(12) United States Patent
Ackermann et al.

(10) Patent No.: US 10,835,738 B2
(45) Date of Patent: Nov. 17, 2020

(54) NASAL STIMULATION DEVICES AND METHODS

(71) Applicant: Oculeve, Inc., South San Francisco, CA (US)

(72) Inventors: Douglas Michael Ackermann, Reno, NV (US); James Donald Loudin, Alhambra, CA (US); John Wardle, San Clemente, CA (US); Janusz Kuzma, Bayview (AU)

(73) Assignee: Oculeve, Inc., San Francisco, CA (US)

( * ) Notice: Subject to any disclaimer, the term of this patent is extended or adjusted under 35 U.S.C. 154(b) by 398 days.

(21) Appl. No.: 15/674,294

(22) Filed: Aug. 10, 2017

(65) Prior Publication Data

US 2017/0368332 A1    Dec. 28, 2017

Related U.S. Application Data

(63) Continuation of application No. 15/256,392, filed on Sep. 2, 2016, now Pat. No. 9,737,702, which is a
(Continued)

(51) Int. Cl.
*A61N 1/05* (2006.01)
*A61N 1/36* (2006.01)
(Continued)

(52) U.S. Cl.
CPC .............. *A61N 1/0546* (2013.01); *A61F 7/12* (2013.01); *A61H 1/00* (2013.01); *A61H 9/0071* (2013.01);
(Continued)

(58) Field of Classification Search
CPC ...... A61N 1/0546; A61N 7/00; A61N 1/0456; A61N 1/36014; A61N 1/36071;
(Continued)

(56) References Cited

U.S. PATENT DOCUMENTS 2,512,882 A    6/1950 Truesdale
2,525,381 A    10/1950 Tower
(Continued)

FOREIGN PATENT DOCUMENTS

CN    1488331 A    4/2004
CN    2693275 Y    4/2005
(Continued)

OTHER PUBLICATIONS

Eye Health (2014). "Watery eyes in cold weather," Oregon Eye Specialists, PC, located at http://www.oregoneyes.net/watery-eyes-in-cold-weather/, 3 total pages.
(Continued)

*Primary Examiner* — Amanda K Hulbert
*Assistant Examiner* — Natasha Patel
(74) *Attorney, Agent, or Firm* — Mintz Levin Cohn Ferris Glovsky and Popeo, P.C.

(57) ABSTRACT

Described here are devices, systems, and methods for treating one or more conditions (such as dry eye) or improving ocular health by providing stimulation to nasal or sinus tissue. Generally, the devices may be handheld or implantable. In some variations, the handheld devices may have a stimulator body and a stimulator probe having one or more nasal insertion prongs. When the devices and systems are used to treat dry eye, nasal or sinus tissue may be stimulated to increase tear production, reduce the symptoms of dry eye, and/or improve ocular surface health.

18 Claims, 58 Drawing Sheets

Related U.S. Application Data continuation of application No. 14/313,937, filed on Jun. 24, 2014, now Pat. No. 9,440,065, which is a continuation of application No. 14/256,915, filed on Apr. 18, 2014, now Pat. No. 8,996,137.

(60) Provisional application No. 61/860,839, filed on Jul. 31, 2013, provisional application No. 61/814,166, filed on Apr. 19, 2013.

(51) Int. Cl.

| | | |
|---|---|---|
| *A61H 1/00* | (2006.01) | |
| *A61F 7/12* | (2006.01) | |
| *A61H 9/00* | (2006.01) | |
| *A61H 21/00* | (2006.01) | |
| *A61H 23/02* | (2006.01) | |
| *A61N 1/378* | (2006.01) | |
| *H02J 7/00* | (2006.01) | |
| *A61N 1/04* | (2006.01) | |
| *A61N 7/00* | (2006.01) | |
| *A61M 31/00* | (2006.01) | |

(52) U.S. Cl.
CPC .......... *A61H 21/00* (2013.01); *A61H 23/02* (2013.01); *A61H 23/0218* (2013.01); *A61H 23/0245* (2013.01); *A61H 23/0263* (2013.01); *A61N 1/0456* (2013.01); *A61N 1/3615* (2013.01); *A61N 1/36046* (2013.01); *A61N 1/36071* (2013.01); *A61N 1/36132* (2013.01); *A61N 1/36146* (2013.01); *A61N 1/36171* (2013.01); *A61N 1/36175* (2013.01); *A61N 1/3787* (2013.01); *A61N 7/00* (2013.01); *H02J 7/0044* (2013.01); *A61H 2201/0153* (2013.01); *A61H 2201/0173* (2013.01); *A61H 2201/025* (2013.01); *A61H 2201/0207* (2013.01); *A61H 2201/0214* (2013.01); *A61H 2201/10* (2013.01); *A61H 2201/165* (2013.01); *A61H 2201/5002* (2013.01); *A61H 2201/5005* (2013.01); *A61H 2201/5015* (2013.01); *A61H 2201/5035* (2013.01); *A61H 2201/5038* (2013.01); *A61H 2201/5043* (2013.01); *A61H 2205/023* (2013.01); *A61H 2205/024* (2013.01); *A61M 31/00* (2013.01); *A61N 2007/0043* (2013.01)

(58) Field of Classification Search
CPC .......... A61N 1/36132; A61N 1/36146; A61N 1/3615; A61N 1/36171; A61N 1/36175; A61N 1/3787; A61N 1/36046; A61N 2007/0043; A61H 9/0071; A61H 21/00; A61H 23/02; A61H 23/0218; A61H 23/0245; A61H 23/0263; A61H 1/00; A61H 2201/0153; A61H 2201/0173; A61H 2201/0207; A61H 2201/0214; A61H 2201/025; A61H 2201/10; A61H 2201/165; A61H 2201/5002; A61H 2201/5005; A61H 2201/5015; A61H 2201/5035; A61H 2201/5038; A61H 2201/5043; A61H 2205/023; A61H 2205/024; H02J 7/0044; A61F 7/12; A61M 31/00

See application file for complete search history.

(56) References Cited

U.S. PATENT DOCUMENTS

| | | |
|---|---|---|
| 3,620,219 A | 11/1971 | Barker |
| 3,709,228 A | 1/1973 | Barker et al. |
| 3,885,550 A | 5/1975 | MacLeod |
| D257,495 S | 11/1980 | Bros et al. |
| 4,495,676 A | 1/1985 | Hartmetz |
| 4,520,825 A | 6/1985 | Thompson et al. |
| 4,539,988 A | 9/1985 | Shirley et al. |
| 4,590,942 A | 5/1986 | Brenman et al. |
| 4,628,933 A | 12/1986 | Michelson |
| 4,681,121 A | 7/1987 | Kobal |
| 4,684,362 A | 8/1987 | Holt |
| 4,706,680 A | 11/1987 | Keusch et al. |
| 4,735,207 A | 4/1988 | Nambu et al. |
| 4,777,954 A | 10/1988 | Keusch et al. |
| 4,780,932 A | 11/1988 | Bowman et al. |
| 4,868,154 A | 9/1989 | Gilbard et al. |
| 4,926,880 A | 5/1990 | Claude et al. |
| 4,957,480 A | 9/1990 | Morenings |
| 4,988,358 A | 1/1991 | Eppley et al. |
| 5,025,807 A | 6/1991 | Zabara |
| 5,072,724 A | 12/1991 | Marcus |
| 5,078,733 A | 1/1992 | Eveleigh et al. |
| 5,090,422 A | 2/1992 | Dahl et al. |
| 5,099,829 A | 3/1992 | Wu |
| 5,147,284 A | 9/1992 | Fedorov et al. |
| 5,324,316 A | 6/1994 | Schulman et al. |
| 5,342,410 A | 8/1994 | Braverman |
| 5,345,948 A | 9/1994 | O'Donnell, Jr. |
| 5,352,445 A | 10/1994 | Lavaux |
| 5,360,438 A | 11/1994 | Fisher |
| 5,498,681 A | 3/1996 | Askari et al. |
| 5,514,131 A | 5/1996 | Edwards et al. |
| 5,533,470 A | 7/1996 | Rose |
| 5,545,617 A | 8/1996 | Dartt et al. |
| 5,571,101 A | 11/1996 | Ellman et al. |
| 5,607,461 A | 3/1997 | Lathrop |
| 5,611,970 A | 3/1997 | Apollonio et al. |
| 5,640,978 A | 6/1997 | Wong |
| 5,683,436 A | 11/1997 | Mendes et al. |
| 5,697,957 A | 12/1997 | Noren et al. |
| 5,707,400 A | 1/1998 | Terry et al. |
| 5,713,833 A | 2/1998 | Milligan |
| 5,720,773 A | 2/1998 | Lopez-Claros |
| 5,733,282 A | 3/1998 | Ellman et al. |
| 5,735,817 A | 4/1998 | Shantha |
| 5,792,100 A | 8/1998 | Shantha |
| 5,794,614 A | 8/1998 | Gruenke et al. |
| 5,800,685 A | 9/1998 | Perrault |
| 5,843,140 A | 12/1998 | Strojnik |
| 5,900,407 A | 5/1999 | Yerxa et al. |
| 5,904,658 A | 5/1999 | Niederauer et al. |
| 5,935,155 A | 8/1999 | Humayun et al. |
| 5,948,006 A | 9/1999 | Mann |
| 6,001,088 A | 12/1999 | Roberts et al. |
| 6,020,445 A | 2/2000 | Vanderlaan et al. |
| 6,035,236 A | 3/2000 | Jarding et al. |
| 6,050,999 A | 4/2000 | Paraschac et al. |
| 6,051,017 A | 4/2000 | Loeb et al. |
| 6,083,251 A | 7/2000 | Shindo |
| 6,102,847 A | 8/2000 | Stielau |
| 6,152,916 A | 11/2000 | Bige |
| 6,200,626 B1 | 3/2001 | Grobe, III et al. |
| 6,205,359 B1 | 3/2001 | Boveja |
| 6,208,902 B1 | 3/2001 | Boveja |
| 6,240,316 B1 | 5/2001 | Richmond et al. |
| 6,246,911 B1 | 6/2001 | Seligman |
| 6,270,796 B1 | 8/2001 | Weinstein |
| 6,272,382 B1 | 8/2001 | Faltys et al. |
| 6,275,737 B1 | 8/2001 | Mann |
| 6,277,855 B1 | 8/2001 | Yerxa |
| 6,284,765 B1 | 9/2001 | Caffrey |
| 6,324,429 B1 | 11/2001 | Shire et al. |
| 6,327,504 B1 | 12/2001 | Dolgin et al. |
| 6,366,814 B1 | 4/2002 | Boveja et al. |
| 6,405,079 B1 | 6/2002 | Ansarinia et al. |
| 6,438,398 B1 | 8/2002 | Pflugfelder et al. |
| 6,458,157 B1 | 10/2002 | Suaning |
| 6,505,077 B1 | 1/2003 | Kast et al. |
| 6,526,318 B1 | 2/2003 | Ansarinia et al. |
| 6,535,766 B1 | 3/2003 | Thompson et al. |
| 6,537,265 B2 | 3/2003 | Thanavala et al. |

(56) References Cited

U.S. PATENT DOCUMENTS

| | | |
|---|---|---|
| 6,539,253 B2 | 3/2003 | Thompson et al. |
| 6,562,036 B1 | 5/2003 | Ellman et al. |
| 6,564,102 B1 | 5/2003 | Boveja |
| 6,578,579 B2 | 6/2003 | Burnside et al. |
| 6,604,528 B1 | 8/2003 | Duncan |
| 6,641,799 B2 | 11/2003 | Goldberg |
| 6,658,301 B2 | 12/2003 | Loeb et al. |
| 6,662,052 B1 | 12/2003 | Sarwal et al. |
| 6,684,879 B1 | 2/2004 | Coffee et al. |
| 6,701,189 B2 | 3/2004 | Fang et al. |
| 6,748,951 B1 | 6/2004 | Schmidt |
| 6,792,314 B2 | 9/2004 | Byers et al. |
| 6,829,508 B2 | 12/2004 | Schulman et al. |
| 6,853,858 B2 | 2/2005 | Shalev |
| 6,871,099 B1 | 3/2005 | Whitehurst et al. |
| 6,879,859 B1 | 4/2005 | Boveja |
| 6,885,888 B2 | 4/2005 | Rezai |
| 6,895,279 B2 | 5/2005 | Loeb et al. |
| 7,024,241 B1 | 4/2006 | Bornzin et al. |
| 7,054,692 B1 | 5/2006 | Whitehurst et al. |
| 7,067,307 B2 | 6/2006 | Hochleitner et al. |
| 7,069,084 B2 | 6/2006 | Yee |
| 7,117,033 B2 | 10/2006 | Shalev et al. |
| 7,142,909 B2 | 11/2006 | Greenberg et al. |
| 7,146,209 B2 | 12/2006 | Gross et al. |
| 7,169,163 B2 | 1/2007 | Becker |
| 7,190,998 B2 | 3/2007 | Shalev et al. |
| 7,225,032 B2 | 5/2007 | Schmeling et al. |
| 7,228,184 B2 | 6/2007 | Heath |
| 7,247,692 B2 | 7/2007 | Laredo |
| 7,317,947 B2 | 1/2008 | Wahlstrand et al. |
| 7,330,762 B2 | 2/2008 | Boveja et al. |
| 7,346,389 B1 | 3/2008 | Newsome |
| 7,346,398 B2 | 3/2008 | Gross et al. |
| 7,369,897 B2 | 5/2008 | Boveja et al. |
| 7,442,191 B2 | 10/2008 | Hovda et al. |
| 7,460,911 B2 | 12/2008 | Cosendai et al. |
| 7,477,947 B2 | 1/2009 | Pines et al. |
| 7,502,652 B2 | 3/2009 | Gaunt et al. |
| 7,547,447 B2 | 6/2009 | Yiu et al. |
| 7,565,204 B2 | 7/2009 | Matei et al. |
| 7,599,737 B2 | 10/2009 | Yomtov et al. |
| 7,636,597 B2 | 12/2009 | Gross et al. |
| 7,650,186 B2 | 1/2010 | Hastings et al. |
| D613,408 S | 4/2010 | Gausmann et al. |
| D614,303 S | 4/2010 | Gausmann et al. |
| D614,774 S | 4/2010 | Gausmann et al. |
| 7,725,176 B2 | 5/2010 | Schuler et al. |
| 7,725,195 B2 | 5/2010 | Lima et al. |
| D617,443 S | 6/2010 | Grenon et al. |
| 7,758,190 B2 | 7/2010 | Korb et al. |
| 7,778,703 B2 | 8/2010 | Gross et al. |
| 7,778,711 B2 | 8/2010 | Ben-David et al. |
| 7,792,591 B2 | 9/2010 | Rooney et al. |
| 7,805,200 B2 | 9/2010 | Kast et al. |
| 7,805,202 B2 | 9/2010 | Kuzma et al. |
| 7,805,203 B2 | 9/2010 | Ben-David et al. |
| 7,809,442 B2 | 10/2010 | Bolea et al. |
| 7,835,794 B2 | 11/2010 | Greenberg et al. |
| 7,846,124 B2 | 12/2010 | Becker |
| 7,860,570 B2 | 12/2010 | Whitehurst et al. |
| 7,873,421 B2 | 1/2011 | Karell |
| 7,879,032 B1 | 2/2011 | Garito et al. |
| 7,879,079 B2 | 2/2011 | Tu et al. |
| D638,128 S | 5/2011 | Prokop et al. |
| 7,981,095 B2 | 7/2011 | Grenon et al. |
| 7,993,381 B2 | 8/2011 | Mac et al. |
| 7,998,202 B2 | 8/2011 | Lesh |
| 8,002,783 B2 | 8/2011 | Vercellotti et al. |
| 8,019,419 B1 | 9/2011 | Panescu et al. |
| 8,019,441 B2 | 9/2011 | Wallace et al. |
| 8,080,047 B2 | 12/2011 | Yu |
| 8,083,787 B2 | 12/2011 | Korb et al. |
| 8,145,322 B1 | 3/2012 | Yao et al. |
| 8,155,746 B2 | 4/2012 | Maltan et al. |
| 8,165,680 B2 | 4/2012 | Greenberg et al. |
| 8,204,591 B2 | 6/2012 | Ben-David et al. |
| 8,231,218 B2 | 7/2012 | Hong et al. |
| 8,251,983 B2 | 8/2012 | Larson et al. |
| 8,295,529 B2 | 10/2012 | Petersen et al. |
| 8,318,070 B2 | 11/2012 | Shiah et al. |
| D681,839 S | 5/2013 | Nathanson |
| 8,489,189 B2 | 7/2013 | Tronnes |
| 8,494,641 B2 | 7/2013 | Boling et al. |
| 8,521,292 B2 | 8/2013 | Wei et al. |
| 8,626,298 B2 | 1/2014 | Simon |
| 8,676,324 B2 | 3/2014 | Simon et al. |
| 8,728,136 B2 | 5/2014 | Feldman |
| 8,918,181 B2 | 12/2014 | Ackermann et al. |
| 8,936,594 B2 | 1/2015 | Wolf et al. |
| 8,986,301 B2 | 3/2015 | Wolf et al. |
| 8,996,137 B2 | 3/2015 | Ackermann et al. |
| 9,079,042 B2 | 7/2015 | Tiedtke et al. |
| 9,095,723 B2 | 8/2015 | Ackermann et al. |
| 9,265,956 B2 | 2/2016 | Ackermann et al. |
| 9,440,065 B2 | 9/2016 | Ackermann et al. |
| 9,687,652 B2 | 6/2017 | Franke et al. |
| 9,717,627 B2 | 8/2017 | Kuzma et al. |
| 9,737,702 B2 | 8/2017 | Ackermann et al. |
| 9,737,712 B2 | 8/2017 | Franke et al. |
| 9,764,150 B2 | 9/2017 | Loudin et al. |
| 9,770,583 B2 | 9/2017 | Gupta et al. |
| 9,821,159 B2 | 11/2017 | Ackermann et al. |
| 9,956,397 B2 | 5/2018 | Loudin et al. |
| D826,420 S | 8/2018 | Ackermann et al. |
| 10,143,846 B2 | 12/2018 | Ackermann et al. |
| D837,396 S | 1/2019 | Ackermann et al. |
| 10,207,108 B2 | 2/2019 | Franke et al. |
| 2001/0018918 A1 | 9/2001 | Burnside et al. |
| 2001/0020177 A1 | 9/2001 | Gruzdowich et al. |
| 2002/0013594 A1 | 1/2002 | Dinger et al. |
| 2002/0035358 A1 | 3/2002 | Wang |
| 2002/0049290 A1 | 4/2002 | Vanderbilt et al. |
| 2002/0188331 A1 | 12/2002 | Fang et al. |
| 2003/0014089 A1 | 1/2003 | Chow et al. |
| 2003/0045909 A1 | 3/2003 | Gross et al. |
| 2003/0045911 A1 | 3/2003 | Bruchmann et al. |
| 2003/0114899 A1 | 6/2003 | Woods et al. |
| 2003/0120323 A1 | 6/2003 | Meadows et al. |
| 2003/0130809 A1 | 7/2003 | Cohen et al. |
| 2003/0133877 A1* | 7/2003 | Levin ............... A61K 9/0043 424/45 |
| 2003/0139784 A1 | 7/2003 | Morimoto et al. |
| 2003/0176892 A1 | 9/2003 | Shalev |
| 2003/0176898 A1 | 9/2003 | Gross et al. |
| 2003/0192784 A1 | 10/2003 | Zhou et al. |
| 2003/0229381 A1 | 12/2003 | Hochmair et al. |
| 2003/0233134 A1 | 12/2003 | Greenberg et al. |
| 2003/0233135 A1 | 12/2003 | Yee |
| 2004/0050392 A1 | 3/2004 | Tu et al. |
| 2004/0059466 A1 | 3/2004 | Block et al. |
| 2004/0092992 A1 | 5/2004 | Adams et al. |
| 2004/0098036 A1 | 5/2004 | Bergersen |
| 2004/0098067 A1 | 5/2004 | Ohta et al. |
| 2004/0127942 A1 | 7/2004 | Yomtov et al. |
| 2004/0138646 A1 | 7/2004 | Walla |
| 2004/0147973 A1 | 7/2004 | Hauser et al. |
| 2004/0151930 A1 | 8/2004 | Rouns et al. |
| 2004/0220644 A1* | 11/2004 | Shalev ............... A61N 1/0546 607/45 |
| 2005/0004621 A1 | 1/2005 | Boveja et al. |
| 2005/0004625 A1 | 1/2005 | Chow |
| 2005/0010250 A1 | 1/2005 | Schuler et al. |
| 2005/0010266 A1 | 1/2005 | Bogdanowicz |
| 2005/0101967 A1 | 5/2005 | Weber et al. |
| 2005/0101994 A1 | 5/2005 | Yamazaki et al. |
| 2005/0105046 A1 | 5/2005 | Tung |
| 2005/0137276 A1 | 6/2005 | Yahiaoui et al. |
| 2005/0159790 A1 | 7/2005 | Shalev et al. |
| 2005/0197675 A1 | 9/2005 | David et al. |
| 2005/0251061 A1 | 11/2005 | Schuler et al. |
| 2005/0256570 A1 | 11/2005 | Azar |
| 2005/0267542 A1 | 12/2005 | David et al. |
| 2005/0268472 A1 | 12/2005 | Bourilkov et al. |

(56) References Cited

U.S. PATENT DOCUMENTS

| | | |
|---|---|---|
| 2006/0004423 A1 | 1/2006 | Boveja et al. |
| 2006/0018872 A1 | 1/2006 | Tew et al. |
| 2006/0036296 A1 | 2/2006 | Greenberg et al. |
| 2006/0074450 A1 | 4/2006 | Boveja et al. |
| 2006/0089673 A1 | 4/2006 | Schultheiss et al. |
| 2006/0095077 A1 | 5/2006 | Tronnes et al. |
| 2006/0095108 A1 | 5/2006 | Chowdhury et al. |
| 2006/0100668 A1 | 5/2006 | Ben-David et al. |
| 2006/0107958 A1 | 5/2006 | Sleeper |
| 2006/0142822 A1 | 6/2006 | Tulgar |
| 2006/0161225 A1 | 7/2006 | Sormann et al. |
| 2006/0195169 A1 | 8/2006 | Gross et al. |
| 2006/0206155 A1 | 9/2006 | Ben-David et al. |
| 2006/0206162 A1 | 9/2006 | Wahlstrand et al. |
| 2006/0216317 A1 | 9/2006 | Reinhard et al. |
| 2006/0235430 A1 | 10/2006 | Le et al. |
| 2006/0239482 A1 | 10/2006 | Hatoum et al. |
| 2006/0259098 A1 | 11/2006 | Erickson |
| 2006/0271024 A1 | 11/2006 | Gertner et al. |
| 2006/0271108 A1 | 11/2006 | Libbus et al. |
| 2006/0276738 A1 | 12/2006 | Becker |
| 2007/0031341 A1 | 2/2007 | DiMauro et al. |
| 2007/0038250 A1 | 2/2007 | He et al. |
| 2007/0038267 A1 | 2/2007 | Shodo et al. |
| 2007/0060815 A1 | 3/2007 | Martin et al. |
| 2007/0060954 A1 | 3/2007 | Cameron et al. |
| 2007/0083245 A1 | 4/2007 | Lamensdorf et al. |
| 2007/0123938 A1 | 5/2007 | Haller et al. |
| 2007/0135868 A1 | 6/2007 | Shi et al. |
| 2007/0150034 A1 | 6/2007 | Rooney et al. |
| 2007/0219600 A1 | 9/2007 | Gertner et al. |
| 2007/0237797 A1 | 10/2007 | Peyman |
| 2007/0237825 A1 | 10/2007 | Levy et al. |
| 2007/0248930 A1 | 10/2007 | Brawn |
| 2007/0250119 A1 | 10/2007 | Tyler et al. |
| 2007/0250135 A1 | 10/2007 | Bartz-Schmidt et al. |
| 2007/0255333 A1 | 11/2007 | Giftakis et al. |
| 2007/0276314 A1 | 11/2007 | Becker |
| 2007/0276451 A1 | 11/2007 | Rigaux |
| 2007/0295327 A1 | 12/2007 | Bottomley |
| 2007/0299420 A1 | 12/2007 | Peyman |
| 2007/0299462 A1 | 12/2007 | Becker |
| 2008/0009897 A1 | 1/2008 | Duran Von Arx |
| 2008/0021515 A1 | 1/2008 | Horsager et al. |
| 2008/0082057 A1 | 4/2008 | Korb et al. |
| 2008/0082131 A1 | 4/2008 | Llanos |
| 2008/0109046 A1 | 5/2008 | Lima et al. |
| 2008/0109054 A1 | 5/2008 | Hastings et al. |
| 2008/0114424 A1 | 5/2008 | Grenon et al. |
| 2008/0132933 A1 | 6/2008 | Gerber |
| 2008/0132969 A1 | 6/2008 | Bennett et al. |
| 2008/0140141 A1 | 6/2008 | Ben-David et al. |
| 2008/0183242 A1 | 7/2008 | Tano et al. |
| 2008/0183243 A1 | 7/2008 | Shodo et al. |
| 2008/0208287 A1 | 8/2008 | Palermo et al. |
| 2008/0208335 A1 | 8/2008 | Blum et al. |
| 2008/0221642 A1 | 9/2008 | Humayun et al. |
| 2008/0269648 A1 | 10/2008 | Bock |
| 2008/0288036 A1 | 11/2008 | Greenberg et al. |
| 2008/0294066 A1 | 11/2008 | Hetling et al. |
| 2009/0005835 A1 | 1/2009 | Greenberg et al. |
| 2009/0012573 A1 | 1/2009 | Karell et al. |
| 2009/0018582 A1 | 1/2009 | Ishikawa et al. |
| 2009/0024187 A1 | 1/2009 | Erickson et al. |
| 2009/0024189 A1 | 1/2009 | Lee et al. |
| 2009/0036945 A1 | 2/2009 | Chancellor et al. |
| 2009/0043185 A1 | 2/2009 | McAdams et al. |
| 2009/0056709 A1 | 3/2009 | Worsoff |
| 2009/0099600 A1 | 4/2009 | Moore et al. |
| 2009/0099623 A1 | 4/2009 | Bentwich et al. |
| 2009/0099626 A1 | 4/2009 | de Juan, Jr. et al. |
| 2009/0101139 A1 * | 4/2009 | Karell .................. A61F 5/08 128/200.24 |
| 2009/0124965 A1 | 5/2009 | Greenberg et al. |
| 2009/0138061 A1 | 5/2009 | Stephens et al. |
| 2009/0156581 A1 | 6/2009 | Dillon et al. |
| 2009/0157142 A1 | 6/2009 | Cauller et al. |
| 2009/0157145 A1 | 6/2009 | Cauller |
| 2009/0157147 A1 | 6/2009 | Cauller et al. |
| 2009/0192571 A1 | 7/2009 | Stett et al. |
| 2009/0192575 A1 | 7/2009 | Carbunaru et al. |
| 2009/0204142 A1 | 8/2009 | Becker |
| 2009/0239235 A1 | 9/2009 | DeMaria et al. |
| 2009/0241840 A1 | 10/2009 | Mills |
| 2009/0264966 A1 | 10/2009 | Blum et al. |
| 2009/0281594 A1 | 11/2009 | King et al. |
| 2009/0281596 A1 | 11/2009 | King et al. |
| 2009/0299418 A1 | 12/2009 | Shalev et al. |
| 2009/0306738 A1 | 12/2009 | Weiss et al. |
| 2009/0312818 A1 | 12/2009 | Horsager et al. |
| 2010/0030150 A1 | 2/2010 | Paques et al. |
| 2010/0076423 A1 | 3/2010 | Muller |
| 2010/0087896 A1 | 4/2010 | McCreery |
| 2010/0094280 A1 | 4/2010 | Muller |
| 2010/0100165 A1 | 4/2010 | Swanson et al. |
| 2010/0139002 A1 | 6/2010 | Walker et al. |
| 2010/0152708 A1 | 6/2010 | Li et al. |
| 2010/0161004 A1 | 6/2010 | Najafi et al. |
| 2010/0168513 A1 | 7/2010 | Pless et al. |
| 2010/0179468 A1 | 7/2010 | Becker |
| 2010/0211132 A1 | 8/2010 | Nimmagadda et al. |
| 2010/0241195 A1 | 9/2010 | Meadows et al. |
| 2010/0256609 A1 * | 10/2010 | Hillis .................... A61B 5/411 604/890.1 |
| 2010/0274164 A1 | 10/2010 | Juto |
| 2010/0274224 A1 | 10/2010 | Jain et al. |
| 2010/0274313 A1 | 10/2010 | Boling et al. |
| 2010/0280509 A1 | 11/2010 | Muller et al. |
| 2010/0288275 A1 | 11/2010 | Djupesland et al. |
| 2010/0311688 A1 | 12/2010 | Chapin et al. |
| 2010/0318159 A1 | 12/2010 | Aghassian et al. |
| 2011/0021975 A1 | 1/2011 | Covello |
| 2011/0028807 A1 | 2/2011 | Abreu |
| 2011/0028883 A1 | 2/2011 | Juan, Jr. et al. |
| 2011/0076775 A1 | 3/2011 | Stewart et al. |
| 2011/0077551 A1 | 3/2011 | Videbaek |
| 2011/0077698 A1 | 3/2011 | Tsampazis et al. |
| 2011/0081333 A1 | 4/2011 | Shantha et al. |
| 2011/0082518 A1 | 4/2011 | Filippello |
| 2011/0093043 A1 | 4/2011 | Torgerson et al. |
| 2011/0151393 A1 | 6/2011 | Frey, II et al. |
| 2011/0152969 A1 | 6/2011 | Zehnder et al. |
| 2011/0184490 A1 | 7/2011 | Horsager et al. |
| 2011/0202121 A1 | 8/2011 | Wen |
| 2011/0218590 A1 | 9/2011 | DeGiorgio et al. |
| 2011/0234971 A1 | 9/2011 | Yeh |
| 2011/0270067 A1 | 11/2011 | Faraji et al. |
| 2011/0270348 A1 | 11/2011 | Goetz |
| 2011/0275734 A1 | 11/2011 | Scales et al. |
| 2011/0276107 A1 * | 11/2011 | Simon ................ A61N 1/36021 607/46 |
| 2011/0282251 A1 | 11/2011 | Baker et al. |
| 2011/0295336 A1 | 12/2011 | Sharma et al. |
| 2011/0313330 A1 | 12/2011 | Loushin et al. |
| 2011/0313480 A1 | 12/2011 | De Vos |
| 2011/0313481 A1 | 12/2011 | De Vos |
| 2011/0313488 A1 | 12/2011 | Hincapie Ordonez et al. |
| 2012/0053648 A1 | 3/2012 | Neher et al. |
| 2012/0112903 A1 | 5/2012 | Kaib et al. |
| 2012/0130398 A1 | 5/2012 | Ackermann et al. |
| 2012/0133887 A1 | 5/2012 | Huang |
| 2012/0197338 A1 | 8/2012 | Su et al. |
| 2012/0232615 A1 | 9/2012 | Barolat et al. |
| 2012/0232618 A1 | 9/2012 | Feldman |
| 2012/0234332 A1 | 9/2012 | Shantha |
| 2012/0253249 A1 | 10/2012 | Wilson et al. |
| 2012/0298105 A1 | 11/2012 | Osorio et al. |
| 2012/0315329 A1 | 12/2012 | Ahn et al. |
| 2012/0316557 A1 | 12/2012 | Sartor et al. |
| 2012/0323214 A1 | 12/2012 | Shantha |
| 2012/0323227 A1 | 12/2012 | Wolf et al. |
| 2012/0323232 A1 | 12/2012 | Wolf et al. |
| 2012/0330376 A1 | 12/2012 | Flynn et al. |
| 2013/0006095 A1 | 1/2013 | Jenkins et al. |

(56) References Cited

U.S. PATENT DOCUMENTS

| | | | |
|---|---|---|---|
| 2013/0006326 A1* | 1/2013 | Ackermann | A61N 1/36046 607/53 |
| 2013/0053733 A1 | 2/2013 | Korb et al. | |
| 2013/0053737 A1 | 2/2013 | Scerbo | |
| 2013/0065765 A1 | 3/2013 | Selifonov et al. | |
| 2013/0072755 A1 | 3/2013 | Papania et al. | |
| 2013/0085551 A1 | 4/2013 | Bachinski et al. | |
| 2013/0158451 A1 | 6/2013 | Juto et al. | |
| 2013/0158626 A1 | 6/2013 | DeGiorgio et al. | |
| 2013/0172790 A1 | 7/2013 | Badawi | |
| 2013/0178937 A1 | 7/2013 | Vassallo et al. | |
| 2013/0197321 A1 | 8/2013 | Wilson | |
| 2013/0253387 A1 | 9/2013 | Bonutti et al. | |
| 2013/0261706 A1 | 10/2013 | Mirro et al. | |
| 2013/0270491 A1 | 10/2013 | Park et al. | |
| 2013/0274824 A1 | 10/2013 | Otto et al. | |
| 2013/0274831 A1 | 10/2013 | Otto et al. | |
| 2013/0282070 A1 | 10/2013 | Cowan et al. | |
| 2013/0304154 A1 | 11/2013 | Goodman et al. | |
| 2013/0310887 A1 | 11/2013 | Curtis | |
| 2013/0336557 A1 | 12/2013 | Cruzat et al. | |
| 2014/0012182 A1 | 1/2014 | Shantha et al. | |
| 2014/0056815 A1 | 2/2014 | Peyman | |
| 2014/0081353 A1 | 3/2014 | Cook et al. | |
| 2014/0088463 A1 | 3/2014 | Wolf et al. | |
| 2014/0148872 A1 | 5/2014 | Goldwasser et al. | |
| 2014/0156000 A1 | 6/2014 | Campin et al. | |
| 2014/0163580 A1 | 6/2014 | Tischendorf et al. | |
| 2014/0214115 A1 | 7/2014 | Greiner et al. | |
| 2014/0214118 A1 | 7/2014 | Greiner et al. | |
| 2014/0214120 A1 | 7/2014 | Simon et al. | |
| 2014/0214124 A1 | 7/2014 | Greiner et al. | |
| 2014/0214125 A1 | 7/2014 | Greiner et al. | |
| 2014/0257205 A1 | 9/2014 | Schaller | |
| 2014/0257433 A1 | 9/2014 | Ackermann et al. | |
| 2014/0277429 A1 | 9/2014 | Kuzma et al. | |
| 2014/0316310 A1 | 10/2014 | Ackermann et al. | |
| 2014/0316396 A1 | 10/2014 | Wolf et al. | |
| 2014/0316485 A1 | 10/2014 | Ackermann et al. | |
| 2014/0324147 A1 | 10/2014 | Wagner | |
| 2014/0362339 A1 | 12/2014 | Imafuku | |
| 2014/0371565 A1 | 12/2014 | Glasser | |
| 2014/0371812 A1 | 12/2014 | Ackermann et al. | |
| 2015/0088156 A1 | 3/2015 | Ackermann et al. | |
| 2015/0182145 A1 | 7/2015 | Gazdzinski | |
| 2015/0238754 A1 | 8/2015 | Loudin et al. | |
| 2015/0335900 A1 | 11/2015 | Ackermann et al. | |
| 2015/0343202 A1 | 12/2015 | Picaud et al. | |
| 2015/0362755 A1 | 12/2015 | Lee et al. | |
| 2016/0022992 A1 | 1/2016 | Franke et al. | |
| 2016/0058615 A1 | 3/2016 | Camras et al. | |
| 2016/0080720 A1 | 3/2016 | Fullam | |
| 2016/0114163 A1 | 4/2016 | Franke et al. | |
| 2016/0158548 A1 | 6/2016 | Ackermann et al. | |
| 2016/0270656 A1 | 9/2016 | Samec et al. | |
| 2016/0367795 A1 | 12/2016 | Ackermann et al. | |
| 2016/0367806 A1 | 12/2016 | Kahook | |
| 2017/0049619 A1 | 2/2017 | Kahook | |
| 2017/0157401 A1 | 6/2017 | Loudin et al. | |
| 2017/0188947 A1 | 7/2017 | Connor | |
| 2017/0239459 A1 | 8/2017 | Loudin et al. | |
| 2017/0252563 A1 | 9/2017 | Franke et al. | |
| 2017/0312521 A1 | 11/2017 | Franke et al. | |
| 2017/0340884 A1 | 11/2017 | Franke et al. | |
| 2017/0354536 A1 | 12/2017 | Kuzma et al. | |
| 2017/0368359 A1 | 12/2017 | Loudin et al. | |
| 2018/0064940 A1 | 3/2018 | Ackermann et al. | |
| 2018/0064941 A1 | 3/2018 | Ackermann et al. | |
| 2018/0064942 A1 | 3/2018 | Franke et al. | |
| 2018/0153394 A1 | 6/2018 | Franke et al. | |
| 2018/0154137 A1 | 6/2018 | Ackermann et al. | |
| 2018/0154161 A1 | 6/2018 | Ackermann et al. | |
| 2018/0161579 A1 | 6/2018 | Franke et al. | |
| 2018/0280688 A1 | 10/2018 | Loudin et al. | |
| 2019/0022392 A1 | 1/2019 | Franke et al. | |
| 2019/0167978 A1 | 6/2019 | Ackermann et al. | |
| 2019/0217095 A1 | 7/2019 | Franke et al. | |
| 2019/0282804 A1 | 9/2019 | Ackermann et al. | |
| 2019/0290922 A1 | 9/2019 | Ackermann et al. | |
| 2019/0308009 A1 | 10/2019 | Loudin et al. | |
| 2019/0344077 A1 | 11/2019 | Ackermann et al. | |
| 2020/0030615 A1 | 1/2020 | Loudin et al. | |
| 2020/0038238 A1 | 2/2020 | Kuzma et al. | |

FOREIGN PATENT DOCUMENTS

| | | |
|---|---|---|
| CN | 101087822 A | 12/2007 |
| CN | 101503491 A | 8/2009 |
| CN | 101589085 A | 11/2009 |
| CN | 101616663 A | 12/2009 |
| CN | 101829120 A | 9/2010 |
| CN | 101939043 A | 1/2011 |
| CN | 102266592 A | 12/2011 |
| CN | 103467652 A | 12/2013 |
| DE | 102006048819 A1 | 4/2008 |
| EP | 0 109 935 A1 | 5/1984 |
| EP | 1 497 483 | 1/2005 |
| EP | 1 651 307 | 5/2006 |
| EP | 1 919 553 | 5/2008 |
| EP | 1 958 661 A1 | 8/2008 |
| EP | 2 205 193 | 7/2010 |
| EP | 2 205 314 | 7/2010 |
| EP | 2102681-0001 | 10/2012 |
| EP | 2199000-0001 | 3/2013 |
| EP | 3263175 A1 | 1/2018 |
| GB | 2 129 690 B | 3/1987 |
| GB | 2 456 002 A | 7/2009 |
| JP | S60500241 A | 2/1985 |
| JP | 2002-519138 A | 7/2002 |
| JP | 2002-325851 A | 11/2002 |
| JP | 2002-539859 A | 11/2002 |
| JP | 2004-508847 A | 3/2004 |
| JP | 2004526510 A | 9/2004 |
| JP | 2005-502409 A | 1/2005 |
| JP | 2005-052461 A | 3/2005 |
| JP | 2005-144178 A | 6/2005 |
| JP | 2005521489 A | 7/2005 |
| JP | 2005-528169 A | 9/2005 |
| JP | 2006-515900 A | 6/2006 |
| JP | 2006-311917 A | 11/2006 |
| JP | 2007-044323 A | 2/2007 |
| JP | 2007-521385 A | 8/2007 |
| JP | 2007-528751 A | 10/2007 |
| JP | 2008-55000 A | 3/2008 |
| JP | 2008-183248 A | 8/2008 |
| JP | 2008-541850 A | 11/2008 |
| JP | 2009-506836 A | 2/2009 |
| JP | 2009-523503 A | 6/2009 |
| JP | 2010-505563 A | 2/2010 |
| JP | 2010-051562 A | 3/2010 |
| JP | 2010506654 A | 3/2010 |
| JP | 2010-537777 A | 12/2010 |
| JP | 2011-030734 A | 2/2011 |
| JP | 2011-524780 A | 9/2011 |
| JP | 2012-100708 A | 5/2012 |
| JP | 2012-115545 A | 6/2012 |
| JP | 2012-200558 A | 10/2012 |
| JP | 2013-528416 A | 7/2013 |
| JP | 2013-542838 A | 11/2013 |
| RU | 2338492 C1 | 11/2008 |
| WO | WO-00/01320 A2 | 1/2000 |
| WO | WO-00/56393 A1 | 9/2000 |
| WO | WO-00/62672 A1 | 10/2000 |
| WO | WO-01/05388 A2 | 1/2001 |
| WO | WO-01/85094 A2 | 11/2001 |
| WO | WO-02/078592 A2 | 10/2002 |
| WO | WO-03/023907 A1 | 3/2003 |
| WO | WO-03/082080 A2 | 10/2003 |
| WO | WO-2003/087433 A1 | 10/2003 |
| WO | WO-03/101535 A1 | 12/2003 |
| WO | WO-2004/026106 A2 | 4/2004 |
| WO | WO-2004/026106 A3 | 4/2004 |
| WO | WO-2004/043217 A2 | 5/2004 |
| WO | WO-2004/043217 A3 | 5/2004 |

(56) References Cited

FOREIGN PATENT DOCUMENTS

| | | |
|---|---|---|
| WO | WO-2004/091453 A1 | 10/2004 |
| WO | WO-2004/112893 A2 | 12/2004 |
| WO | WO-2004/112893 A3 | 12/2004 |
| WO | WO-2005/007234 A2 | 1/2005 |
| WO | WO-2005/007234 A3 | 1/2005 |
| WO | WO-2005/030025 A2 | 4/2005 |
| WO | WO-2005/030025 A3 | 4/2005 |
| WO | WO-2005/060984 A1 | 7/2005 |
| WO | WO-2006/127366 A1 | 11/2006 |
| WO | WO-2007/028003 A2 | 3/2007 |
| WO | WO-2007/079543 A1 | 7/2007 |
| WO | WO-2008/048321 A1 | 4/2008 |
| WO | WO-2008/156501 A2 | 12/2008 |
| WO | WO-2008/156501 A3 | 12/2008 |
| WO | WO-2009/035571 A2 | 3/2009 |
| WO | WO-2009/035571 A3 | 3/2009 |
| WO | WO-2009/048580 A1 | 4/2009 |
| WO | WO-2009/070709 A1 | 6/2009 |
| WO | WO-2009/154457 A2 | 12/2009 |
| WO | WO-2010/003011 A1 | 1/2010 |
| WO | WO-2010/027743 A1 | 3/2010 |
| WO | WO-2010/069317 A1 | 6/2010 |
| WO | WO-2010/076904 A1 | 7/2010 |
| WO | WO-2010/099818 A1 | 9/2010 |
| WO | WO-2010/123704 A2 | 10/2010 |
| WO | WO-2011/011373 A1 | 1/2011 |
| WO | WO-2012/068247 A1 | 5/2012 |
| WO | WO-2012/139063 A2 | 10/2012 |
| WO | WO-2012/139063 A3 | 10/2012 |
| WO | WO-2012/155188 A1 | 11/2012 |
| WO | WO-2012/174161 A1 | 12/2012 |
| WO | WO-2013/055940 A2 | 4/2013 |
| WO | WO-2013/055940 A3 | 4/2013 |
| WO | WO-2013/157320 A1 | 10/2013 |
| WO | WO-2013/162793 A1 | 10/2013 |
| WO | WO-2013/165697 A1 | 11/2013 |
| WO | WO-2013/166353 A1 | 11/2013 |
| WO | WO-2013/055940 A2 | 5/2014 |
| WO | WO-2013/055940 A3 | 5/2014 |
| WO | WO-2014/138709 A1 | 9/2014 |
| WO | WO-2014/165124 A1 | 10/2014 |
| WO | WO-2014/172693 A2 | 10/2014 |
| WO | WO-2014/172693 A3 | 10/2014 |
| WO | WO-2015/130707 A2 | 9/2015 |
| WO | WO-2015/130707 A3 | 9/2015 |
| WO | WO-2016/015025 A1 | 1/2016 |
| WO | WO-2016/025323 A1 | 2/2016 |
| WO | WO-2016/065211 A1 | 4/2016 |
| WO | WO-2016/065213 A1 | 4/2016 |
| WO | WO-2016/065215 A1 | 4/2016 |
| WO | WO-2017/192572 A1 | 11/2017 |
| WO | WO-2014/153218 A1 | 9/2019 |

OTHER PUBLICATIONS

Friedman et al. (2016). "A nonrandomized, open-label study to evaluate the effect of nasal stimulation on tear production in subjects with dry eye disease," Clin. Ophthal. 10:795-804.
Friedman, N. J. (2010) "Impact of Dry Eye Disease and Impact on Quality of Life." Current Opinion in Ophthalmology. 21:310-316.
Galor, A. et al. (2014). "Environmental factors affect the risk of dry eye syndrome in a United States veteran population," Opth. 121:972-973.
Harvard Health Publishing (2010). "Dry eyes and what you can try," Harvard Medical School, 2 total pages.
McDonald, MD, Marguerite et al. "Hydroxypropyl Cellulose Ophthalmic Inserts (Lacrisert) Reduce the Signs and Symptoms of Dry Eye Syndrome and Improve Patient Quality of Life." Transactions of the American Ophthalmological Society, (2009), 107:214-222.
Petrov, A. et al. (2016). "SkQ1 Ophthalmic Solution for Dry Eye Treatment: Results of a Phase 2 Safety and Efficacy Clinical Study in the Environment and During Challenge in the Controlled Adverse Environment Model," Adv. Ther. 33:96-115.
Van Setten, G. et al. (2016). "Evidence of seasonality and effects of psychrometry in dry eye disease," Acta Opth. 94:499-506.
Vapor Pressure Data for H2O (2012). Handbook of Chemistry and Physics, 73rd edition, 1 total page.
Yu, PhD, Junhua, et al. "The Economic Burden of Dry Eye Disease in the United States: a Decision Tree Analysis." Cornea, (Apr. 2011), 30(4):379-387.
Acar, M. et al. (2013). "Ocular surface assessment in patients with obstructive sleep apnea-hypopnea syndrome," Sleep Breath 17(2):583-588.
Amparo (2013). "Topical Interleukin 1 Receptor Antagonist for Treatment of Dry Eye Disease," JAMA Ophth. 131(6):E1-E9.
Anonymous (2007). "The epidemiology of dry eye disease: report of the Epidemiology Subcommittee of the International Dry Eye WorkShop (2007)," Ocul. Surf. 5(2):93-107.
Bajpai et al. (2012). "Preparation, Characterization and Water Uptake Behavior of Polysaccharide Based Nanoparticles," Prog. Nanotech. Nanomat. 1(1):9-17.
Baraniuk et al. (2007). "Nasonasal Reflexes, the Nasal Cycle, and Sneeze," Curr. Allergy and Asthma Reports 7:105-111.
Baroody FM, Foster KA, Markaryan A, et al. Nasal ocular reflexes and eye symptoms in patients with allergic rhinitis. Ann Allergy Asthma Immunol 2008;100:194-199.
Baroody FM, Shenaq D, DeTineo M, et al. Fluticasone furoate nasal spray reduces the nasal-ocular reflex: a mechanism for the efficacy of topical steroids in controlling allergic eye symptoms. J Allergy Clin Immunol 2009; 123:1342-1348.
Boberg-Ans J. (1955). "Experience in clinical examination of corneal sensitivity: corneal sensitivity and the naso-lacrimal reflex after retrobulbar anaesthesia," Br. J. Ophthalmol. 39(12):705-726.
Calonge (2001). "The Treatment of Dry Eye," Survey Ophth. 45(2):S227-S239.
Cipriano et al. (2014). "Superabsorbent Hydrogels That Are Robust and Highly Stretchable," Am. Chem Soc. 47(13):4445-4452.
Corrected Notice of Allowance dated Feb. 23, 2015, for U.S. Appl. No. 14/256,915, filed Apr. 18, 2014, 2 pages.
Corrected Notice of Allowance dated Jun. 9, 2017, for U.S. Appl. No. 14/920,860, filed Oct. 22, 2015, 2 pages.
Corrected Notice of Allowance dated Jul. 17, 2017, for U.S. Appl. No. 15/256,392, filed Sep. 2, 2016, 2 pages.
Dart et al. (2002). "Effects of 25% Propylene Glycol Hydrogel (Solugel) on Second Intention Wound Healing in Horses," Vet. Surg. 31(4):309-313.
Drummond PD. Lacrimation and cutaneous vasodilatation in the face induced by painful stimulation of the nasal ala and upper lip. J Auton Nerv Syst 1995;51:109-16.
Elsby et al. (1967). "Lacrimal Secretion in the Cat," Br. J. Pharm. Chemother. 29(1):1-7.
Extended European Search Report dated Nov. 18, 2016, for EP Application No. 14 785 631.4, filed on Apr. 18, 2014, 7 pages.
Final Office Action for U.S. Appl. No. 14/256,916, dated Apr. 8, 2015, 16 pages.
Final Office Action for U.S. Appl. No. 14/313,937 dated Apr. 29, 2015, 13 pages.
Final Office Action for U.S. Appl. No. 14/630,471, dated Sep. 26, 2016, 22 pages.
Final Office Action for U.S. Appl. No. 14/256,916, dated Aug. 19, 2016, 19 pages.
Final Office Action dated Sep. 23, 2016, for U.S. Appl. No. 14/809,109, filed Jul. 24, 2015, 10 pages.
Final Office Action dated Feb. 1, 2017, for U.S. Appl. No. 14/920,852, filed Oct. 22, 2015, 20 pages.
Fujisawa et al. (2002). "The Effect of Nasal Mucosal Stimulation on Schirmer Tests in Sjogren's Syndrome and Dry Eye Patients," Lac. Gland Tear Film Dry Eye Syndrome 3 506:1221-1226.
Gupta et al. (1997). "Nasolacrimal Stimulation of Aqueous Tear Production," Cornea 16(6):645-648.
Heigle TJ, Pflugfelder SC. Aqueous tear production in patients with neurotrophic keratitis. Cornea 1996;15:135-138.
Holzer P. Capsaicin: cellular targets, mechanisms of action, and selectivity for thin sensory neurons. Pharmacol Rev 1991;43:143-201.

(56) References Cited

OTHER PUBLICATIONS

Ikemura et al. (2008). "UV-VIS Spectra and Photoinitiation Behaviors of Acylphosphine Oxide and Bisacylphosphine Oxide Derivatives in unfilled, Light-Cured Dental Resins," Dent. Mat. J. 27:765-774.
International Search Report and Written Opinion received for PCT Application No. PCT/US2015/042130, dated Oct. 28, 2015.
International Search Report and Written Opinion received for PCT Patent Application No. PCT/US2014/034733, dated Dec. 5, 2014.
International Search Report and Written Opinion received for PCT Patent Application No. PCT/US2015/017379, dated Jul. 24, 2015.
International Search Report and Written Opinion received for PCT Patent Application No. PCT/US2015/057023, dated Mar. 4, 2016.
International Search Report dated Feb. 10, 2016, for PCT Patent Application No. PCT/US2015/57021, filed on Oct. 22, 2015, 4 pages.
Krupin T, Cross DA, Becker B. Decreased basal tear production associated with general anesthesia. Arch Ophthalmol 1977;95:107-108.
Lora et al. (2009). "Lacrimal Nerve Stimulation by a Neurostimulator for Tear Production," Invest. Ophth. Vis. Science 50(13):172.
Loth S, Bende M. Effect of nasal anaesthesia on lacrimal function after nasal allergen challenge. Clin Exp Allergy 1994;24:375-376.
Meng, I.D. et al. (2013). "The role of corneal afferent neurons in regulating tears under normal and dry eye conditions," Exp. Eye Res. 117:79-87.
Mallepally et al. (2013). "Superabsorbent Alginate Aerogels," J. Supercritical Fluids 79:1-5.
Non-Final Office Action received for U.S. Appl. No. 14/256,915, dated Aug. 13, 2014, 11 pages.
Non-Final Office Action received for U.S. Appl. No. 14/256,916, dated Sep. 12, 2014, 24 pages.
Non-Final Office Action received for U.S. Appl. No. 14/313,937, dated Nov. 19, 2014, 12 pages.
Non-Final Office Action dated Jun. 14, 2016, for U.S. Appl. No. 14/630,471, filed Feb. 24, 2015, 24 pages.
Non-Final Office Action received for U.S. Appl. No. 14/809,109, dated Apr. 8, 2016, 8 pages.
Non-Final Office Action Received for U.S. Appl. No. 14/920,860, dated Aug. 17, 2016, 11 pages.
Non-Final Office Action received for U.S. Appl. No. 14/256,916, dated Nov. 19, 2015, 20 pages.
Non-Final Office Action Received for U.S. Appl. No. 14/313,937, dated Oct. 6, 2015, 7 pages.
Non-Final Office Action Received for U.S. Appl. No. 14/920,852, dated Aug. 1, 2016, 20 pages.
Non-Final Office Action dated Sep. 30, 2016, for U.S. Appl. No. 15/256,392, filed Sep. 2, 2016, 14 pages.
Non-Final Office Action dated Feb. 14, 2017, for U.S. Appl. No. 14/630,471, filed Feb. 24, 2015, 23 pages.
Non-Final Office Action dated Apr. 19, 2017, for U.S. Appl. No. 14/256,916, filed Apr. 18, 2014, 19 pages.
Non-Final Office Action dated Jul. 17, 2017, for U.S. Appl. No. 15/598,063, filed May 17, 2017, 9 pages.
Non-Final Office Action dated Jul. 31, 2017, for U.S. Appl. No. 14/920,852, filed Oct. 22, 2015, 18 pages.
Notice of Allowance received for U.S. Appl. No. 14/256,915, dated Nov. 26, 2014, 7 pages.
Notice of Allowance received for U.S. Appl. No. 14/313,937, dated Feb. 19, 2016, 8 pages.
Notice of Allowance received for U.S. Appl. No. 14/313,937, dated May 2, 2016, 7 pages.
Notice of Allowability dated Dec. 19, 2016, for U.S. Appl. No. 14/809,109, filed Jul. 24, 2015, 8 pages.
Notice of Allowance dated Jan. 19, 2017, for U.S. Appl. No. 14/920,860, filed Oct. 22, 2015, 5 pages.
Notice of Allowance dated Mar. 21, 2017, for U.S. Appl. No. 14/809,109, filed Jul. 24, 2015, 8 pages.
Notice of Allowance dated Apr. 17, 2017, for U.S. Appl. No. 15/256,392, filed Sep. 2, 2016, 10 pages.
Notice of Allowance dated Apr. 20, 2017, for U.S. Appl. No. 14/920,860, filed Oct. 22, 2015, 5 pages.
Notice of Allowance dated May 26, 2017, for U.S. Appl. No. 14/630,471, filed Feb. 24, 2015, 5 pages.
Pasqui et al. (2012). "Polysaccharide-Based Hydrogels: The Key Role of Water in Affecting Mechanical Properties," Polymers 4(3):1517-1534.
Philip G, Baroody FM, Proud D, et al. The human nasal response to capsaicin. J Allergy Clin Immunol 1994;94:1035-1045.
Roessler et al. (2009). "Implantation and Explantation of a Wireless Epiretinal Retina Implant Device: Observations During the EPIRET3 Prospective Clinical Trial," Invest. Ophthal. Visual Science 50(6):3003-3008.
Ruskell (2004). "Distribution of Pterygopalatine Ganglion Efferents to the Lacrimal Gland in Man," Exp. Eye Res. 78(3):329-335.
Sall et al. (2000). "Two Multicenter, Randomized Studies of the Efficacy and Safety of Cyclosporine Ophthalmic Emulsion in Moderate to Severe Dry Eye Disease," Ophth. 107(4):631-639.
Shaari et al. (1995). "Rhinorrhea is decreased in dogs after nasal application of botulinum toxin," Oto. Head Neck Surg. 112(4):566-571.
Stjernschantz et al. (1979). "Electrical Stimulation of the Fifth Cranial Nerve in Rabbits: Effects on Ocular Blood Flow, Extravascular Albumin Content and Intraocular Pressure," Exp. Eye Res. 28(2):229-238.
Stjernschantz et al. (1980). "Vasomotor effects of Facial Nerve Stimulation: Noncholinergic Vasodilation in the eye," Acta Phys. Scand. 109(1):45-50.
Tsubota (1991). "The Importance of the Schirmer Test with Nasal Stimulation," Am. J. Ophth. 111:106-108.
Velikay-Parel et al. (2011). "Perceptual Threshold and Neuronal Excitability as Long-Term Safety Evaluation in Retinal Implants," Invest. Opht. Visual Science E-Abstract 2590, 2 pages.
Written Opinion received for PCT Patent Application No. PCT/US2015/57021, dated Feb. 10, 2016, 5 pages.
Zilstorff-Pedersen (1965). "Quantitative Measurements of the Nasolacrimal Reflex," Arch. Oto. 81:457-462.
Olsen (Feb. 1998), Human Sclera: Thickness and Surface Area, American Journal of Ophthalmology, 125(2):237-241.
Ahmed, E. M. et al. (2013, e-published Jul. 18, 2013). "Hydrogel: Preparation, characterization, and applications: A review," Cairo University, Journal of Advanced Research (2015) 6, 105-121.

* cited by examiner

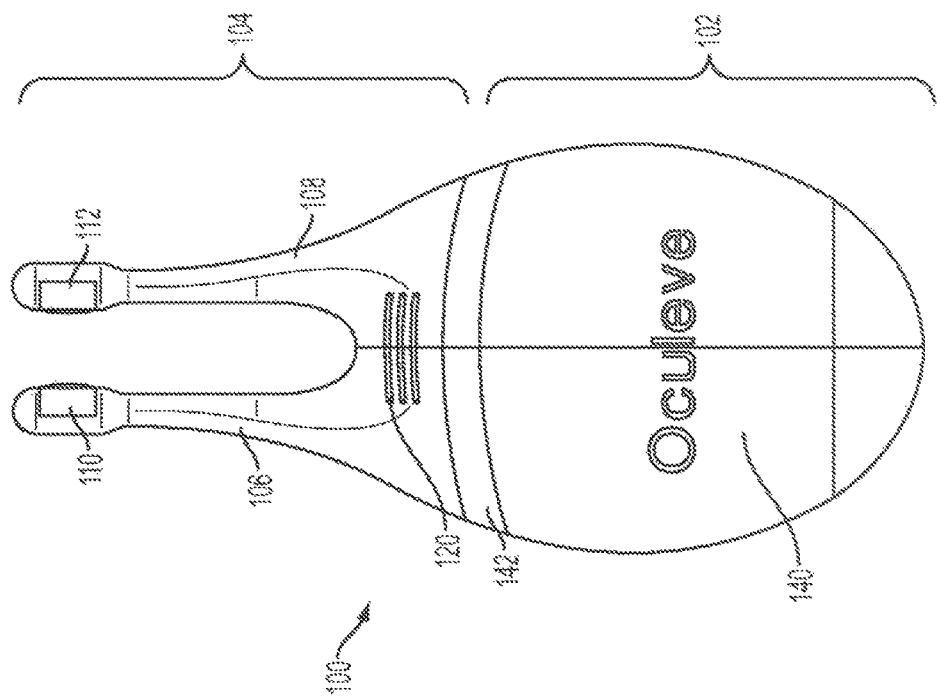
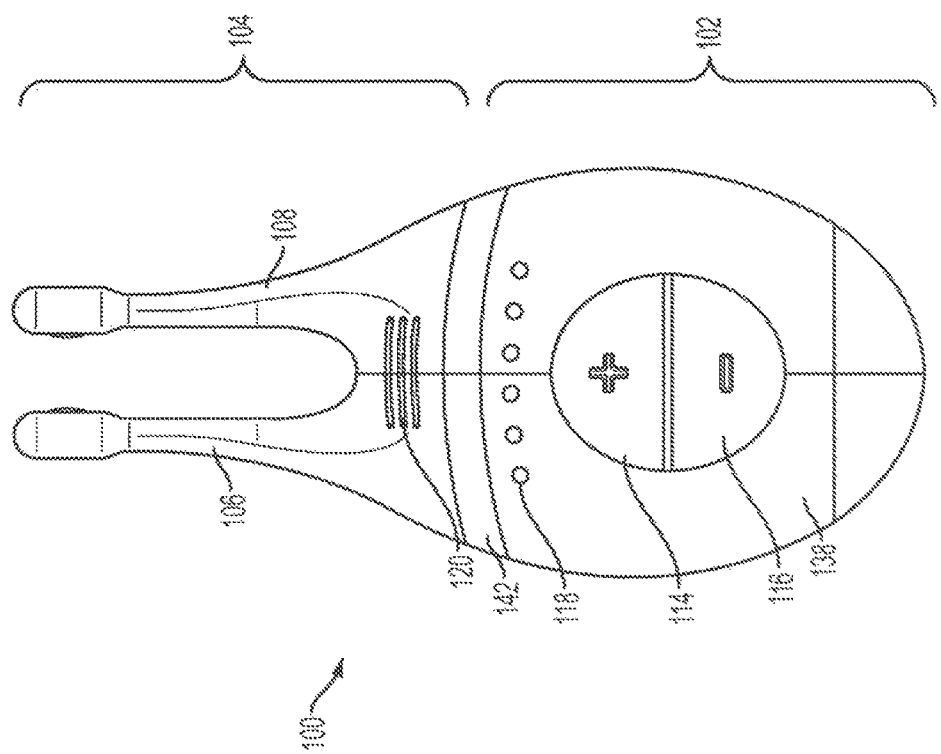

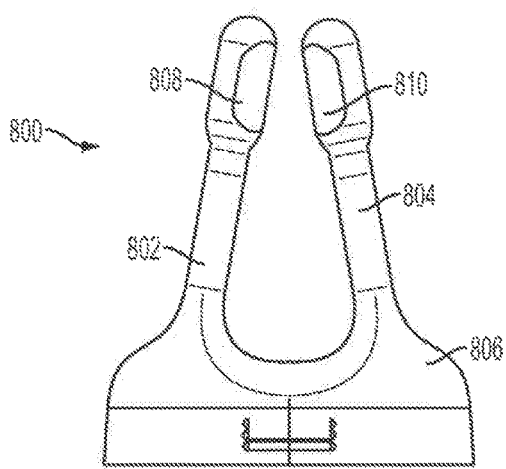
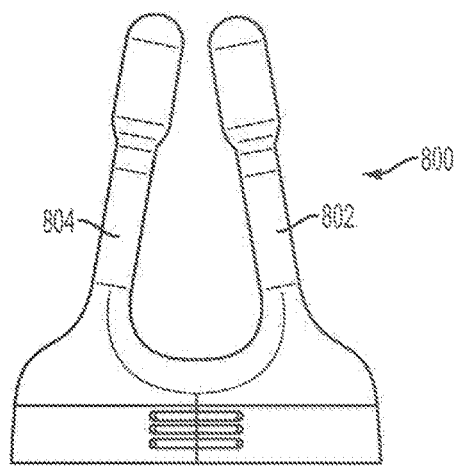
FIG. 8A  FIG. 8B
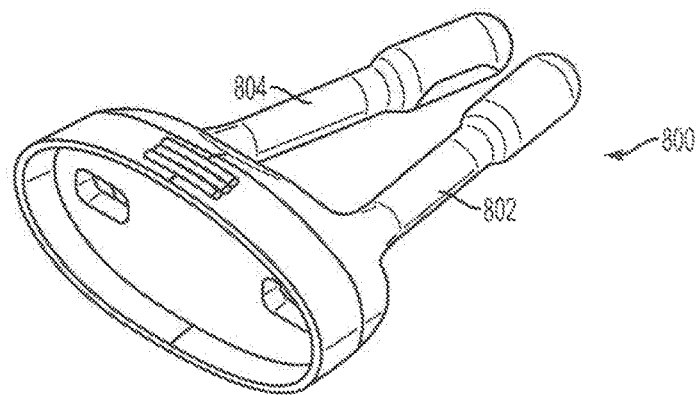
FIG. 8C

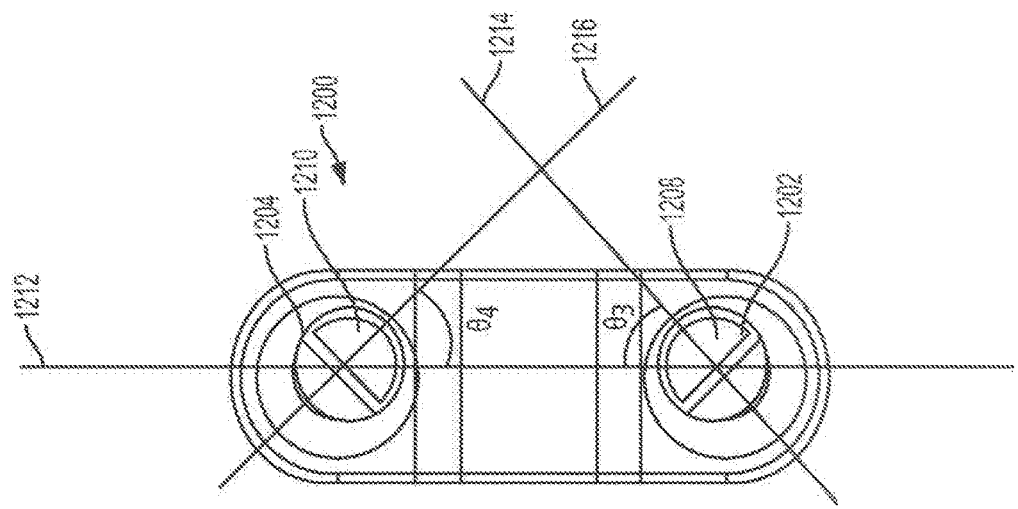
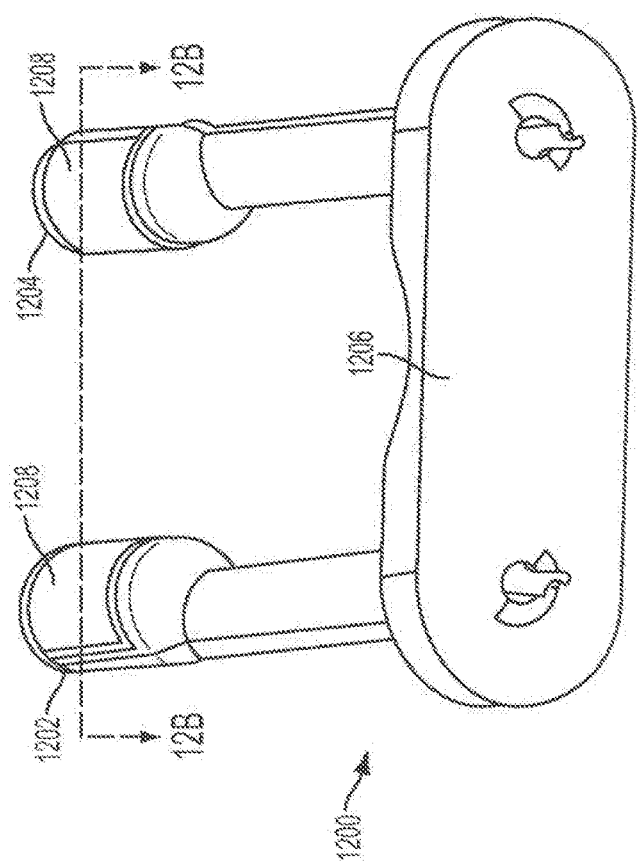
FIG. 12B
FIG. 12A

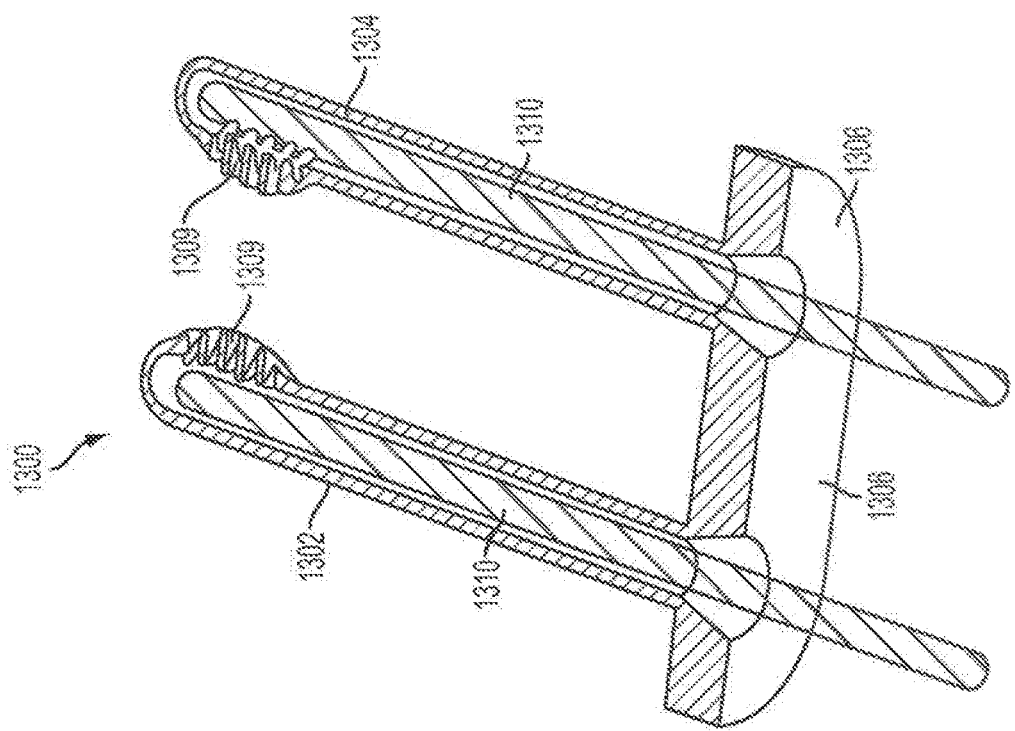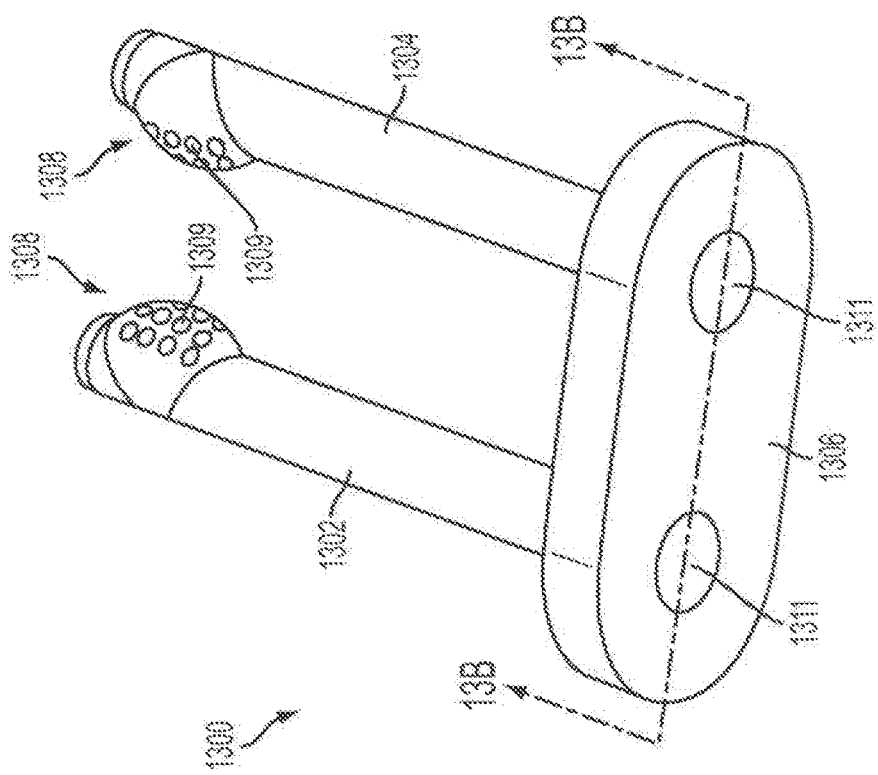

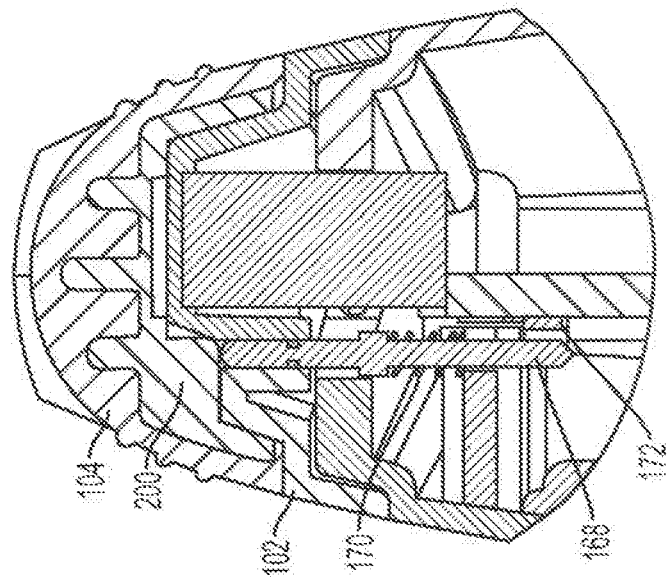
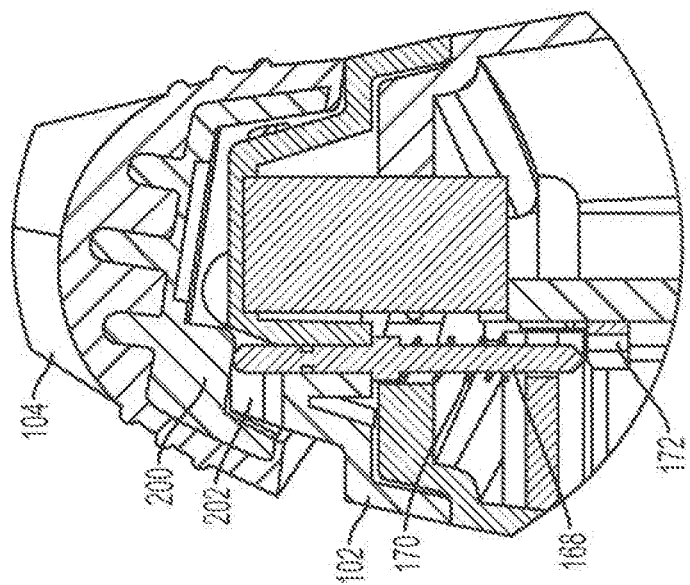

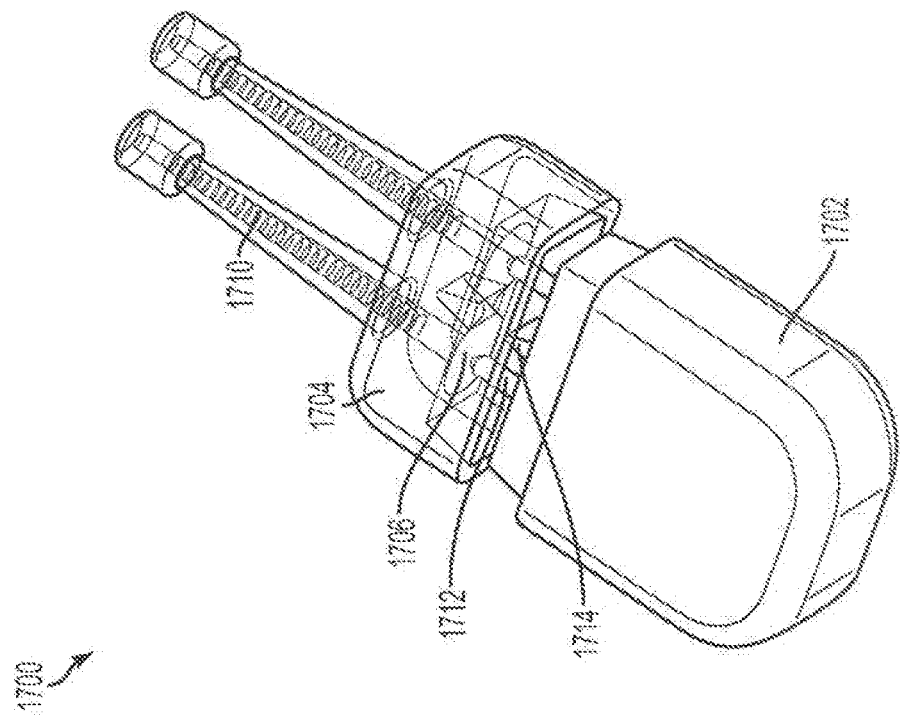
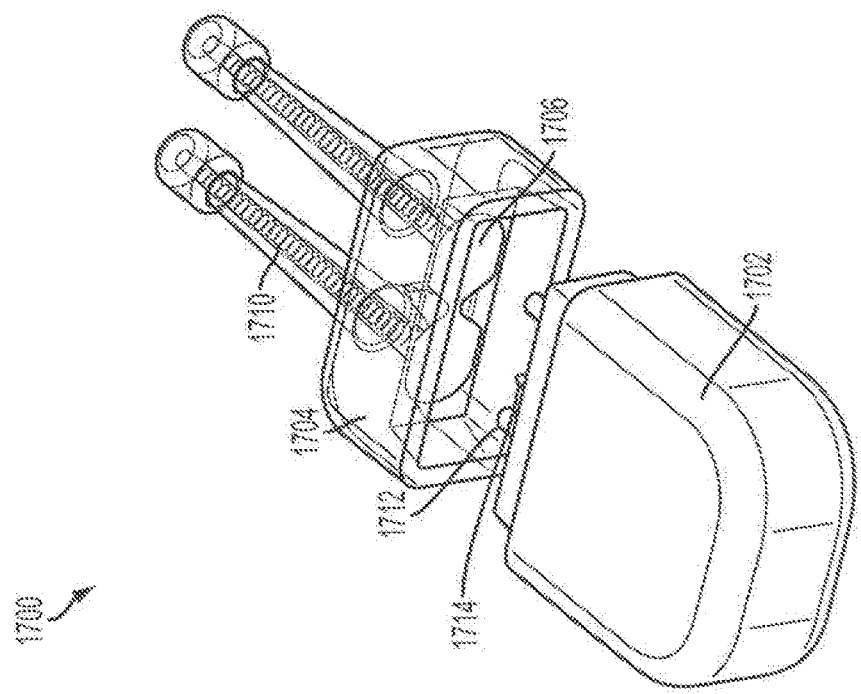

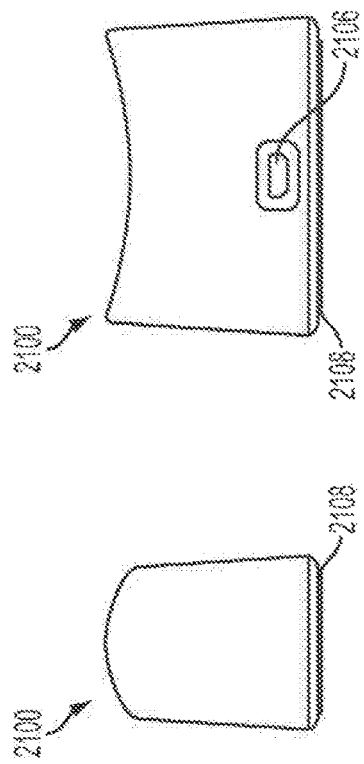
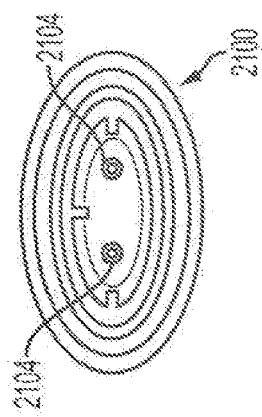
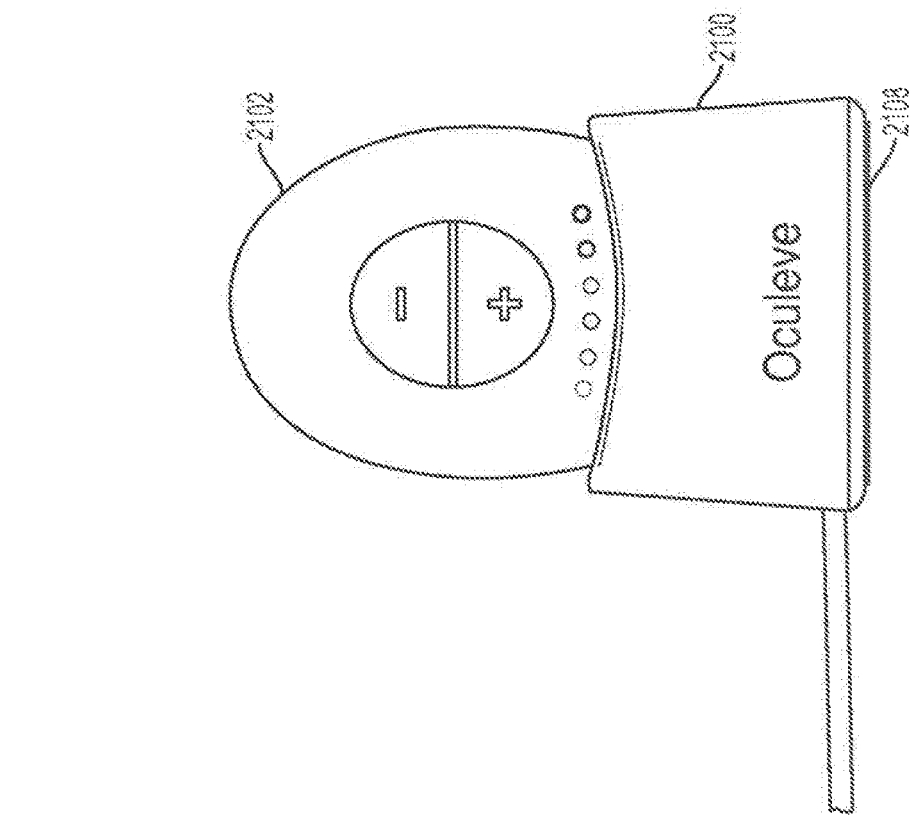
FIG. 21C
FIG. 21D
FIG. 21B
FIG. 21A

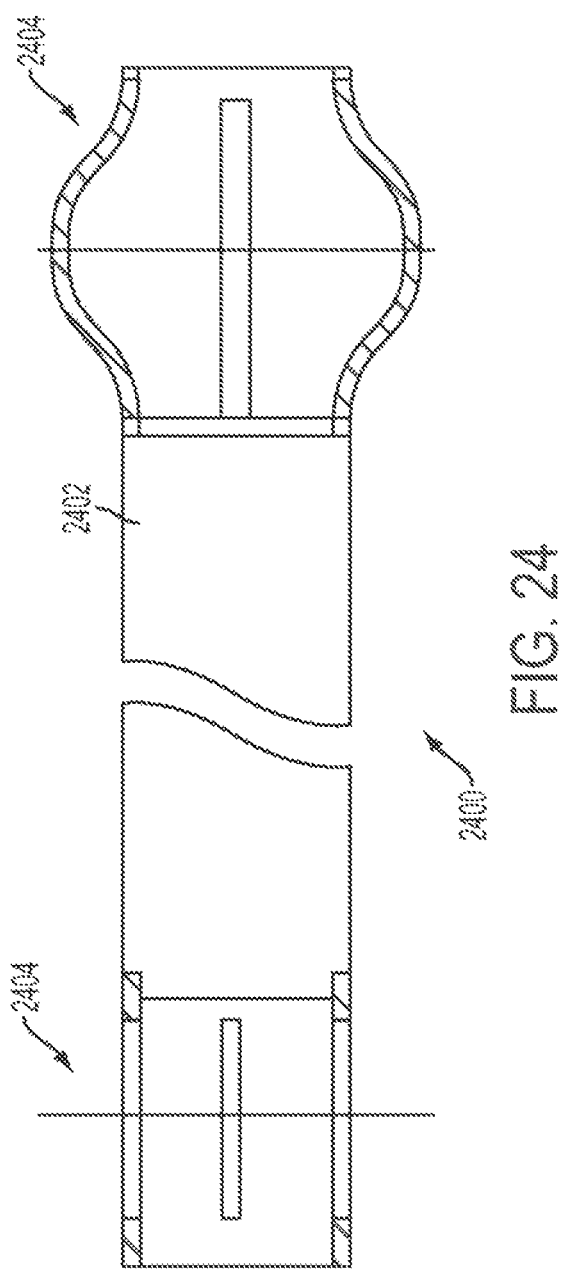

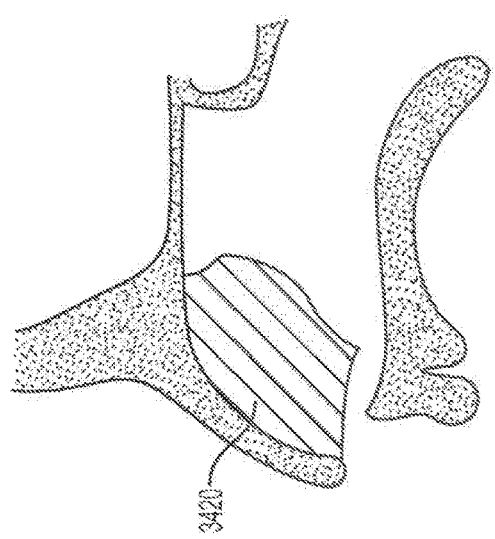
FIG. 34B
FIG. 34C
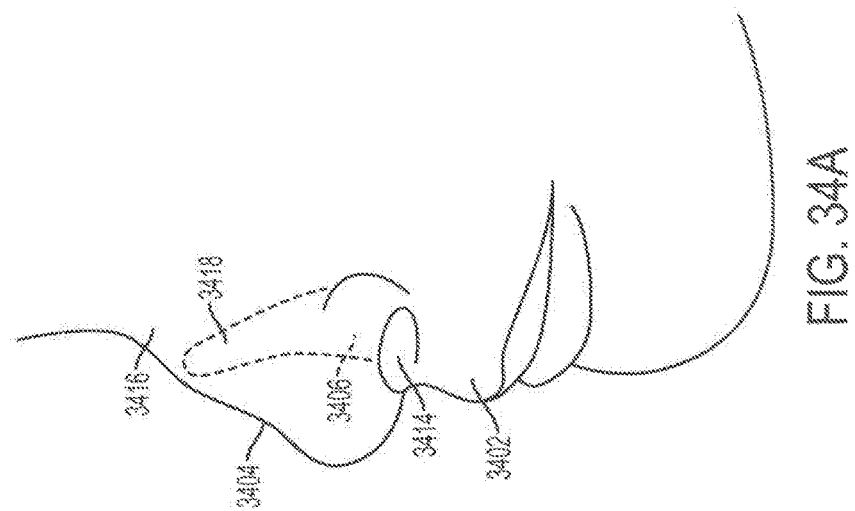
FIG. 34A

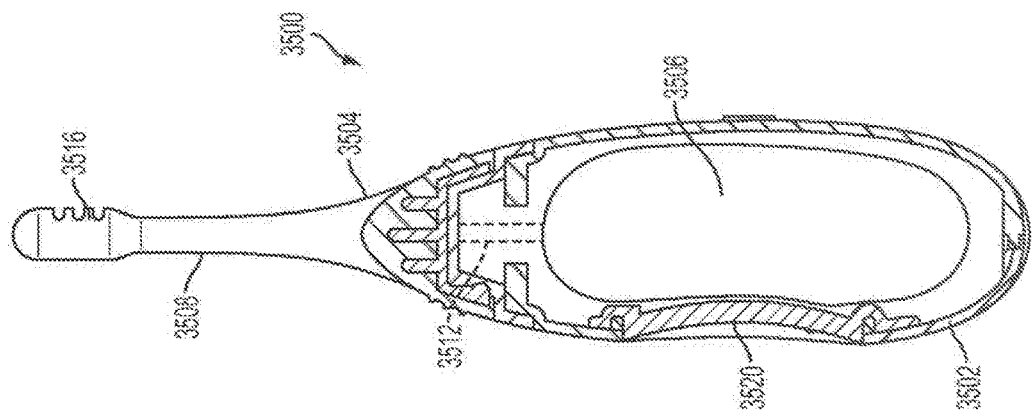
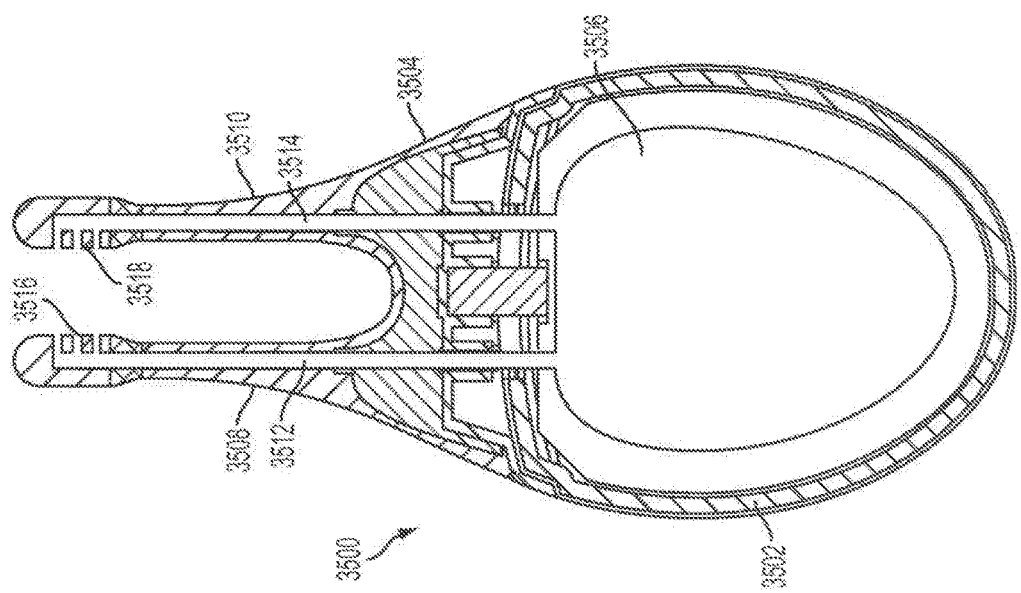

NASAL STIMULATION DEVICES AND METHODS

CROSS-REFERENCE TO RELATED APPLICATIONS

This application is a continuation of U.S. patent application Ser. No. 15/256,392, filed on Sep. 2, 2016, which is a continuation of U.S. patent application Ser. No. 14/313,937, filed on Jun. 24, 2014, issued as U.S. Pat. No. 9,440,065, which is a continuation of U.S. patent application Ser. No. 14/256,915, filed on Apr. 18, 2014, issued as U.S. Pat. No. 8,996,137, which claims priority to U.S. Provisional Patent Application No. 61/814,166, filed on Apr. 19, 2013, and titled "NASAL STIMULATION DEVICES AND METHODS," and to U.S. Provisional Patent Application No. 61/860,839, filed on Jul. 31, 2013, and titled "NASAL STIMULATION DEVICES AND METHODS," each of which is incorporated by reference herein in its entirety.

BACKGROUND OF THE INVENTION

Dry Eye Disease ("DED") is a condition that affects millions of people worldwide. More than 40 million people in North America have some form of dry eye, and many millions more suffer worldwide. DED results from the disruption of the natural tear film on the surface of the eye, and can result in ocular discomfort, visual disturbance and a reduction in vision-related quality of life. Activities of daily living such as driving, computer use, housework and reading have also been shown to be negatively impacted by DED. Patients with severe cases of DED are at risk for serious ocular health deficiencies such as corneal ulceration, and can experience a quality of life deficiency comparable to that of moderate-severe angina.

The etiology of DED is becoming increasingly well understood. DED is progressive in nature, and fundamentally results from insufficient tear coverage on the surface of the eye. This poor tear coverage prevents healthy gas exchange and nutrient transport for the ocular surface, promotes cellular desiccation and creates a poor refractive surface for vision. Poor tear coverage typically results from: 1) insufficient aqueous tear production from the lacrimal glands (e.g. secondary to post-menopausal hormonal deficiency, auto-immune disease, LASIK surgery, etc.), and/or 2) excessive evaporation of aqueous tear resulting from dysfunction of the meibomian glands. Low tear volume causes a hyperosmolar environment that induces an inflamed state of the ocular surface. This inflammatory response induces apoptosis of the surface cells which in turn prevents proper distribution of the tear film on the ocular surface so that any given tear volume is rendered less effective. This initiates a vicious cycle where more inflammation can ensue causing more surface cell damage, etc. Additionally, the neural control loop, which controls reflex tear activation, is disrupted because the sensory neurons in the surface of the eye are damaged. As a result, fewer tears are secreted and a second vicious cycle develops that results in further progression of the disease (fewer tears cause nerve cell loss, which results in fewer tears, etc.).

There is a wide spectrum of treatments for DED, however, none provides substantial efficacy for treatment of the condition. Treatment options include: Artificial tear substitutes, ointments, gels, warm compresses, environmental modification, topical cyclosporine, omega-3 fatty acid supplements, punctal plugs and moisture chamber goggles. Patients with severe disease may further be treated with punctal cautery, systemic cholinergic agonists, systemic anti-inflammatory agents, mucolytic agents, autologous serum tears, PROSE scleral contact lenses and tarsorrhaphy. Despite these treatment options, DED continues to be considered one of the most poorly treated diseases in ophthalmology. Accordingly, it would be desirable to have a more effective treatment for dry eye.

BRIEF SUMMARY OF THE INVENTION

Described here are devices, systems, and methods for treating one or more conditions (such as dry eye) by providing stimulation to nasal or sinus tissue. Generally, the devices and systems may be configured to stimulate nasal or sinus tissue. The devices may be handheld or implantable. In some variations, the devices may comprise a stimulator body and a stimulator probe, where the stimulator probe comprises one or more nasal insertion prongs. The stimulus delivered by the stimulators described here may in some variations be electrical; in other variations, it may be mechanical, thermal, chemical, light-based, magnetic, or the like. When the devices and systems are used to treat dry eye, the methods may comprise stimulating nasal or sinus tissue to increase tear production, reduce the symptoms of dry eye, and/or improve ocular health. The methods may further comprise treating dry eye by regular activation of the nasolacrimal reflex.

In some variations, the devices described here comprise devices for stimulating nasal tissue of a subject. In some variations, the device comprises a stimulator body and a stimulator probe connected to the stimulator body, wherein the stimulator probe comprises a nasal insertion prong, and wherein the stimulator body comprises a control subsystem to control a stimulus to be delivered to the subject via the stimulator probe. In some of these variations, the stimulator probe comprises at least two nasal insertion prongs. In some of these variations, the at least two nasal insertion prongs are self-aligning when inserted into the nostrils of the subject. In some of these variations, the stimulator probe comprises at least one electrode. In some of these variations, the stimulus is electrical. In some of these variations, the electrode comprises a hydrogel. In others of these variations, the electrode comprises one or more of platinum, platinum-iridium, gold, or stainless steel. In some variations, the stimulus is a biphasic pulse waveform. In some of these variations, the biphasic pulse waveform is symmetrical. In some of these variations, the frequency of the biphasic pulse waveform is between 20 Hz and 80 Hz. In some variations, the stimulator probe is releasably connected to the stimulator body. In some of these variations, the device comprises a disabling mechanism that prevents stimulus delivery to the subject when the stimulator probe is reconnected to the stimulator body after being disconnected from the stimulator body. Additionally or alternatively, the device may comprise a lockout mechanism that prevents the stimulator probe from being reconnected to the stimulator body after being disconnected from the stimulator body. In some variations, the stimulator body is reusable and the stimulator probe is disposable. In some variations, the device further comprises a detachable protective cap. In some variations, the device further comprises a user interface. In some of these variations, the user interface comprises one or more operating mechanisms to adjust one or more parameters of the stimulus. Additionally or alternatively, the user interface may comprise one or more feedback elements.

In some variations, the systems described here comprise systems for stimulating nasal tissue of a subject. In some variations, the system comprises a stimulator comprising a stimulator probe comprising a nasal insertion prong and a stimulator body comprising a rechargeable power source and a control subsystem to control a stimulus to be delivered to the subject via the nasal insertion prong, and a base station to recharge the rechargeable power source. In some of these variations, the stimulator comprises memory to store data, and the base station is configured to retrieve data from the stimulator. Additionally or alternatively, the stimulator probe is removably connectable to the stimulator body, and wherein the stimulator probe blocks access to the rechargeable power source when connected to the stimulator body.

In some variations, the methods described here comprise methods of tear production in a subject. In some variations, the method comprises positioning a probe in contact with the nasal mucosa of the subject, and delivering a stimulus via the probe to produce tears. In some of these variations, the method further comprises positioning a second probe in contact with the nasal mucosa of the subject. In some variations, the stimulus is electrical. In some of these variations, the stimulus is delivered for a 5 minute period, and the Schirmer score over the 5 minute period is at least 3 mm greater than a basal Schirmer score of the patient. In some of these variations the Schirmer score over the 5 minute period is at least 5 mm greater than a basal Schirmer score of the patient. In some of these variations, the stimulus is a biphasic pulse waveform. In some of these variations, the biphasic pulse waveform is symmetrical. In some variations, the stimulus is pulsed. In some variations, the method further comprises positioning a probe in contact with the nasal mucosa of the subject and delivering a stimulus via the probe to produce tears on a second occasion. In some variations, the stimulus is mechanical. In some variations, the stimulus is chemical.

In some variations, the methods described here comprise methods of improving ocular health in a patient. In some variations, the methods comprise positioning a probe in a nasal cavity of the patient, and delivering stimulation to the nasal tissue of the patient via the probe at least once daily during a treatment period comprising at least 2 days to improve the ocular health of the patient, wherein improved ocular health is measured by decreased dry eye symptoms. In some of these variations, the probe comprises at least one electrode, and the stimulation is electrical. In some of these variations, decreased dry eye symptoms are measured by the Ocular Surface Disease Index, and the Ocular Surface Disease Index decreases by at least 10% within the treatment period, wherein the treatment period comprises 7 days. In some of these variations, the Ocular Surface Disease Index decreases by at least 20% within the treatment period. In some variations, decreased dry eye symptoms are measured by the Ocular Surface Disease Index, and the Ocular Surface Disease Index decreases by at least 40% within the treatment period, wherein the treatment period comprises 90 days. In some of these variations, the Ocular Surface Disease Index decreases by at least 50% within the treatment period. In some variations, the stimulation activates the nasolacrimal reflex. In some variations, the probe is positioned in contact with nasal mucosa of the patient. In some variations, the probe is positioned in contact with the septum. In some variations, the probe is positioned in contact with the columella. In some variations, the probe is positioned in contact with the tissue adjacent to the interface between the nasal bone and the upper lateral cartilage. In some variations, the probe is positioned in contact with nasal mucosa of the patient. In some variations, the method further comprises positioning a second probe in a second nasal cavity of the patient. In some variations, the probe comprises at least one electrode. In some of these variations, the electrical stimulation comprises a biphasic pulse waveform. In some of these variations, the biphasic pulse waveform is symmetrical. In some of these variations, the frequency of the biphasic pulse waveform is between 20 Hz and 80 Hz. In others of these variations, the stimulation is mechanical. In others of these variations, the stimulation is chemical. In others of these variations, the stimulation is thermal.

In some variations, the methods described here comprise methods of improving ocular health in a patient. In some variations, the methods comprise positioning a probe in a nasal cavity of the patient, and delivering stimulation to the nasal tissue of the patient via the probe at least once daily during a treatment period comprising at least 2 days to improve the ocular health of the patient, wherein improved ocular health is measured by decreased corneal staining or conjunctival staining. In some variations, the probe comprises at least one electrode, and the stimulation is electrical. In some of these variations, improved ocular health is measured by decreased corneal staining, and corneal staining decreases by at least 10% within the treatment period, wherein the treatment period comprises 7 days. In some of these variations, corneal staining decreases by at least 20% within the treatment period. In some variations, improved ocular health is measured by decreased corneal staining, and corneal staining decreases by at least 50% within the treatment period, wherein the treatment period comprises 90 days. In some of these variations, corneal staining decreases by at least 60% within the treatment period. In some variations, improved ocular health is measured by decreased conjunctival staining, and wherein conjunctival staining decreases by at least 5% within the treatment period, wherein the treatment period comprises 7 days. In some of these variations, conjunctival staining decreases by at least 10% within the treatment period. In some variations, improved ocular health is measured by decreased conjunctival staining, and wherein conjunctival staining decreases by at least 30% within the treatment period, wherein the treatment period comprises 90 days. In some of these variations, conjunctival staining decreases by at least 40% within the treatment period. In some variations, the stimulation activates the nasolacrimal reflex. In some variations, the probe is positioned in contact with nasal mucosa of the patient. In some variations, the probe is positioned in contact with the septum. In some variations, the probe is positioned in contact with the columella. In some variations, the probe is positioned in contact with the tissue adjacent to the interface between the nasal bone and the upper lateral cartilage. In some variations, the probe is positioned in contact with nasal mucosa of the patient. In some variations, the method further comprises positioning a second probe in a second nasal cavity of the patient. In some variations, the probe comprises at least one electrode. In some of these variations, the electrical stimulation comprises a biphasic pulse waveform. In some of these variations, the biphasic pulse waveform is symmetrical. In some of these variations, the frequency of the biphasic pulse waveform is between 20 Hz and 80 Hz. In others of these variations, the stimulation is mechanical. In others of these variations, the stimulation is chemical. In others of these variations, the stimulation is thermal.

In some variations, the methods described here comprise methods of improving ocular health in a patient. In some variations, the methods comprise positioning a probe in a nasal cavity of the patient, and delivering stimulation to the nasal tissue of the patient via the probe at least once daily during a treatment period comprising at least 2 days to improve the ocular health of the patient, wherein improved ocular health is measured by increased tear production. In some of these variations, the probe comprises at least one electrode, and the stimulation is electrical. In some of these variations, increased tear production is measured by increased basal tear production, and basal tear production increases by at least 1 mm on the Schirmer Tear Test within the treatment period, wherein the treatment period comprises 7 days. In some of these variations, basal tear production increases by at least 2 mm on the Schirmer Tear Test within the treatment period. In some variations, increased tear production is measured by increased basal tear production, and basal tear production increases by at least 2 mm on the Schirmer Tear Test within the treatment period, wherein the treatment period comprises 90 days. In some of these variations, basal tear production increases by at least 3 mm on the Schirmer Tear Test within the treatment period. In some variations, the stimulation activates the nasolacrimal reflex. In some variations, the probe is positioned in contact with nasal mucosa of the patient. In some variations, the probe is positioned in contact with the septum. In some variations, the probe is positioned in contact with the columella. In some variations, the probe is positioned in contact with the tissue adjacent to the interface between the nasal bone and the upper lateral cartilage. In some variations, the method further comprises positioning a second probe in a second nasal cavity of the patient. In some variations, the probe comprises at least one electrode. In some of these variations, the electrical stimulation comprises a biphasic pulse waveform. In some of these variations, the biphasic pulse waveform is symmetrical. In some of these variations, the frequency of the biphasic pulse waveform is between 20 Hz and 80 Hz. In others of these variations, the stimulation is mechanical. In others of these variations, the stimulation is chemical. In others of these variations, the stimulation is thermal.

In some variations, the methods described here comprise methods of improving ocular health in a patient. In some variations, the methods comprise positioning a probe in a nasal cavity of the patient, and delivering stimulation to the nasal tissue of the patient via the probe at least once daily during a treatment period comprising at least 2 days to improve the ocular health of the patient, wherein improved ocular health is measured by at least two of decreased Ocular Surface Disease Index, decreased corneal staining, decreased conjunctival staining, increased basal tear production, and increased acute tear production. In some of these variations improved ocular health is measured by at least three of decreased Ocular Surface Disease Index, decreased corneal staining, decreased conjunctival staining, increased basal tear production, and increased acute tear production. In some of these variations, ocular health is measured by at least four of decreased Ocular Surface Disease Index, decreased corneal staining, decreased conjunctival staining, increased basal tear production, and increased acute tear production.

BRIEF DESCRIPTION OF THE DRAWINGS

FIGS. 1A, 1B, 1C, 1D, 1E show perspective, front, back, cut-away back, and cut-away side views, respectively, of an illustrative variation of a handheld stimulator.

FIGS. 8A, 8B, and 8C depict back, front, and perspective views, respectively, of a stimulator probe suitable for the handheld stimulators described here.

FIGS. 12A and 12B show perspective and cut-away top views, respectively, of a variation of a stimulator probe suitable for the handheld stimulators described here.

FIGS. 13A and 13B show perspective and cut-away perspective views, respectively, of a variation of a stimulator probe suitable for the handheld stimulators described here.

FIGS. 15B-15C illustrate an example of one mechanism for measuring how long a stimulator probe has been connected to the stimulator body.

FIGS. 17A-17E show an example of a handheld stimulator comprising a mechanical fuse.

FIGS. 21A-21D depict portions of a stimulator system comprising a stimulator and a base station. FIG. 21A shows a front view of the stimulator body docked in the base station, while FIGS. 21B, 21C, and 21D depict side, back, and top views, respectively, of the base station.

FIG. 22A shows a front view of the stimulator body docked in the base station, while FIGS. 22B, 22C, and 22D show top, bottom, and side views, respectively, of the base station.

FIG. 23A shows perspective views of the base station and an undocked stimulation, while FIG. 23B shows a perspective view of the stimulator body docked in the base station.

FIG. 24 shows a cut-away side view of a variation of an implantable stimulator.

FIGS. 34A-34C illustrate relevant anatomical locations.

FIGS. 35A-35B depict cut-away front and side views, respectively, of a handheld stimulator configured to deliver one or more chemical agents.

DETAILED DESCRIPTION OF THE INVENTION

Described here are devices, systems, and methods for treating one or more conditions (such as dry eye) by providing stimulation to nasal or sinus tissue. Generally, the devices and systems may be configured to stimulate nasal or sinus tissue. The devices may be handheld or implantable. In some variations, the devices may comprise a stimulator body and a stimulator probe, where the stimulator probe comprises one or more nasal insertion prongs. The stimulus delivered by the stimulators described here may in some variations be electrical; in other variations, they may be mechanical, thermal, chemical, light-based, magnetic, or the like. When the devices and systems are used to treat dry eye, the methods may comprise stimulating nasal or sinus tissue to increase tear production, reduce the symptoms of dry eye, or improve ocular health.

Handheld Stimulators

Figure 1A:
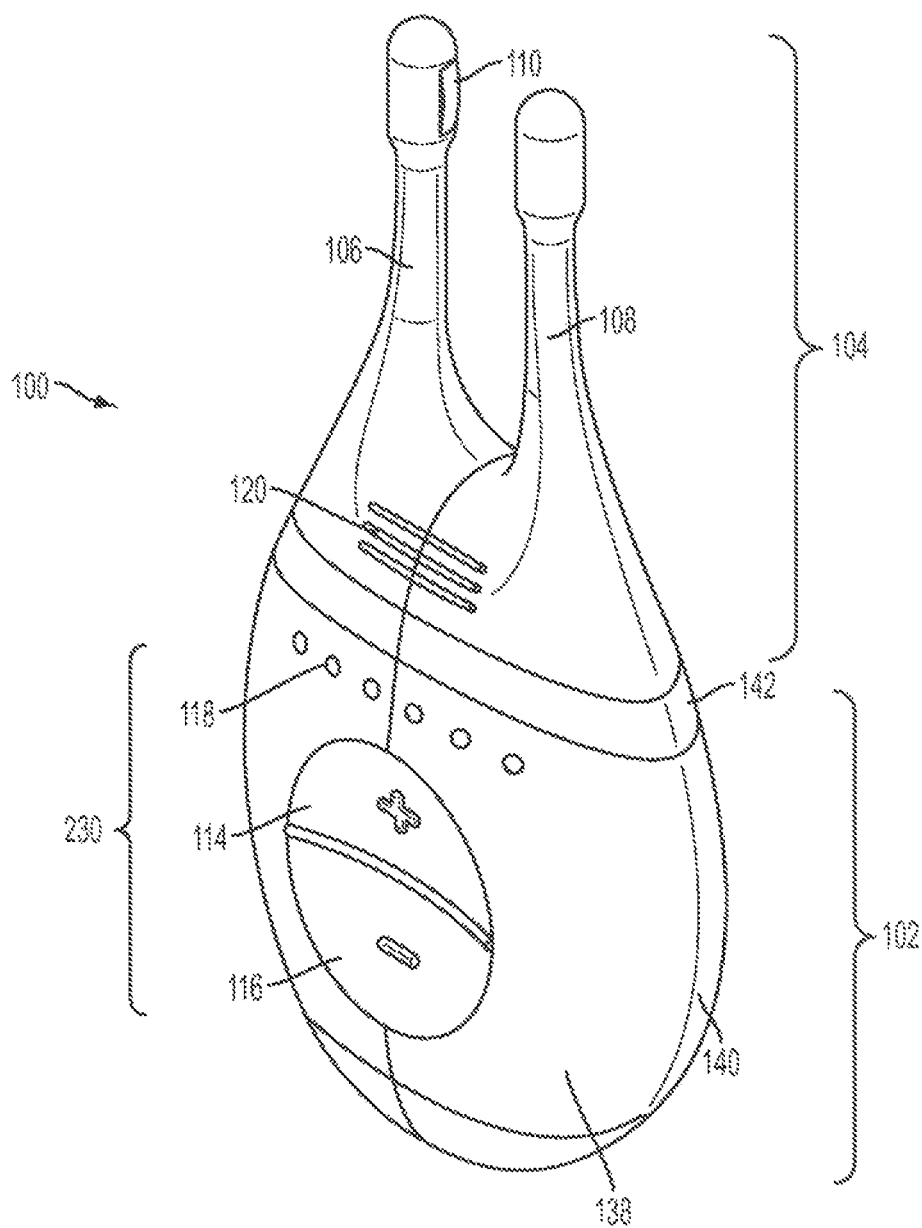
Figure 1E:
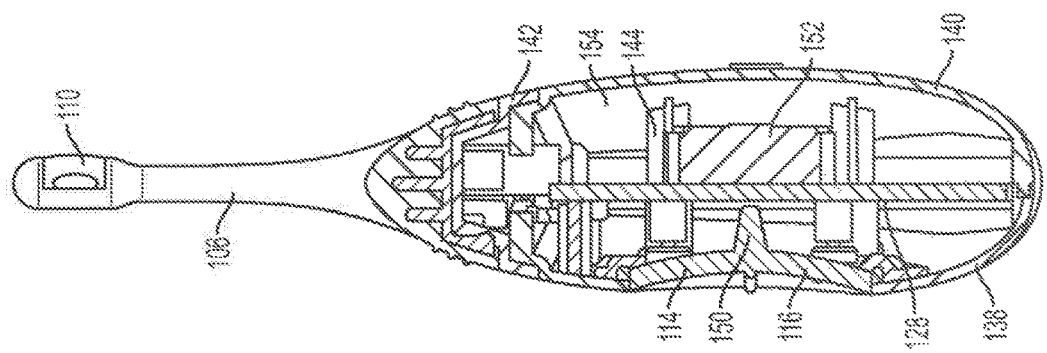

Some variations of the stimulation systems described here may comprise a handheld stimulator. FIGS. 1A, 1B, 1C, 1D, 1E show perspective, front, back, cut-away back, and cut-away side views, respectively, of an illustrative variation of a handheld stimulator 100, respectively. FIG. 2 shows a block diagram schematically representing the stimulator 100. As shown in FIGS. 1A-1E, the stimulator 100 may comprise a stimulator body 102 and a stimulator probe 104. Generally, the stimulator body 102 may be configured to generate a stimulus that may be delivered to the subject. The stimulator body 102 may comprise a front housing 138, back housing 140, and proximal housing 142, which may fit together to define a body cavity 154. The body cavity 154 may contain a control subsystem 136 and a power source 152, which together may generate and control the stimulus.

The stimulus may be delivered to a subject via the stimulator probe 104. In some variations the stimulator body 102 and stimulator probe 104 may be reversibly attachable, as described in more detail below. In other variations, the stimulator probe may be permanently connected to the stimulator body. Some or all of the stimulator 100 may be disposable. In variations where the stimulator body is permanently attached to the stimulator probe, the entire stimulator may be disposable. In other variations, one or more portions of the stimulator 100 may be reusable. For example, in variations where the stimulator probe 104 is releasably connected to the stimulator body 102, the stimulator body 102 may be reusable, and the stimulator probe 104 may be disposable and periodically replaced, as described in more detail below.

The stimulator probe 104 may comprise at least one nasal insertion prong, which may be configured to be at least partially inserted into the nasal cavity of a subject or patient. In the handheld stimulator variation shown in FIGS. 1A-1E, the stimulator probe 104 may comprise two nasal insertion prongs 106 and 108. The stimulator probe 104 may further comprise ridges 120, which may allow the patient to more easily grip the probe 104.

In some variations, the stimulus may be electrical. In these instances, each nasal insertion prong may comprise at least one electrode. As shown, the probe 104 may comprise a first electrode 110 on nasal insertion prong 106 and a second electrode 112 on nasal insertion prong 108. As shown in the cut-away view of the stimulator 100 in FIG. 1D, the electrodes 110 and 112 may be connected to leads 130 and 132 located within prongs 106 and 108, respectively. The leads 130 and 132 may in turn be connected to connectors 122 and 124, respectively. Connectors 122 and 124 may extend through lumens 208 and 210 in the proximal housing 142, and may connect directly or indirectly to the control subsystem 136 and power source 152. As such, the electrical stimulus may travel from the control subsystem 136 through the connectors 122 and 124, through the leads 130 and 132, and through the electrodes 110 and 112.

The stimulator body 102 may comprise a user interface 230 comprising one or more operating mechanisms to adjust one or more parameters of the stimulus, as described in more detail below. The operating mechanisms may provide information to the control subsystem 136, which may comprise a processor 232, memory 234, and/or stimulation subsystem 236. In some variations, the operating mechanisms may comprise first and second buttons 114 and 116. In some variations, pressing the first button 114 may turn on the stimulator and/or change one or more parameters of the stimulus (e.g., increase the intensity of the stimulus, change the stimulation pattern, or the like), while pressing the second button 116 may turn off the stimulator and/or change one or more parameters of the stimulus (e.g., decrease the intensity of the stimulus, change the stimulation pattern, or the like). Additionally or alternatively, the user interface may comprise one or more feedback elements (e.g., based on light, sound, vibration, or the like). As shown, the user feedback elements may comprise light-based indicators 118, which may provide information to the user, as described in more detail below.

Stimulator Body

As described briefly above, the stimulator body may comprise a housing, a user interface, a control subsystem, and a power source.

Housing

Figure 3A:
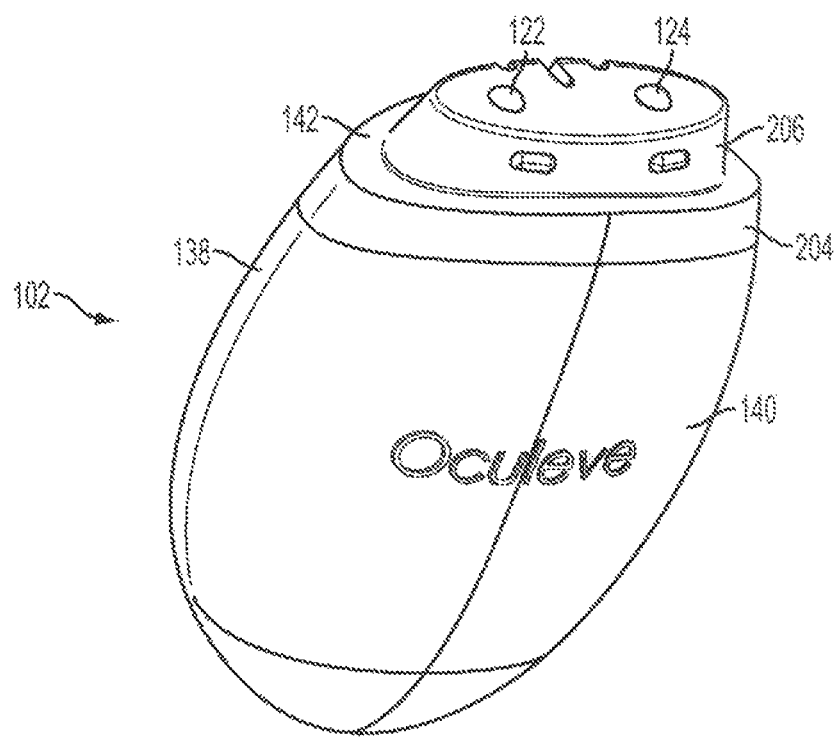
FIG. 3A and FIGS. 3B-3C show perspective view and exploded views, respectively, of a stimulator body suitable for the handheld stimulators described here.
Figure 3B:
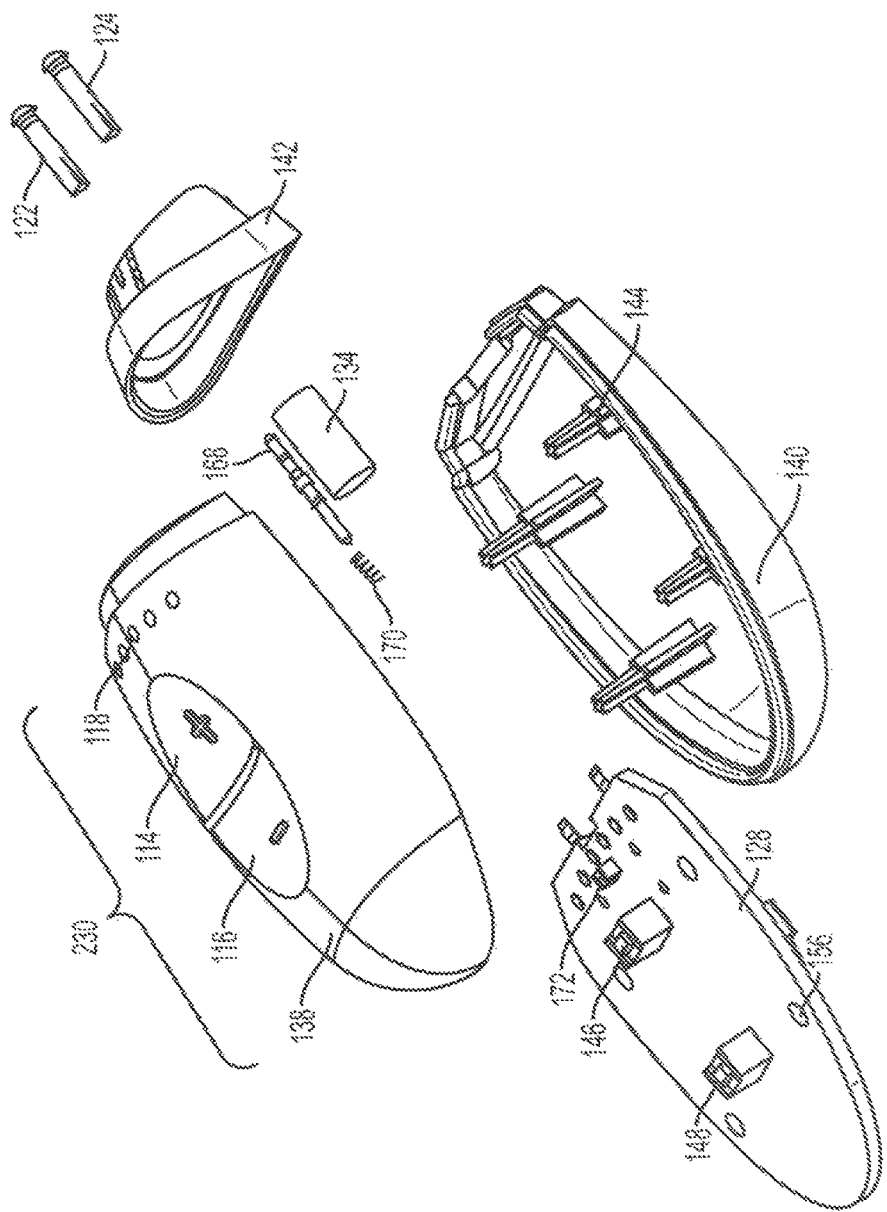
Figure 3C:
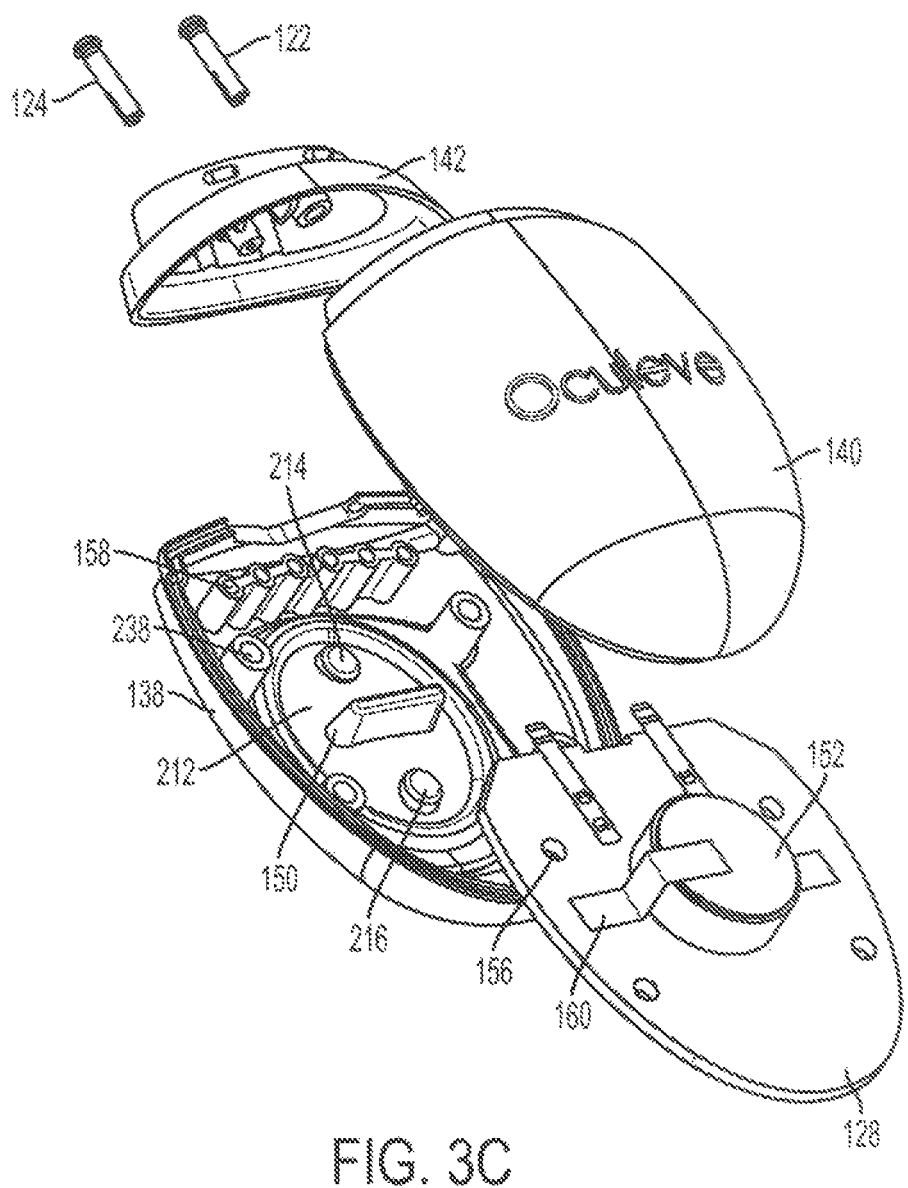
Figure 4:
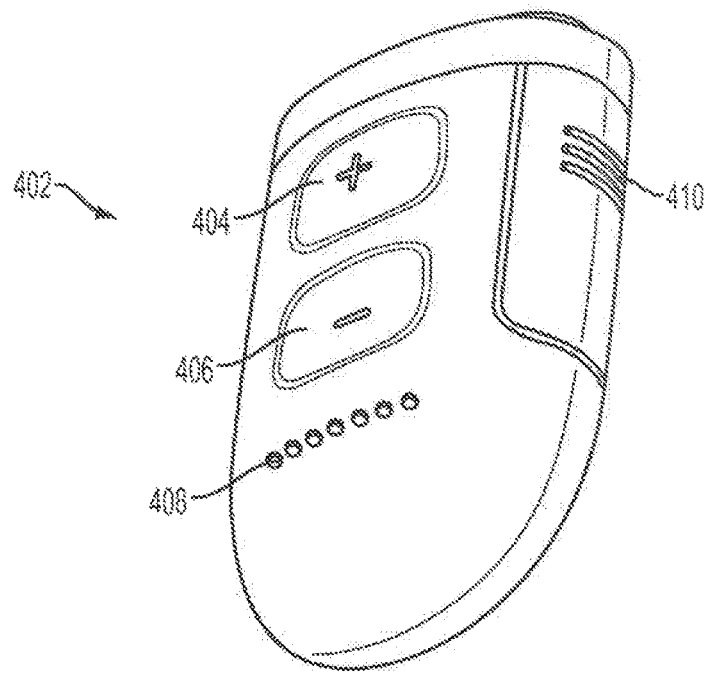
FIG. 4 shows a perspective view of another variation of a stimulator body suitable for the handheld stimulators described here.
Figure 5:
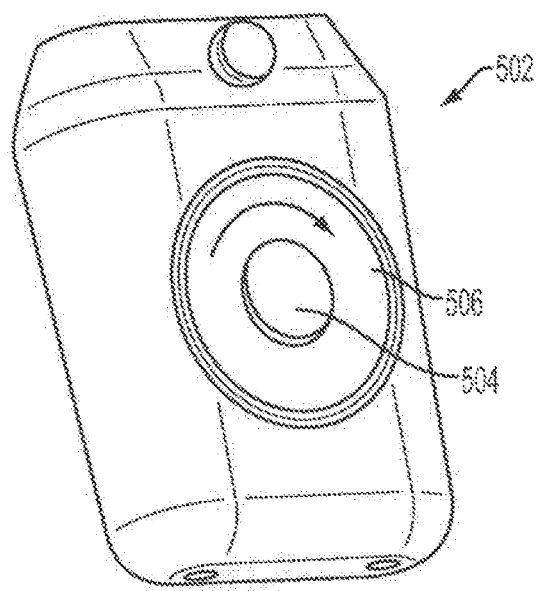
FIG. 5 shows a perspective view of another variation of a stimulator body suitable for the handheld stimulators described here.

FIG. 3A and FIGS. 3B-3C show a perspective view and exploded views, respectively, of the stimulator body 102. The stimulator body 102 may have any suitable shape. In some variations, it may be desirable for the stimulator body 102 to be shaped such that it can be easily gripped by a user, such that it can be held with one hand, such that it can be placed upright on a surface, and/or such that it can be easily and/or discretely carried in a pocket or purse. As shown in FIG. 3A, the stimulator body 102 may have a truncated ovoid shape. However, it should be appreciated that the stimulator body may have other shapes. For example, as shown in FIG. 4, a stimulator body 402 may have a flat proximal end and a rounded distal end. As another example, as shown in FIG. 5, a stimulator body 502 may have a generally rectangular shape, with rounded corners and a tapered proximal end. In other variations, the stimulator body may have a rectangular shape, a rounded rectangular shape, a circular shape, a cylindrical shape, a triangular shape, a teardrop, or the like, each of which may or may not be truncated. The proximal end of the stimulator body 102 (formed by proximal housing 142) may have a shape that is complementary to the bottom of the stimulator probe 104, as described in more detail below.

As mentioned above, the stimulator body may comprise a housing formed by a front housing 138, a back housing 140, and a proximal housing 142. These may fit together to form the exterior of the stimulator body. The front housing 138 and back housing 140 may fit together with any suitable attachment mechanism. For example, the front 138 and back 140 housings may fit together with a tongue-and-groove joint. The proximal housing 142 may comprise a proximal portion 204, which may fit over the proximal ends of the front and back housings 138 and 140, and a distal portion 206, which may fit within a portion of the stimulator probe 104, as described in more detail below. The housing formed by the front 138, back 140, and proximal 142 housings may comprise any number of suitable openings for elements of the stimulator body. For example, the proximal housing 142 may comprise two lumens 208 and 210 that may be configured to receive connectors 122 and 124, described in more detail below. The front housing 138 may comprise an opening configured to receive a portion of the user interface 230, described in more detail below. It should be appreciated that while the housing is described here as comprising front, back, and proximal housings, the housing may be constructed from any number of separate housing components (e.g., two, three, four, five, or more).

In some instances, it may be desirable for the stimulator body to be sealed, such that it may be waterproof or the like. In some of these instances, when the housing comprises a front housing 138, back housing 140, and proximal housing 142, the three housing portions may attach so as to be watertight. For example, the tongue-and-groove joint described above may be watertight. In some variations, the stimulator body 102 may further comprise one or more seals located at the interface between the front housing 138 and the back housing 140, and/or between the front 138 and back 140 housings and the proximal housing 142. In variations in which the housing comprises openings for other elements of the stimulator body (e.g., connectors 122 and 124, a release mechanism, or the like), the interface between those elements and the stimulator housing may be watertight, and/or may comprise seals.

In some variations, it may be desirable for each of the front housing 138, back housing 140, and proximal housing 142 to be formed from the same material in order to improve the ability of the front housing 138, back housing 140, and proximal housing 142 to maintain a tight seal and to exhibit similar expansion/contraction properties with changes in temperature. In some variations, the front housing 138, back housing 140, and top housing 142 may each comprise a rigid material, such as a rigid plastic. For example, the front 138, back 140, and top 142 housings may comprise a thermoplastic such as acrylonitrile butadiene styrene (ABS), polycarbonate, polyetherimide (e.g., ULTEM™ polyetherimide). However, the housing may comprise any suitable material or materials. Furthermore, it should be appreciated that in some variations the front housing 138, back housing 140, and/or proximal housing 142 may comprise different materials.

Figure 3D:
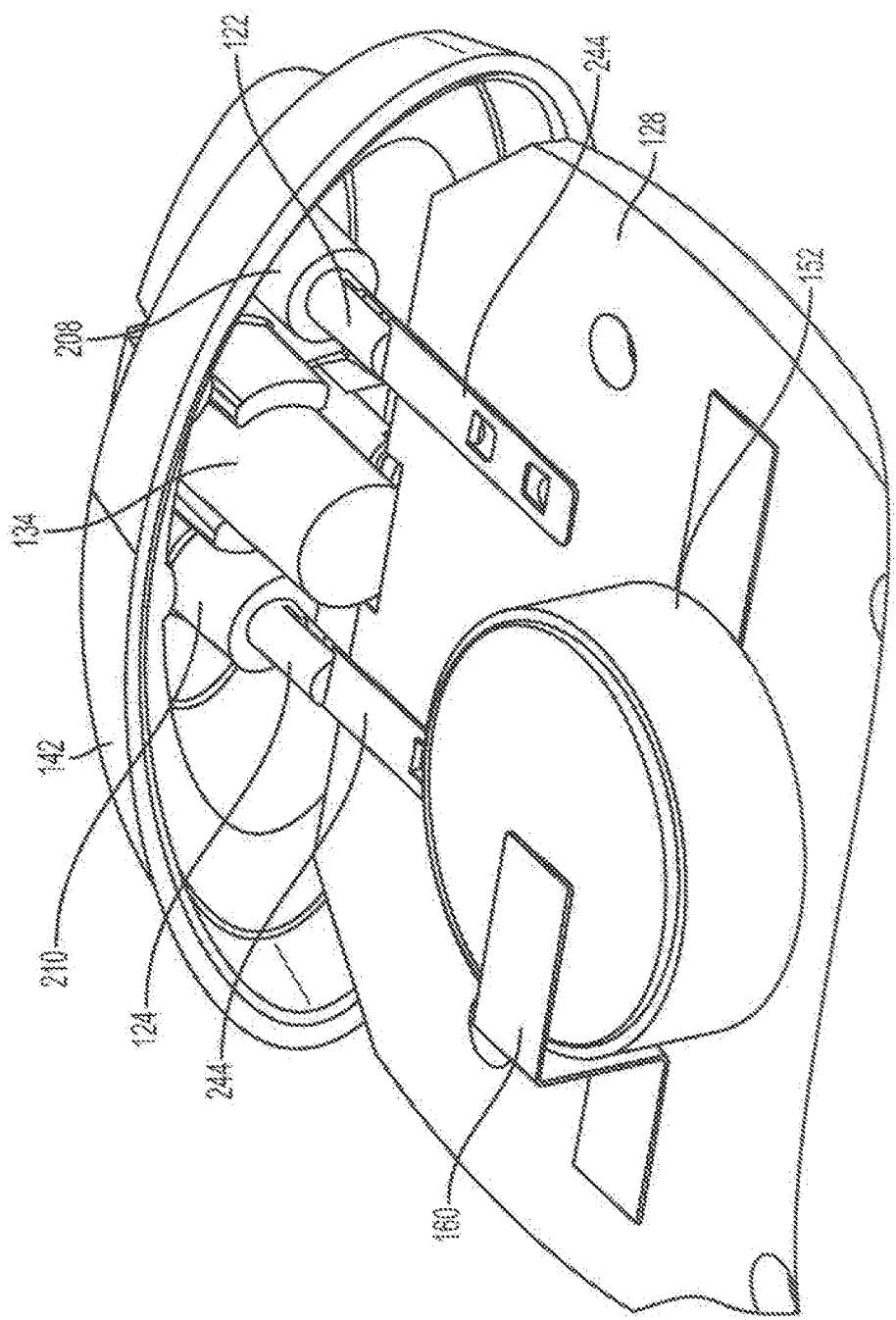
FIG. 3D shows a perspective view of a portion of the stimulator body of FIGS. 3A-3C.

In some variations the housing may comprise an alignment mechanism. The alignment mechanism may assist in aligning the stimulator body with the stimulator probe in variations in which the stimulator body and stimulator probe are detachable, and/or it may assist in keeping the stimulator body and stimulator probe connected. Additionally or alternatively, in which the stimulator system comprises a base station (as described in more detail below), it may assist in aligning the stimulator body with the base station in variations and/or it may assist in keeping the stimulator body and the base station connected. In variations in which the stimulator is configured to be attached to a charging cable, the alignment mechanism may assist in aligning the stimulator or a portion of the stimulator with a charging cable and/or keeping the stimulator and charging cable attached. In some variations, the alignment mechanism may comprise a magnet. FIG. 3D shows a perspective view of a portion of the stimulator body 102. A magnet 134 may be connected to the interior surface of the proximal housing 142 as shown. In other variations, a magnet may be connected to the interior of another portion of the housing, or to the exterior of any portion of the housing. In variations in which the magnet 134 may assist in aligning the stimulator body 102 with the stimulator probe 104, the stimulator probe 104 may comprise a magnet or ferromagnetic material in a corresponding location. In variations in which the magnet 134 may assist in aligning the stimulator body 102 to a base station, the base station may comprise a magnet or ferromagnetic material in a corresponding location, as described in more detail below.

In some variations the housing may comprise a weight. It may in some instances be desirable for the stimulator to have a sufficient weight such that it has a substantial feel when held by a user. In some variations, the alignment mechanism (e.g., a magnet) may further serve as a weight. Additionally or alternatively, the weight may comprise a dense material or materials (e.g., iron or steel). The weight may be located in any suitable location within the housing. In some instances, the weight may be attached to the interior of the housing, to a printed circuit board comprising the control subsystem (described in more detail below), or threaded within pins holding a printed circuit board in place (e.g. pins 144 in stimulator body 102).

In some variations, the stimulator bodies described here may comprise features to assist the user in holding the device. For example, stimulator 402 shown in FIG. 4 may comprise ridges 410 on both sides of the stimulator body 402. These ridges 410 may act as grips for the user to hold onto. It should be appreciated that any of the stimulator bodies (e.g., stimulator body 102) described here may comprise any suitable features to assist the user in holding the device, such as any texturized surface, a high-friction material (e.g., rubber), indentations, or the like.

User Interface

In instances where the stimulators described here comprise a user interface, the user interface may comprise one or more operating mechanisms, which may allow the user to control one or more functions of the stimulator. For example, the operating mechanisms may allow the user to power the device on or off, start or stop the stimulus, change the intensity of the stimulus, change the duration of the stimulus, change the stimulus pattern, or the like. In some variations, the operating mechanisms may be able to activate or deactivate different functions, and/or may be able to change different parameters, based on their manner of operation (e.g., pressing a button briefly, pressing a button for a prolonged period, pressing a button with a particular pattern of pressing actions, rotating a dial by different angles or different speeds). Each of the one or more operating mechanisms may be any suitable structure, such as but not limited to a button, slider, lever, touch pad, knob, or deformable/squeezable portion of the housing, and a stimulator may comprise any combination of different operating mechanisms.

In one variation, the one or more operating mechanisms may comprise one or more buttons. The stimulator body 102, for example, may comprise two buttons 114 and 116. In the variation shown, the two buttons 114 and 116 may be located on a single a flexible membrane 212. The flexible membrane 212 may comprise any suitable material or materials, such as but not limited to a flexible polymer, such as a thermoplastic elastomer (e.g., a thermoplastic elastomer alloy (e.g., VERSAFLEX™ thermoplastic elastomer), thermoplastic polyurethane, or the like), silicone, or the like. In some variations in which the flexible membrane is located within the front housing 138, the flexible membrane 212 may be attached to the front housing 138 such that they are chemically bound. In some variations, they may be connected via overmolding, transfer molding, or two-shot molding. However, it should be appreciated that the flexible membrane 212 may be attached to the housing in any other suitable manner, such as via bonding.

The flexible membrane 212 may be separated into two buttons 114 and 116 by a divider 150. As shown in FIGS. 1E and 3C, the divider 150 may extend interiorly into the body cavity 154 from the interior surface of the flexible membrane 212. The end of the divider 150 may press against a fixed surface within the body cavity 154 of the stimulator body 154. For example, the end of the divider 150 may press against a portion of the printed circuit board (PCB) (128) that forms the control subsystem 136, described in more detail below. The divider 150 may thus serve as an inflection point on the flexible membrane 212, such that each of the two buttons 114 and 116 may be pressed separately by the user. The divider 150 may also serve to resist separation between the flexible membrane 212 and the housing (e.g., by breaking the adhesion between the housing and the flexible membrane) by limiting the movement of the flexible membrane 212 into the body cavity 154.

If the user presses one of buttons 114 or 116, the movement of the button may be transferred to the control subsystem 136. As shown in FIG. 3C, the interior surface of the flexible membrane 212 may comprise two raised surfaces 214 and 216 on the interior surface of buttons 114 and 116, respectively. When button 114 or 116 is depressed, the corresponding raised surface 214 or 216 may press against PCB button 146 or 148 (shown in FIG. 3D), respectively, located in the printed circuit board 128, in order to transmit information to the control subsystem 136. While the stimulator body 102 is shown as having two buttons formed on a single flexible membrane, it should be appreciated that in other variations, two or more buttons may be separately formed. An example of such buttons is shown in FIG. 4, which shows separate first and second buttons 404 and 406.

In stimulator body 102, pressing the top button 114 may power on the stimulator 100 when the stimulator 100 is off. In some variations in which the stimulator is capable of differing stimulus intensities, the stimulator may be powered on to the last stimulus intensity from before the stimulator was powered off. When the stimulator 100 is on, pressing the top button 114 may increase the intensity of the stimulus (for example, when the stimulus is electrical, pressing the top button 114 may increase the amplitude of the stimulus waveform). Conversely, pressing the bottom button 116 may decrease the intensity of the stimulus (for example, when the stimulus is electrical, pressing the bottom button 116 may decrease the amplitude of the stimulus waveform). Pressing the bottom button 116 also may in some instances power off the stimulator 100. For example, pressing and holding the bottom button 116 may power off the stimulator 100; or additionally or alternatively, pressing the bottom button 116 when the stimulus intensity is at its lowest level may power off the stimulator 100. However, it should be appreciated that additionally or alternatively, the stimulator 100 may power off without user input (e.g., after a period of idle time). In some variations, the stimulator 100 may provide feedback to the user to indicate that the buttons are being pressed (or that other operating mechanisms are being operated). For example, pressing the buttons or operating any of a stimulator's operating mechanisms may be accompanied by a sound, vibration, tactile click, light, or the like, but need not be.

The operating mechanisms of the stimulators described here may have any number of other suitable configurations. For example, in another variation of the stimulator body 502 shown in FIG. 5, the stimulator body 502 may comprise a button 504 and a ring-shaped slider 506. The button 504 may be pressed to perform one or more stimulator functions (e.g., powering the device on or off, starting and stopping stimulation, as described in more detail regarding stimulator 100), and the ring-shaped slider 506 may be rotated to perform one or more stimulator functions (e.g., changing intensity of the stimulation, changing the duration of the stimulation, as described in more detail regarding stimulator 100).

In some variations, the stimulators may be configured to provide feedback or otherwise convey information to a user. This may be done visually, audibly, or via tactile feedback. For example, the user interface of the stimulator may comprise one or more light-based status indicators (e.g., LEDs), which may light up to convey information to a user.

The number and/or location of illuminated status indicators, and/or their color, may convey information to the user. For example, the number and/or locations of illuminated status indicators may indicate the intensity of the stimulus or the charge or charging status of any rechargeable battery; the color (e.g., red) of the illuminated status indicator(s) may indicate a low battery or need to replace the stimulator probes (as explained in more detail below); and/or flashing lights may indicate that the stimulator is currently charging. In stimulator 100, the user interface 230 may comprise one or more light-based status indicators 118. The light-based status indicators 118 may comprise one or more light sources (e.g., LEDs) located on the printed circuit board 128, which may be connected to or located near light-transmitting elements 158 on the front housing 138. The light-transmitting elements 158 may transmit light from a light source on the printed circuit board 128 to the exterior of the housing, where it may be perceived by a user. In some variations, the light-transmitting elements 158 may comprise fiber optics (e.g., light pipes). In other variations, the light-transmitting elements 158 may comprise translucent or transparent epoxy) in the front housing 138. While the light-based status indicators 118 are shown as being located on front housing 138, it should be appreciated that they may be in any suitable location, such as on the back housing 140, the top housing 142, or the stimulator probe 104.

Additionally or alternatively, in some variations the stimulator body may comprise a display, which may be configured to convey information to a user via text and/or images. Additionally or alternatively, the stimulator body may comprise a speaker or buzzer configured to produce one or more speech prompts or other sounds. Additionally or alternatively, the stimulator body may be configured to vibrate. When the stimulator body is configured to vibrate, the duration and/or repetition of the vibration may convey information to the user. It should be appreciated that when the stimulator is configured to deliver a mechanical stimulus (e.g., vibration), as described in more detail below, vibration and/or noise caused by the mechanical stimulus delivery may be used to convey information to the user.

It should be appreciated that while the user interfaces described above are located on the stimulator bodies (e.g., stimulator body 102), in other variations, all of a portion of the user interface of the stimulator may be located on the stimulator probe. Additionally or alternatively, all or a portion of the user interface may be located on a separate unit, which may be physically or wirelessly attached to the stimulator. For example, in variations where the stimulator is configured to connect to a computer or mobile device (such as cellular telephone, tablet, wearable computer (e.g., optical head-mounted displays such as Google GLASS™ wearable computing device), or the like, as will be discussed in more detail below), the mobile device may act as a user interface. For example, the mobile device may act as a display to convey information to the user or may allow the user to control or program the device.

Control Subsystem

Generally, the control subsystem may be configured to control a stimulus to be delivered to a subject via the stimulator probe. The control subsystem may be contained within the housing the stimulator. The control subsystem may be connected to the operating mechanisms of the stimulator (e.g., the buttons), which may allow the control subsystem to receive input from a user. The control subsystem may also be connected to mechanisms configured to provide feedback or otherwise convey information to a user. In some variations, such as stimulator 100, the control subsystem 136 may be located on a printed circuit board 128. When the control subsystem 136 is located on a printed circuit board 128, the printed circuit board 128 may be fixed within the body cavity 154 of the stimulator body 102 in any suitable manner. In some variations, the printed circuit board 128 may be held in place relative to the housing by pins 144. As shown in FIG. 3B, the interior surface of back housing 140 may comprise four pins 144. The pins 144 may be configured to fit through corresponding openings 156 in the printed circuit board 128, and may be further configured to fit into receiving recesses 238 in the front housing 138. It should be appreciated that in other variations in which the printed circuit board is secured by pins, the housing may comprise any number of pins 144, which may be located on any portion of the housing.

The control subsystem 136 may include any circuitry or other components configured to operate the stimulators as described here. In some variations the control subsystem may comprise a processor 232, memory 234, and/or a stimulation subsystem 236. Generally, the processor may be configured to control operation of the various subsystems of the control subsystem. For example, the processor 232 may be configured to control the stimulation subsystem 236 to control parameters of the stimulation provided by the stimulation subsystem 236. The memory 234 may be configured to store programming instructions for the stimulator, and the processor 232 may use these programming instructions in controlling operation of the stimulator. The stimulation subsystem 236 may be configured to generate a stimulation signal and deliver the stimulation signal to a patient via the stimulator probe. In other variations, the control subsystem 136 may comprise a finite state machine.

In some variations, the control subsystem 136 may comprise a detection/recording subsystem. In these variations, the detection/recording subsystem may be configured to monitor one or more parameters of a subject (e.g., subject impedance), the stimulation delivered to the subject (e.g., date and time of stimulation, duration of the stimulation, amplitude of the stimulation signal, pulse width, frequency), and/or the stimulator itself (e.g., diagnostic data). The detection/recording subsystem may record some or all of this data to the memory. Additionally or alternatively, the control subsystem 136 may be configured to accept and record user input regarding subject symptomology, subject activity, or the like.

Additionally or alternatively, the control subsystem may comprise a communications subsystem. The communication subsystem may be configured to facilitate communication of data and/or energy between the stimulator and an external source. For example, in some variations the communications subsystem may be configured to allow the stimulator to communicate wirelessly (e.g., via WiFi, BLUETOOTH™ wireless technology, or the like) with an external device (e.g., an external programmer, base station, laptop or other computer, mobile device such as a mobile phone, tablet, wearable computer (e.g., optical head-mounted displays such as Google GLASS™ wearable computing device), or the like), and may comprise an antenna, coil, or the like. Additionally or alternatively, the communication subsystem may be configured to communicate with an external device (e.g., a flash drive, a laptop or other computer, a mobile device such as a mobile phone, palm pilot, or tablet, or the like) via a wired transmission line. In these variations, the stimulator may comprise one or more ports (e.g., a USB port), connectors and/or cables configured to physically connect the stimulator to an external device, such that data and/or energy may be transmitted between the stimulator and the external device.

The control subsystem may in some variations comprise safety mechanisms, such as limits on the voltage, current, frequency, and duration of the stimulus when the stimulus is electrical. In some variations, some of these safety mechanisms may be part of the stimulation subsystem. For example, the stimulation subsystem 236 of the control subsystem 136 of stimulator 100 may limit the voltage and current that may be delivered to the patient. In some variations, the voltage may be limited by a voltage regulator. In some of these variations, the voltage limit may be between about 1 V and about 100 V. In some of these variations, the voltage limit may be between about 5 V and 50 V, between about 10 V and 25 V, or between about 15 V and 20 V. In some variations, the voltage may be regulated via a boost regulator connected to the power source 152, but it should be appreciated that any suitable voltage regulator may be used. In some variations, the current may be limited by a resistor in series with the load or a current-limiting transistor, or any other suitable combinations of elements. In some variations, the current limit may be about between about 1 mA to about 30 mA, between about 5 mA to about 20 mA, or about 10 mA. In some variations, the stimulation subsystem 236 may be capacitively coupled by one or more series capacitors on the output. This capacitive coupling may prevent DC currents from being applied to the patient, and may limit the total charge injection and pulse duration.

Additionally or alternatively, some or all of the safety mechanisms of the control subsystem 136 may be part of the processor 232. For example, the processor 232 may comprise software that limits the frequency to within an allowed range. In some variations, the frequency may be limited to between about between about 0.1 Hz and about 200 Hz, between about 10 Hz and about 60 Hz, between about 25 Hz and about 35 Hz, between about 50 Hz and about 90 Hz, between about 65 Hz and about 75 Hz, between about 130 Hz and about 170 Hz, between about 145 Hz and about 155 Hz, or between about 145 Hz and about 155 Hz. Additionally or alternatively, the processor 232 may comprise software that limits the stimulus intensity (e.g., the current or voltage). In some of these variations, the voltage limit may be between about 5 V and 50 V, between about 10 V and 25 V, or between about 15 V and 20 V. In some variations, the current limit may be about between about 1 mA to about 30 mA, between about 5 mA to about 20 mA, or about 10 mA. The processor 232 may additionally or alternatively comprise software that limits the stimulus duration. In some variations, the duration may be limited to about 1 minute, about 2 minutes, about 3 minutes, about 5 minutes, about 10 minutes, or the like. In some variations in which the stimulator probe 104 is removably connected to the stimulator body 102, the control subsystem 136 may prevent the delivery of current by the stimulation subsystem 236 when the stimulator probe 104 is disconnected from the stimulator body 102. For example, the control subsystem 136 may prevent delivery of current when the mechanism described with respect to FIGS. 15B-15C does not detect an attached stimulator probe. Additionally or alternatively, the control subsystem 136 may prevent delivery of current by the stimulation subsystem 236 when the stimulator probe 104 is not in contact with a patient's tissue.

Power Source

The stimulator may comprise a power source. The power source may be any suitable power supply capable of powering one or more functions of the stimulator, such as one or more batteries, capacitors, or the like. As shown in FIGS. 3C-3D, in some variations the power source may comprise a lithium coin cell battery 152. The battery 152 may be secured in place via any suitable method, such as a clip 160 attached to the printed circuit board 128 comprising the control subsystem 136. In some variations, the power source may be rechargeable, as described in more detail below.

While the stimulator body 102 comprises a power source, in other variations the stimulator body need not comprise a power source. In some variations, the stimulator body may comprise a port, cord, or other mechanism for connecting the stimulator to an external power source (such as a wall outlet or separate battery pack), which in turn may be used to power one or more portions of the stimulator. In some other variations, such a port, cord, or other mechanism may be used to recharge a rechargeable power source. The stimulator body 102 may comprise such a port (e.g., a USB port) at any suitable location, such as between the connectors 122 and 124 on the proximal housing 142, on the back housing 140, on the front housing 138, or at the proximal end of the stimulator body 102 between the front 138 and back housings 140.

Stimulator Probe

The stimulator probe of the stimulator may comprise one or more nasal insertion prongs, which may be configured to extend at least partially into a nasal cavity of a subject. FIGS. 6A, 6B, 6C, 6D, and FIGS. 6E-6F depict back, side, cut-away back, cut-away top, and perspective views, respectively, of the stimulator probe 104 of stimulator 100. As shown there, the stimulator probe 104 may comprise a first nasal insertion prong 106 and a second nasal insertion prong 108. The first and second prongs 106 and 108 may be connected via a base member 126. The base member 126 may be configured to hold at least a portion of the first and second prongs in fixed relation to each other.

Prongs & Base

The nasal insertion prongs 106 and 108 may generally be configured to be inserted a subject's nostrils. As shown in FIGS. 6A-6F, each nasal insertion prong 106 and 108 may comprise an elongate portion 162 and 164, respectively. Each elongate portion 162 and 164 may have at its distal end a distal portion 176 and 178. In some variations, the distal portions 176 and 178 may have a diameter (or greatest cross-sectional dimension) that is larger than the diameter (or greatest cross-sectional dimension) of the elongate portion 162 and 164 of the prongs proximal to the distal portions. This may allow a portion of the distal portions 176 and/or 178 (e.g., the electrodes, described below) to be brought into contact with a subject's tissue, while the elongate portions 162 and 164 are not in contact with the subject's tissue. For example, the diameter of the nasal insertion prongs 106 and 108 at the distal portions 176 and 178 may in some instances be between about 3 mm and about 7 mm, while the diameter of the elongate portions 162 and 164 may be between about 1 mm and about 6 mm proximal to the distal portions. More specifically, in some variations the diameter of the nasal insertion prongs at the distal portions 176 and 178 may be about 5 mm, and the diameter of the elongate portions 162 and 164 may be about 3 mm. The proximal portion of the elongate portions 162 and 164 may flare outward (i.e., have an increasing diameter or greatest cross-sectional dimension) toward the base member, which may in some variations act as a stop to limit the distance that the nasal insertion prongs 106 and 108 may be advanced into the nose of a user.

Figure 6A:
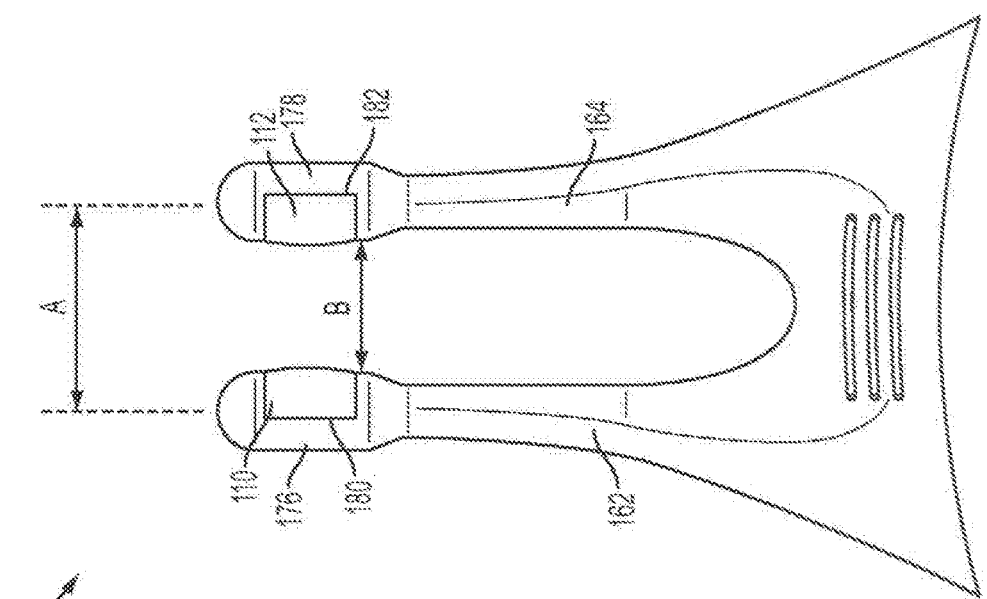
FIGS. 6A, 6B, 6C, 6D, and FIGS. 6E-6F depict back, side, cut-away back, cut-away top, and perspective views, respectively, of a stimulator probe suitable for the handheld stimulators described here.
Figure 6B:
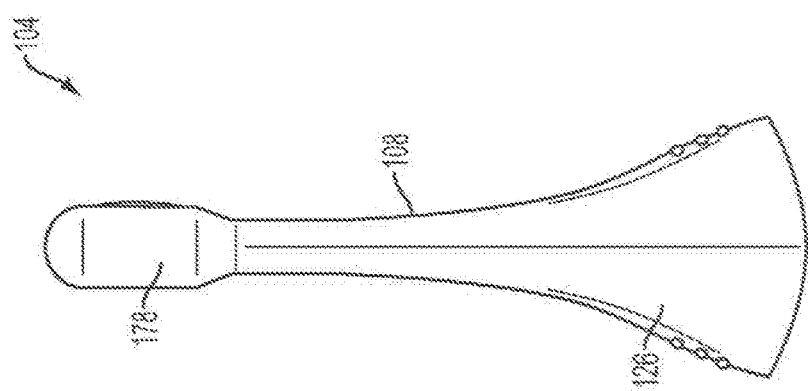
Figure 6C:
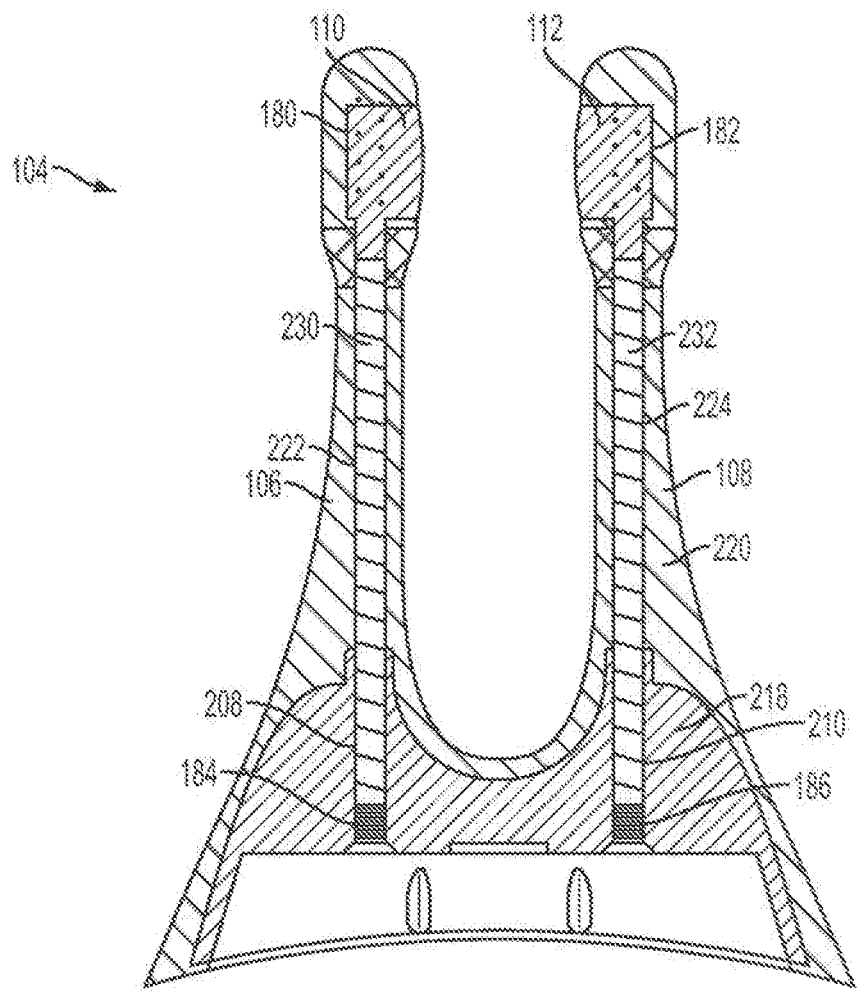
Figure 6D:
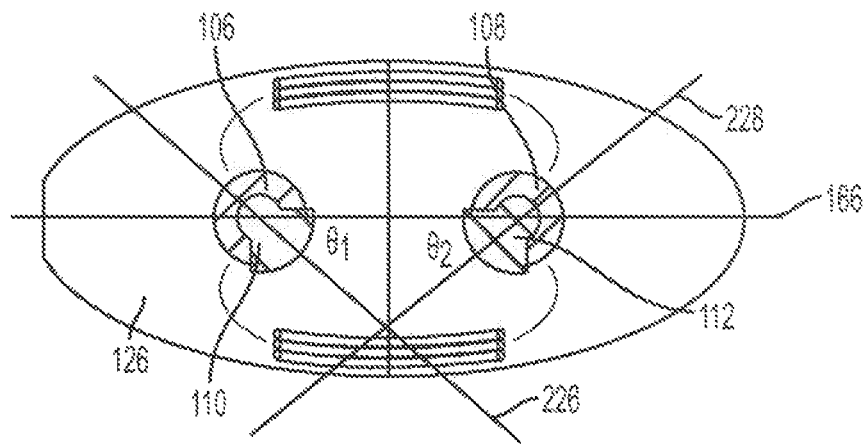
Figure 6E:
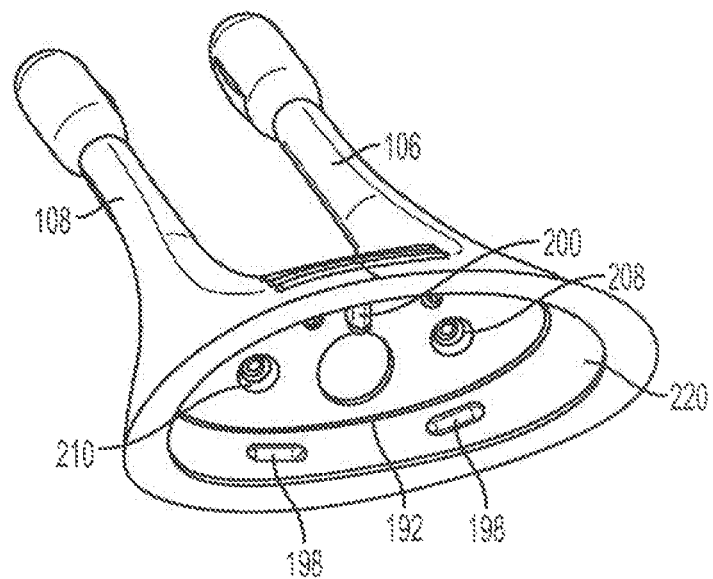
Figure 6F:
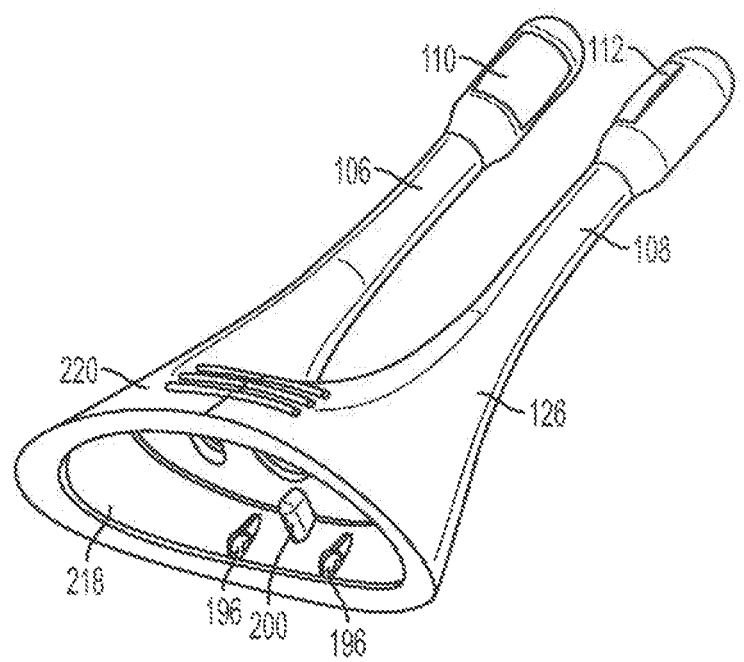
Figure 6G:
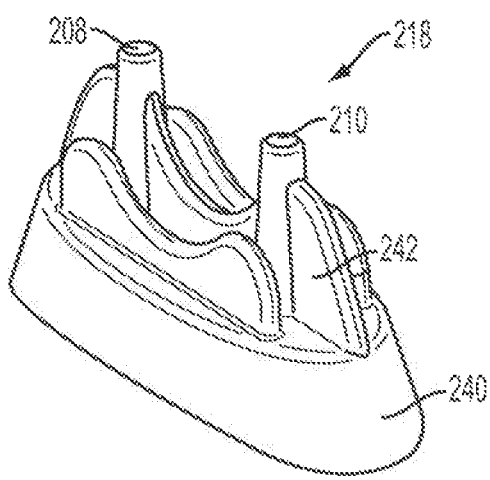
FIG. 6G depicts a perspective view of a rigid support of the stimulator probe of FIGS. 6A-6F.

The first and second nasal insertion prongs 106 and 108 may be connected to each other via a base member 126. In the variation shown in FIGS. 6A-6F, the prongs 106 and 108 may be integrally formed with the base member 126 by a rigid support 218 and a flexible overlay 220, as shown in FIG. 6C. The rigid support 218 may provide support to the base of the nasal insertion prongs 106 and 108 and may interface with the top of the stimulator body 102, as described in more detail below. The rigid support 218 may comprise any suitable material or materials, such as a rigid plastic. For example, in some variations, the rigid support 218 may comprise a thermoplastic such as acrylonitrile butadiene styrene (ABS), polycarbonate, polyetherimide (e.g., ULTEM™ polyetherimide). It may in some instances be desirable for the rigid support 218 to comprise the same material as a portion of the stimulator body 102 (e.g., the proximal housing 142 (described above)), in order to improve the ability to attach the stimulator probe 104 to the stimulator body 102, as described in more detail below. In some variations, the rigid support 218 may comprise a bottom portion 240 configured to interface with the stimulator body 102, and a top portion comprising one or more supports 242 (e.g., as shown in FIG. 6G, three supports 242). The top portion may further comprise two lumens 208 and 210, configured to receive leads as described below. In some variations, the supports 242 may be saddle-shaped.

The flexible overlay 220 may form the nasal insertion prongs 106 and 108 and may wrap around the rigid support 218 to form the base member 126. The flexible overlay 220 may comprise any suitable material or materials. The flexible overlay 220 may comprise a more flexible material than the rigid support 218. For example, in some variations the flexible overlay 220 may comprise a flexible polymer, such as a thermoplastic elastomer (e.g., thermoplastic elastomer alloys (e.g., VERSAFLEX™ thermoplastic elastomer), thermoplastic polyurethanes, or the like), silicone, or the like. Although the nasal insertion prongs 106 and 108 may be integrally formed with the base member 126 in stimulator probe 104, in other variations, the nasal insertion prongs may separately formed from the base member, as shown for example in FIGS. 9A-9F, FIGS. 10A-10C, and FIG. 14, which are described in more detail below.

The base member 126 may allow the nasal insertion prongs 106 and 108 to be manipulated as a single unit (and disposed as a single unit, in instances where the stimulator probe is disposable). In some variations, the base member 126 may act as a stop to limit the distance that the nasal insertion prongs 106 and 108 may be advanced into the nose of a user. Additionally or alternatively, one or more of the nasal insertion prongs may include a flange or other mechanical stop to limit the distance that the prongs may be inserted into a user's nose. The base member 126 may further help to control the relative orientation of the prongs. For example, as shown in FIGS. 6A-6F, the two nasal insertion prongs 106 and 108 may be connected to the base member 126 such that the two prongs are oriented substantially parallel to each other. In some variations, having the nasal insertion prongs oriented substantially parallel to each other may provide advantages in manufacturing and may aid in nasal insertion.

Figure 7A:
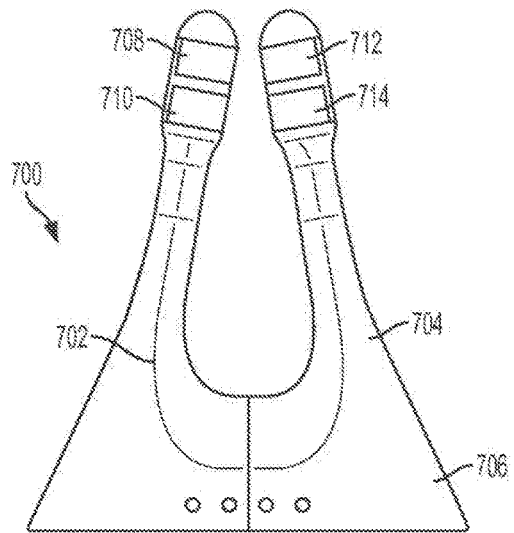
FIGS. 7A, 7B, and 7C depict back, front, and perspective views, respectively, of a stimulator probe suitable for the handheld stimulators described here.
Figure 7B:
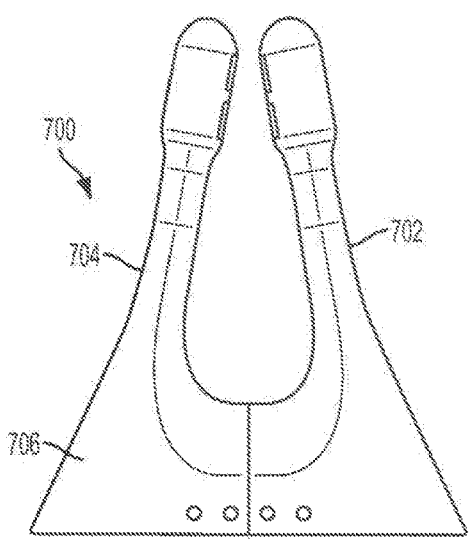
Figure 7C:
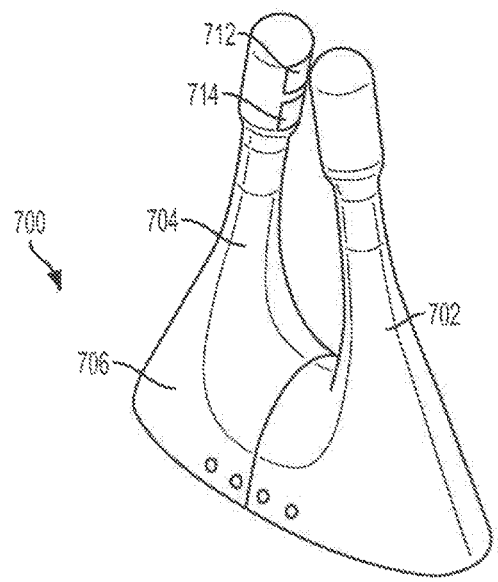

However, in other variations, the nasal insertion prongs may not be oriented parallel to each other. For example, in some variations, the nasal insertion prongs may be angled toward each other. For example, FIGS. 7A-7C and FIGS. 8A-8C show variations of stimulator probes suitable for use with the stimulators described here. As shown in FIGS. 7A-7C, stimulator probe 700 may comprise first and second nasal insertion prongs 702 and 704, respectively, connected to a base member 706. The nasal insertion prongs 702 and 704 may be connected to the base member 706 such that they are angled toward each other. Similarly, as shown in FIGS. 8A-8C, stimulator probe 800 may comprise first and second nasal insertion prongs 802 and 804, respectively, connected to a base member 806 such that they are angled toward each other.

The two nasal insertion prongs may be positioned with any suitable distance between them (e.g., between about 3 mm and about 15 mm). In some variations, it may be desirable for the distance between the two nasal insertion prongs to be such that they fit simultaneously into each of the user's nostrils on either side of the septum. Additionally or alternatively, it may be desirable for the distance to be such that the nasal insertion prongs are configured to self-align to the desired stimulation location (described in more detail below) when inserted into the user's nasal cavities. In some of these variations, the distance between the central longitudinal axes of the two nasal insertion prongs 106 and 108 (labeled as distance "A" in FIG. 6A) may be between about 12 mm and about 16 mm. The diameter of the nasal insertion prongs at the distal portions 176 and 178 may in some instances be about 3 mm to about 7 mm as described above, and thus the distance between the distal portions (labeled as distance "B" in FIG. 6A) may be about 5 mm to about 11 mm. More specifically, in some variations the distance between the central axes of the two nasal insertion prongs 106 and 108 may be about 14 mm, and the diameter of the nasal insertion prongs at the distal portions 176 and 178 may be about 5 mm, and thus the distance between the distal portions may be about 11 mm.

The one or more nasal insertion prongs may have any suitable length. In some variations, the length of the nasal insertion prongs may be such that when inserted into the nasal cavity, at least a portion (e.g., distal portions 176 and 178) is capable of reaching the area of the nasal cavity that is desired to be stimulated. For example, the length of the nasal insertion prongs may be such that when inserted into the nasal cavity, at least a portion is capable of reaching the nasal mucosa or other area desired to be stimulated, as described in more detail below. In some variations, the length of the nasal insertion prongs extending from the base member (i.e., the farthest the nasal insertion prongs could be inserted into the nasal cavity) may be between about 25 mm and about 45 mm. In other variations, the length of the nasal insertion prongs extending from the base member may be between about 30 mm and about 40 mm. For example, in some variations the nasal insertion prongs 106 and 108 may have a length extending from the base member 126 of about 37.5 mm (labeled as distance "C" in FIG. 6A). While the two nasal insertion prongs of stimulator probe 104 are shown as having the same fixed length, in other variations different prongs of a stimulator probe may different lengths. In some variations, one or more prongs may have an adjustable height. For example, in some of these variations, a prong may be configured to telescope to alter the height of the prong. In other variations, the prongs may be removable from the base member, and prongs having different lengths may be attached to the base member. Furthermore, while the prongs are shown as being substantially straight, it should be appreciated that in other variations the prongs may comprise one or more bends or curves.

The nasal insertion prong dimensions and configuration described with respect to stimulator probe 104 may allow the nasal insertion prongs 106 and 108 to self-align to the desired stimulation location when inserted into a user's nasal cavities. The length of the nasal insertion prongs is desirably long enough such that the prongs can reach the desired stimulation location (e.g., the nasal mucosa superior to the columella, such as near the interface between the nasal bone and the upper lateral cartilage) in a range of patients. However, it should be appreciated that in some instances it may be desirable to stimulate the columella. For those patients having a larger distance between the columella and the desired stimulation location, a longer portion of the nasal insertion prongs may be inserted into the nasal cavities. For those patients having a shorter distance between the columella and the desired stimulation location, a shorter portion of the nasal insertion prongs may be inserted into the nasal cavities. Because the patient's nasal cavities may narrow from inferior to superior, as the nasal stimulation prongs are advanced superiorly into the nasal cavities toward the desired stimulation location, the nasal tissue may generate a force pressing the nasal insertion prongs medially. When the nasal insertion prongs comprise a flexible material (e.g., a flexible polymer, such as a thermoplastic elastomer (e.g., a thermoplastic elastomer alloy (e.g., VERSAFLEX™ thermoplastic elastomer), thermoplastic polyurethane, or the like), silicone, or the like) as described herein, the nasal insertion prongs may flex medially, bringing them into contact with the desired stimulation location (e.g., the nasal mucosa on or near the septum, such as on the septum near the interface between the nasal bone and the upper lateral cartilage), as described in more detail below.

In some variations, it may be desirable to have a particular flexibility or range of flexibilities in order to allow the nasal insertion prongs to self-align to the desired stimulation location when inserted into a user's nasal cavities. In these variations, properties of the nasal insertion prongs (e.g., the Young's modulus, thickness of the flexible material or materials, the properties of the leads located within the prongs (described in more detail below)) may be chosen to allow self-alignment. Generally, it may be desirable for the prongs to be stiff enough such that they can be pushed into the nasal cavities without buckling, while being flexible enough to self-align and/or to be atraumatic to the nasal tissue during regular use and insertion, and/or during a sudden movement (e.g., a sneeze). This may also improve comfort for the user. In some variations, the desired hardness of the material may be between about 40 D and about 90 D, between about 50 D and about 80 D, between about 60 D and about 70 D, or about 65 D. In addition to having material properties that may be atraumatic to nasal tissue, it may be desirable for the distal tips of the nasal insertion prongs to have rounded edges to help minimize the risk of tissue damage during advancement of the prongs into the nose.

Electrodes

When the stimulators described here are configured to deliver an electrical stimulus, at least one of the nasal insertion prongs may comprise one or more electrodes configured to deliver a stimulus to tissue. In variations where a stimulator comprises two nasal insertion prongs, each of the two nasal insertion prongs may comprise at least one electrode. Having multiple electrode-bearing prongs may allow the stimulator to provide bipolar stimulation (and/or bilateral stimulation of two nostrils), as will be discussed in more detail below.

Figure 11B:
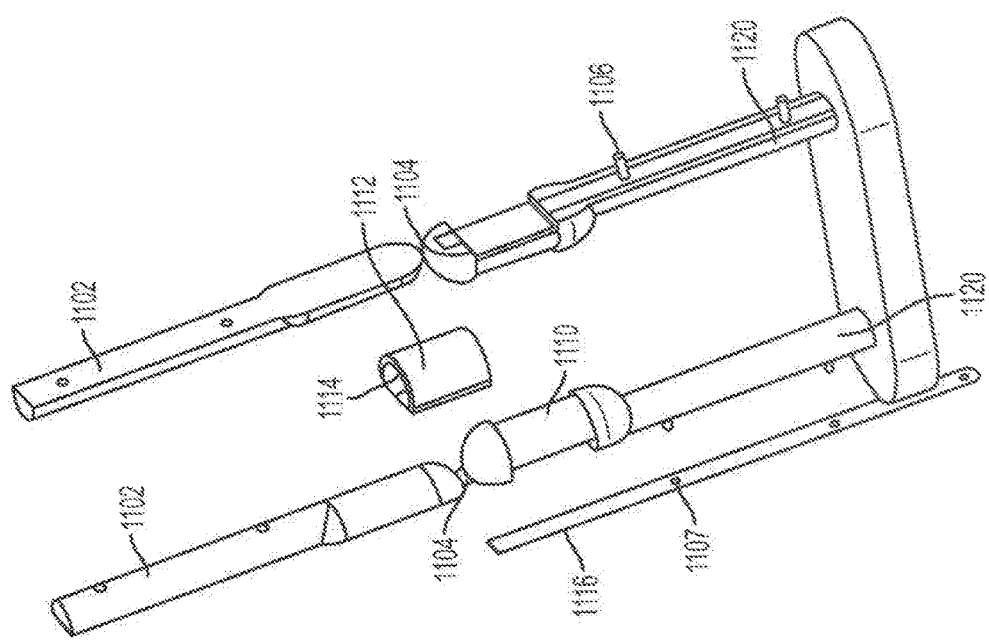
FIG. 11B shows one manner in which the stimulator probe of FIG. 11A may be constructed.
Figure 11A:
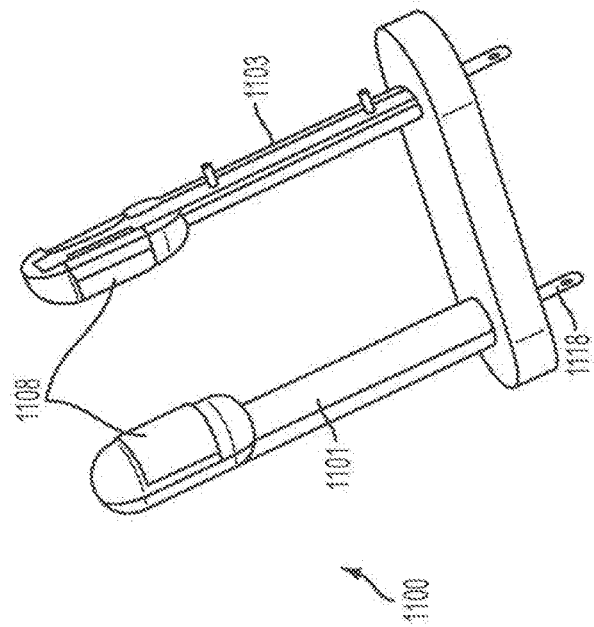
FIG. 11A depicts a perspective view of a variation of a stimulator probe suitable for the handheld stimulators described here.
Figure 12C:
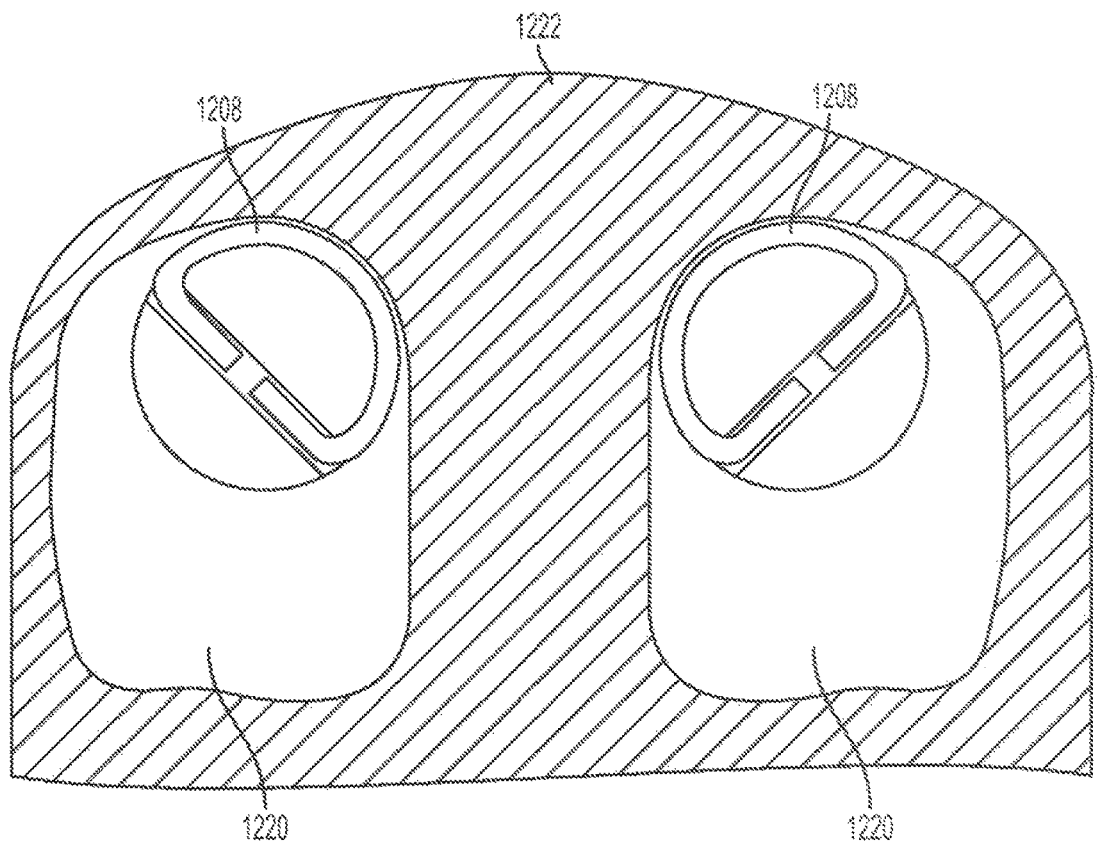
FIG. 12C shows a cross-sectional view of the stimulator probe of FIGS. 12A-12B positioned in the nose of a user.

When a nasal insertion prong or prongs of the stimulators describe here comprise one or more electrodes, the electrodes may have any suitable design. In variations in which the electrodes comprise an arc of a cylindrical surface, such as in the variation shown in FIGS. 6A-6F, the electrodes 110 and 112 may comprise about a 100 degree arc of a cylindrical surface. That is, openings 180 and 182 in the distal portions 176 and 178 of the nasal insertion prongs may comprise about a 100 degree arc of a cylinder, and the electrodes 110 and 112 may be located within the openings 180 and 182. In other variations, the electrodes may be any suitable arc length of a cylinder. For example, in some instances, the electrodes may be semi-cylindrical, as shown in FIGS. 7A-7C, 11A-11B, and 12A-12C (discussed further below). As shown in FIGS. 12A-12C, for example, the stimulator probe 1200 may comprise a first nasal insertion prong 1202 and a second nasal insertion prong 1204 connected by a base member 1206, with each prong having an electrode 1208. The electrodes 1208 may be semi-cylindrical. In other instances, the electrodes may be a partial cylinder having an arc greater than 100 degrees (e.g., between about 110 degrees and about 270 degrees, about 110 degrees, about 120 degrees, about 180 degrees, about 270 degrees, or the like). In yet other instances, an electrode may be a partial cylinder having an arc less than 100 degrees (e.g., between about 30 degrees about 95 degrees, about 90 degrees, about 45 degrees, or the like).

Although the electrodes described above may comprise an arc of a cylindrical surface, it should be appreciated that the electrodes described here may have any suitable shape. In some other variations, for example, the electrodes may comprise two or more adjacent arcs of a cylindrical surface. For example, the nasal insertion prongs 702 and 704 of stimulator probe 700 may comprise two semi-cylindrical electrodes 708 and 710 or 712 and 714, respectively. In yet other variations, the electrodes may comprise a portion of an arc of a cylindrical surface, wherein the portion of the arc comprises rounded edges. As example is shown in FIGS. 8A-8C, which shows electrodes 808 and 810 of nasal insertion prongs 802 and 804, respectively. In some other variations, for example, an electrode may be ellipsoid or spherical, ovoid, or the like. In yet other variations, the electrodes may comprise an array of electrodes, as shown for example in FIGS. 13A-13B (described in more detail below). In some variations, having an array of electrodes may allow a stimulus to be delivered to tissue even if one or more of the electrodes in the array fails, and/or may facilitate unilateral stimulation with a single nasal insertion prong.

When the nasal insertion prongs comprise one or more electrodes, the center of the electrodes may be angled relative to the axis intersecting the first and second prongs. In some variations, the electrodes may be angled such that when the first nasal insertion prong is positioned in a first nostril and the second nasal insertion prong is positioned in the second nostril, the electrodes may be directed toward the front of the nose. When an electrical stimulus is delivered through the electrodes of the first and second nasal insertion prongs and, the stimulation energy may be directed toward the front of the nose. This may allow for selective activation of nerves in the front of the septum and nasal mucosa, while minimizing activation of nerves toward the rear of the nasal septum. This may reduce negative side effects that may occur from stimulation of nerves that innervate the teeth, as described in more detail below. Specifically, in the variation of the stimulator probe 104, as shown in FIG. 6D, the center of the electrode 110 of the first nasal insertion prong 106 (shown by line 226) may be rotated at an angle $\theta_1$ relative to the axis 166 intersecting the first 106 and second 108 nasal insertion prongs, while the center of the electrode 112 of the second nasal insertion prong 108 (shown by line 228) may be rotated at an angle $\theta_2$ relative to the axis 166. Similarly, in the variation of the stimulator probe 1200 shown in FIGS. 12A-12C, the center of the electrode 1208 of the first prong 1202 (represented by line 1214) may be rotated at an angle $\theta_3$ relative to the axis 1212 intersecting the first 1202 and second 1204 nasal insertion prongs, while the center of the electrode 1210 of the second prong 1204 (represented by line 1216) may be rotated at an angle $\theta_4$ relative to the axis 1212.

The angles $\theta_1$ and $\theta_2$ of the stimulator probe 104, or $\theta_3$ and $\theta_4$ of the stimulator probe 1200, may be the same or different, and may be any suitable value (e.g., about 45 degrees, about 90 degrees, about 180 degrees, between about 0 degrees and about 90 degrees, between about 15 and about 75 degrees, or the like). In some variations, the center of the electrodes may face each other (e.g., angles $\theta_1$ and $\theta_2$ or $\theta_3$ and $\theta_4$ may be zero). In the variation shown in FIGS. 6D and 12B, the angles $\theta_1$, $\theta_2$, $\theta_3$, and $\theta_4$ may each be 45 degrees. As such, when the stimulator probe 104 or 1200 is positioned such that the first nasal insertion prong is positioned in a first nostril and the second nasal insertion prong is positioned in the second nostril, the electrodes may be directed partially toward the front of the nose, as described in more detail herein. For example, FIG. 12C shows electrodes 1208 positioned in nostrils 1220 against septum 1222 and directed partially toward the front of the nose.

The electrodes may be positioned on any suitable longitudinal portion or portions of the nasal insertion prongs. The position of the electrode along the prong may at least partially determine the placement of the electrode relative to tissue when the stimulator probe is advanced into the nose. In some variations, an electrode may be located at an intermediate position along a prong of stimulator. For example, in the variation of the stimulator probes depicted in FIGS. 6A-6F, the electrodes 110 and 112 may be located at an intermediate position along the nasal insertion prongs, within the distal portions 176 and 178 the prongs but not at the distal tip of the prongs. The electrodes 110 and 112 may be located any suitable distance from the distal tip of the prongs, such as between about 0.1 mm and about 4 mm, about 4 mm and about 8 mm, or more than 8 mm from the distal dip of the prongs (e.g., 1 cm from the distal tip). In some variations, the electrodes 110 and 112 may be located about 2.5 mm from the distal tip of the prongs. In some variations, the electrodes may be locate such that when inserted into the nasal cavity, the electrodes are capable of reaching the nasal mucosa or other area desired to be stimulated. In some variations, distance from the base member of the stimulator probe to the longitudinal center of the electrode (i.e., the farthest the center of the electrode could be inserted into the nasal cavity) may be between about 25 mm and about 45 mm. In other variations, the distance from the base member of the stimulator probe to the longitudinal center of the electrode may be between about 30 mm and about 40 mm. For example, in some variations the distance from the base member of the stimulator probe to the longitudinal center of the electrode may be about 32.5 mm (labeled as distance "D" in FIG. 6A). The electrode may have any suitable length, such as between about 1 mm and about 10 mm, between about 3 mm and about 7 mm, about 5 mm, or more than about 10 mm.

In other variations, an electrode may be connected to a distal end of a nasal insertion prong. In the variation of the stimulator probe 1400 shown in FIG. 14 (described in more detail below), each of the first 1402 and second 1404 nasal insertion prongs may comprise an electrode 1414 and 1415, respectively, positioned at a distal end thereof. Generally, when the electrodes are positioned at the distal end of the prongs, it may be desirable to provide an electrode having no edges or rounded edges to help minimize the risk of tissue damage during advancement of the electrodes into the nose. For example, the spherical electrodes 1414 and 1415 may be relatively atraumatic to nasal or sinus tissue as the first 1402 and/or second 1404 prongs are advanced into the nose.

The electrode(s) described here may be made from one or more conductive materials. In some variations, the electrodes may comprise metals (e.g., stainless steel, titanium, tantalum, platinum or platinum-iridium, other alloys thereof, or the like), conductive ceramics (e.g., titanium nitride), liquids, gels, or the like. In some variations, the electrode may comprise one or more materials configured to promote electrical contact between electrodes of the stimulator probe and tissue (i.e., all of an electrodes or a portion of the electrode, such as a covering). In some instances, the impedance provided by tissue may be at least partially dependent on the presence or absence of fluid-like materials (e.g., mucous) in the nasal cavity. The material(s) may help to minimize the impact of subject tissue impedance by providing a wet interface between the electrode and tissue, which may act to normalize the impedance experienced by the electrodes. This may in turn normalize the output and sensation experienced by the user.

In the variation shown in FIGS. 6A-6F, the electrode may comprise a hydrogel. In hydrogel may be any suitable hydrogel, including the hydrogels described in U.S. Provisional Patent Application No. 61/944,340, filed on Feb. 25, 2014, and titled "Polymer Formulations for Nasolacrimal Stimulation," the contents of which are hereby incorporated by reference in their entirety. The hydrogel may be located within the openings 180 and 182 of the distal portions 176 and 178 of the nasal insertion prongs 106 and 108. As described above, the hydrogel electrode may form about a 100 degree arc of a cylinder, although it should be appreciated that the hydrogel electrode may in other variations have other shapes (e.g., a smaller or larger arc, as described in detail herein). The hydrogel may fill the openings 180 and 182 and the adjacent portions of the central lumens 222 and 224 of the nasal insertion prongs. As such, the hydrogel may surround the axial portion of the leads (described in more detail below) located adjacent to the openings 180 and 182. In some variations, the distal portions 176 and 178 of the nasal insertion prongs may further be covered by a thin hydrogel skin. The hydrogel skin may help to retain the hydrogel electrodes within the distal portions 176 and 178 of the nasal insertion prongs 106 and 108. Additionally or alternatively, in variations having a hydrogel skin, the hydrogel skin may improve manufacturability (e.g., by allowing the electrodes to be formed by dip coating). In some variations, the distal portions 176 and 178 of the nasal insertion prongs 106 and 108 may comprise retention columns located between the surface of the electrode and the central lumens 222 and 224. The retention columns may help to retain the leads within the central lumens, and when the electrodes comprise a hydrogel, may help to retain the hydrogel within the opening 180 and 182.

In other instances, the electrodes may comprise one or more coverings that may be configured to connect to a stimulator probe to at least partially cover an electrode of the stimulator probe. In some variations, the covers may comprise a hydrogel. In some variations, the covers may comprise a foam or porous material which may be impregnated with a gel or liquid. Because the impedance provided by tissue may be at least partially dependent on the presence or absence of fluid-like materials, these covers may normalize the impedance experienced by the electrodes. For example, in the variation of the stimulator probe 1400 shown in FIG. 14, the stimulator probes 1402 and 1404 may comprise one or more foam covers 1418, which may be configured to fit over and cover the electrodes 1414 and 1415. The covers 1418 may comprise a foam material, which may be impregnated or otherwise filled with a conductive liquid or gel. When placed in contact with dry nasal tissue, the gel or liquid may wet the nasal tissue to reduce the impedance of the tissue, which may result in a more consistent impedance experienced by the electrodes 1415 and 1415. In some variations, the covers 1418 may be re-wettable to replace or replenish the gel or liquid. In other variations, the electrodes may be coated with a hydrogel. However, it should be appreciated that the electrodes need not comprise one or more such coverings to normalize impedance.

Leads

When a nasal insertion prong or prongs of the stimulators described here comprise one or more electrodes, the electrodes may comprise leads. When the stimulator probe is connected to a stimulator body, the leads may contact the circuitry of the stimulator body to electrically connect the electrodes to the stimulator body circuitry, as described in more detail below. As such, the leads may extend at least partially through each of the nasal insertion prongs. The leads may be formed from one or more conductive materials (e.g., stainless steel, titanium, platinum or platinum-iridium, other alloys thereof, or the like), conductive ceramics (e.g., titanium nitride), and may be positioned such that at least a portion of each lead contacts a respective electrode to provide a conduction pathway between the lead and the electrode.

The leads of stimulator probe 104 can be seen in the cut-away view in FIG. 6C. As shown there, the leads 130 and 132 may each comprise a spring. The springs comprising leads 130 and 132 may comprise any suitable biocompatible conductive material or materials. For example, in some variations, the springs may comprise stainless steel. In other variations, the springs may comprise gold or platinum. In some variations, the springs may comprise two or more materials (e.g., stainless steel with gold plating). The leads 130 and 132 may extend through the central lumens 222 and 224 of the nasal insertion prongs 106 and 108, respectively. A portion of the leads (e.g., the distal ends) may contact the electrodes. For example, distal ends of the leads 130 and 132 may extend through the hydrogel forming electrodes 110 and 112, as described in more detail herein. In variations in which the leads comprise springs, the wound coil of the springs may allow for a greater conductive surface between the leads and the hydrogel electrode as compared to a single straight wire. Additionally or alternatively, the wound coil of the springs 130 and 132 may grip the hydrogel electrode, thus better retaining it within the distal portions 176 and 178 of the nasal insertion prongs 106 and 108. The proximal ends of the leads 130 and 132 may extend through the lumens 208 and 210 through the rigid support 218, such that the proximal ends of the leads are able to contact the circuitry of the stimulator body, as described in more detail below. In variations in which the leads comprise springs, the proximal ends 184 and 186 of the springs may have a tighter pitch than the rest of the springs. This may create a more even surface to contact the circuitry of the stimulator body. The spring force may also promote contact between the leads and the circuitry of the stimulator body, as described in more detail below. Additionally or alternatively, the proximal ends 184 and 186 may have a different (e.g., greater) coil diameter than the rest of the springs, which may also improve the contact between the leads and a portion of the stimulator body.

Figure 9A:
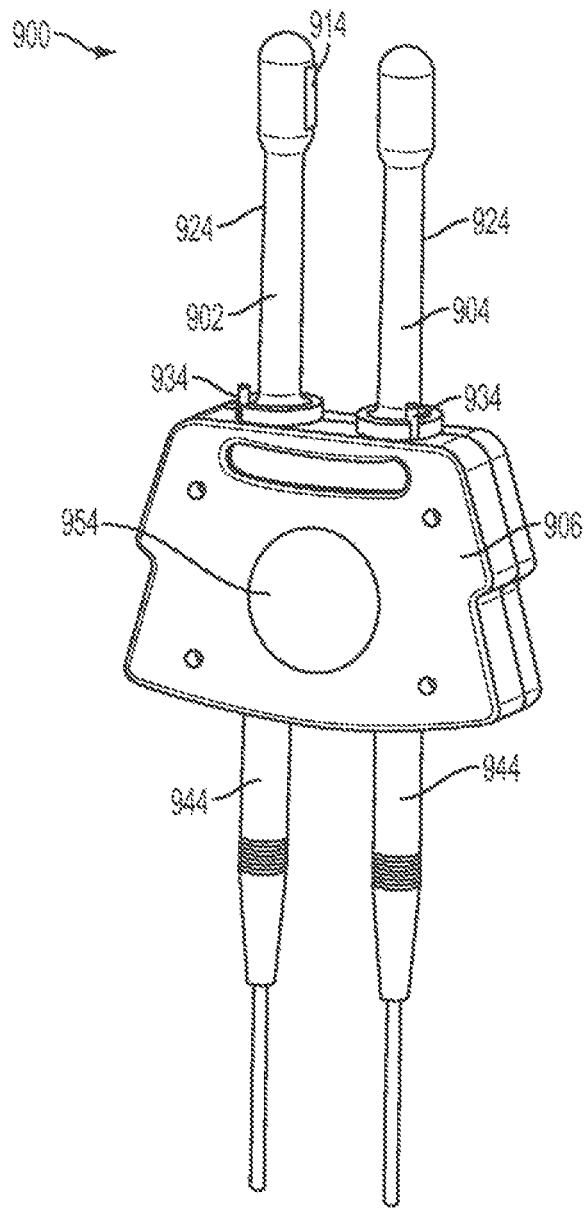
FIG. 9A shows a perspective view of a stimulator probe suitable for the handheld stimulators described here.
Figure 9C:
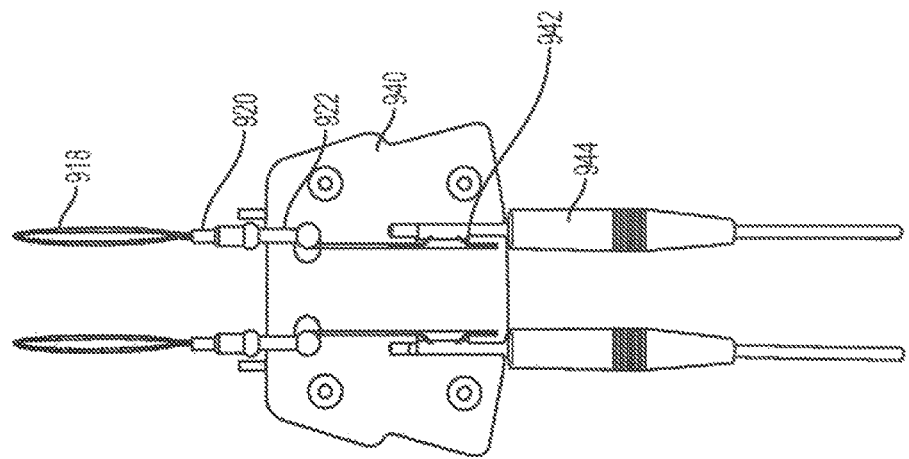
FIG. 9C shows an assembled view of the stimulator probe of FIG. 9A without sleeves and without a first plate.
Figure 9B:
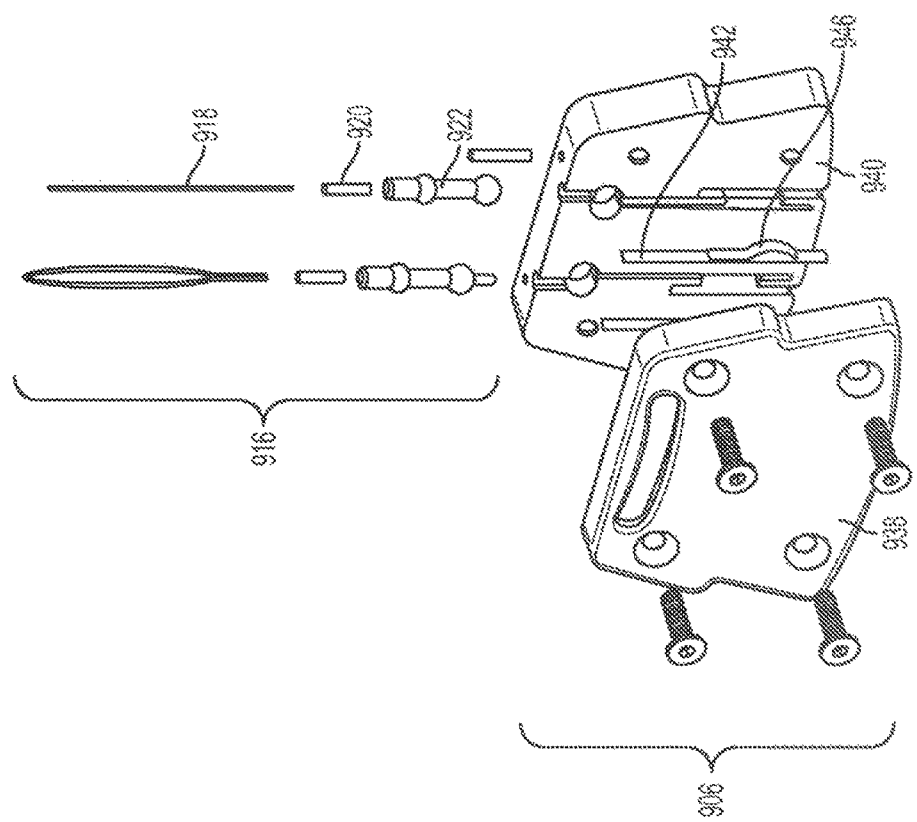
FIG. 9B shows an exploded view of the stimulator probe of FIG. 9A without sleeves.
Figure 9F:
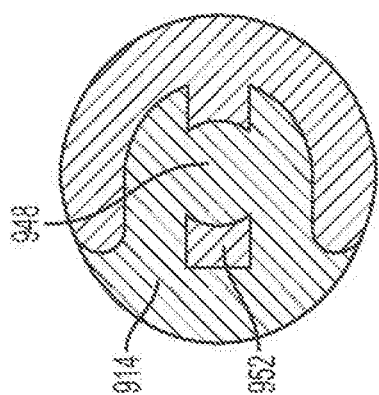
FIGS. 9D-9F show perspective, side cut-away, and cross-sectional views of a sleeve of the stimulator probe of FIG. 9A.
Figure 9E:
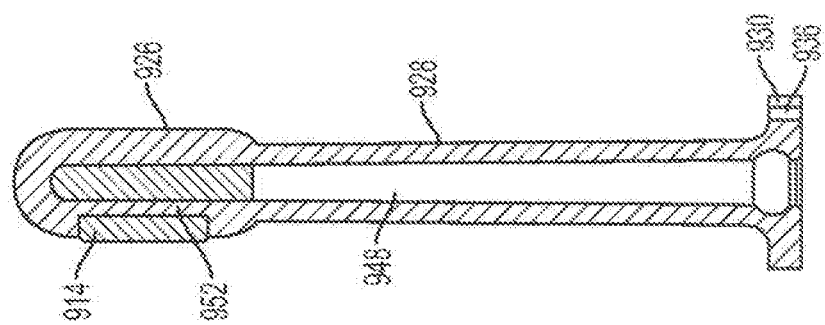
Figure 9D:
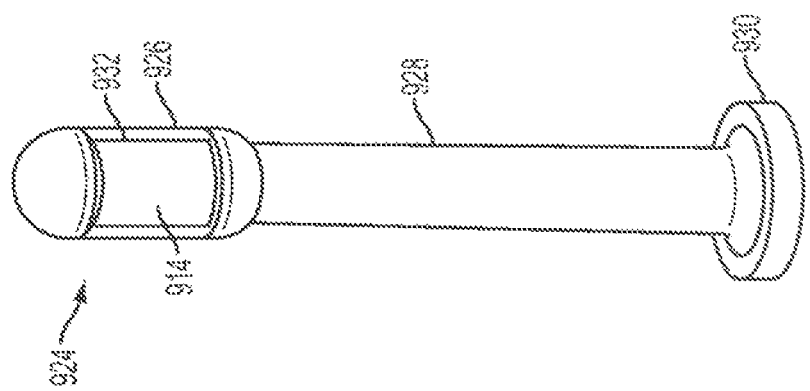
Figure 10C:
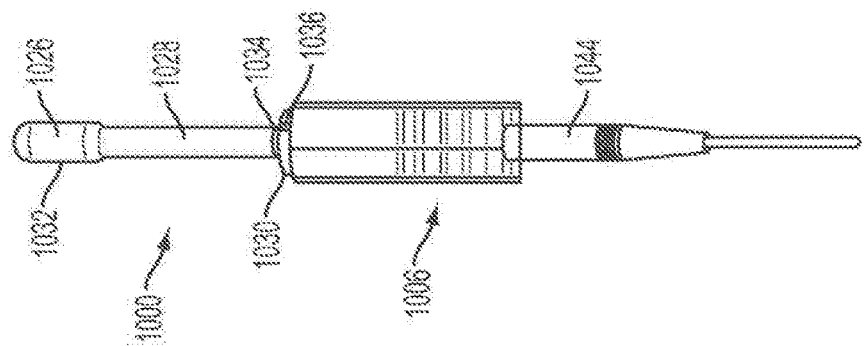
FIGS. 10A, 10B, and 10C show perspective, back cut-away, and side views, respectively, of a stimulator probe suitable for the handheld stimulators described here.
Figure 10B:
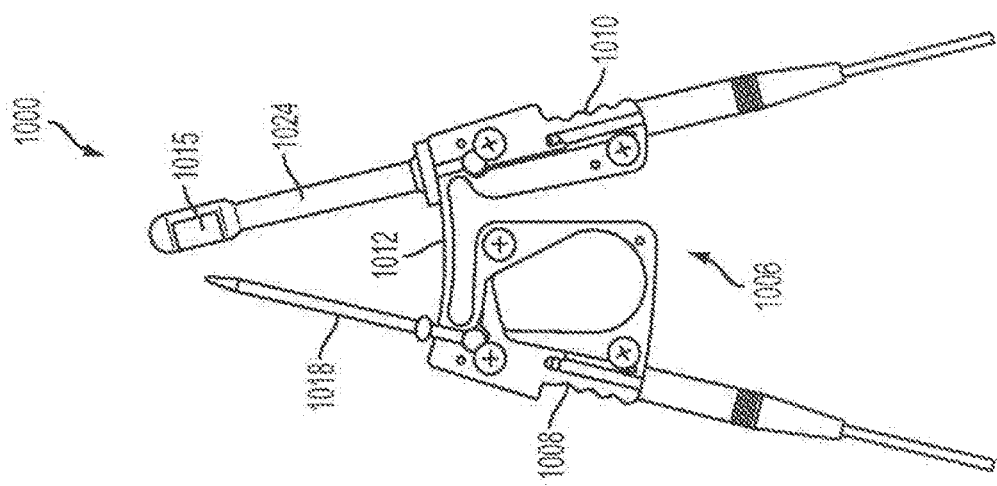
Figure 10A:
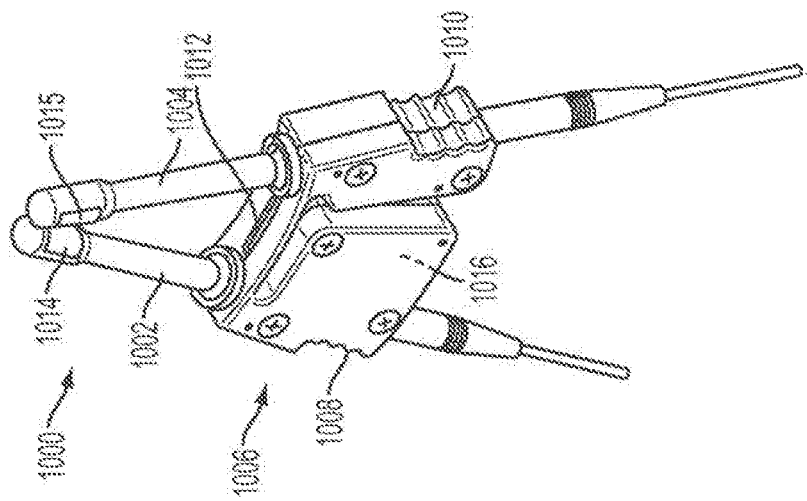

It should be appreciated the leads need not comprise springs. In other variations, for example, stimulator probes may comprise leads comprising a conductive loop. An example is shown in FIGS. 9A-9F. As shown there, a stimulator probe 900 may comprise a first 902 and a second 904 nasal insertion prong, each comprising an electrode 914. The first 902 and second 904 nasal insertion prongs may be substantially parallel, and may each be attached to a base member 906. The first 902 and second 904 nasal insertion prongs may each comprise a sleeve 924, described in more detail below. As shown in the exploded view of FIG. 9B with the sleeves 924 removed, the nasal insertion prongs 902 and 904 may each further comprise a lead 916 comprising a conductive loop 918. The conductive loop 918 may comprise any suitable material or materials as described herein. In some variations, the conductive loop 918 may comprise Nitinol. In some variations, the conductive loop 918 may comprise a coating, which may enhance its electrochemical properties. The coating may comprise, for example, platinum or gold. The conductive loops 918 may each be formed by crimping together two ends of a wire with crimp tubes 920. The crimp tubes 920 may be welded to posts 922, which may be configured to be attached to the base member 906. The posts 922 may comprise any suitable conductive material or materials as described herein. In some variations the posts 922 may comprise stainless steel. Leads comprising conductive loops, such as conductive loops 918, may be desirable in combination with sleeves that are removable (as described below), since loops may be less likely to injure a user than a single wire. In yet other variations, however, the stimulator probes described here may comprise leads comprising a single metal post, as shown in FIGS. 10A-10C and described in more detail below.

The leads 916 may be attached to the base member 906 in any suitable manner. As shown in the exploded view of FIG. 9B, the posts 922 of the leads 916 may be held within first 938 and second 940 plates of the base member 906. An assembled view of the stimulator probe 900 without the first plate 938 of the base member 906 is shown in FIG. 9C. The stimulator probe 900 may further comprise contact springs 942, which may be attached to the posts 922 (e.g., via laser welding). The contact springs 942 may be formed from any suitable conductive material or materials as described herein, and may be configured to electrically connect the leads 916 to the circuitry of the stimulator body. For example, the contact springs may comprise a flexible region 946 that is configured to contact a portion of cable connectors 944 of a stimulator body (not shown) when the cable connectors 944 are reversibly inserted into the base member 906 of the stimulator probe 900, as shown in FIG. 9C.

The exterior of the nasal insertion prongs 902 and 904 may be formed by sleeves 924 covering the leads 916 of stimulator probe 900. The sleeves 924 may comprise any suitable material or materials, which may desirably be biocompatible, flexible, injection-moldable, and/or non-conductive. For example, the sleeves 924 may comprise a thermoplastic elastomer (e.g., a thermoplastic elastomer alloy (e.g., VERSAFLEX™ thermoplastic elastomer), thermoplastic polyurethane, or the like), silicone, or the like. As shown in FIG. 9D, the sleeves 924 may comprise a distal portion 926, an elongate middle portion 928, and a base 930. As shown in the cut-away view of FIG. 9E and cross-sectional view of FIG. 9F, the sleeves 924 may further comprise a central lumen 948, which may be configured to receive a lead 916. The distal portion 926 and/or base 930 may have a larger diameter (or largest cross-sectional dimension) that is greater than the elongate middle portion 928, similar to the nasal insertion prongs 106 and 108 described with respect to stimulator 100. This may allow a portion of the distal portions 926 (e.g., the electrodes, described below) to be brought into contact with a subject's tissue, while the elongate portions 928 are not in contact with the subject's tissue.

Like the nasal insertion prongs 106 and 108 of stimulator probe 102, the nasal insertion prongs 902 and 904 may have any suitable distance between them, including all of the distances described with respect to the prongs of stimulator probe 102. Nasal insertion prongs 902 and 904 may also have any suitable length, including all of the distances described with respect to the prongs of stimulator probe 102. Similarly, the nasal insertion prongs 902 and 904 may have a particular flexibility or range of flexibilities in order to allow the nasal insertion prongs to self-align to the desired stimulation location when inserted into a user's nasal cavities, as described with respect to the prongs of stimulator probe 102.

The distal portions 926 of sleeves 924 may each comprise an opening 932, and the electrode 914 may be formed within the opening 932 of the distal portion 926. As described with respect to electrodes 110 and 112 of stimulator 100, the electrodes 914 may comprise a portion of the cylindrical surface. As shown in the cross-sectional view of the sleeve 924 in FIG. 9F, the electrodes 914 may comprise about a 100 degree arc of a cylindrical surface, but it should be appreciated that the electrode may have any suitable size or shape, as described in more detail with respect to electrodes 110 and 112 of stimulator probe 102. Like the electrodes 110 and 112 of stimulator probe 102 and described in more detail, the electrodes 914 may be angled relative to the axis intersecting the first and second prongs, such that the electrodes may be directed at least partially toward the front of the nose, which may allow for selective activation of the nerves in the front of the nasal septum. The electrodes 914 may be formed by a hydrogel located within the openings 932, and may comprise any suitable material, including a hydrogel. Like the electrodes 110 and 112 of stimulator probe 102, in variations in which the electrode 914 comprises a hydrogel, the hydrogel may be any suitable hydrogel, including the hydrogels described in U.S. Provisional Patent Application No. 61/944,340, filed on Feb. 25, 2014, and titled "Polymer Formulations for Nasolacrimal Stimulation," the contents of which were previously incorporated by reference in their entirety. Similarly, in some variations the distal portions 926 of the sleeves 924 may further be covered by a thin hydrogel skin. In some variations, the sleeves 924 may comprise a retention column 952 located between the surface of the electrode and the central lumen 948. The retention column 952 may help to retain the lead within the central lumen 948 of the sleeve 924, and when the electrode 914 comprises a hydrogel, may help to retain the hydrogel within the opening 932.

The base 930 of the sleeves 924 may comprise a notch 936 configured to align with a rod 934 on the base member 906 of the stimulator probe 900. The sleeves 924 may be reversibly removable from the stimulator probe 900. In some variations, the sleeves 924 may be disposable, while the remainder of the stimulator probe 900 is reusable. The rod 934 and notch 936 may assist the user in properly aligning the sleeve 924 with the base member 906. In combination with an indicator on the stimulator probe 906 of the direction in which to hold the probe when inserting it into the nose (e.g., a thumb groove 954), the proper alignment of the sleeves 924 with the base member 906 may be desirable in order to orient the electrodes 914 toward the front of the nose when inserted, for the reasons described in more detail herein.

Insulation

Generally, when the stimulator probes described here are configured to delivery an electrical stimulus, the external surfaces of the any of the stimulator probes described herein may be insulated, with the exception of the electrodes. This may help to prevent inadvertent stimulation of other tissue (e.g., by direct tissue contact with a lead instead of with an electrode). Accordingly, in some variations, the prongs may be formed from or otherwise coated with one or more insulating materials (e.g., PTFE, silicone, combinations thereof, or the like). For example, in the variation of the stimulator probe shown in FIGS. 6A-6F, the first and second prongs may be formed from an insulating material such as a flexible polymer (e.g., a thermoplastic elastomer (e.g., thermoplastic elastomer alloys (e.g., VERSAFLEX™ thermoplastic elastomer), thermoplastic polyurethanes, or the like), silicone, or the like), and the leads may be positioned inside the prongs such that they are electrically insulated from the exterior surfaces of the first and second prongs during use of the stimulator probe, as described herein. Accordingly, in these instances, electrical stimulation energy provided to the leads may be delivered via the electrodes. Similarly, the material of sleeves 924 of stimulator probe 900, and the sleeves 1024 of stimulator probe 1000, may be insulating.

Other Stimulator Probe Designs

The stimulator probes for use with the stimulators here may have any suitable design. For example, FIGS. 11A-11B show another variation of a stimulator probe 1100. In the variation shown there, the first 1101 and second 1103 nasal stimulation prongs may be formed from an insulating material such as silicone, and the leads 1118 may be positioned inside the nasal stimulation prongs such that they are electrically insulated from the exterior surfaces of the first 1101 and second 1103 nasal stimulation prongs during use of the stimulator probe 1100. Accordingly, in these instances, stimulation energy provided to the leads 1118 may be delivered via the electrodes 1108.

The stimulator probe 1100 may be constructed in any suitable manner. FIG. 11B shows one example of a manner in which the stimulation probe 1100 of FIG. 11A may be constructed. As shown there, the first 1101 and second nasal stimulation prongs 1103 may each be formed from a first piece 1120 and a second piece 1102, which each may be formed from one or more insulating materials, such as described in more detail herein. In some variations, the first piece 1120 and second piece 1102 may be formed as separate pieces. In other variations, such as shown in FIG. 11B, the first piece 1120 and second piece 1102 may be formed with a living hinge 1104 connecting the first piece 1120 and second piece 1102, such that the first 1120 and second 1102 pieces may be folded at the living hinge 1104 to bring the first 1120 and second 1102 pieces together. In some variations, the first 1120 and/or second 1102 pieces may comprise one or more pegs 1106. These pegs 1106 may help to hold the first piece 1120 relative to the second piece 1102. Additionally, in some variations the leads 1118 may comprise one or more apertures 1107 extending therethrough. In these variations, a lead 1118 may be positioned between first 1120 and second 1102 pieces such that the pegs 1106 extend through the apertures 1107 in the leads 1118. This may, in turn, control and maintain the position of a lead 1118 relative to the first 1120 and second 1102 pieces as well as a respective electrode 1108.

The first piece 1120 may comprise a semi-cylindrical segment 1110 configured to receive the electrode 1108. As shown in FIG. 11B, the electrode 1108 may be formed as a hydrogel sheet 1112 on a backing layer 1114. The hydrogel sheet 1112 may be wrapped around the semi-cylindrical segment 1110, which may cause the hydrogel sheet 1112 to take on a semi-cylindrical shape. When the second piece 1102 is connected to the first piece 1120 to enclose the lead 1118, the hydrogel sheet 1112 may be locked into place. For example, in some variations, the lead 1118 may comprise one or more teeth 1116 or other projections extending from a surface of the lead 1118. When the first piece 1120 and second piece 1102 are connected to enclose the lead 1110, the teeth 1116 or other projections may press into the hydrogel sheet 1112. This engagement between the teeth 1116 and the hydrogel sheet 1112 may mechanically hold the hydrogel sheet 1112 in place as well as provide an electrical connection between the lead 1118 and the electrode 1108. Stimulator probe 1200 shown in FIGS. 12A-12C may have similar features and may be constructed in a similar manner as stimulator probe 1100, but may have electrodes 1208 angled toward each other, as described in more detail herein.

FIGS. 13A and 13B show perspective and cut-away perspective views, respectively, of another variation of a stimulator probe 1300 suitable for use with the stimulators described here. As shown there, the stimulator probe 1300 may comprise first 1302 and second 1304 nasal stimulation prongs connected by a base member 1306, although it should be appreciated that the stimulator probe 1300 may be configured with any suitable number of nasal stimulation prongs as discussed below. The first 1302 and second 1304 nasal stimulation prongs may be formed from or covered with an insulating material or materials, such as discussed here, and may each additionally comprise a lumen 1311 extending at least partially through each nasal stimulation prong. Each nasal stimulation prong may further comprise an electrode region 1308 comprising a plurality of apertures 1309 extending through the prong from an exterior surface of the prong to the lumen 1311. A conductive lead 1310 may be positioned at least partially inside of each lumen 1311, and the apertures 1309 may facilitate an electrical connection between the leads 1310 and tissue. For example, in some variations an electrically conductive gel or solution (e.g., a hydrogel, saline) may be positioned inside of the apertures 1309 to provide a conductive pathway between the lead 1310 and tissue positioned externally of the prong, thereby allowing the electrode region 1308 to provide stimulation to tissue. While the stimulator probe 1300 is described here as configured to delivery an electrical stimulus, it should be appreciated that the plurality of apertures 1309 may also be configured to deliver other forms of stimuli (e.g., chemical stimuli), as described in more detail below.

In some variations, the stimulator probes described here may be configured to adjust the distance between at least a portion of the first and second nasal insertion prongs. It may in some instances be desirable to adjust the distance between at least a portion of the first and second nasal insertion prongs (e.g., the electrodes) in order to accommodate different nose sizes, achieve better contact between a portion of the nasal insertion prongs and the nasal tissue, hold the nasal insertion prongs in place, or the like.

Figure 14:
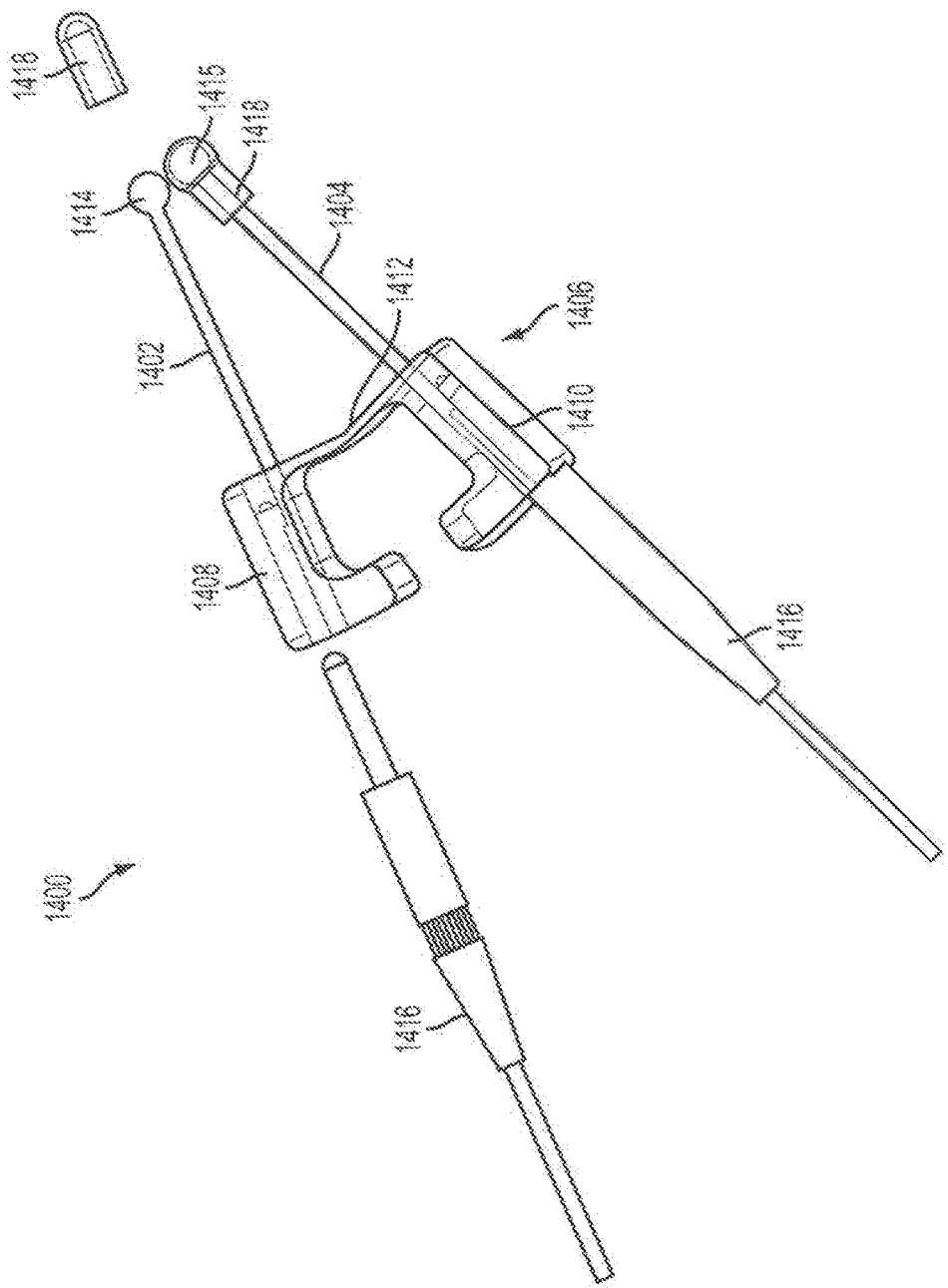
FIG. 14 depicts a perspective view of a variation of a stimulator probe suitable for the handheld stimulators described here.

In some of the variations in which the stimulator probe is configured to adjust the distance between at least a portion of the first and second nasal insertion prongs, the stimulator probe may be configured to adjust the angle between the first and second prongs. For example, FIG. 14 shows a variation of a stimulator probe 1400 suitable for use with the stimulators described here. As shown there, the stimulator probe 1400 may comprise first 1402 and second 1404 nasal insertion prongs connected to a base member 1406. The base member 1406 may be configured to rotate the first nasal insertion prong 1402 relative to the second nasal insertion prong 1404. The base member 1406 may comprise a first grip 1408, a second grip 1410, and a connector 1412 connecting the first grip 1408 and the second grip 1410. Generally, the connector 1412 may be configured to act as a pivot point or flexible hinge to allow the first grip 1408 to rotate relative toward the second grip 1410. For example, in the variation of the stimulator probe 1400 shown in FIG. 14, the connector 1412 may comprise a strip of resilient material that may bend or otherwise deflect when the first grip 1408 is pushed toward the second grip 1410. In other variations, the connector may comprise a hinge rotatably connecting the first grip and the second grip. As the first grip 1408 rotates toward the second grip 1410 (via the connector 1412), the first prong 1402 may be configured to rotate away from the second prong 1404, which may increase the distance between the distal ends of the first 1402 and second 1404 nasal insertion prongs.

In some of these variations, the first grip and second grip may be biased toward a specific orientation, such that the base member returns toward the predetermined orientation when forces on the base member are removed. For example, the first 1402 and second 1404 nasal insertion prongs of stimulator probe 1400 may be connected to the base member 1406 such that each of the first 1402 and second 1404 nasal insertion prongs are biased at an angle toward each other, as shown in FIG. 14. As shown there, the nasal insertion prongs may be biased toward a configuration in which the distal ends of the first 1402 and second 1404 prongs are separated by an initial distance (e.g., between about 3 mm and about 15 mm). The first grip 1408 and second grip 1410 may be pressed toward each other to rotate the first 1402 and second 1404 nasal insertion prongs away from each other, which may increase the distance between the first 1402 and second 1404 prongs. As the first 1408 and second grips 1410 are released, the return bias may cause the first grip 1408 and second group 1410 to rotate away from each other, which may in turn return the distal ends of the first 1402 and second 1404 prongs to their initial separation distance.

When the first 1402 and second 1404 prongs are inserted into respective first and second nasal cavities to position nasal tissue (e.g., a nasal septum) between the prongs (as will be discussed in more detail below), the first 1402 and second 1404 prongs may be rotated away from each other prior to insertion into the respective nasal cavities. Once positioned in the nasal cavities, the force applied to the first 1408 and second 1410 grips may be released and the return bias may rotate the first 1402 and second 1404 prongs toward each other. If the initial separation distance between the first 1402 and second 1404 prongs is less than the width of the nasal tissue positioned between the prongs, the return bias of the stimulator probe 1400 may press the distal ends of the first 1402 and second 1404 prongs against tissue. This may help to increase electrode apposition with tissue, and in some instances may act to hold the stimulator probe 1400 in place relative to tissue. To remove the stimulator probe 1400 from tissue, the first 1402 and second 1404 prongs may again be rotated away from each other to release the tissue positioned between the prongs.

When the distal ends of the first 1402 and second 1404 nasal insertion prongs comprise electrodes 1414 and 1415, changing the distance between the distal ends of the nasal insertion prongs may correspondingly change the distance between the electrodes 1414 and 1415. As described elsewhere herein, the electrodes 1414 and 1415 of stimulator probe 1400 may comprise one or more conductive materials, may have a relatively atraumatic shape (e.g., a spherical shape, and may comprise one or more foam covers 1418.

FIGS. 10A, 10B, and 10C show perspective, back cutaway, and side views, respectively, of another stimulator probe configured to adjust the angle between first and second nasal insertion prongs. As shown there, the stimulator probe 1000 may comprise first 1002 and second 1004 nasal insertion prongs connected to a base member 1006. The base member 1006 may be configured to rotate the first nasal insertion prong 1002 relative to the nasal insertion second prong 1004. The base member 1006 may comprise a first grip 1008, a second grip 1010, and a connector 1012 connecting the first grip 1008 and the second grip 1010. Like connector 1412 of stimulator probe 1400, the connector 1012 may be configured to act as a pivot point or flexible hinge to allow the first grip 1008 to rotate relative toward the second grip 1010. The connector 1012 may comprise a strip of resilient material that may bend or otherwise deflect when the first grip 1008 is pushed toward the second grip 1010. As the first grip 1008 rotates toward the second grip 1010 (via the connector 1012), the first prong 1002 may be configured to rotate away from the second prong 1004, which may increase the distance between the distal ends of the first 1002 and second 1004 prongs.

The first 1002 and second 1004 nasal insertion prongs may be connected to the base member 1006 such that each of the first 1002 and second 1004 nasal insertion prongs are biased at an angle toward each other, as shown in FIGS. 10A-10C, such that the distal ends of the first 1002 and second 1004 prongs are separated by an initial distance (e.g., between about 1 mm and about 20 mm, between about 5 mm and about 10 mm, between about 10 mm and about 15 mm, about 12 mm). The first grip 1008 and second grip 1010 may be pressed toward each other to rotate the first 1002 and second 1004 nasal insertion prongs away from each other, which may increase the distance between the first 1002 and second 1004 nasal insertion prongs. As the first 1008 and second grips 1010 are released, the return bias may cause the first grip 1008 and second group 1010 to rotate away from each other, which may in turn return the distal ends of the first 1002 and second 1004 prongs to their initial separation distance.

When the first 1002 and second 1004 prongs are inserted into respective first and second nasal cavities to position nasal tissue (e.g., a nasal septum) between the prongs (as will be discussed in more detail below), the first 1002 and second 1004 nasal insertion prongs may be rotated away from each other prior to insertion into the respective nasal cavities. Once positioned in the nasal cavities, the force applied to the first 1008 and second 1010 grips may be released and the return bias may rotate the first 1002 and second 1004 nasal insertion prongs toward each other. If the initial separation distance between the first 1002 and second 1004 nasal insertion prongs is less than the width of the nasal tissue positioned between the prongs, the return bias of the stimulator probe 1000 may press the distal ends of the first 1002 and second 1004 nasal insertion prongs against tissue. This may help to increase electrode apposition with tissue in variations in which the probes comprise electrodes, and in some instances may act to hold the stimulator probe 1000 in place relative to tissue. To remove the stimulator probe 1000 from tissue, the first 1002 and second 1004 prongs may again be rotated away from each other to release the tissue positioned between the prongs. When the distal portions of the first 1002 and second 1004 nasal insertion prongs comprise electrodes 1014 and 1015, as described below, changing the distance between the distal ends of the nasal insertion prongs may correspondingly change the distance between the electrodes 1014 and 1015.

In some variations, the stimulator may comprise a buzzer. The buzzer may create a buzzing noise when stimulus is being delivered by the stimulator probe, which may provide feedback to the user that the stimulator is working. For example, stimulator probe 1000 may comprise a buzzer 1016. As shown in FIG. 10A, the buzzer 1016 may be located on the base member 1006 between the first 1008 and second 1010 grips in a way that still allows the prongs to be rotated relative to each other. In some instances, the buzzer 1016 may be attached to the first grip 1008. Additionally or alternatively, the base member 1006 may comprise other electrical components (e.g., a controller, memory, or the like).

The first 1002 and second 1004 nasal insertion prongs may each comprise leads comprising a metal post 1018, which may be covered by sleeves 1024. The metal posts 1018 may comprise any suitable conductive material or materials (e.g., stainless steel, titanium, titanium nitride, platinum, alloys thereof or the like). The sleeves may have the same properties as described with respect to sleeves 924. As described in more detail with respect to sleeves 924, the sleeves 1024 may comprise any suitable material or materials, which may desirably be biocompatible, flexible, injection-moldable, and/or non-conductive. For example, the sleeves 1024 may comprise a thermoplastic elastomer (e.g., a thermoplastic elastomer alloy (e.g., VERSAFLEX™ thermoplastic elastomer), thermoplastic polyurethane, or the like), silicone, or the like. The sleeves 1024 may comprise a distal portion 1026, an elongate middle portion 1028, and a base 1030. The distal portion 1026 and/or base 1030 may have a larger diameter (or largest cross-sectional dimension) that is greater than the elongate middle portion 1028, similar to the nasal insertion prongs 106 and 108 described with respect to stimulator 100. The distal portion 1026 may comprise an opening 1032, and the electrode 1014 may be formed by a hydrogel located within the opening 1032 of the distal portion 1026. The electrodes 1014 may comprise a portion of the cylindrical surface. The base 1030 of the sleeves 1024 may comprise a notch 1036 configured to align with a rod 1034 on the base member 1006 of the stimulator probe 1000. The sleeves 1024 may be reversibly removable from the stimulator probe 1000. In some variations, the sleeves 1024 may be disposable, while the remainder of the stimulator probe 1000 may reusable.

In some of the variations in which the stimulator probe is configured to adjust the distance between at least a portion of the first and second nasal insertion prongs, the stimulator may be configured such that the distance between the two nasal insertion prongs is adjustable, independent of adjusting the angle between the two nasal insertion prongs. For example, in variations in which the nasal insertion prongs are connected by a base member, one or more of the nasal insertion prongs may be capable of sliding relative to the base member. Additionally or alternatively, the base member may be adjustable in size (e.g., may comprise two pieces, each comprising a nasal insertion prong, that are configured to slide apart or together) to alter the spacing between the prongs.

While the nasal insertion prongs described herein may be connected via a base member, it should be appreciated that in other variations, each prong may be individually connected to the stimulator body, which may allow the prongs to be individually disconnected and/or replaced. Thus, in other variations where a stimulator comprises two or more nasal insertion prongs, the prongs may not be connected to each other. In variations where individual nasal insertion prongs are directly connected to a stimulator body, the connection between the nasal insertion prongs and the stimulator body may control the relative positioning of the nasal insertion prongs. It should also be appreciated that in some variations where the stimulator probe includes a base member or other structure connecting two or more nasal insertion prongs, the stimulator probe may be configured such that individual prongs may be disconnected from the stimulator probe and replaced.

While the stimulator probes are described in some instances herein with respect to delivery of an electrical stimulus, it should be appreciated that the stimulators described here may be configured to deliver other types of stimuli, including mechanical, chemical, or other forms of stimulation. In variations in which the stimulators are configured to deliver a mechanical stimulus, the nasal insertion prongs may be configured to deliver vibrational energy to nasal tissue. In variations where a stimulator comprises one or more prongs configured to be inserted at least partially into a nasal cavity (such as described herein), the prongs may be configured to vibrate relative to tissue. In variations where a stimulator is implanted in a nasal or sinus cavity, one or more portions of the stimulator may be configured to vibrate. In some of these variations, the vibration may be generated using one or more magnets positioned externally of the body. In these variations, mechanical energy may be used to activate mechanical receptors in afferent neurons.

Additionally or alternatively, the nasal insertion prongs may be configured to deliver ultrasonic energy to tissue. In these variations, the nasal insertion prongs (and stimulator bodies) may be configured to have similar physical properties as described herein, although the nasal insertion prongs need not comprise electrodes. Instead, the nasal insertion prongs or the stimulator body may comprise vibrating motors in variations configured to vibrate all or a portion of the nasal insertion prongs, or may comprise one or more ultrasound transducers configured to deliver ultrasonic energy. In some variations, the ultrasound transducers may be located in place of the electrodes described herein.

In some other variations, the stimulators described here may be configured to deliver thermal, light-based, and/or magnetic stimuli. In some variations, stimulators may be configured to deliver one or more pulses of air to tissue via the nasal insertion prongs, which may stimulate tissue. The pulses of air may be generated via a source of compressed air, or the like. In some variations, the gas may be warmed or cooled (e.g., mechanically or via one or more thermally-activated fibers). In other variations, the nasal insertion prongs may be heated or cooled to provide thermal stimulation to tissue. Additionally or alternatively, the stimulator may comprise one or more light-generating or magnetic field-generating elements, which may be used to stimulate nasal or sinus tissue via the nasal insertion prongs.

In yet other variations, the stimulator probes may be configured to deliver one or more chemical agents to nasal tissue. The chemical agent may be one or more drugs, such as a histamine receptor agonist, nicotinic agonist, or the like. In other variations, the chemical agent may contain one or more irritants, such as ammonia, benzene, nitrous oxide, capsaicin (e.g., propanethial S-oxide), mustard oil, horseradish, crystalline silica, or the like. The nasal insertion prongs may in these instances comprise delivery ports for delivering one or more chemical agents, and may additionally comprise lumens connecting the delivery ports to one or more reservoirs located in the base member of the stimulation probe and/or in the stimulator body.

For example, FIGS. 35A-35B depict cut-away views of a handheld stimulator 3500 configured to deliver one or more chemical agents. As shown there, the stimulator 3500 may comprise a stimulator body 3502 and a stimulator probe 3504, which may be permanently or detachably connected. The stimulator body 3502 may comprise a reservoir 3506 configured to hold one or more chemical agents. The chemical agents may be held in any suitable form. The stimulator probe 3504 may comprise one or more nasal insertion prongs (here, two nasal insertion prongs 3508 and 3510). The reservoir 3506 may be connected via lumens 3512 and 3514 to delivery ports 3516 and 3518 located on the nasal insertion prongs 3508 and 3510. The user may be able to cause delivery of the one or more chemical agents using an operating mechanism (e.g., button 3520 on the stimulator body 3502). In some variations, such as shown in FIGS. 35A-35B, the applying pressure to the button 3520 may cause the button 3520 to press on the reservoir 3506, causing the one or more chemical agents to flow through the lumens 3514 and 3514 and out the delivery ports 3516 and 3518. The chemical agents may be in any suitable vehicle (e.g., liquid, aerosol, gas, etc.). However, it should be appreciated that in other variations, stimulators configured to deliver one or more chemical agents may comprise an automated delivery mechanism, such as one or more pumps connected to internal circuitry and/or intelligence. In some instances, these stimulators may be configured to deliver electrical stimulation (such as described herein) to nasal or sinus tissue to promote or otherwise facilitate the uptake of one or more chemical agents by the tissue (e.g., by iontophoresis).

While the stimulator probes in the figures described herein are shown as having two nasal stimulation prongs, it should be appreciated that in other variations the stimulator probe may have any suitable number of prongs (e.g., one, two, or three or more prongs). For example, in some variations where the stimulator is configured for monopolar stimulation, the stimulator probe may comprise a single nasal insertion prong. Similarly, the stimulators may comprise any suitable number of electrodes (e.g., one, two, three, or four or more electrodes), and the electrodes may be positioned on any suitable portion of the stimulator (e.g., the stimulator body and/or a stimulator probe). In some variations where a stimulator comprises two prongs (such as described in more detail herein), a first prong may comprise an electrode while the second prong may not include an electrode. These variations may find particular utility in instances where the stimulator is configured to deliver monopolar stimulation (or unilateral stimulation of a single nostril). In these variations, the non-electrode bearing nasal insertion prong may be configured to help hold tissue between the two prongs (as described in more detail herein), or may be configured to deliver non-electrical energy from the prong (e.g., vibratory energy, thermal energy, or the like, as discussed in more detail herein).

Connection Between Stimulator Body & Probe

Physical Connection

The stimulator probes described here (and any prongs thereof) may be connected to a stimulator body in any suitable manner. In some variations, a stimulator probe may be configured to directly connect to a stimulator body. In these variations, at least a portion of the stimulator probe may have a fixed location and orientation with respect to the stimulator body when the two are connected. In some of these variations, the stimulator probe may be permanently connected to the stimulator body. For example, the stimulator probe and stimulator body may be formed together such that they are permanently connected. In other variations, the stimulator probe may clip, latch, snap onto, or otherwise mechanically connect to the stimulator body. In some of these variations, the stimulator probe may be releasably connected to the stimulator body, such that the stimulator probe may be disconnected from the stimulator body after being connected.

Figure 15A:
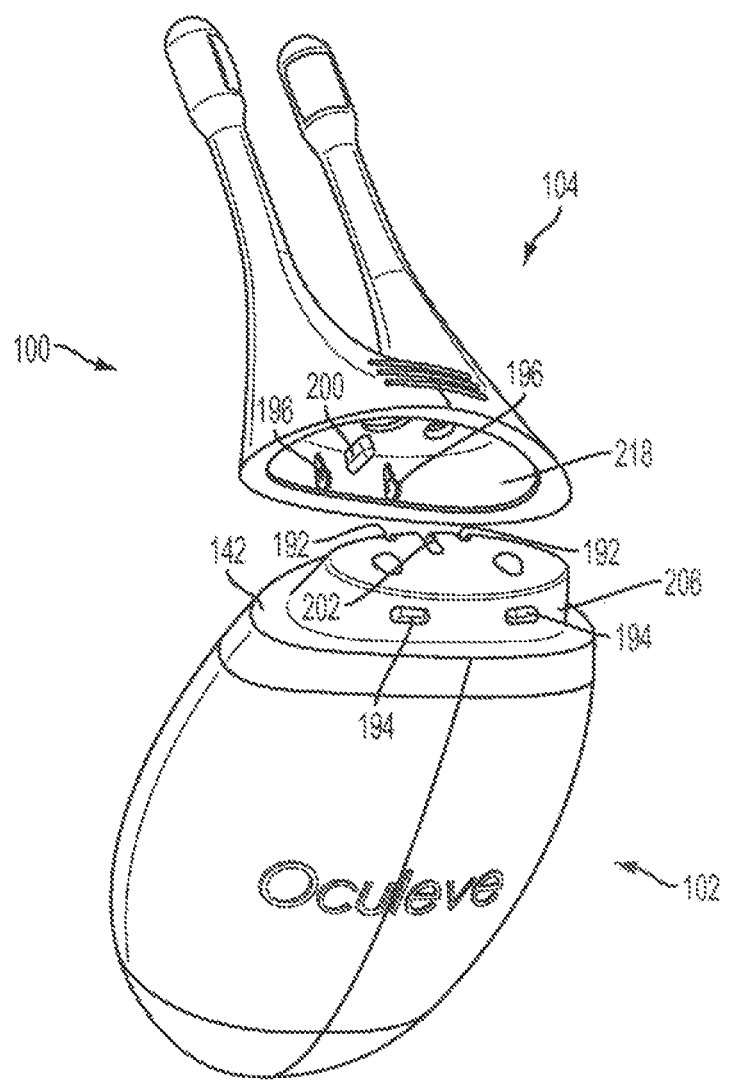
FIG. 15A depicts a perspective view of the stimulator of FIGS. 1A-1E with the stimulator probe disconnected from the stimulator body.

For example, stimulator body 102 and stimulator probe 104 of stimulator 100 may be removably connected such that a portion of the stimulator probe 104 directly contacts and connects to the stimulator body 104. FIG. 15A depicts a perspective view of the stimulator 100 showing the connection mechanism. As shown there, the distal portion 206 of the top housing 142 of the stimulator body 102 and the proximal portion of the stimulator probe 104 may comprise corresponding and complementary shapes, which may allow the stimulator body 102 and stimulator probe 104 to be attached. For example, the distal portion 206 of the top housing 142 of the stimulator body and the proximal surface of the rigid support 218 of the stimulator probe 104 may comprise features that allow them to be reversibly attached. For example, in the variation shown the distal portion 206 of the top housing 142 of the stimulator body 102 may comprise two notches 192 on a first side and two notches 194 on a second side. The proximal surface of the rigid support 218 of stimulator probe 104 may comprise four corresponding tabs: two tabs 196 on a first side and two tabs 198 on a second side (shown in FIG. 6E). The stimulator body 102 and stimulator probe 104 may be snapped together by first placing tabs 198 of the stimulator probe 104 into the notches 194 of stimulator body 102, and then manipulating the probe 104 and body 102 such that the first side of the simulator body 102 is rotated toward the first side of the stimulator probe 104. In doing so, the tabs 196 of the stimulator probe 104 may be rotatably inserted into the notches 192 of the stimulator body 102. The tabs 196 and 198 and notches 192 and 194 may have increased height and depth, respectively, at their proximal ends, such that the probe 104 and body 102 are held together by the tabs and notches when connected.

Conversely, the stimulator probe 104 may be removed from the stimulator body 102 by rotating the first side of the probe 104 and first side of the body 102 away from each other. It may be desirable for the stimulator to be configured such that when a user inserts the stimulator probe 104 into his/her nasal cavities, if the user presses a portion of the stimulator prongs (e.g., the electrodes) against tissue (e.g., tissue near the front of the nose), the force on the stimulator probe reinforces the connection between the stimulator probe 104 and the stimulator body 102. That is, the force from the user's tissue may desirably tend to push the first side of the stimulator body 102 toward the first side of the stimulator probe 104. If, instead, the force tended to push the first side of the probe 104 and the first side of the body 102 away from each other, there could be an increased risk of the probe being inadvertently disconnected from the stimulator body during stimulation. In some variations, as described in more detail below, the stimulator probe 104 may further comprise tab 200 configured to fit into notch 202 of stimulator body 102, which may help the control subsystem 136 to register the connection of the stimulator probe 104 to the stimulator body 102.

It should be appreciated that in other variations, the stimulator body and stimulator probe may have any suitable features for being attached, such as other snapping mechanisms (e.g., having different shapes or different numbers of features), magnets, friction fits, a latching mechanism, or the like. For example, in some variations the stimulator body may comprise a magnet (e.g., magnet 134 of stimulator body 102) connected to the interior surface of the proximal housing of the stimulator body, as described in more detail herein. The stimulator probe may comprise a magnet or ferromagnetic material in a corresponding location (e.g., in the base member of the stimulator probe), which may retain the stimulator probe on the stimulator body.

Figure 16B:
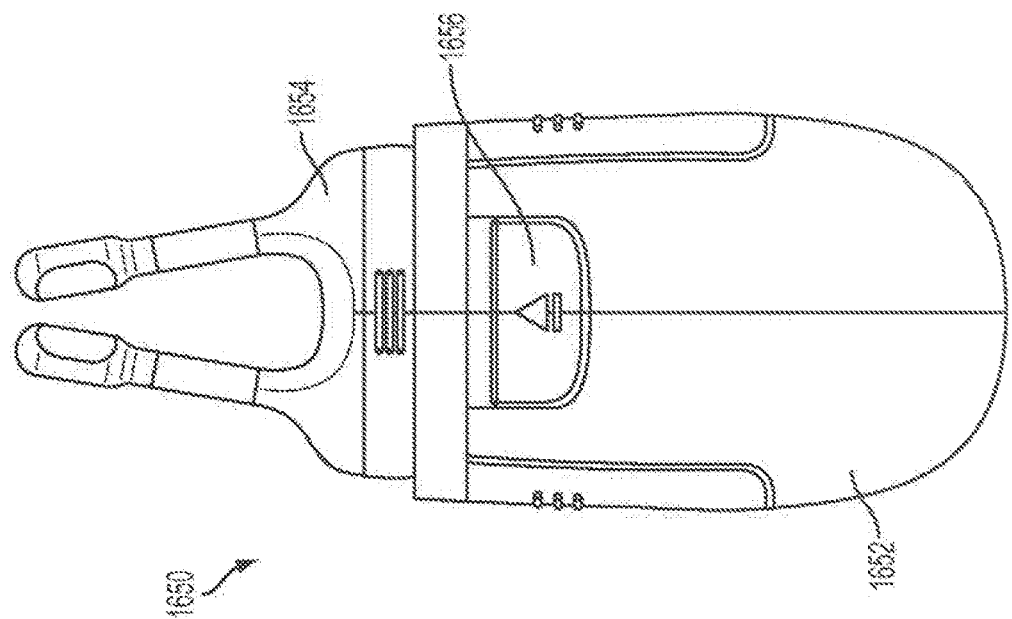
FIGS. 16A and 16B show side views of other variations of handheld stimulators.
Figure 16A:
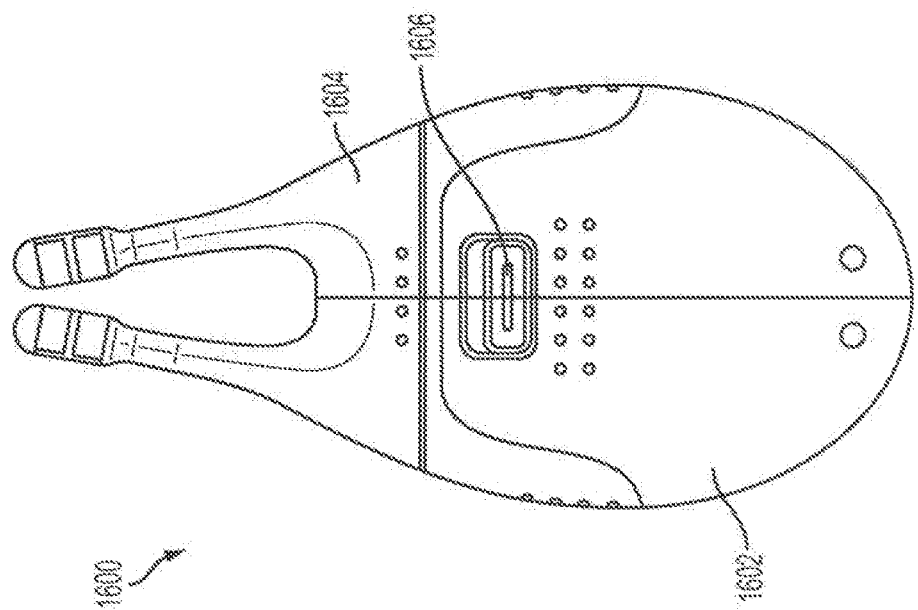

In some variations where the stimulator body is releasably connected to the stimulator probe, the stimulator may comprise a release mechanism, although the stimulator need not comprise a release mechanism. In some variations, the release mechanism may comprise a button, switch, lever, or the like, which may be activated to disconnect the stimulator probe from the stimulator body. In other variations, the release mechanism may be controlled by the control subsystem. Example of release mechanisms are shown in FIGS. 16A and 16B. In the stimulator 1600 of FIG. 16A, the stimulator probe 1604 may be configured to releasably connect to stimulator body 1602. The stimulator body 1602 may comprise a release mechanism 1606, which may decouple the stimulator probe 1604 from the stimulator body 1602. The release mechanism 1606 may be manually manipulated by the user and may comprise a sliding button; as the button is moved from the position shown in FIG. 16A to a distal position, the stimulator probe 1604 may be released. Similarly, in the stimulator 1650 of FIG. 16B, the stimulator probe 1654 may be configured to releasably connect to stimulator body 1652. The stimulator body 1652 may comprise a release mechanism 1656, which may decouple the stimulator probe 1654 from the stimulator body 1652. The release mechanism 1656 may be manually manipulated by the user. In some variations, the release mechanism 1656 may comprise a sliding button; as the button is moved from the position shown in FIG. 16B to a distal position, the stimulator probe 1654 may be released. In some variations, the release mechanism 1656 may comprise a push button; as the button is pushed inward, the stimulator probe 1654 may be released. In some variations, the release mechanism 1656 may release the stimulator probe 1654 by moving a portion of an attachment mechanism (e.g., a tab, hook, or the like). In some variations comprising a release mechanism, the release mechanism may comprise a seal to waterproof any openings.

In other variations, the stimulator probe and the stimulator body may be indirectly connected via a cable, cord, or the like. In these variations, the stimulator probe and stimulator body may be movable relative to each other while they are connected. For example, in the variation of the stimulator probe 1400 shown in FIG. 14, the stimulator probe 1400 may be configured to connect to a stimulator body (not shown) via one or more cable connectors 1416. In the variation shown in FIG. 14, the cable connectors 1416 may be releasably connected to the stimulator probe 1400. In these variations, the cable connectors 1416 may be permanently or releasably connected to the stimulator body. In other variations, the cable connectors 1416 may be permanently connected to the stimulator probe 1400. In these variations, the cable connectors 1416 may be releasably connected to the stimulator body (e.g., to allow the stimulator probe 1400 to be releasably connected to the stimulator body) or permanently connected to the stimulator body (e.g., to allow the stimulator probe 1400 to be permanently connected to the stimulator body). The stimulator probes 900 and 1000 in FIGS. 9A-9F and 10A-10C, respectively, may similarly be indirectly connected via a cable, cord, or the like to a stimulator body, such as via cable connectors 944 and 1044, respectively.

Electrical Connection

Generally, when the stimulators described here are configured to deliver an electrical stimulus, the electrodes of the stimulator may be electrically connected to the stimulator circuitry, such that the stimulator may generate a stimulus and deliver it to tissue via one or more of the electrodes. Accordingly, the stimulators described here may comprise one or more electrical connections configured to electrically connect the electrode via a lead to a portion of the stimulator body (e.g., a stimulation subsystem housed in the stimulator body). In variations in which the stimulator probe and stimulator body are indirectly connected, the indirect connection (e.g., a cable, cord, or the like) may serve as the electrical connection between the stimulator circuitry and the electrodes. In variations in which the stimulator probe and the stimulator body are directly connected, the stimulator body and stimulator probe may comprise conductive elements configured to electrically connect the electrodes of the stimulator probe to the stimulator circuitry when the body and probe are connected.

Figure 1D:
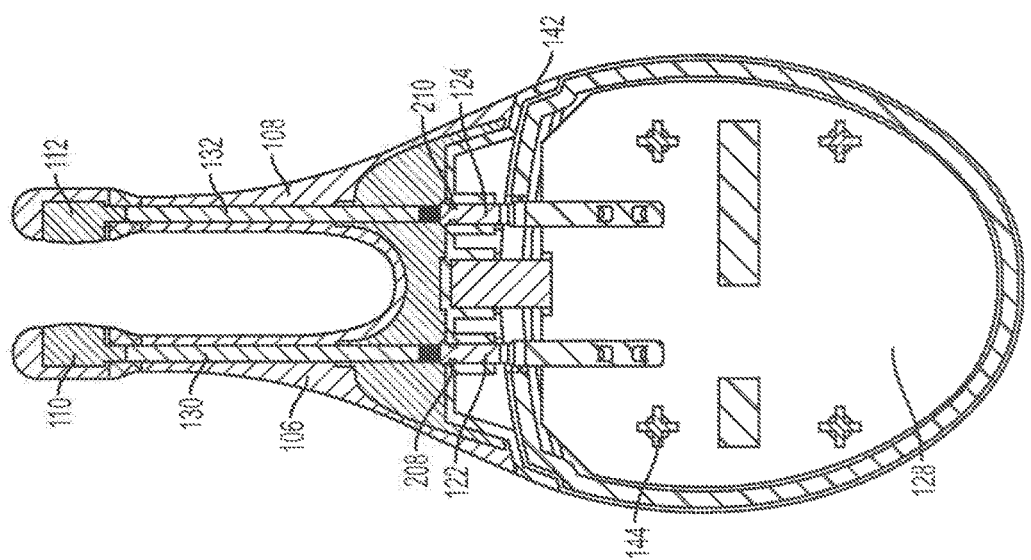
Figure 2:
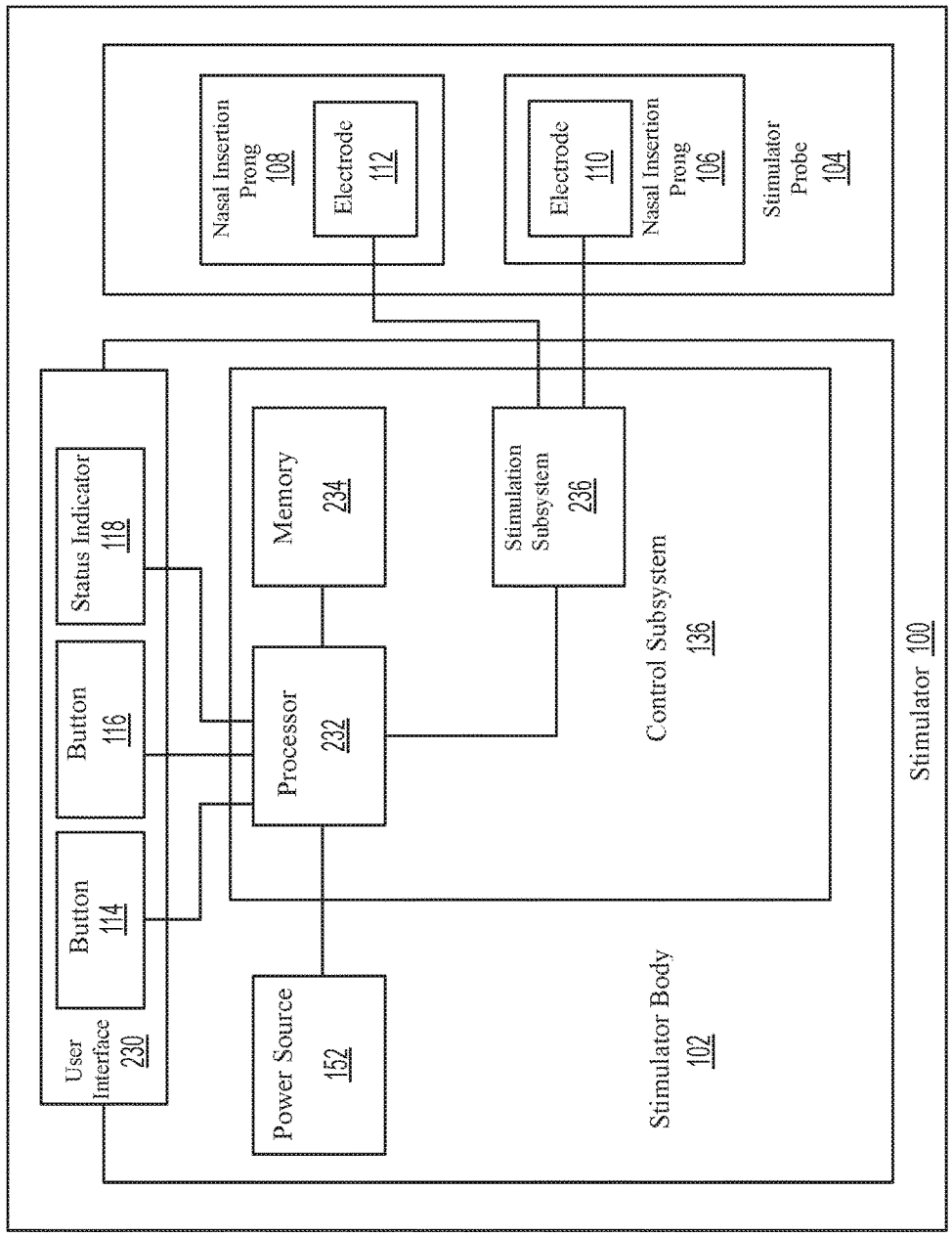
FIG. 2 shows a block diagram schematically representing a variation of a stimulator.

For example, as shown in FIG. 1D, the electrodes 110 and 112 of stimulator probe 104 may be connected to leads 130 and 132 located within nasal insertion prongs 106 and 108, respectively. The corresponding stimulator body 102 may comprise connectors 122 and 124 directly or indirectly connected to the control subsystem 136 and power source 152. The distal ends of the connectors 122 and 124 may be configured to connect with the proximal ends of the leads 130 and 132 of the stimulator probe 104. As shown in FIG. 3A, in some variations the distal ends of the connectors may comprise a rounded surface. As described above, in variations in which the leads comprise springs, the proximal ends of the springs may have a tighter pitch than the rest of the springs. This may create a more even surface to contact proximal ends of the connectors, and thus may allow for a better electrical connection between the leads of the stimulator probe 104 and the connectors of the stimulator body 102.

When the proximal ends of the springs of stimulator probe 104 are in contact with the connectors 122 and 124 of the stimulator body 102, the springs may be compressed. This compression may cause the springs to generating a restoring force. The restoring force may promote contact between the springs and the connectors 122 and 124. However, in variations in which the stimulator probe 104 is removably connectable to the stimulator body 102, the restoring force may also act against the force of the connection mechanism holding together the stimulator probe and the stimulator body (e.g., notches 192 and 194 and tabs 196 and 198). Thus, it may be desirable for the spring stiffness to be low enough that the restoring force of the springs does not cause the stimulator probe to disconnect from the stimulator body.

The connectors 122 and 124 may extend through lumens 208 and 210 in the proximal housing 142, and the proximal ends may be directly or indirectly attached to the control subsystem. As shown in FIG. 3D, the proximal ends of the connectors 122 and 124 may comprise slots configured to receive the distal ends of contact strips 244. The proximal ends of contact strips 244 may be attached to the control subsystem 136 (i.e., may be attached to the printed circuit board 128). The connectors and contact strips may comprise any suitable conductive material or materials, such as but not limited to stainless steel, titanium, copper, nickel, brass, zinc, or the like, which may in some instances be gold-plated.

It should be appreciated that the stimulator body and stimulator probe may additionally or alternatively be inductively coupled, such that power may be transferred from the stimulator body to the stimulator probe via induction. In these variations, the stimulator body and stimulator probe may each comprise a coil. In some variations, each of the coils may be wrapped around a ferromagnetic (e.g., iron) core, but need not be. In some variations, the coil of the stimulator body and/or stimulator probe may be a printed coil.

Disposable Design

In some variations, some or all of the stimulator may be disposable. In variations where the stimulator body is permanently attached to the stimulator probe, the entire stimulator may be disposable. In other variations, one or more portions of the stimulator may be reusable. For example, in variations where the stimulator probe is releasably connected to the stimulator body, the stimulator body may be reusable, and the stimulator probe may be disposable. As such, the stimulator probe may be periodically replaced, such as will be described in more detail below. In yet other variations, a portion of the stimulator probe may be disposable (e.g., the stimulator probe may comprise disposable sleeves or disposable prongs) and may be periodically replaced. In some variations, the stimulators described here may comprise features that encourage or require a user to replace a stimulator or stimulator components after a certain period or on a regular basis in order to main proper hygiene.

In variations in which the entire stimulator is disposable (e.g., when the stimulator probe is integrally formed with or permanently attached to the stimulator body), the stimulator may be configured to become non-operational after a certain period of time and/or use. In some of these variations, the stimulator may be configured to limit the duration of stimulation that may be provided by the stimulator; after the duration limit, the stimulator may be configured to become non-operational. For example, the stimulator may have a power source that is only sufficient to power stimulus delivery for a predetermined duration (e.g., one hour of stimulation). Once the power source has been depleted, a user may need to replace the spent stimulator with a new stimulator. In some of these variations, the stimulator may be configured such that the power source cannot be accessed without rendering the device inoperable, which may help prevent users from replacing the power source.

As another example, the stimulator additionally or alternatively may be programmed to limit the duration or amount of stimulus delivery with a given stimulator. In some of these variations, the stimulator may be configured to measure and store the duration of stimulation provided by the stimulator over time (which may be cumulatively added over a plurality of different treatment sessions). When the duration reaches a threshold limit (e.g., about 10 minutes, about 30 minutes, about one hour, about 2 hours, or longer than 2 hours), the stimulator may be programmed to switch to an inoperable state, whereby the stimulator may not be activated to provide additional stimulation. As another example, the stimulator additionally or alternatively may be configured to limit the number of treatment sessions provided by the stimulator. In some of these variations, the stimulator may be configured to measure and store the number of treatment sessions provided by the stimulator. When the number of treatment sessions reaches a threshold limit (e.g., five uses, ten uses, fifteen uses, or more than fifteen uses), the stimulator may be programmed to switch to an inoperable state, whereby the stimulator may not be activated to provide additional stimulation.

In these or other variations in which the entire stimulator is disposable, the stimulator may additionally or alternatively be configured to become non-operational after a certain period of time after its first use. The stimulator may be configured to limit the duration since the first use of the stimulator; after the duration limit, the stimulator may be configured to become non-operational. In some of these variations, the stimulator may be configured to store date and time information regarding the first use of the stimulator. The stimulator may be further configured to switch to an inoperable state when a predetermined amount of time (e.g., one day, two days, five days, one week, two weeks, or longer than two weeks) has passed from the first use of the stimulator.

In any of these variations, the stimulator may be configured to limit the duration of stimulus delivery, the number of treatment sessions, or the duration since first use via a control subsystem, which may in some instances comprise intelligence such as a microcontroller, programmable logic (e.g., a field-programmable gate array), or an application-specific integrated circuit (ASIC) configured to measure, store, and limit the duration and/or number of treatment sessions and/or the time since first use of the stimulator. In any of these variations, when the device moves to an inoperable state, the user may need to replace the inoperable stimulator with a new stimulator.

In variations in which the stimulator body is reusable and all or a portion of the stimulator probe is disposable, the stimulator may be configured to encourage and/or require the user to replace all or a portion of the stimulator probe. In some of these variations, the disposable portion probe or portion of the probe may comprise a recyclable material. In some of these variations, the stimulator may be configured such that the stimulator probe or a portion thereof becomes inoperable after being attached to the stimulator body for a predetermined amount of time (e.g., between about 1 hour and about 24 hours, between about 1 day and about 7 days, between about 1 week and about 4 weeks, between about 1 month and about 3 months, or longer than about 3 months), after a predetermined number of treatment sessions, and/or after a predetermined duration of stimulation (e.g., between about 2 minutes and about 30 minutes, between about 30 minutes and about 1 hour, between about 1 hour and about 3 hours, between about 3 hours and 12 hours, or longer than about 12 hours).

For example, in some variations of stimulators comprising one or more electrodes, the electrodes of the stimulator probe may become inoperable after being attached to the stimulator body for a predetermined amount of time, after a predetermined number of treatment sessions, and/or after a predetermined duration of stimulation. For example, in some variations it may be desirable to promote oxidation of one or more of the electrodes during stimulation. In these variations, the electrode may be configured to form a non-conductive (or reduced conductivity) layer on the surface of the electrode. In some variations, this may interfere with the ability of the electrode to stimulate tissue, and eventually the oxide layer may substantially prevent any electrical energy from being supplied to the user. In some instances, to form such a layer, the stimulator may be configured to deliver biphasic pulses using the electrodes, wherein the biphasic pulses are not charge-balanced. By not charge-balancing the stimulation pulses, charge may accumulate on one or more of the electrodes and/or leads, which may facilitate oxidation of the metal of the electrode and/or lead. The rate of the oxidation may be controlled at least partially by the materials of the electrode and/or lead and the parameters of the pulses delivered by stimulator, and the rate of oxidation may be tailored to achieve a predetermined treatment duration or number of treatment sessions before formation of an oxide layer may render the stimulator inoperable. As another example, in some variations, an electrode of a stimulator probe additionally or alternatively may be configured to change color over time (e.g., as a result of delivering stimulation, as a result of carbon dioxide exposure, as a result of oxidation), such that a user may be prompted to change the stimulator probe when the electrode reaches a certain color. In these variations, the stimulator probe or a portion of the stimulator probe (e.g., nasal insertion prongs or sleeves comprising the electrodes) may be replaced when the electrodes of the stimulator probe are unable to provide stimulation or when the stimulator encourages replacement via the color change.

As yet another example, in some variations the stimulator may be programmed to render the stimulator probe inoperable and/or to encourage replacement of the stimulator probe or a portion thereof (e.g., disposable prongs or sleeves) after being attached to the stimulator body for a predetermined amount of time, after a predetermined number of treatment sessions, and/or after a predetermined duration of stimulation. In some of these variations, the stimulator may be programmed to measure the duration of stimulation provided using a specific stimulator probe or portion thereof, the number of treatment sessions provided using a specific stimulator probe or portion thereof, and/or the duration of attachment of a specific stimulator probe or portion thereof to the stimulator, via mechanisms described in more detail below. In variations where the stimulator is programmed to measure multiple of the above-listed parameters, if the measurement reaches a threshold value, the stimulator may be configured to alert the user and/or to enter an inoperable state until the current stimulator probe or portion thereof is replaced. In variations where the stimulator is programmed to measure multiple of the above-listed parameters, the stimulator may be configured to alert the user and/or enter the inoperable state when any of the measured parameters reaches its threshold value, or the stimulator may require multiple of the measured parameters to reach their corresponding threshold values in order to alert the user and/or enter an inoperable state. The stimulator may alert the user in any suitable manner, including visual feedback (e.g., generating a prompt on a display, activating a LED, notifying the user on another device, such as a computer or mobile device, or the like), audio feedback (e.g., generating one or more beeps or audio prompts), and/or tactile feedback (e.g., vibrating the stimulator). Similarly, in variations in which the stimulator has entered its inoperable state, the stimulator may additionally or alternatively be configured to instruct the user to replace the stimulator probe. This may also be done in any suitable manner, including visual, audio, or tactile feedback as described above, and herein throughout.

An example of one mechanism for measuring how long a stimulator probe 104 has been connected to the stimulator body 102 is shown in FIGS. 15B-15C. The mechanism may comprise a detector connected to the memory of the control subsystem, which may record how long the detector detects the stimulator probe. In some variations, the detector may comprise an LED or laser and a sensor (e.g., a photodiode) to detect the light emitted by the LED or laser. The transmission of light to the sensor may be blocked when the stimulator probe is connected to the stimulator body. FIGS. 15B-15C illustrate a sensor 172 configured to detect light from an LED or laser (not shown). Movable rod 168 is shown in a first position in FIG. 15B, when the stimulator probe 104 has not yet be fully connected to stimulator body 102. The movable rod 168 may be biased by a spring 170 such that when the stimulator probe 104 is not connected to the stimulator body 102, the movable rod 168 does not block the transmission of light from the LED or laser to the sensor 172. When the stimulator probe 104 is attached to the stimulator body 102 (as shown in FIG. 15C), a portion of the stimulator probe (e.g., tab 200) may enter notch 202 of the stimulator body 102 and may press on the movable rod 168, causing the moveable rod 168 to block the transmission of light to the sensor 172. The sensor 172 may transmit this information to the control subsystem 136, which may allow the stimulator 100 to measure the duration of attachment. When a predetermined attachment duration is reached, the probe 104 may be disabled, or the user may be encouraged to replace the stimulator probe 104 in any of the manners described herein. The duration may be, for example, between about 1 hour and 24 hours, between about 1 day and 7 days, between 1 week and about 4 weeks, between about 1 month and 6 months, or longer than 6 months. The stimulator may be configured to do so via intelligence in the control subsystem 136, such as a microcontroller, programmable logic (e.g., a field-programmable gate array), or an application-specific integrated circuit (ASIC).

It should be appreciated that any suitable method may be used to determine whether and for how long a stimulator probe is attached. For example, the stimulator body may be configured to measure the capacitance across the connectors 122 and 124. As another example, the stimulator body may be configured to detect an RFID chip located in the stimulator probe. Based on the identifier associated with the RFID chip, the stimulator may also be configured to determine whether the stimulator probe is new. As yet another example, the stimulator body may comprise two electrical connections that may be short circuited when the stimulator probe is attached. For example, the stimulator body may comprise two conductive pads on the proximal housing 142, which may be electrically connected via a foil strip on the proximal end of the stimulator probe when the stimulator probe is attached to the stimulator body. The control subsystem 136 may be configured to detect whether the two conductive pads are short circuited. As yet another example, the stimulator body may comprise a magnetic sensor (e.g., a Hall effect sensor) configured to detect a magnet that may be located in the stimulator probe. As yet another example, the stimulator body may comprise a coil, while the probe may comprise a conductor (e.g., a conductive foil). The coil may be configured to inductively detect the presence of the conductor in the stimulator probe when the probe is connected to the stimulator body.

Additionally or alternatively, in some variations the stimulator may be configured to alert the user and/or enter an inoperable state when a used stimulator probe is attached to the stimulator body. The stimulator may alert the user in any suitable manner, and may additionally or alternatively be configured to instruct the user to replace the stimulator probe, as described herein. In these variations, the stimulators may comprise a mechanism for determining whether the attached stimulator probe is new (i.e., whether the stimulator probe has been previously attached to a stimulator body or not). In some variations, the mechanism for determining whether the stimulator probe is new may comprise a fuse. In some variations, the fuse may temporarily short circuit the stimulator circuitry while the probe is being connected to the stimulator body.

Figure 17B:
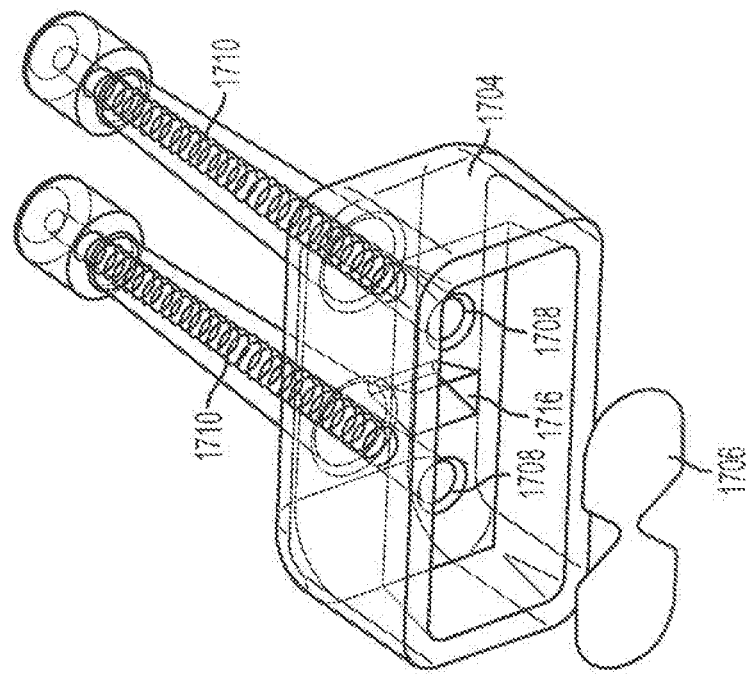
Figure 17A:
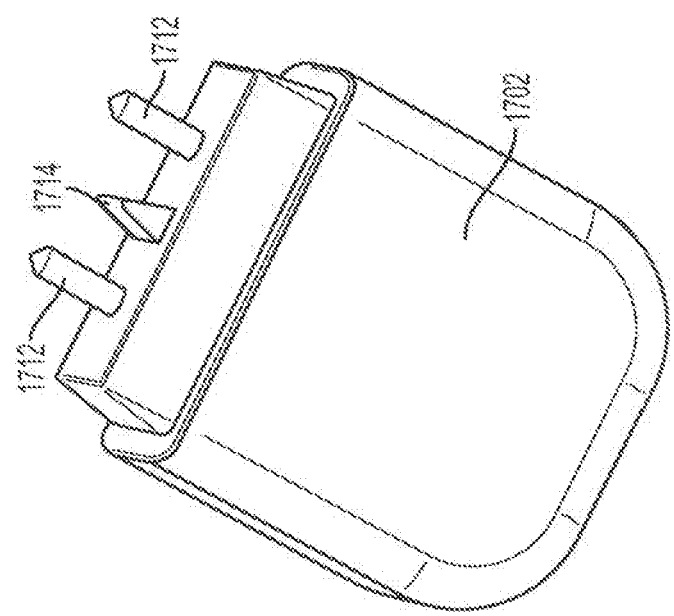
Figure 17E:
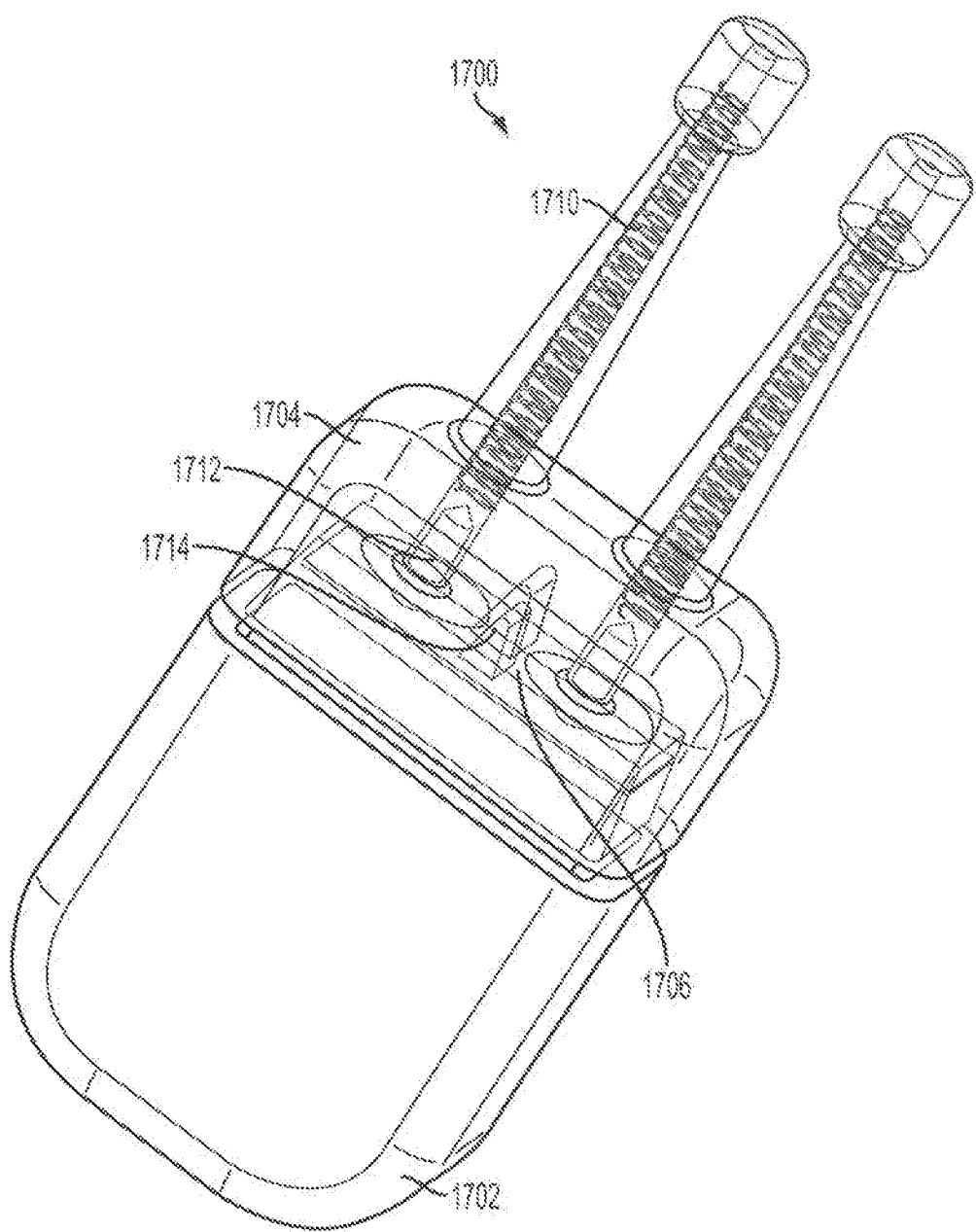

In some variations, the fuse may be a mechanical fuse. FIGS. 17A-17E show one example of a stimulator 1700 comprising a stimulator body 1702 and a stimulator probe 1704, and comprising mechanical fuse. Stimulator probe 1704 is shown as translucent in FIGS. 17A-17E for explanatory purposes. The stimulator probe 1702 may comprise a thin conductive strip 1706 (e.g., aluminum, metalized plastic, or the like), as shown in an exploded view in FIG. 17A. As shown in FIG. 17C, the conductive strip 1706 may be attached to the proximal surface of the stimulator probe 1704. The conductive strip 1706 may comprise an adhesive (e.g., contact glue) on its distal side in order to attach it to the proximal surface of the stimulator probe 1704. When attached to the stimulator probe 1704, the conductive strip 1706 may cover openings 1708 in the stimulator probe 1704 through which the leads 1710 are configured to contact the electrical connectors 1712 of the stimulator body 1702. The distal surface of the stimulator body 1702 may comprise a protrusion 1714. The protrusion 1714 may have a sharp edge or point, and may further comprise a non-conductive material (e.g., a plastic). As the stimulator probe 1704 is attached to the stimulator body 1702, the conductive strip 1706 of the stimulator probe 1704 may come into contact with the two electrical connectors 1712 of the stimulator body 1702, as shown in FIG. 17D. The conductive strip 1706 may thus electrically connect the two electrical connectors 1712, causing a short circuit between the two connectors. As the stimulator probe 1704 is further pressed down and connected to the stimulator body 1702, as shown in FIG. 17E, the protrusion may break the conductive strip 1706 into two electrically separate pieces. (The stimulator probe 1704 may comprise a recess 1716 configured to receive the protrusion 1714.) When the conductive strip 1706 is broken, it may no longer create a short circuit between the two electrical connectors 1712.

Thus, a short circuit as the stimulator probe 1704 is connected indicates that the stimulator probe 1704 has not been previously attached to a stimulator body 1702. Instead, if the stimulator probe 1704 is not new and has been previously attached to a stimulator body 1702, the conductive strip 1706 may be already broken. Placing the used stimulator probe 1704 onto the stimulator body 1702 thus may not cause the stimulator circuitry to short circuit. Whether or not this short circuit occurs may be detected by any suitable mechanism. For example, the stimulator may comprise a micro-controller, and an analog voltage proportional to the load voltage may be connected to an analog-to-digital port on the micro-controller. When the stimulator probe 1704 is placed onto the stimulator body 1702, the micro-controller may apply a test voltage across the two electrical connectors 1712. If the connectors 1712 are connected via the conductive strip 1706 (i.e., a new stimulator probe is being place on the stimulator body), the sampled voltage may be about 0 V. In contrast, if the electrical connectors 1712 are not connected via the conductive strip 1706 (i.e., a used stimulator probe is being placed on the stimulator body), the sampled voltage will be greater than about 0 V. This non-zero sampled voltage may be registered by the micro-controller. If the micro-controller registers a non-zero sampled voltage, it may disable stimulus delivery. As such, the mechanical fuse may function as a disabling mechanism that prevents stimulus delivery to the subject when the stimulator probe is reconnected to the stimulator body after being disconnected from the stimulator body. It should be appreciated that the fuse may have other suitable designs. In some variations, the fuse may comprise an electrical fuse that may be blown during the initial delivery of a stimulus.

One or more mechanisms for determining when a stimulator probe is attached (e.g., a mechanism to record when the stimulator probe is connected, as described with respect to FIGS. 15B-15C, and/or a mechanism to determine when a new probe is attached to the stimulator, as described with respect to FIGS. 17A-17E) may also be used in some variations to render the stimulator probe inoperable and/or to encourage replacement of the stimulator probe or a portion thereof (e.g., disposable prongs or sleeves) after a predetermined number of treatment sessions, and/or after a predetermined duration of stimulation. In some of these variations, attachment of the stimulator probe may be registered using one or more of these mechanisms, and the stimulator may be programmed to measure the duration of stimulation or number of treatment sessions provided using that stimulator probe. The stimulator may be configured to do so via intelligence in a control subsystem, such as a microcontroller, programmable logic (e.g., a field-programmable gate array), or an application-specific integrated circuit (ASIC).

In some variations, the stimulators described here may be configured such that it may be necessary to replace a disposable stimulator probe in order to recharge the stimulator or to replace a power supply of the stimulator. For example, in some variations where the stimulator comprises one or more electrical contacts or ports configured to connect to an external power source, the stimulator probe may be configured to cover or otherwise block access to the electrical contacts/ports when the stimulator probe is connected to the stimulator body. In these variations, it may be necessary to remove the stimulator probe to provide access to the electrical contacts/ports (which may in some variations disable the stimulator probe, as described in more detail below). Similarly, in variations where the stimulator body includes a replaceable power source (e.g., one or more batteries), the stimulator probe may block access to the replaceable power source such that the stimulator probe may need to be disconnected from the stimulator body prior to replacing the power source.

Figure 22A:
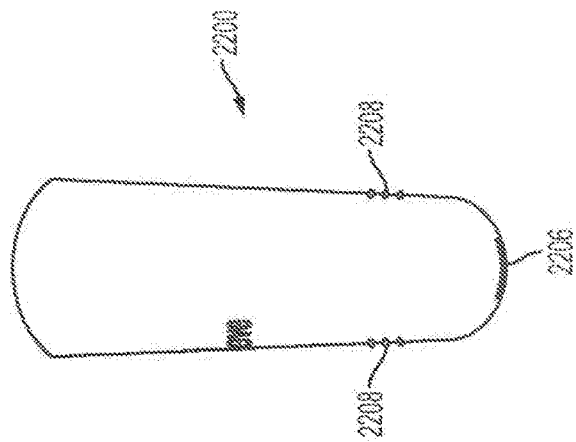
FIGS. 22A-22D depict portions of another variation of a stimulator system comprising a stimulator and a base station.

In variations where a stimulation system comprises a base station (as described in more detail below), a stimulator may be configured such that the stimulator cannot be connected to the base station while a stimulator probe is attached to the stimulator body. For example, in the variations of the stimulation systems shown in FIGS. 21A-21D, 22A-22D, and 23A-23B described in more detail below, the base station may comprise a recess sized and configured to receive the stimulator body to operationally connect the stimulator body to the base station. Specifically, the recess may be sized such that the stimulator body can fit within the recess when the stimulator probe is disconnected from the stimulator body (as illustrated in FIGS. 21A, 22A, and 23B), but is prevented from fitting in the recess when the stimulator probe is attached to the stimulator body. In these variations, it may be necessary to first disengage the stimulator probe. Accordingly, to utilize one or more functions of the base station, a user may need to first decouple a stimulation probe from the stimulator body before connecting the stimulator body to the base station.

In some variations, the stimulator probe may comprise a lockout mechanism that prevents the stimulator probe from being reconnected to the stimulator body after being disconnected from the stimulator body. For example, the stimulator may be configured such that the stimulator probe is disabled when disengaged from the stimulator body (e.g., when the probe is disengaged from the stimulator body in order to connect the stimulator body to the base station). This may prevent the stimulator probe from being reused. For example, in the variation of the stimulator system 2300 in FIGS. 23A-23B, the disposable stimulator probe 2306 may comprise a frangible connector 2318 (which in some instances may also act as a lead to connect an electrode to the stimulator body 2304). The frangible connector 2318 may connect to the stimulator body 2304 to releasably couple the stimulator probe 2306 to the stimulator body 2304. The stimulator 2302 may be configured such that frangible connector 2318 is broken when the stimulator probe 2306 is disengaged from the stimulator body 2304. For example, the stimulator body 2304 may comprise a release mechanism 2320, such that the release mechanism 2320 decouples the stimulator probe 2306 from the stimulator body 2304 and breaks the frangible connector 2318. With the frangible connector 2318 broken, the stimulation probe 2306 may be prevented from being reconnected to the stimulator body 2304. Additionally or alternatively, when the stimulator probe is disconnected from the stimulator body, one or more of the elements holding the stimulator probe and stimulator body may break or be otherwise deformed. For example, in some variations stimulator 100 may be modified such that one or more of the tabs 196 or 198 may break off of the stimulator probe 104 when the stimulator probe is removed from the stimulator body 102. This may prevent the stimulator probe 104 from being securely reconnected to the stimulator body 102.

Cap & Case

Figure 19B:
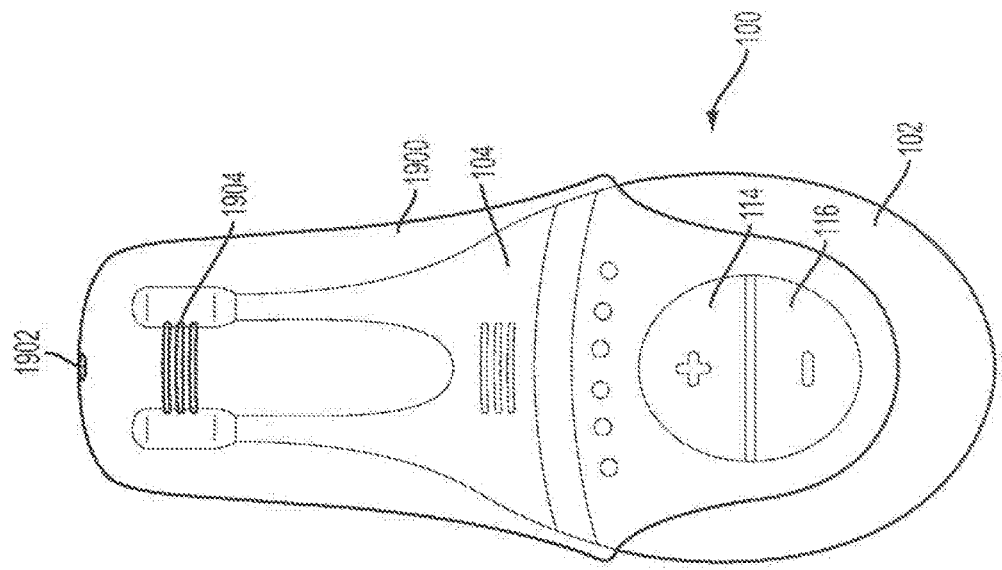
FIGS. 19A and 19B show perspective and front views, respectively, of the handheld stimulator of FIGS. 1A-1E with an attached cap.
Figure 19A:
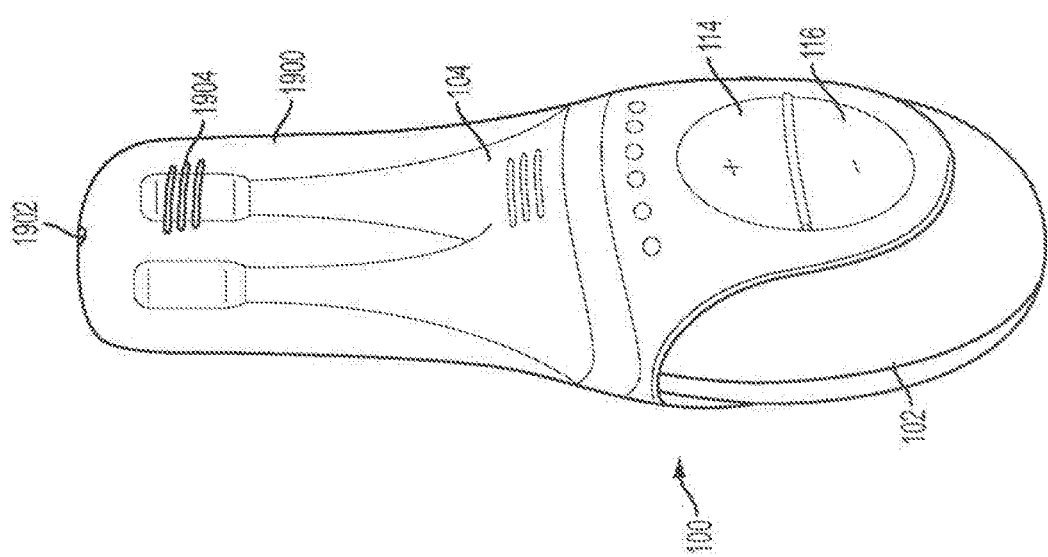

In some variations, the stimulators described here may comprise a cap to protect the stimulator probe. For example, FIGS. 19A and 19B show perspective and front views, respectively, of stimulator 100 with an attached cap 1900. As shown there, the cap 1900 may fit over the stimulator probe 104, which may protect the probe from contamination. More particularly, it may be desirable for the cap to protect the nasal insertion prongs, and especially the electrodes, from contamination. The cap 1900 may have any suitable shape. In some variations, the cap 1900 may cover the operating mechanisms when attached to the stimulator. This may prevent the operating mechanisms from being inadvertently or accidentally manipulated. As shown in FIGS. 19A-19B, the cap 1900 may cover the buttons 114 and 116 of the stimulator body 102, while leaving the sides of stimulator body 102 exposed. This may allow a user to more easily grip the stimulator body 102 in order to remove the cap 1900. In some variations the cap may comprise a texturized surface or other gripping features to assist with removal, such as ridges 1904 shown on cap 1900. The cap or other enclosure may comprise any suitable material or materials, such as a plastic or synthetic resin. In some variations the cap or other enclosure may be translucent or transparent, while in other variations it may be opaque.

The cap or other enclosure may in some variations comprise one or more features to control the exposure of the stimulator probes to the air. When the probes comprise a hydrogel or other liquid or wet material, the amount of exposure of air may affect the rate at which the hydrogel or other liquid or wet material dries out. For example, in some variations the caps may comprise one or more openings to allow for air flow underneath the cap or other enclosure. Cap 1900, for example, may comprise an opening 1902 at the distal end of the cap. In some variations the cap may be generally conformed to the shape of the stimulator probe (e.g., by comprising recesses having shapes corresponding to the stimulator prongs' shape and configured to receive the prongs), such that the air within the cap is minimal; in other variations, the cap may not be conformed to the shape of the stimulator probe, such that there is more air circulating within the cap around the stimulator probe.

Figure 19C:
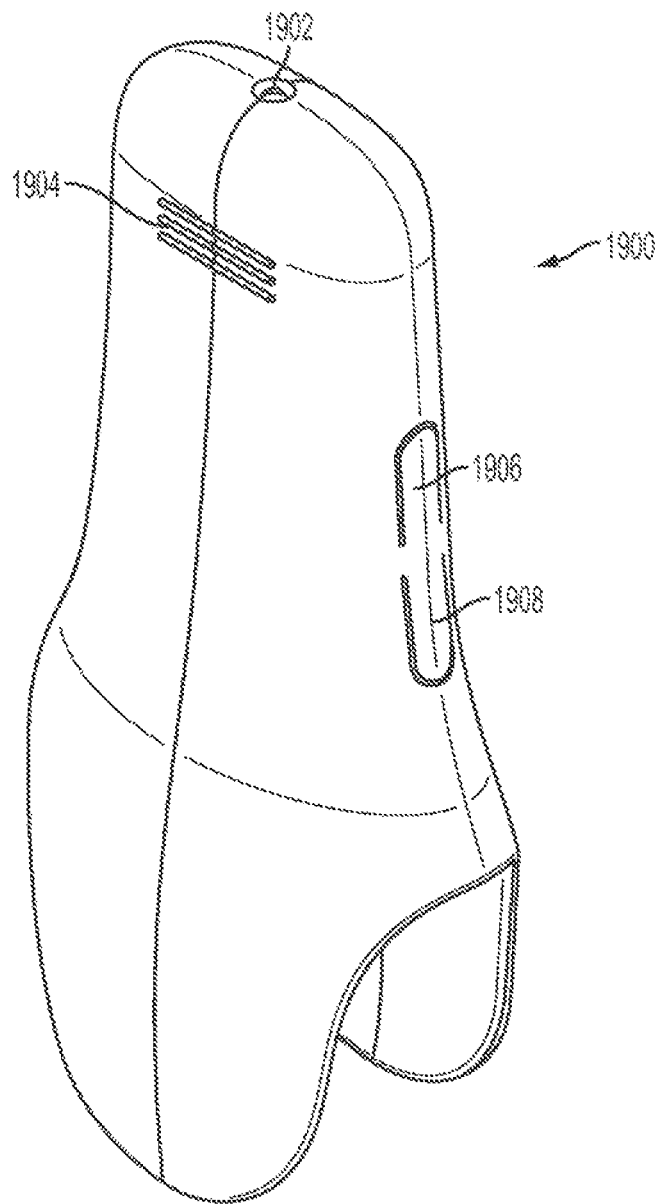
FIG. 19C shows a perspective view of a cap.

In some variations, the cap may comprise one or more features to promote attachment of the cap to the stimulator body. For example, in some variations the cap may comprise tabs or bosses, which may be configured to mate with indentations or cavities on the stimulator. Additionally or alternatively, the stimulator may comprise tabs or bosses, which may be configured to mate with indentations or cavities on the cap. In some of these variations, the flexibility of the cap material may allow cap to be placed on the stimulator. Additionally or alternatively, the cap may comprise one or more living hinges or cutaways 1906 and 1908, such as shown in FIG. 19C. The living hinges or cutaways may allow the cap to flex in order to slide past a raised feature on the stimulator (e.g., a tab or boss); for example, squeezing the top cutaway 1906 may cause the bottom portion 1908 to rotate away from the stimulator, allowing the bottom portion 1908 to slide past a raised feature when attaching or removing the cap 1900. Additionally or alternatively, the cap material and/or shape may promote attachment of the cap to the stimulator body. For example, the cap may be flexible in order to flex to slide over a thicker portion of the stimulator while being attached, and then the cap may relax into a conformal position upon reaching a thinner portion of the stimulation.

Figure 20:
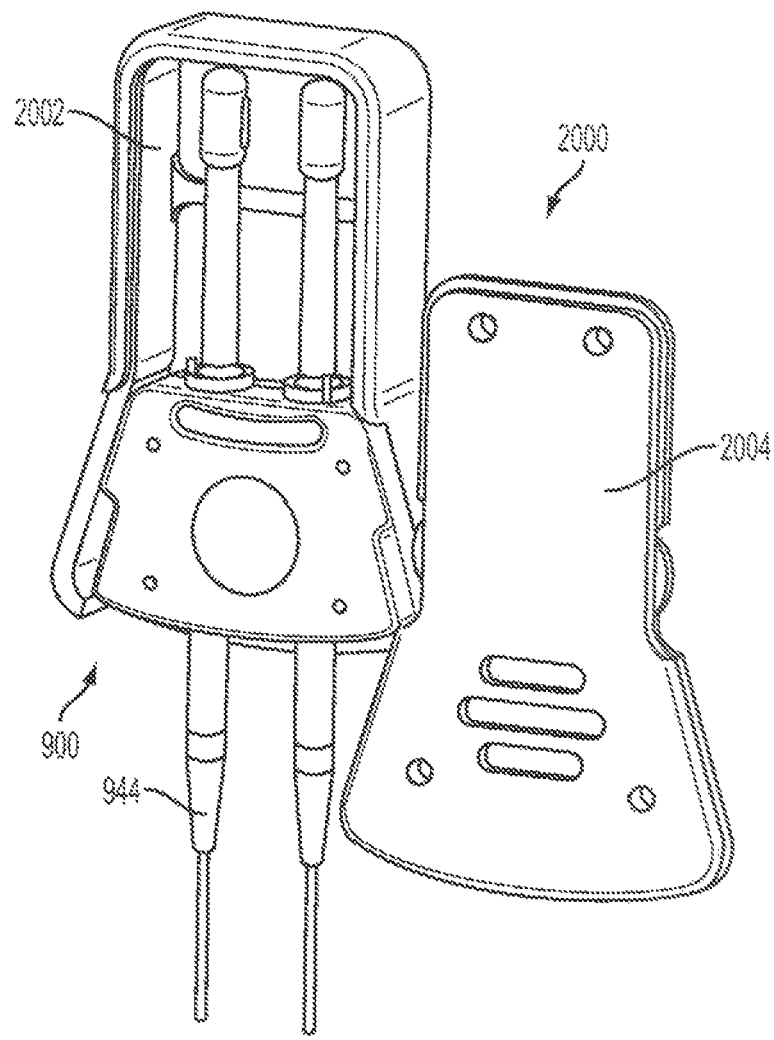
FIG. 20 shows a perspective view of the handheld stimulator of FIGS. 9A-9F with an attached cap.

In yet other variations, the cap or enclosure may comprise two or more pieces, which may be connected to cover all or a portion of the stimulator. In some variations, the two or more pieces may be fully separable, while in other variations the pieces may be permanently connected (e.g., via a hinge). An example of an enclosure comprising two pieces is shown in FIG. 20. FIG. 20 shows a perspective view of the stimulator of FIGS. 9A-9F with another variation of enclosure. As shown there, the enclosure 2000 may comprise a cover 2002 configured to receive the stimulator probe 900, and a cover lid 2004 configured to attach to the cover 2002 to protect the stimulator probe 900. In the variation shown in FIG. 20, the cover lid 2004 may slide onto the cover 2002. As shown, the enclosure 2000 may comprise an opening configured to allow the cable connectors 944 to extend out of the enclosure 2000. In other variations, the cap or enclosure may comprise a top portion and a bottom portion that may connect in the middle to enclose the stimulator.

Figure 36B:
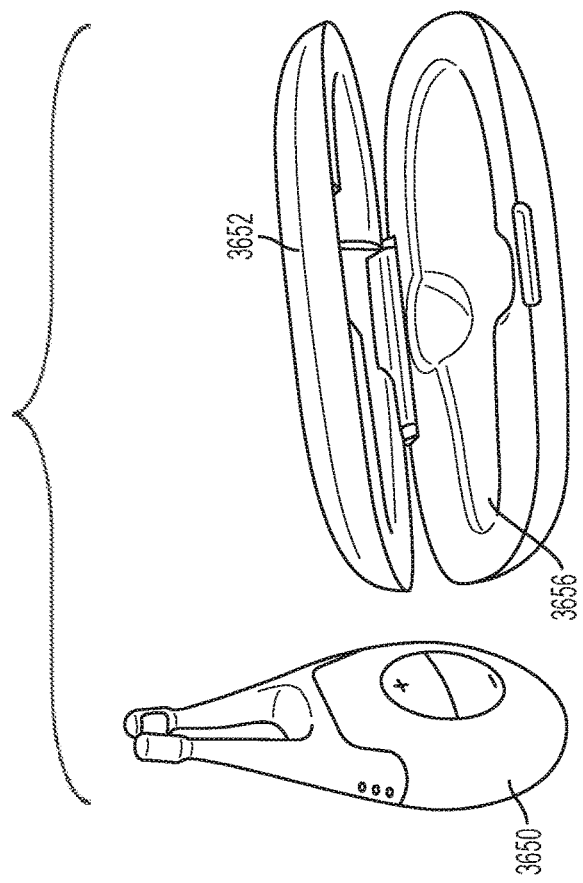
FIG. 36B depicts a perspective view of a stimulator and a case for the stimulator.
Figure 36A:
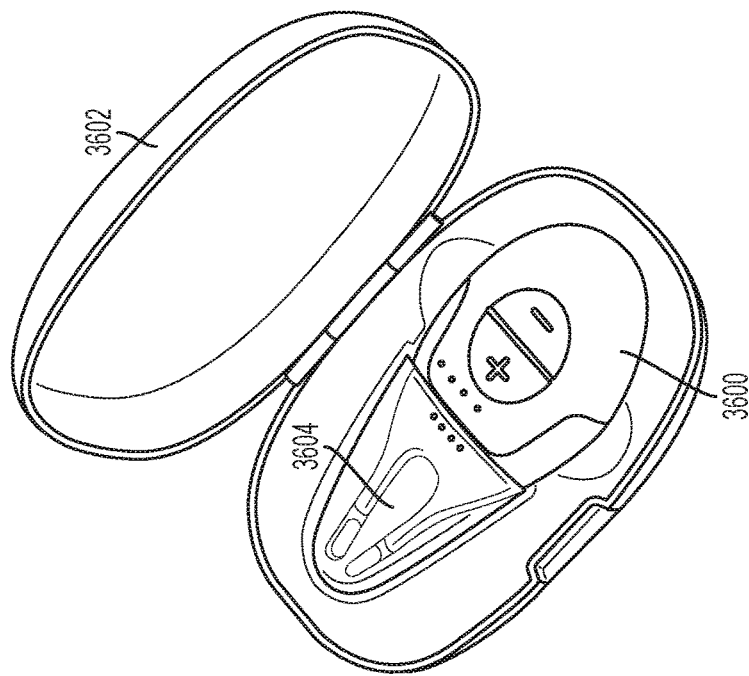
FIG. 36A depicts a perspective view of a stimulator in a case.

Additionally or alternatively, the stimulation systems described here may comprise a case configured to hold the stimulator. Like a cap, a case may protect the probe (more particularly, the nasal insertion prongs) from contamination. In some variations, the case may be configured to hold the stimulator while the stimulator has a cap attached. On such variation is shown in FIG. 36A, which shows a stimulator 3600 sitting within a case 3602. As shown, the stimulator 3600 may be placed into a recess of the case 3602 with a cap 3604 attached. The case 3602 may latch closed in order to protect the stimulator 3600. In other variations, the case may be configured to hold the stimulator without a cap attached, as shown in FIG. 36B. As shown there, a case 3652 may comprise a recess 3656 configured to receive a stimulator 3650 without a cap. In yet other variations, the case may be configured to hold a stimulator body and a stimulator probe when disconnected. In some variations, the case may be configured to charge the stimulator in variations in which the stimulator comprises a rechargeable power source. In these variations, the case may comprise a recess configured to receive a stimulator body. The case may comprise one or more electrical contacts configured to connect to one or more corresponding electrical contacts on the stimulator body, or the stimulator body and case may be configured such that the case may inductively charge the stimulator (as described in more detail with regard to the base station herein), and the case may comprise a power source and/or a port configured to connect to a power source. In some variations, the case may contain compartments, recesses, or the like to hold accessories, such as but not limited to tools for cleaning the nasal insertion prongs (e.g., alcohol wipes), additional disposable components (e.g., stimulator prongs, sleeves), a connector cable, or the like.

Base Station

In some variations, the stimulation systems described here may comprise a base station configured to connect to a portion of the stimulator, the stimulator having a stimulator body and a stimulator probe. The base station may be configured to releasably connect to one or more portions of the stimulator, and may be configured to perform one or more functions when connected to the stimulator. FIGS. 21A-21D depict a portion of a stimulator system comprising a base station 2100 as described here. FIG. 21A shows a front view the stimulator body 2102 docked in the base station 2100, while FIGS. 21B, 21C, and 21D depict side, back, and top views of the base station 2100, respectively. The stimulator body 2102 and stimulator probe (not shown) may include any of the elements of the stimulators described herein. In variations where the stimulator body 2102 comprises a rechargeable power source (such as a rechargeable battery, capacitor, or the like), the base station 2100 may be configured to recharge the rechargeable power source. For example, the base station 2100 may comprise one or more electrical contacts 2104, which may be configured to electrically connect to corresponding electrical contacts on the stimulator body 2102. In some variations, these electrical contacts may be the same electrical contacts that connect the stimulator probe and the stimulator body (e.g., electrical contacts similar to connectors 122 and 124 of stimulator 100). This electrical connection may allow the base station 2100 to charge the power source of the stimulator body 2102.

In some variations, the base station may comprise a safety mechanism that prevents power delivery to the electrical contacts unless the stimulator is connected. For example, the base station may comprise a sensor configured to detect the stimulator. After the stimulator is detected, power may be delivered to the contacts. In one variation, the sensor may comprise a magnetic field sensor (e.g., a Hall effect sensor), and the stimulator may comprise a magnet. When the stimulator is placed in the base station, the magnetic field sensor may detect the presence of the magnet in the stimulator and may in turn cause power to be delivered to the contacts.

It should be appreciated that in other variations, the base station may additionally or alternatively be configured to inductively charge the stimulator. For example, the base station may comprise a primary coil, which may or may not be wrapped around a ferromagnetic (e.g., iron) core, and the stimulator body may comprise a secondary coil, which may or may not be wrapped around a ferromagnetic core. When the stimulator body is placed in the base station, the coils and iron cores may form a complete transformer, allowing power to be inductively transferred from the base station to the stimulator body. Additionally or alternatively, it should be recognized that inductive power transfer may also be used to transfer power from the stimulator body to the stimulator probe, as described in more detail above.

The base station may be powered in any suitable manner. In some variations, the base station may be connectable to an external power source (e.g., a wall outlet or separate battery back), which may provide power to the stimulator and/or the base station. In some variations, the base station may comprise a power cable, which may be permanently attached via a strain relief. In other variations, such as the variation of the base station 2100 shown in FIGS. 21A-21D, the base station may comprise a port 2106 (e.g., a USB port or micro-USB port), which may connect the base station 2100 to an external power source. It should be appreciated that the base station 2100 may include any suitable port or connector for connecting the base station to an external power source. Additionally or alternatively, the base station may comprise a power source (e.g., one or more batteries) operable to power the base station 2100 (and to recharge the stimulator in variations where the stimulator is rechargeable). The power source may or may not be rechargeable.

The base station 2100 may be configured to rest on a surface (e.g., a counter or table), and may comprise a weight and/or a bottom surface with increased friction (e.g., a rubber pad 2108) to help keep the base station 2100 in place. In variations in which the stimulator comprises a magnet or material attracted to a magnetic field (e.g., iron, nickel, cobalt, alloys thereof and the like), the base station may comprise a magnet in a corresponding location in order to hold the stimulator in place within the base station. For example, the base station may comprise a magnet located between the electrical contacts, which may be configured to attract a magnet in the stimulator body (e.g., in a base station configured to receive stimulator body 102, the base station may comprise a magnet configured to attract the magnet 134 attached to the interior of proximal housing 142.).

Figure 22B:
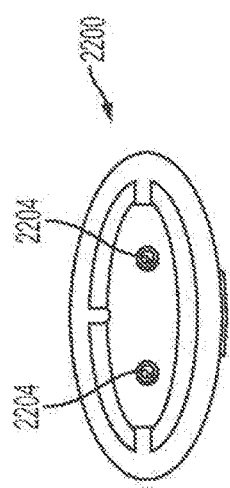
Figure 22C:
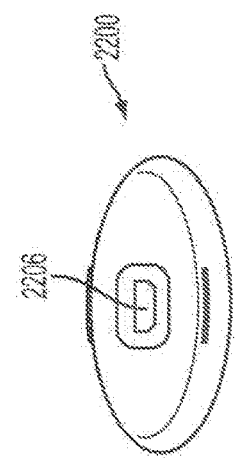
Figure 22D:
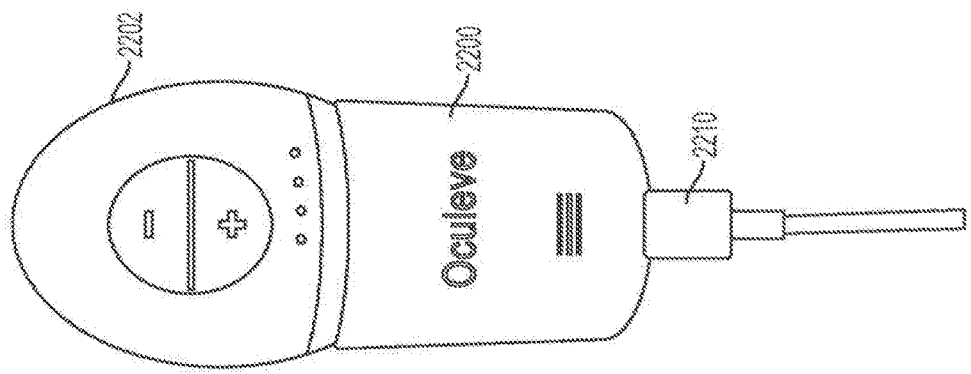

FIGS. 22A-22D depict another variation of a stimulator system comprising a base station as described here. FIG. 22A shows a front view the stimulator body 2202 docked in the base station 2200, while FIGS. 22B, 22C, and 22D depict top, bottom, and side views of the base station 2200, respectively. The base station 2200 may have similar features as base station 2100 described above but may be have a different shape configured to lie on its side on a surface, as opposed to having a flat bottom surface. Like base station 2100, it may be configured to connect to stimulator body 2202 via electrical contacts 2204 and may comprise a port 2206 to connect the base station 2200 to an external power source (e.g., via a USB cable 2210). The base station 2200 may comprise and a magnet in order to hold the stimulator in place. In some variations, the base station 2200 may comprise ribs 2208 to help the user grip the base station 2200 in order to remove the stimulator body 2202 from the base station 2200.

Figure 18:
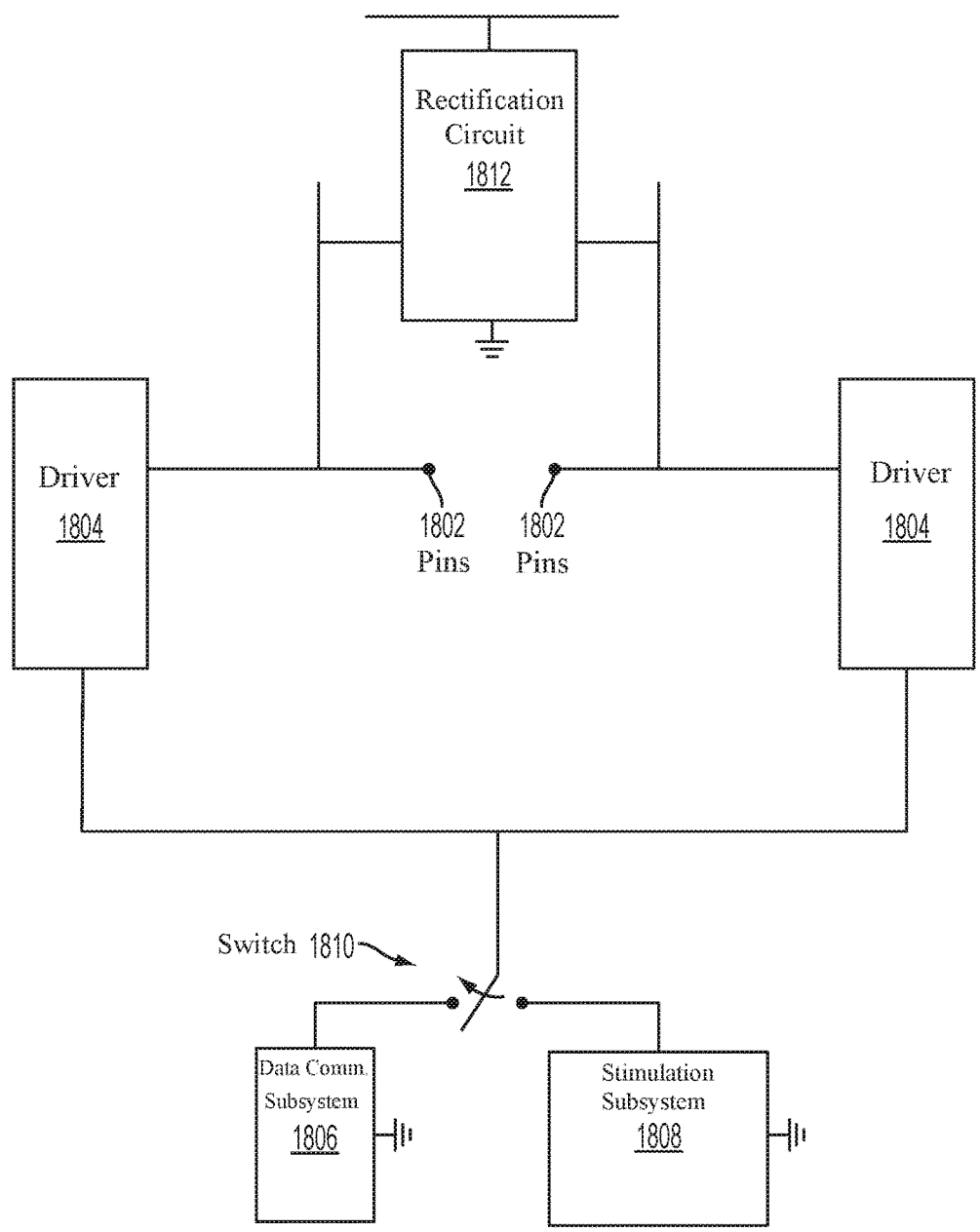
FIG. 18 illustrates a schematic diagram of stimulator circuitry.

In instances where the stimulator is configured to record or otherwise store data (e.g., the frequency or duration of stimulation), the base station may be configured to retrieve data from the stimulator. For example, in variations where the stimulator and base station are configured to be electrically connected, data may be transmitted via this electrical connection (e.g., the connection between connectors 122 and 124 of stimulator body 102 and electrical contacts 2104 of base station 2100 or electrical contacts 2204 of base station 2200). FIG. 18 illustrates a schematic diagram of stimulator circuitry allowing for the same pins 1802 to be used to transfer data from the stimulator body to the base station, to transmit a stimulus from the stimulator body to the stimulator probe, and to charge a rechargeable power source in the stimulator body using the base station. As shown, the pin drivers 1804 may take input signals either from a data communication subsystem 1806 or a stimulation subsystem 1808. The input to the drivers 1804 may be determined by a switch 1810. In some variations, the switch 1810 may comprise a gate, state machine, or a microcontroller. The pins 1802 may also be used to charge the stimulator. A rectification circuit 1812 may be configured to rectify a charging input signal without interfering with any output stimulation or data waveform. In some variations, the rectification circuit may comprise a full wave rectifier comprising rectification diodes, but it should be appreciated that any suitable circuit may be used. Time blocks for each function may be synchronized in order for the system to perform each function.

Additionally or alternatively, the base station may be configured to wirelessly transmit or receive data from the stimulator. In variations where data may be transmitted between the stimulator and the base station, the base station may be configured to provide programming instructions to the stimulator. The base station may be configured to be attached to an external computing device, to transfer data downloaded from the stimulator and/or receive programming instructions to be provided to the stimulator. In variations where the base station comprises a port (such as a USB port), the port may be used to attach the base station to an external computing device.

Figure 23A:
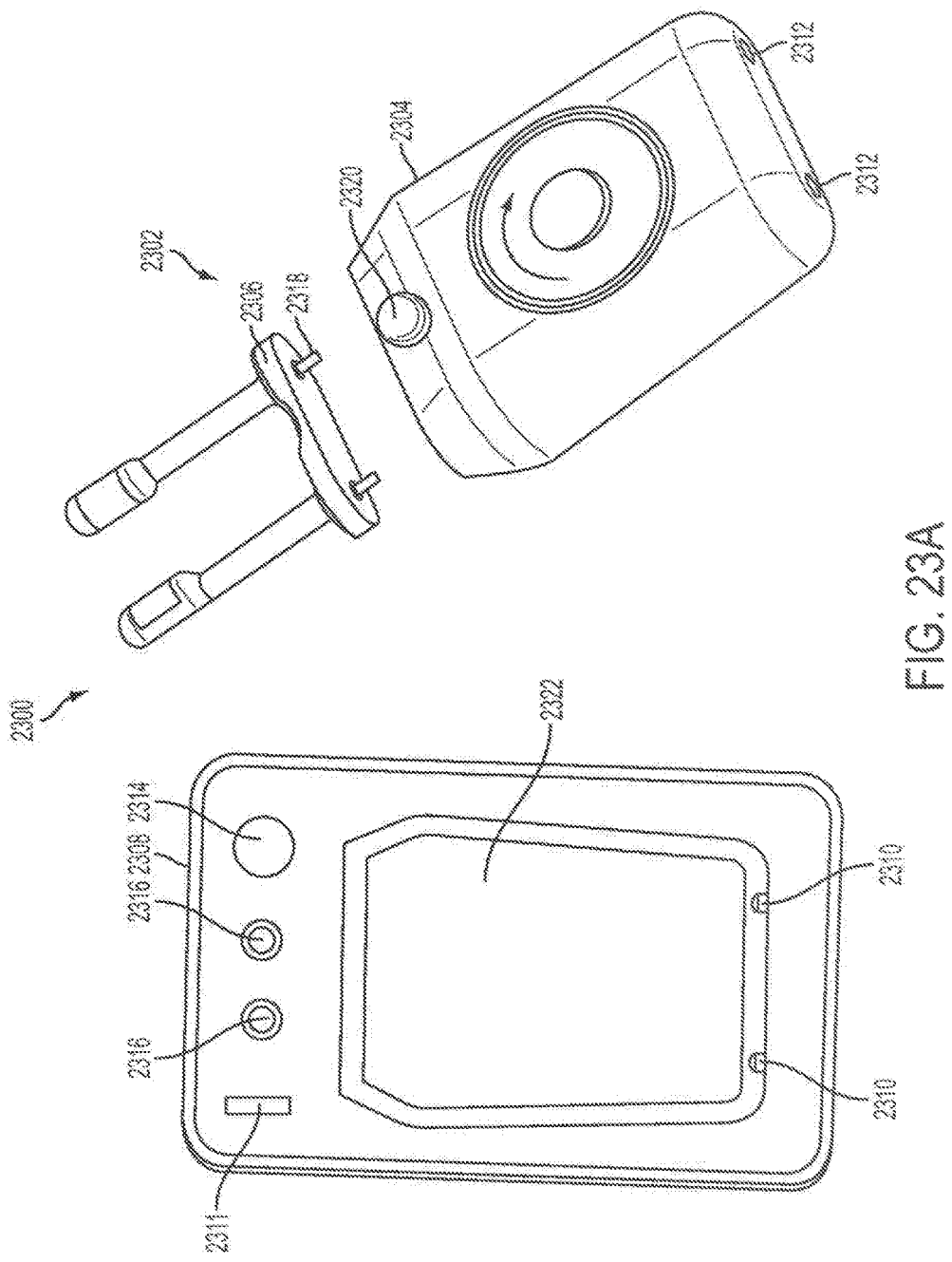
FIGS. 23A-23B show another variation of a stimulator system comprising a stimulator and a base station.
Figure 23B:
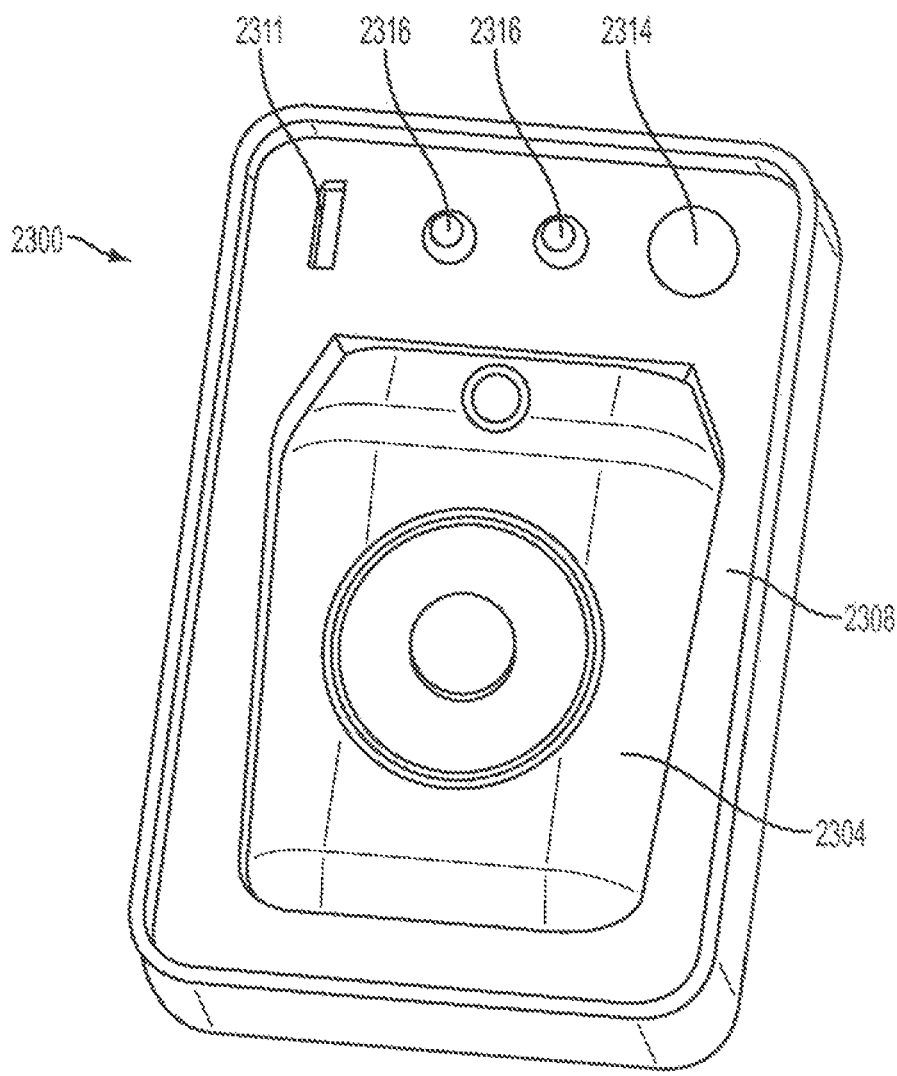

In some variations, the base station may be configured to perform one or more diagnostic tests on the stimulator when the stimulator is connected to the base station. For example, FIGS. 23A-23B show a variation of a stimulator system comprising a base station that may be configured to test the operational status of the stimulator, and alert a user as to whether the stimulator is ready for subsequent use. In the variation of the base station shown in FIGS. 23A-23B, the base station 2308 may comprise a recess 2322 configured to receive the stimulator body 2304 when the stimulator probe 2306 is detached from the stimulator body 2304. The base station 2308 may comprise one or more electrical contacts 2310, which may be configured to electrically connect to corresponding electrical contacts 2312 on the stimulator body 2304. The base station 2308 may comprise a test button 2314 and one or more status indicators 2316. A user may press or otherwise activate the test button 2314 to initiate a diagnostic test of the stimulator 2302 when stimulator body 2304 is placed into recess 2322 (as shown in FIG. 23B).

The status indicators 2316 may communicate the results of the diagnostic test to the user. For example, in some variations the status indicators 2316 may comprise a first light and a second light, wherein the first light is activated when the diagnostic test determines that the stimulator 2302 is operational, and the second light is activated when the diagnostic test results in an error or otherwise determines that the stimulator 2302 is not presently operational. In other variations, the status indicator 2316 may include a single light that changes color depending on the results. It should be appreciated that the base station 2308 need not provide visual status indicators to the user, and may be configured to provide feedback in any suitable manner (e.g., via visual feedback, auditory feedback, tactile/vibratory feedback, combinations thereof and the like). It should be appreciated that the base stations described herein may be configured to receive/connect to the handheld or the implantable stimulators as described here.

In some variations, the systems described here may further comprise a cap configured to fit over the stimulator while the stimulator is connected to the base station. The cap may attach to the base station, and may assist in securing the stimulator to the base station. In some variations, the cap may be translucent or transparent, while in other variations, the cap may be opaque for discreteness. Additionally or alternatively, the base station may comprise a recess configured to receive another portion of the stimulation system, such as a stimulator probe or a cap.

External Device Connection

In some variations the stimulators described here may be configured to connect to an external device, such as a mobile device (e.g., a cellular telephone, a tablet, a wearable computer (e.g., optical head-mounted displays such as Google GLASS™ wearable computing device), or the like), a computer, or the like. The stimulators may be configured to connect to an external device through any suitable connection method. In some variations the connection method may be wireless (e.g., via WiFi, BLUETOOTH™ wireless technology, or the like), and the stimulator may comprise an antenna or the like. Additionally or alternatively, the connection method may be via a wired transmission line. In these variations, the stimulator may comprise one or more ports (e.g., a USB port), connectors and/or cables configured to physically connect the stimulator to an external device. In some variations, the stimulators may use a wireless or wired connection to connect to the internet, via which they may be connected to an external device. In these variations, the device may be at a distant location (e.g., at the manufacturer, at a physician's office, or the like).

In instances in which the stimulators are configured to connect to an external device, the device may be configured to perform one or more operations associated with the stimulator. For example, in variations where the stimulator is configured to collect data (e.g., one or more subject parameters, stimulation timing or parameters, stimulator diagnostic information, such as described in more detail herein) and store that data in a memory unit of the stimulator, connection of the stimulator to the device may allow for transfer of data stored in the stimulator's memory unit to the device. Specifically, the device and stimulator may be programmed such that upon connection of the device and the stimulator, the device may download the recorded data stored in the stimulator's memory. In some variations, once data has been transferred from the stimulator to the device, the stimulator may be configured to delete this data from the stimulator memory. Because the amount of memory available in the device may be greater than that in the stimulator, this transfer may increase the data that may be accumulated for a subject.

In addition to or instead of transferring data stored in the stimulator memory, a device may be configured to collect and store real-time data from the stimulator when the two are connected. In some of these variations, the stimulator may also be configured to store this data in the stimulator memory. In some instances, the device may be configured to transmit data (e.g., via internet connection, cellular data network, or the like) from the device to an external location (e.g., to a database where the data may be analyzed, to a physician's office to allow the physician to monitor the data and, in some instances, provide feedback).

In some variations, the device may be configured to solicit input from a user. For example, if the stimulator is used to provide stimulation while attached to a device, the device may be configured to solicit the user to input data regarding the subject's experience (e.g., a subject's level of comfort/discomfort, status of subject's symptoms). In some variations, the device may be configured to present data (and/or analysis of the data) to a user. For example, the device may be configured to display information regarding the frequency of stimulation, the average duration of stimulation, a graph of subject comfort levels over time, or the like. In some variations, the device may be configured to share the data or analysis of the data with the manufacturer, clinicians, friends, or others.

Implantable Stimulators

In some variations of the stimulation systems described here, the stimulation system may comprise a stimulator configured to be implanted, either permanently or temporarily, in a subject. It should be appreciated that the implantable stimulators need not be surgically implanted. In some of these instances, the implantable stimulator may be configured such that the stimulator may be inserted and/or removed by a user. In others of these instances, the implantable stimulator may be configured to be inserted and/or removed by a medical professional. In other instances, the stimulator may be configured to be implanted in or otherwise attached to tissue within a nasal or sinus cavity.

Figure 25:
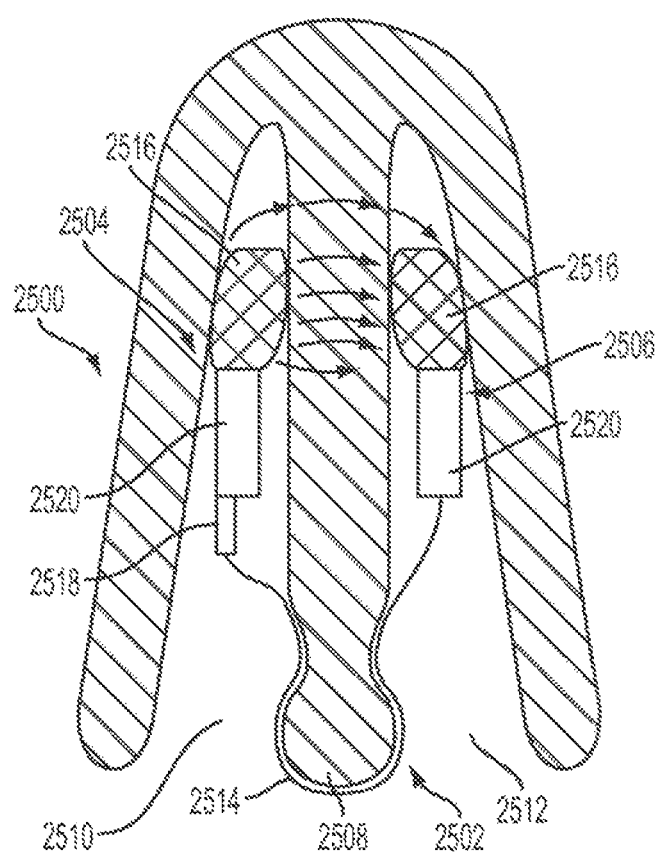
FIG. 25 shows a cross-sectional view of an implantable stimulator positioned in the nasal cavities.

As mentioned above, in some variations an implantable stimulator may be configured for placement and/or removal by a user. For example, FIG. 25 depicts a cross-sectional view of a user's nose having a septum 2508 and nostrils 2510 and 2512 having a variation of an implantable stimulator 2500 located therein. As shown there, the stimulator 2500 may comprise a clip 2502, a first stimulator unit 2504 attached to a first end of the clip 2502, and a second stimulator unit 2506 attached to a second end of the clip 2502. Generally, the clip 2502 may be configured to temporarily connect the stimulator 2500 to a nasal septum 2508 of a user, which may position the first stimulator unit 2504 in the first nostril 2510 and the second stimulator unit 2506 in the second nostril 2512.

In some variations, the clip 2502 may comprise a u-shaped portion 2514 configured to receive and clamp to a portion of the nasal septum 2508. This engagement between the clip 2502 and the nasal septum 2508 may limit advancement of the stimulator 2500 into the nose (e.g., to prevent over-insertion of the stimulator 2500). The clip 2502 may exert sufficient pressure on the septum 2508 so as to resist removal of the stimulator 2500 from the nose. Accordingly, the clip 2502 may allow the stimulator to be positioned in the nose of a user, and the user may wear the stimulator for as long as needed without needing to actively hold the stimulator in the nose. The clip 2502 may be removed by flexing the clip 2502 to disengage it from the septum. As such, the patient may be able to insert and remove the stimulator 2500 him- or herself. In some variations, the clip 2502 may be at least partially formed from one or more shape memory materials (e.g., a nickel-titanium alloy), such that the clip 2502 may be deformed to disengage the clip 2502 from the septum 2508 and may return to its original shape. In some variations, the clip 2502 may be curved such that the stimulation unit or units are directed toward the front of the septum, as described herein. In some variations in which the stimulator 2500 is configured to deliver an electrical stimulus, an exterior portion of the clip 2502 may be formed from one or more insulating materials, such as described herein (e.g., PTFE, silicone, combinations thereof, or the like), and an interior portion may include an electrically conductive core (e.g., a wire of any suitable metal, such as silver, stainless steel, platinum, alloys thereof, or the like) electrically connecting the first stimulator unit 2504 to the second stimulator unit 2506. In these variations, the insulating outer portion of the clip 2502 may prevent inadvertent electrical stimulation between the clip 2502 and the subject.

While shown in FIG. 25 as having a first stimulator unit 2504 and a second stimulator unit 2506, it should be appreciated that in some variations the stimulator 2500 may comprise only a first stimulator unit 2504. Generally, when the stimulator is configured to deliver an electrical stimulus, each stimulator unit may comprise one or more electrodes 2516. While shown in FIG. 25 as being formed from an expandable wire mesh/braid electrode, each electrode 2516 may be configured in any manner as described in more detail herein. For example, in some variations, it may be desirable for the stimulator units to comprise a smooth surface to prevent tissue abrasion. In some variations, it may be desirable for the stimulator units to comprise a radially expandable structure that may expand to contact the nasal mucosa when inserted into the nostrils. Additionally or alternatively, it may be desirable for the electrode to be directed toward the front of the nose (e.g., by the electrode comprising only a front-facing portion of the stimulator unit), as described in more detail herein. When the stimulator comprises only a first stimulator unit 2504, the first stimulator unit 2504 may provide unilateral stimulation to the first nostril 2510 via electrodes of the first stimulator unit 2504. In variations where the stimulator 2500 comprises first 2504 and second 2506 stimulator units, the stimulator may be configured to provide unilateral stimulation of the first nostril 2510 (e.g., via electrodes of the first stimulator unit 2504, with a return electrode in the first nostril or elsewhere), unilateral stimulation of the second nostril 2512 (e.g., via electrodes of the second stimulator unit 2506, with a return electrode in the second nostril or elsewhere), or bilateral stimulation (e.g., via electrodes of the first 2504 and second 2506 stimulator units). The stimulator may be configured such that the electrodes 2516 are placed in contact with any suitable tissue structure or structures (e.g., the nasal mucosa above the columella, such as the nasal mucosa superior to the columella (e.g., the nasal mucosa near the interface between the nasal bone and the upper lateral cartilage) when the clip 2502 is connected to the nasal septum.

Generally, the first 2504 and/or second 2506 stimulator units may comprise a housing 2520, which may include any of the control circuitry described with respect to the handheld stimulators described here. For example, the stimulator may comprise a control subsystem having a processor, a stimulation subsystem, and a memory. In some variations the control subsystem may have a detection subsystem. Additionally or alternatively, the stimulator may comprise a communication subsystem. In some of these variations, the stimulator may be configured to wirelessly receive and/or transmit data and/or power via a coil 2518 or other antenna. For example, in some of these variations, the stimulator may be configured to connect to an external device (such as an external programmer, laptop or other computer, or to a mobile device, as discussed in more detail herein). The stimulator circuitry may be housed in a single housing 2520 (e.g., a housing 2520 of the first stimulator unit 2504 or a housing 2520 of the second stimulator unit), or may be divided between multiple housings (e.g., a housing 2520 of the first stimulator unit 2504 and a housing 2520 of the second stimulator unit).

In some variations, the stimulator 2500 may comprise a power source (e.g., a battery) (not shown). In other variations, the stimulator 2500 may be powered wirelessly (e.g., via power received from a coil 2518 or other antenna), such as described in U.S. patent application Ser. No. 13/441,806, filed on Apr. 6, 2012, and titled "Stimulation Devices and Methods", the contents of which is hereby incorporated by reference in its entirety.

Figure 26B:
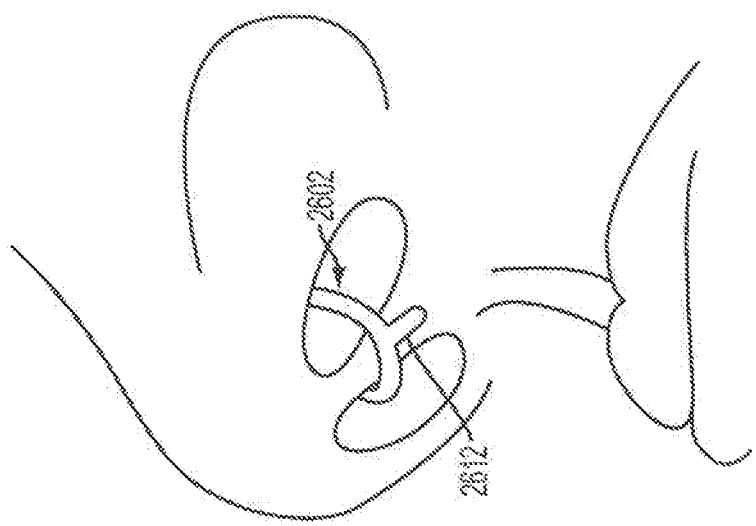
FIG. 26B shows a perspective view of the stimulator probe of FIG. 26A implanted in the nasal cavities.
Figure 26A:
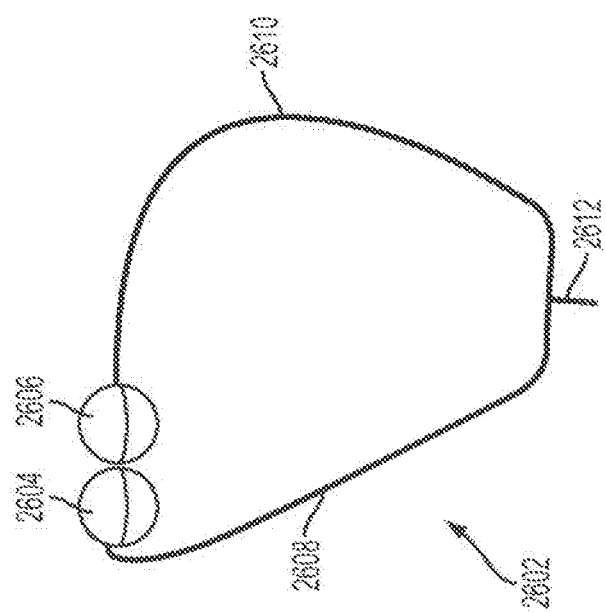
FIG. 26A shows perspective view of a stimulator probe of an implantable stimulator.
Figure 26C:
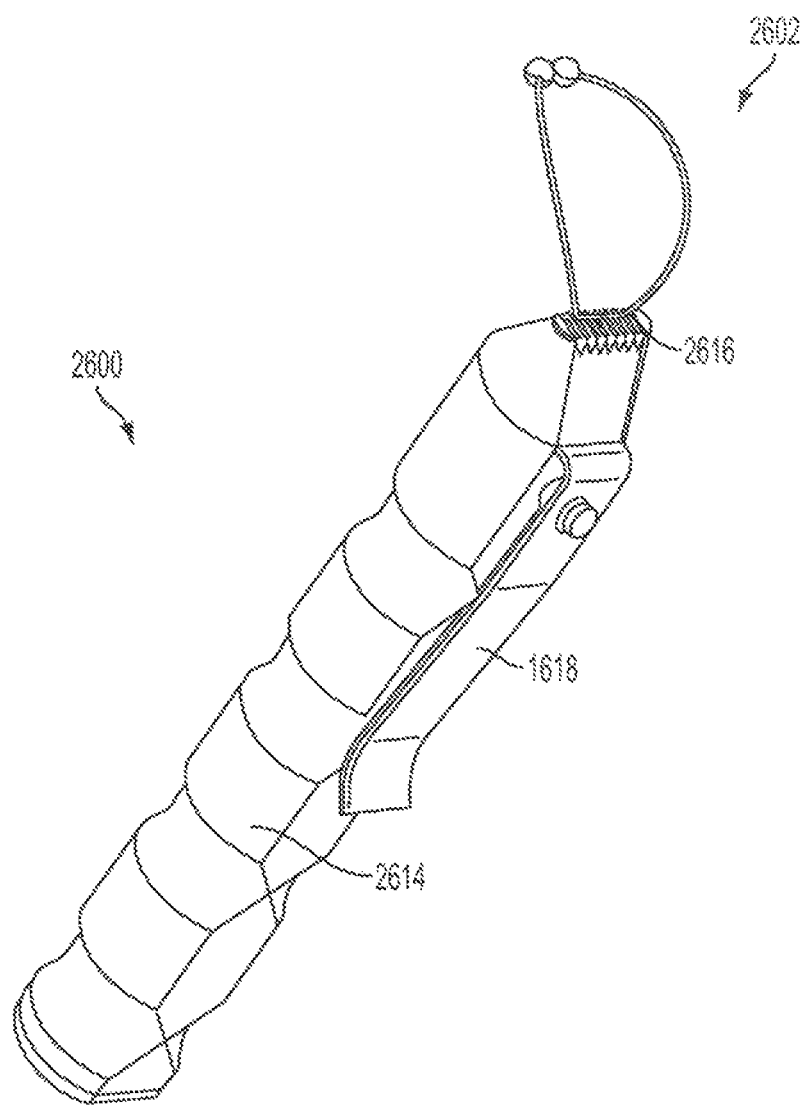
FIG. 26C shows a perspective view of the stimulator probe of FIG. 26A connected to a stimulator body.

FIGS. 26A-26C depict another variation of an implantable stimulator 2600 configured for placement and/or removal by a user. As shown there, the stimulator 2600 may comprise a clip 2602, a first stimulation unit 2604 attached to a first end of the clip 2602, and a second stimulation unit 2606 attached to a second end of the clip 2602. Generally, the clip 2602 may be configured to temporarily connect to a nasal septum of a user, which may position the first stimulation unit 2604 in a first nostril of the user and the second stimulation unit 2606 in a second nostril of the user, as shown in FIG. 26B.

The clip 2602 may comprise a first arm 2608 and a second arm 2610, which may be connected at the base of the clip 2602. This may limit the advancement of the clip 2602 into the nose. The first 2608 and second 2610 arms may curve inwardly toward each other. This curvature may cause the stimulation units 2604 and 2606 to press against the septum of the user when inserted, which may hold the clip 2602 in place and allow the stimulator to be worn in place by the user as long as needed without the user needing to actively hold the stimulator in his/her nose. The clip 2602 may be removed by pulling it downward and/or flexing the clip 2602 to disengage it from the septum. The first 2608 and second 2610 arms may also curve forward when placed in the user's nose. This may cause the stimulation units to contact a desired region of the nasal tissue (e.g., the front of the nasal septum) when the clip is connected to the nasal septum. In some variations in which the stimulator 2600 is configured to deliver an electrical stimulus, the exterior portion of the first 2608 and second 2610 arms may be formed from one or more insulating materials, while the interior portion may comprise an electrically conductive core, as described in more detail with respect to implantable clip 2502.

When the stimulator 2600 is configured to deliver an electrical stimulus, the stimulation units 2604 and 2606 may comprise electrodes. The electrodes may have any suitable design. A shown in FIGS. 26A and 26C, the electrodes may in some variations be spherical, although in other variations the electrodes may be cylindrical, an arc of a cylindrical surface, elliptical, ovoid, or the like, and/or may comprise an array of electrodes. In some variations, the electrodes may comprise an expandable wire mesh/braid electrode, as described with respect to stimulator 2500. The electrodes may comprise one or more conductive materials, including but not limited to conductive metals (e.g., stainless steel, titanium, tantalum, platinum or platinum-iridium, other alloys thereof, or the like), conductive ceramics (e.g., titanium nitride), liquids, gels, or the like. In some variations, the electrode may comprise one or more materials configured to promote electrical contact between electrodes of the stimulator probe and tissue (i.e., all of an electrodes or a portion of the electrode, such as a covering), such as a hydrogel skin, foam or porous material impregnated with a gel or liquid, or the like, as described in more detail with respect to handheld stimulators.

The clip 2602 may further comprise an electrical connector that may be reversibly connectable to a handheld stimulator body 2614. In some variations, as shown in FIG. 26C, the electrical connector may comprise a lead 2612 extending from the base of the clip 2602. In other variations, the electrical connector may comprise one or more conductive areas on the clip 2602 (e.g., areas without insulation). The stimulator body 2614 may comprise an array of contacts 2616 configured to connect to the electrical connector of the clip 2602. In some variations, the stimulation units 2604 and 2606 may act as return electrodes. In other variations, the stimulator 2600 may comprise a distant return (e.g., the conductive bar 2618, which may be in contact with the user's hand). The handheld stimulator body 2614 may have any of the control circuitry described with respect to the handheld stimulators described. When the stimulator 2600 is configured to deliver an electrical stimulus, the stimulator body 2614 may generate an electrical stimulus that may be transmitted to the electrodes 2604 and 2606 via the first 2608 and second 2610 arms.

Figure 27C:
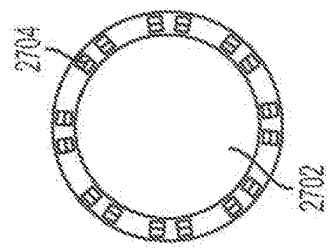
FIGS. 27A-27B and FIGS. 27C-27D depict side and front views, respectively, of a variation of an implantable stimulator.
Figure 27D:
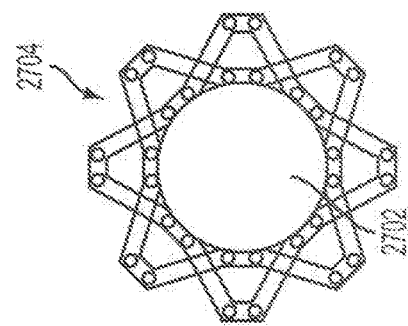
Figure 27A:
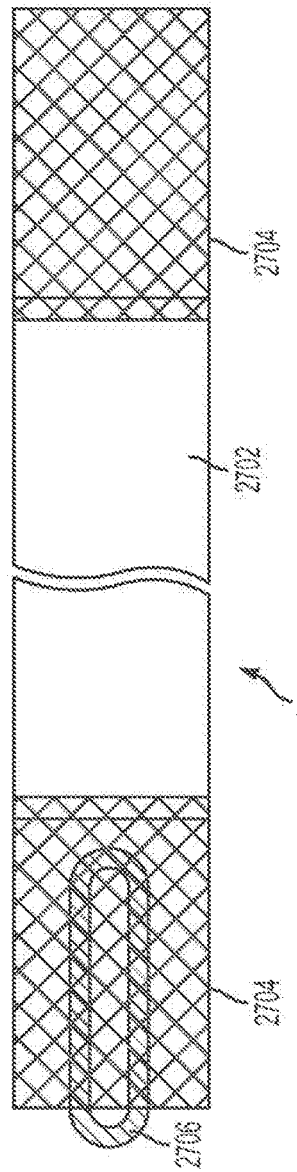
Figure 27B:
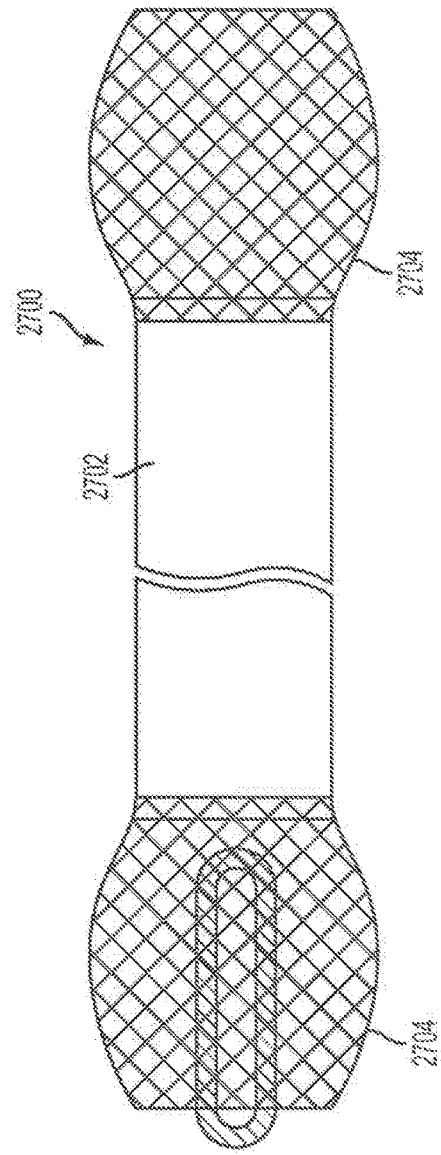

FIGS. 27A-27D show another variation of an implantable simulator 2700. FIGS. 27A and 27B show side views of the implantable stimulator, while FIGS. 27C and 27D show front views of the stimulator 2700. As shown there, the stimulator 2700 may comprise a housing 2702 and a pair of expandable electrodes 2704. Generally, the housing 2702 may house any of the control circuitry as described herein, which may be connected to the electrodes 2704 such that the stimulator 2700 may deliver stimulation to tissue via the electrodes 2704. In some variations, the stimulator 2700 may comprise a coil 2706 or other antenna which may allow the stimulator 2700 to wirelessly communicate with an external device (not shown), such as described in more detail herein.

Figure 27E:
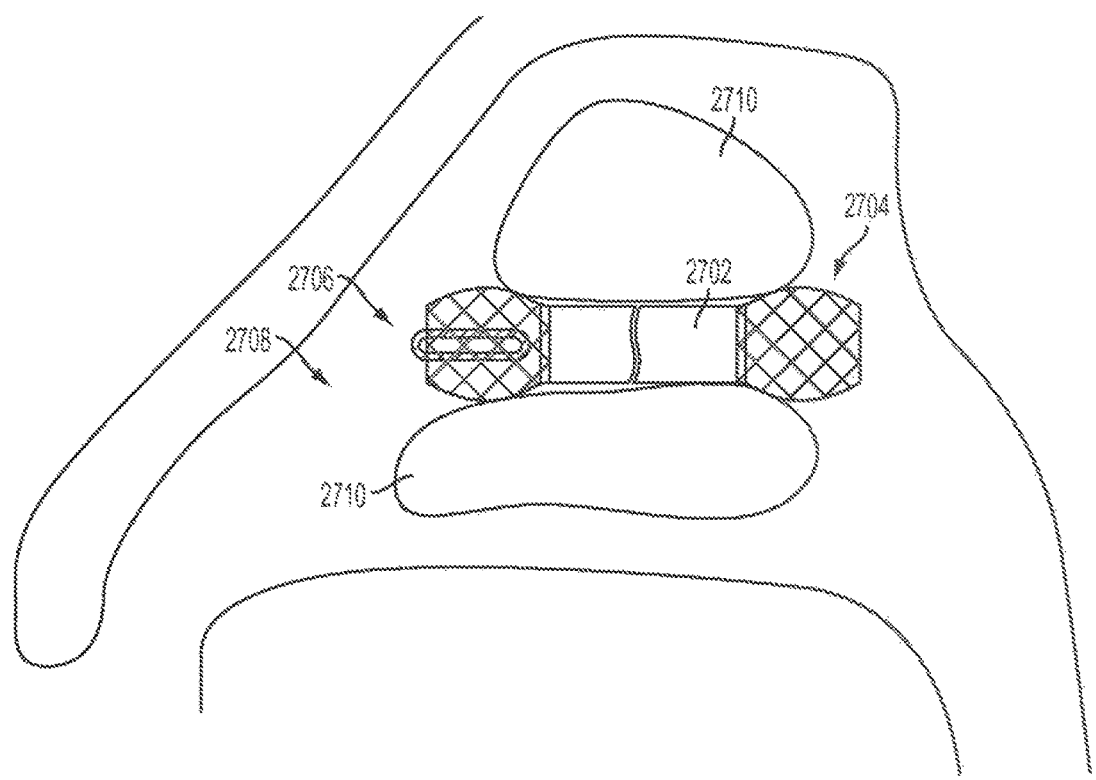
FIG. 27E shows the stimulator of FIGS. 27A-27D positioned in the nasal cavities.

Generally, the expandable electrodes may be moveable between a low-profile configuration (as shown in FIGS. 27A and 27C) and an expanded configuration (as shown in FIGS. 27B and 27D). In some instances, the electrodes may be configured to self-expand from the low-profile configuration to the expanded configuration. Additionally or alternatively, another device (such as a balloon catheter) may be configured to expand the electrodes between the low-profile and expanded configurations. When expanded, the electrodes 2704 may act as an anchor to help hold the stimulator 2700 in place relative to the body. In some variations, it may be desirable for the stimulator units to comprise a smooth surface to prevent tissue ingrowth. For example, as shown in FIG. 27E, the stimulator 2700 may be positioned in a nasal cavity 2708, and the electrodes 2704 may be expanded to anchor the stimulator 2700 in the nasal cavity 2708. In some variations, this may position one or more portions of the electrodes 2704 in contact with nasal mucosal tissue (e.g., tissue of one or more nasal turbinates 2710), which may allow the electrode 2704 to deliver stimulation to the nasal tissue. A stimulator may be positioned in one nostril to deliver unilateral stimulation, or a stimulator may be positioned in each nostril to provide bilateral stimulation. In other instances, a stimulator may be positioned at least partially in a sinus cavity.

Figure 28:
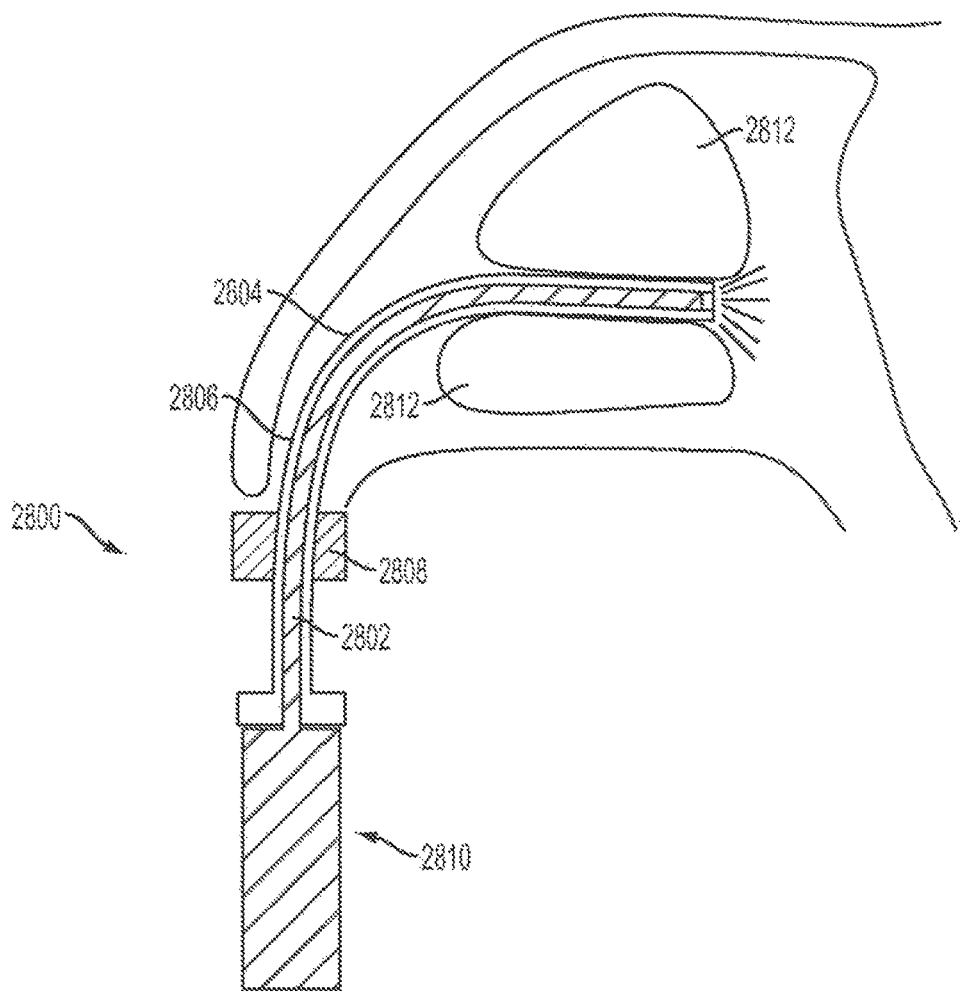
FIG. 28 shows one variation of a delivery device suitable for use with the implantable stimulators described here.

The stimulator 2700 may be delivered in any suitable manner. For example, FIG. 28 shows one variation of a delivery system 2800 suitable for use in delivering the stimulator. As shown there, the delivery system 2800 may comprise a guide catheter 2802. The guide catheter 2802 may be flexible and may be biased toward a configuration comprising a pre-set curve 2804, such that when inserted into the nostril 2806 of a subject, a distal portion of the guide catheter 2802 may be positioned at a desired implantation location (e.g., between turbinates 2812). In some variations, the guide catheter 2802 may comprise a stop sleeve 2808, which may be configured to limit advancement of the guide catheter 2802 into the nose.

With a guide catheter 2802 positioned in the nasal cavity, a stimulator (such as implantable stimulator 2700) may be advanced out of a lumen of the guide (e.g., via a pusher or an endoscope 2810), and a first electrode (or anchor) of the stimulator may be expanded to anchor the first electrode in the nasal cavity. The guide catheter 2802 may be withdrawn to release a second electrode (or anchor) of the stimulator to anchor the second electrode in the nasal cavity. Once the stimulator is delivered to the nasal cavity, the guide catheter 2802 may be withdrawn. In some variations, one or more steps may be visualized using an endoscope 2810, which in some instances may be positioned at least partially through the guide catheter 2802.

While the electrodes 2704 of the stimulator 2700 shown in FIGS. 27A-27E may be configured to be expandable, the electrodes 2704 need not be. In some variations, the stimulator may comprise one or more expandable anchors which may be separate from one or more electrodes of the stimulator. Additionally or alternatively, the stimulator may comprise one or more ribs, stubs, hooks, or barbs which may help to anchor the stimulator in the body.

When the electrodes 2704 are configured to be expandable, they may be formed from any suitable expandable structure. For example, in the variation of the stimulator 2700 shown in FIGS. 27A-27E, the electrodes 2704 may each comprise an expandable braid. In some variations, the braid may be formed from a braided shape memory wire (e.g., a nickel-titanium alloy), which may overlaid with one or more electrically conductive materials (e.g., platinum, a platinum-nickel-titanium alloy, or the like).

In other variations, the electrodes may be formed from an expandable tube. For example, FIG. 24 shows a variation of a stimulator 2400 comprising a housing 2402 and expandable electrodes 2204. As shown there, each electrode 2204 may be formed from a tube, which may be configured to move from a low-profile configuration (as shown in the left electrode 2204 in FIG. 24) and an expanded configuration (as shown in the right electrode 2204 in FIG. 24). In some variations, the tube may be a laser cut tube, which may be formed from a shape memory material (such as a nickel titanium alloy), which may be overlaid with one or more electrically conductive materials (e.g., stainless steel, titanium, tantalum, platinum or platinum-iridium, other alloys thereof, titanium nitride, liquids, gels, or the like). In still other variations, an electrode may be formed at least partially from an expandable foam, which may be impregnated with one or more conductive gels or fluids as discussed in more detail herein.

In still other variations, the stimulation systems described here may comprise a stimulator that is configured to be implanted within or beneath mucosal tissue. The stimulator may be implanted in a nasal or sinus cavity, and may be placed within the mucosa, beneath the mucosa, between mucosa and bone and/or cartilage, within the cartilage, or the like. Generally, the stimulator may comprise a stimulator body and one or more electrodes, and may include any of the stimulators described in U.S. patent application Ser. No. 13/441,806, filed on Apr. 6, 2012 and titled "Stimulation devices and methods", which was previously incorporated by reference in its entirety.

Stimulation Methods

Generally, the stimulators and stimulation systems described herein may be configured to stimulate nasal or sinus tissue. In some variations, the stimulation may be used to cause tear production by a user. Generally, a stimulator (such as described above) may be configured to stimulate one or more nasal or sinus afferents which may activate a lacrimation response via a nasolacrimal reflex. In some instances, this may comprise stimulating one or more branches of the trigeminal nerve or trigeminal nerve afferents. In some of these instances, this may comprise stimulating the ophthalmic branch of the trigeminal nerve. This stimulation may be used to treat various forms of dry eye, including (but not limited to), chronic dry eye, episodic dry eye, seasonal dry eye, aqueous deficient dry eye, or evaporative dry eye.

In some instances, the stimulation may be used as a prophylactic measure to treat users which may be at an increased risk of developing dry eye, such as subjects who will undergo or who have undergone ocular surgery such as refractive vision correction and/or cataract surgery. In other instances, the stimulators may be used to treat ocular allergies. For example, an increase in tear production may flush out allergens and other inflammatory mediators from the eyes. In some instances, the stimulation delivered by the stimulators described herein may be configured to cause habituation of the neural pathways that are activated during an allergic response (e.g., by delivering a stimulation signal continuously over an extended period of time). This may result in reflex habituation which may suppress the response that a user would normally have to allergens.

Location

When an implantable stimulator is used to provide stimulation, the implantable stimulator may be positioned in a nasal or sinus cavity (or multiple nasal or sinus cavities). When a handheld stimulator is used to provide stimulation, one or more prongs of the stimulator may be inserted at least partially into the nose of a user, and a stimulation signal (such as described above) may be delivered to the mucosal tissue.

A portion of the nasal insertion prong(s) may be positioned and/or manipulated to be placed in contact with any suitable tissue. (In variations in which the stimulators are configured to deliver an electrical stimulus, the stimulators may be positioned and/or manipulated to position electrodes into contact with any suitable tissue.) FIGS. 34A-34C illustrate anatomical locations. For example, the nasal insertion prong(s) may be placed in contact with the upper lip 3402, external nasal skin 3404, nasal ala 3406, mucosa of a nasal turbinate (e.g., one or more of the inferior 3408, medial 3410, or superior turbinates 3412), or the like. When the stimulators are used to produce a tearing response as discussed herein, it may be desirable to position a portion of the nasal insertion prongs (e.g., an electrode) in contact with the nasal mucosa of a nasal turbinate. In some instances, the targeted area may comprise tissue innervated by the anterior ethmoidal branch of the nasociliary nerve, as shown by shaded area 3420 in FIG. 34C. In some instances, the targeted area of the nasal mucosa may be superior to the columella 3414. In some of these instances, the targeted area may be near the inferior end of the nasal bone 3416 (i.e., near the interface between the nasal bone 3416 and the upper lateral cartilage 3418). In other variations, the targeted area may be the columella. In some variations, it may be desirable to place a portion of the nasal insertion prong(s) (e.g., an electrode) between about 20 mm and about 35 mm into the nasal cavity of the subject. In some of these variations, it may be desirable to place an electrode between about 25 mm and about 35 mm into the nasal cavity of the subject. As described herein, it may in some instances be desirable to direct the nasal insertion prongs such that a portion (e.g., the electrodes) is directed toward the front of the nose. This may allow for selective activation of nerves in the front of the septum (e.g., the ophthalmic branch of the trigeminal nerve) while minimizing activation of nerves toward the rear of the nasal septum, which may reduce negative side effects that may occur from stimulation of nerves that innervate the teeth, and which may reduce rhinorrhea. It may also in some instances be desirable to direct the nasal insertion prongs so as to reduce negative side effects that may occur from stimulation of the olfactory area.

Electrical Stimulus

In some variations, the stimulation may be delivered unilaterally (e.g., in a single nostril). For example, in variations where a stimulator comprises a single prong, the prong may be placed in a first nostril, and stimulation may be delivered to the first nostril via the prong. It should be appreciated that in some of these variations in which the stimulus is electrical, a pad electrode or other return electrode may be temporarily affixed to or otherwise be placed in contact with an external portion of the nose to act as a return electrode. In some variations where a stimulator comprises two or more prongs, each of the prongs may be placed in a first nostril, and some or all of the prongs may be used to deliver stimulation to mucosal tissue. In other variations where a stimulator comprises two or more prongs, at least one prong may be positioned in a first nostril, and at least one prong may be positioned in a second nostril. In variations in which the stimulus is electrical, some or all of the prongs in the first nostril may be used to deliver unilateral electrical stimulation to the first nostril (e.g., the prongs in the second nostril may remain inactive), or some or all of the prongs in the second nostril may be used to deliver unilateral electrical stimulation to the second nostril.

In some variations, the stimulator may be used to provide bilateral stimulation of the mucosal tissue. In these variations, at least one prong of the stimulator may be positioned in a first nostril and at least one prong of the stimulator may be positioned in a second nostril. In these variations, when the stimulus is electrical, electrical stimulation may be delivered between the prongs in the first nostril and the prongs of the second nostril, which may cause current to flow through the septum.

Electrical Stimulus: Waveforms

When the stimulus is electrical, the electrical stimulus delivered by the stimulators described here may include a waveform or waveforms, which may be tailored for specific treatment regimens and/or specific subjects. The waveforms may be pulse-based or continuous. It should be appreciated that the waveforms described here may be delivered via a bipolar configuration or a monopolar configuration. When the stimulator is configured to deliver a continuous waveform, the waveform may be a sinusoidal, quasi-sinusoidal, square-wave, sawtooth/ramped, or triangular waveform, truncated-versions thereof (e.g., where the waveform plateaus when a certain amplitude is reached), or the like. Generally, the frequency and peak-to-peak amplitude of the waveforms may be constant, but in some variations the stimulator may be configured to vary the frequency and/or amplitude of the waveform. This variation may occur according to a pre-determined plan, or may be configured to occur randomly within given parameters. For example, in some variations the continuous waveform may be configured such that the peak-to-peak amplitude of the waveform varies over time (e.g., according to a sinusoidal function having a beat frequency). In some instances varying the amplitude and/or frequency of a stimulation waveform over time, or pulsing the stimulus on and off (e.g., 1 second on/1 second off, 5 seconds on/5 seconds off), may help reduce subject habituation (in which the subject response to the stimulation decreases during stimulation). Additionally or alternatively, ramping the amplitude of the stimulation waveform at the beginning of stimulation may increase comfort.

When the stimulator is configured to create a pulse-based electrical waveform, the pulses may be any suitable pulses (e.g., a square pulse, a haversine pulse, or the like). The pulses delivered by these waveforms may by biphasic, alternating monophasic, or monophasic, or the like. When a pulse is biphasic, the pulse may include a pair of single phase portions having opposite polarities (e.g., a first phase and a charge-balancing phase having an opposite polarity of the first phase). In some variations, it may be desirable to configure the biphasic pulse to be charge-balanced, so that the net charge delivered by the biphasic pulse is approximately zero. In some variations, a biphasic pulse may be symmetric, such that the first phase and the charge-balancing phase have the same pulse width and amplitude. Having a symmetric biphasic pulse may allow the same type of stimulus to be delivered to each nasal cavity. The pulses of a first phase may stimulate a first side of the nose (while providing a charge-balancing phase to a second side of the nose), while the pulses of the opposite phase may stimulate the second side of the nose (while providing a charge-balancing phase to the first side of the nose). In other variations, a biphasic pulse may be asymmetric, where the amplitude and/or pulse width of the first pulse may differ from that of the charge-balancing phase. Additionally, each phase of the biphasic pulse may be either voltage-controlled or current-controlled. In some variations, both the first phase and the charge-balancing phase of the biphasic pulse may be current-controlled. In other variations, both the first phase and the charge-balancing phase of the biphasic pulse may be voltage-controlled. In still other variations, the first phase of the biphasic pulse may be current-controlled, and the second phase of the biphasic pulse may be voltage-controlled, or vice-versa.

In variations where the waveform comprises a biphasic pulse, the biphasic pulse may have any suitable frequency, pulse widths, and amplitudes. For example, in instances where the stimulators described here are used to treat dry eye or otherwise produce a tearing response by stimulating nasal or sinus tissue, the stimulator may be configured to generate a biphasic pulse waveform at a frequency between about 0.1 Hz and about 200 Hz. In some of these variations, the frequency is preferably between about 10 Hz and about 60 Hz. In some of these variations, the frequency is preferably between about 25 Hz and about 35 Hz. In others of these variations, the frequency is preferably between about 50 Hz and about 90 Hz. In some of these variations, the frequency is preferably between about 65 Hz and about 75 Hz. In other variations, the frequency is preferably between about 130 Hz and about 170 Hz. In some of these variations, the frequency is preferably between about 145 Hz and about 155 Hz. In some variations, high frequencies, such as those between about 145 Hz and about 155 Hz may be too high for each pulse to stimulate/activate the target nerves. As a result, the stimulation may be interpreted by the patient to have an element of randomness, which in turn may help to reduce subject habituation.

Similarly, for the treatment of dry eye, the when the stimulus is electrical and the first phase of the biphasic pulse is current-controlled, the first phase may preferably have an amplitude between about 10 µA and 100 mA. In some of these variations, the amplitude may be preferably between about 0.1 mA and about 10 mA. When the first phase of the biphasic pulse is voltage-controlled, the first phase may preferably have an amplitude between about 10 mV and about 100 V. Additionally, the first phase may preferably have a pulse width between about 1 µs and about 10 ms. In some of these variations, the pulse width may preferably be between about 10 µs and about 100 µs. In other variations, the pulse width may preferably be between about 100 µs and about 1 ms.

When an electrical pulse waveform is an alternating monophasic pulsed waveform, each pulse delivered by the stimulator may have a single phase, and successive pulses may have alternating polarities. Generally, the alternating monophasic pulses are delivered in pairs at a given frequency (such as one or more of the frequencies listed above, such as between 30 Hz and 50 Hz), and may have an inter-pulse interval between the first and second pulse of the pair (e.g., about 100 µs, between 50 µs and 150 µs or the like). Each pulse may be current-controlled or voltage-controlled, and consecutive pulses need not be both current-controlled or both voltage-controlled. In some variations where the pulse waveform is charged-balanced, the waveform may comprise a passive charge-balancing phase after delivery of a pair of monophasic pulses, which may allow the waveform to compensate for charge differences between the pulses.

When a stimulator configured to deliver an electrical stimulus is positioned to place an electrode on either side of the nasal septum, alternating monophasic pulses may promote bilateral stimulation of nasal tissue. The pulses of a first phase may stimulate a first side of the nose (while providing a charge-balancing phase to a second side of the nose), while the pulses of the opposite phase may stimulate the second side of the nose (while providing a charge-balancing phase to the first side of the nose), since nerves may respond differently to anodic and cathodic pulses. The inter-pulse interval may give time for the stimulation provided by a first phase pulse to activate/polarize the target nerves prior to be reversed by an opposite phase pulse.

When a stimulator is configured to deliver a pulse-based waveform, the stimulation amplitude, pulse width, and frequency may be the same from pulse to pulse, or may vary over time. For example, in some variations, the amplitude of the pulses may vary over time. In some variations, the amplitude of pulses may vary according to a sinusoidal profile. In some variations, the stimulation waveform may be a modulated high frequency signal (e.g., sinusoidal), which may be modulated at a beat frequency of the ranges described above. In such variations, the carrier frequency may be between about 100 Hz and about 100 kHz. In other variations, the amplitude of pulses may increase (linearly, exponentially, etc.) from a minimum value to a maximum value, drop to the minimum value, and repeat as necessary. In some variations, the user may be able to control the stimulus during its delivery. After the user has placed a portion of the nasal insertion prong(s) (e.g., the electrode or electrodes) in contact with the nasal tissue, the user may increase the intensity of the stimulus. It may be desirable for the patient to increase the intensity of the stimulus until the stimulus causes paresthesia (e.g., tingling, tickling, prickling). As such, the patient may be able to self-determine the proper stimulation intensity and self-adjust the stimulus to a level effective to achieve the desired result (e.g., tear production). It may be desirable for the user to increase the intensity of the stimulus slowly in order to minimize discomfort.

In some instances, it may be desirable to configure the stimulation waveform to minimize side effects. In some instances, it may be desirable to promote stimulation of larger-diameter nerves (e.g., afferent fibers of the trigeminal nerve), which may promote a therapeutic effect, while reducing the stimulation of smaller nerves (e.g., a-delta fibers, c fibers, sympathetic and parasympathetic fibers), which may result in pain, discomfort, or mucus production. Generally, for smaller pulse-widths, the activation threshold for larger-diameter nerves may be lower than the activation threshold for the smaller nerve fibers. Conversely, for larger pulse-widths, the activation threshold for larger-diameter nerves may be higher than the activation threshold for the smaller nerve fibers. Accordingly, in some instances, it may be desirable to select a pulse width that preferably actuations the larger-diameter nerves. In some variations, the pulse width may be between 30 μs and about 70 μs, or may be between about 30 μs and about 150 μs.

It should be appreciated that the electrical stimulation devices and systems described here may be used for one or more diagnostic functions, to modulate blood flow (e.g., to treat headaches), to promote healing, or the like. Additionally, the stimulation systems, devices, and methods described are herein are intended for use with human users, it should be appreciated that they may be modified for veterinary use.

Chemical Stimulus

In some variations, one or more chemical agents may be delivered to nasal or sinus tissue to treat one or more conditions. For example, in some variations, one or more chemical agents may be used to treat dry eye or otherwise promote a tear-producing response. In some of these variations, the chemical agent may be configured to promote trigeminal nerve activation. The chemical agent may be delivered in any suitable manner. In some variations, the chemical agent may be delivered via a stimulator as described herein. In other variations, the chemical agent may be delivered via an inhaler, a nebulizer, or the like. In other variations, the chemical agent may be delivered via one or more nasal sprays or eye drops (which may drain into the nasal or sinus cavities via a nasolacrimal duct). The chemical agent may comprise one or more of the agents described above.

Mechanical, Thermal, Light-Base, and Magnetic Stimulus

As mentioned above, in some variations the stimulation systems described here may be used to provide mechanical, thermal, light-based and/or magnetic stimulation. In some variations, a stimulator may be used to deliver vibrational energy to nasal or sinus tissue. In variations where a stimulator comprises one or more prongs configured to be inserted at least partially into a nasal cavity (such as the electrical stimulators described herein), the prongs may be inserted at least partially into a nasal cavity and made to vibrate. In variations where a stimulator is implanted in a nasal or sinus cavity, one or more portions of the stimulator may vibrate while implanted. In some of these variations, the vibration may be generated using one or more magnets positioned externally of the body.

Additionally or alternatively, ultrasonic energy may be delivered to tissue by a stimulator comprising one or more ultrasound transducers. In variations in which stimulators are configured to deliver one or more pulses of air to tissue, one or more pulses of air may be delivered to stimulate tissue. The pulses of air may be generated via a source of compressed air, or the like. In some variations, the gas may be warmed or cooled (e.g., mechanically or via one or more thermally-activated fibers). In other variations, one or more portions of a stimulator may be heated or cooled to provide thermal stimulation to tissue. In variations where a stimulator comprises one or prongs configured to be inserted at least partially into a nasal cavity, the stimulator may controllably heat or cool the prongs. Additionally or alternatively, a stimulator may use one or more light-generating or magnetic field-generating elements to stimulate nasal or sinus tissue.

Treatment Regimens

The stimulation methods described herein may be delivered according to one or more treatment regimens to treat a condition. For example, to treat dry eye, stimulation may be delivered to a subject as-needed and/or according to a pre-determined regimen. In some instances, a user may use one of the stimulation devices described herein to provide a round of stimulation when the user experiences symptoms of dry eye. A round of stimulation may have any suitable duration (e.g., between 1 second and 10 minutes).

In other instances, the devices may be used to provide stimulation on a scheduled basis. For example, in some variations the stimulation devices described here may be used to provide a round of stimulation at least once daily, at least once weekly, or the like. In some variations, the stimulation devices may be used to deliver multiple rounds of stimulation each day (e.g., at least two treatments daily, at least three treatments daily, at least four treatments daily, at least five treatments daily, at least six treatments daily, at least seven treatments daily, at least eight treatments daily, between two and ten times daily, between four and eight times daily, or the like). In some variations, the stimulation may be delivered at certain times of day. In other variations, the stimulation may be delivered at any time during the day as desired or determined by the user. When the device is used to provide stimulation on a scheduled basis, in some variations each round of stimulation may be the same length (e.g., about 30 seconds, about 1 minute, about 2 minutes, about 3 minutes, about 4 minutes, about 5 minutes, about 10 minutes, or longer than 10 minutes). In other variations, some rounds of stimulation may have different predetermined lengths. In yet other variations, the user may choose the length of the round of stimulation. In some of these variations, the user may be given a minimum stimulation time (e.g., about 5 seconds, about 10 seconds, about 30 seconds, about 1 minute, about 2 minutes, about 3 minutes, about 5 minutes, or the like) and/or a maximum stimulation time (e.g., about 1 minute, about 2 minutes, about 3 minutes, about 5 minutes, about 10 minutes, about 20 minutes, or the like). In some instances, the delivery schedule or stimulation parameters may be changed based on the time of day (e.g., daytime use vs. nighttime use). In some of these variations, the stimulator may comprise (e.g., as part of a control subsystem) one or more counters and intelligence (e.g., a microcontroller, programmable logic (e.g., a field-programmable gate array), or application-specific integrated circuit (ASIC)). A counter may count oscillator pulses until a certain number have passed, at which point stimulation may be activated. Additionally or alternatively, a counter may measure the duration of stimulation and the intelligence may control the stimulation length.

In instances where the stimulation device is implantable, the stimulation may be delivered on a continuous basis. When an implantable stimulator is used to deliver stimulation non-continuously as discussed herein with respect to handheld stimulators, the implantable stimulator may be configured to deliver stimulation automatically or may be configured to deliver stimulation on command. For example, in some variations the stimulator may be configured to deliver stimulation on a pre-programmed basis (e.g., according to a treatment regimen as discussed herein). In other variations, the stimulator may comprise one or more sensors, and may be configured to deliver stimulation upon detecting a pre-determined condition with the one or more sensors. For example, in some variations, a stimulator may comprise a wetness sensor, and may be configured to deliver stimulation when the wetness sensor registers a certain dry condition in a nasal or sinus cavity. When an implanted stimulator is activated by a user, an external controller may be used (e.g., via a wireless signal such as BLUETOOTH™ wireless technology, near-field RF, far-field RF, or the like) to activate the implanted stimulator.

Treatment Effects

In some variations, the treatment regimens described herein may be used to treat dry eye. Current treatment options for dry eye are limited, and they generally provide limited symptom relief or improvement in ocular health. In contrast to current treatment options, the treatment regimens using the stimulators described herein may provide rapid and marked relief and improvement in ocular health, as measured by numerous indicators, including tear production, patient symptoms, and corneal and conjunctival staining. Both the speed and magnitude of relief and improvement in ocular health that may be achieved is surprising given the much slower and more limited ability to treat dry eye with existing treatments. In some variations, the treatment regimens of providing the stimuli described herein may cause periodic or regular activation of the nasolacrimal reflex, which may in turn treat dry eye and/or improve ocular health. Periodic or regular activation of the nasolacrimal reflex may improve ocular health by several mechanisms of action. For example, the activation of the nasolacrimal reflex may cause tearing, which in turn may deliver growth factors contained in the tears to the ocular surface. These growth factors include epidermal growth factor (EGF). EGF is a polypeptide that stimulates the growth of various tissues, including the cornea, conjunctiva, and goblet cells. In patients with dry eye, the cornea may become damaged due to desiccation and inflammation; EGF may thus play a role in stimulating the healing process for the cornea. Periodic or regular activation of the nasolacrimal reflex may also improve ocular health by increasing resting tear production, which may promote chronic hydration of the ocular surface, as well as by causing periodic or regular significant increases in tear production during activation. Activation of the nasolacrimal reflex may also improve ocular health by causing vasodilation, which may in turn promote ocular health.

Example

A prospective, single phase, open label, single arm, non-randomized study was carried out. Inclusion criteria included males and females 18 year of age or older; a Schirmer's Tear Test (described below) with topical anesthesia of less than or equal to 15 mm in 5 minutes in both eyes at least of two screening visits; at a first screening visit, a Schirmer's Tear Test with topical anesthesia and nasal stimulation with a cotton swab of at least twice or at least 10 mm higher than the first of two unstimulated values in both eyes; a baseline Ocular Surface Disease Index (OSDI) score (described below) of at least 13 with no more than 3 responses of "not applicable" at each of the two screening visits; normal lid anatomy, blinking function, and closure; and corrected visual acuity of 20/200 (Snellen equivalent) or better in each eye at both screening visits.

Subjects were provided a handheld stimulator probe as described herein with respect to FIG. 14, but without electrode covers 1418, and a stimulator body producing a biphasic pulsed waveform with 300 μs per pulse at about 30 Hz and with amplitudes between about 0 mA and about 20 mA. For the duration of the study, subjects were instructed to stop taking their regular dry eye drops but were given over-the-counter artificial tears in unit dose vials to use if their dry eye symptoms became intolerable. Between office study visits, patients were instructed to perform nasal stimulation by placing the nasal insertion prongs of the stimulator probe in both nostrils, turning the device on using the control knob of the stimulator body from the "off" position until a "click" was felt, and then increasing the stimulation intensity by turning the control knob clockwise. Patients were instructed to stimulate at least four times a day (six times per day was encouraged), and more than four times a day as needed for relief of dry eye symptoms. As recorded in patient diaries, patients stimulated for about 30 seconds to about five minutes each time they stimulated, and between once per today and eight times per day.

At each study visit at day 0, day 7-10 ("Day 7"), day 14-17 ("Day 14"), day 26-34 ("Day 30"), days 53-67 ("Day 60"), days 76-104 ("Day 90"), and days 150-210 ("Day 180"), tests to measure ocular health, including tear production, other objective measures of DED, and subject symptom recording were performed prior to and after nasal stimulation in the clinic. These included dry eye symptom measurement, Ocular Surface Disease Index (OSDI), ocular surface staining, tear film breakup time, and Schirmer's Tear Test.

Dry eye symptoms were measured by the subject rating each ocular symptom due to ocular dryness on a scale of 0% (no discomfort) to 100% (maximal discomfort), including the patient's general assessment of dry eye symptom severity, dryness, sticky feeling, burning or stinging, foreign body sensation, blurred vision, photophobia, and/or pain. The rating for each was averaged to determine a symptom rating.

OSDI was measured by the subject answering 12 questions (I. Have you experienced any of the following during the last week: Eyes that are sensitive to light? Eyes that feel gritty? Painful or sore eyes? Blurred vision? Poor vision? II. Have problems with your eyes limited you in performing any of the following during the last week: Reading? Driving at night? Working with a computer or bank machine (ATM)? Watching TV? III. Have your eyes felt uncomfortable in any of the following situations during the last week: Windy conditions? Places or areas with low humidity (very dry)? Areas that are air conditioned?) by circling the number that best represented each answer: 4 (all of the time), 3 (most of the time), 2 (half of the time), 1 (some of the time) or 0 (none of the time). To obtain the total score for the questionnaire, the final score was calculated using the following formula: (A) Add subtotals from Sections I, II, and III=A; (B) Determine total number of questions answered from Sections I, II, and III (do not include N/A)=B; (C) Final OSDI score=A×25 divided by B.

Improvement in ocular surface health was also measured by decreased ocular staining, including corneal and conjunctival staining. While in healthy eyes the tear film may prevent the dye from adhering to the ocular surface, the dye may adhere to the ocular surface of unhealthy eyes. Ocular surface staining was assessed and recorded by carrying out the following steps in order: (1) Lissamine green conjunctival staining was performed using a Lissamine Green Ophthalmic Strip. The strip was wetted with sterile buffered saline and applied to the inferior bulbar conjunctiva. (2) After allowing lissamine green to remain on the eye for 1 minute, the nasal and temporal conjunctival regions were graded on a scale of 0 to 5 using the Oxford pictorial grading scale. (3) Between 1.0 to 5.0 micro-liters of non-preserved, 2% sodium fluorescein on strips were instilled onto the bulbar conjunctiva without inducing reflex tearing. (4) The subject was instructed to blink naturally several times without forced closure of the eyelid to distribute the fluorescein. (5) After allowing fluorescein to remain on the eye for at least 1 minute, the 5 corneal regions were individually graded on a scale of 0 to 5 using the Oxford pictorial grading scale.

Tear film breakup time (TFBUT) was assessed using the following steps: (1) The slit-lamp was set to a magnification of approximately 10×. (2) With adequate fluorescein in place using strips, the subject was asked to stare straight ahead without blinking until told otherwise. A stopwatch was used to record the time between the last complete blink and the first appearance of a growing micelle indicating tear-film breakup. (3) This procedure was repeated in the other eye.

Schirmer's Tear Test with topical anesthetic was used to assess tear production using the following steps: (1) Topical anesthetic drops of 0.5% proparacaine hydrochloride (or other equivalent topical ocular anesthetic) were instilled in both the eyes of the subject. (2) The subject was instructed to keep the eyes closed for one minute. After opening the eyes, excess moisture in the inferior fornix was gently removed with a cotton-tipped applicator. (3) After 5 minutes, Schirmer strips (35 mm×5 mm size filter paper strip) were placed in each eye at the junction of the middle and lateral thirds of the lower eye lid. (4) The test was performed under ambient light. The subject was instructed to look forward and to blink normally during the course of the test. The test was performed in a room with no direct blast of air on the subject's face. (5) Strips were removed after 5 minutes from both eyes and the amount of wetting was recorded. (6) At the first screening visit only, the Schirmer test was repeated a second time as described above with new Schirmer strips. (7) At the first screening visit only, the Schirmer test was repeated a third time as described above with new strips adding cotton swab nasal stimulation. With the strips in place, the examiner inserted cotton swabs and gently probed both nasal middle turbinates of the nose simultaneously. After approximately 2 minutes, the probing could be repeated. The Schirmer strips remained in place until after 5 minutes had elapsed. At the first screening visit, new anesthetic drops were added as necessary. Both basal and acute measurements were taken. Basal Schirmer's Tear Test measurements were baseline tear production measurements, without acute stimulation (e.g., without having stimulated at least within 30 minutes, at least within 2 hours, or the like). Acute Schirmer's Tear Test measurements were taken during stimulation with the patient's device as described above.

Figure 29A:
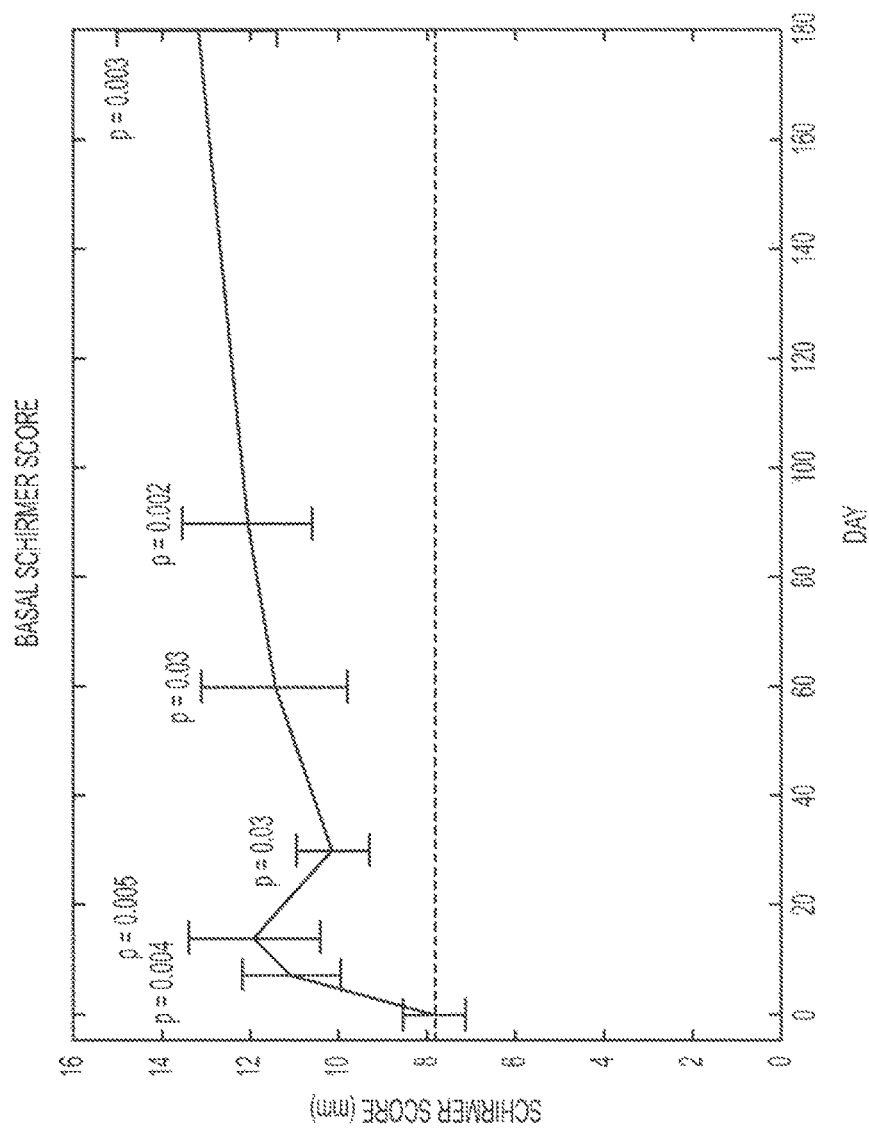
FIG. 29A shows patients' average basal Schirmer scores over time with a treatment regimen as described here.

The average basal Schirmer scores for 24 patients are shown in FIG. 29A and Table 1 below.

TABLE 1

| Day | Basal Schirmer Score (mm) |
| --- | --- |
| 0 | 7.8 |
| 7 | 11.0 |
| 14 | 11.9 |
| 30 | 10.1 |
| 60 | 11.4 |
| 90 | 12.1 |
| 180 | 13.2 |

As shown there, the patients' average basal Schirmer score increased within one week of starting the treatment regimen, increasing by about 3.2 mm during that time. Other treatment options may take significantly longer to show improvement in basal Schirmer scores, and even then the improvement in basal Schirmer score may be significantly less. After 90 days of the treatment regimen described herein, the average basal Schirmer scores were about 4.3 mm higher than before beginning treatment. In contrast, a treatment regimen of topical cyclosporine has been measured to increase basal Schirmer scores by only about 0.3 mm after ninety days of treatment (Sall, et. al. Two Multicenter, Randomized Studies of the Efficacy and Safety of Cyclosporine Ophthalmic Emulsion in Moderate to Severe Dry Eye Disease. *Ophthalmology*, Vol 107(4). 2000; FDA Restasis Statistical Review, CDER 21-023. 1999). Thus, the increase in average basal Schirmer scores over 90 days with the treatment regimen described herein was more than 14 times the increase in average basal Schirmer scores with a treatment of cyclosporine. A treatment regimen of a topical IL-1 agonist was not found to substantially change average Schirmer scores after 12 weeks (Amparo, et al. Topical Interleukin 1 Receptor Antagonist for Treatment of Dry Eye Disease. *JAMA Ophthalmol*, Vol 131(6). 2013).

Figure 29B:
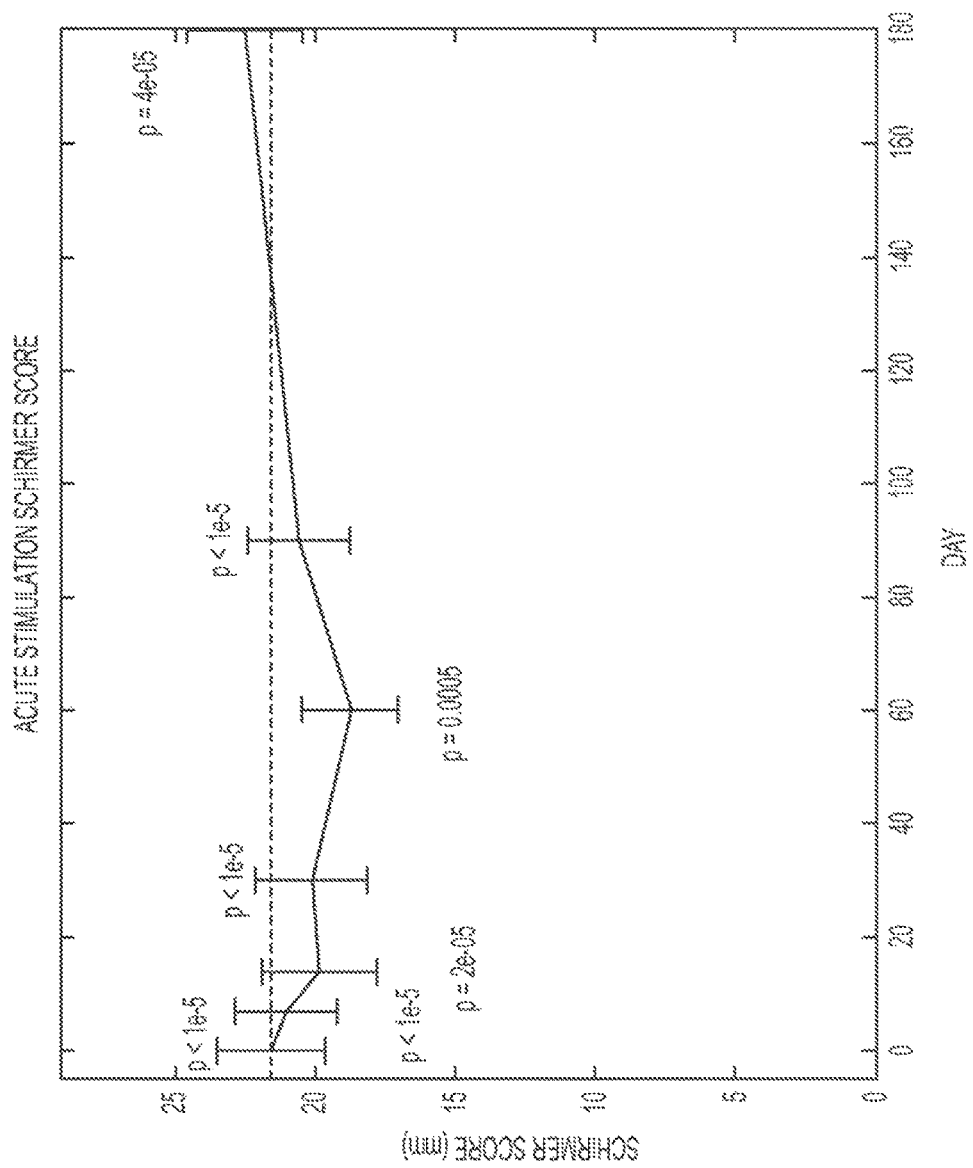
FIG. 29B shows patients' average acute Schirmer scores over time with a treatment regimen as described here.

The acute Schirmer scores for 24 patients are shown in FIG. 29B and Table 2 below.

TABLE 2

| Day | Acute Schirmer Score (mm) |
| --- | --- |
| 0 | 21.6 |
| 7 | 21.0 |
| 14 | 19.8 |
| 30 | 20.1 |
| 60 | 18.7 |
| 90 | 20.5 |
| 180 | 22.5 |

Figure 29C:
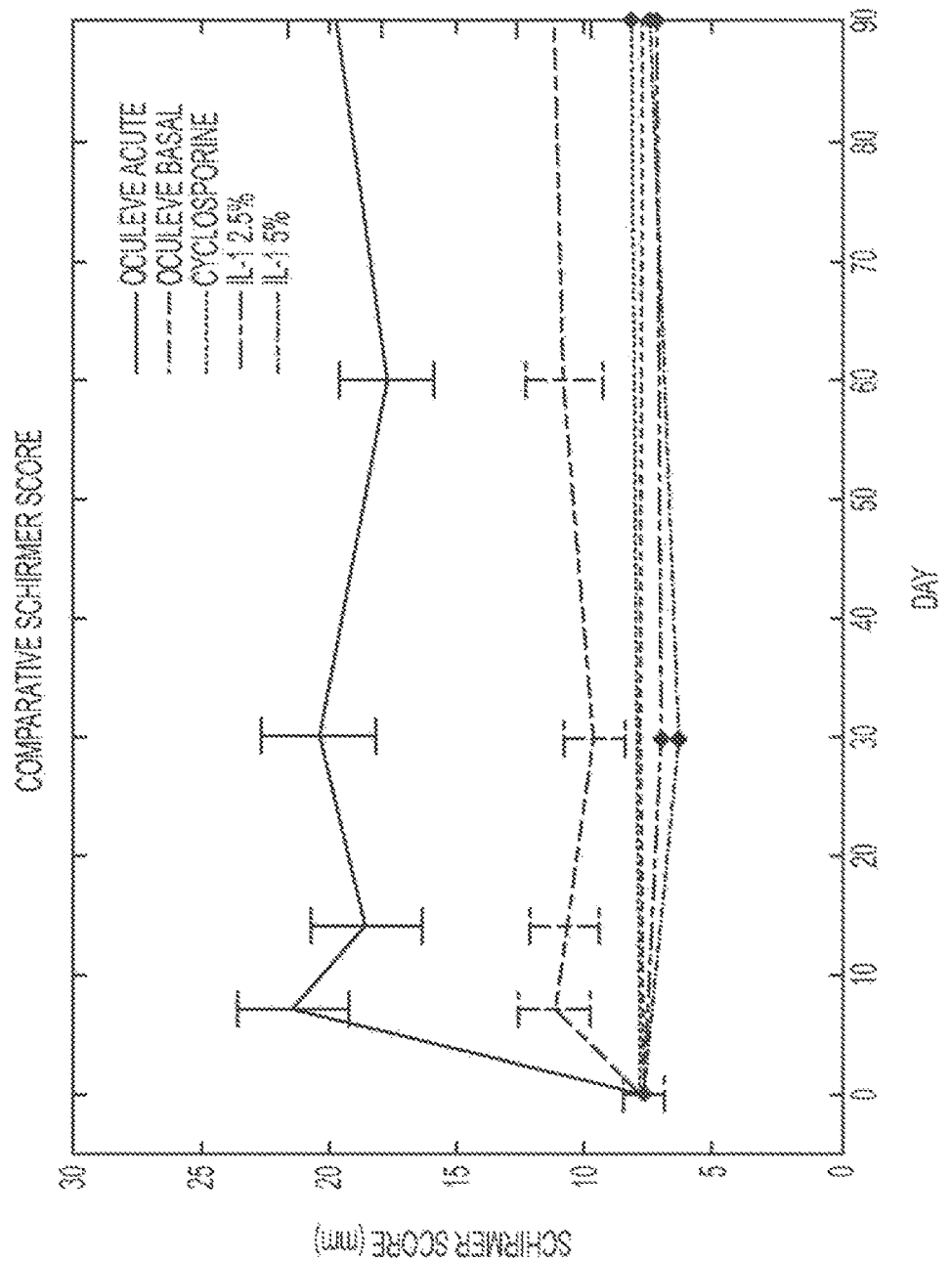
FIG. 29C shows comparative Schirmer score data.

As shown there, the patients' average acute Schirmer scores were between about 18 mm and about 23 mm. Thus, acute stimulation as described here was able to cause average tearing significantly above the basal levels, increasing tearing from basal levels by between about 7 mm and about 14 mm. FIG. 29C shows comparative data for basal and acute Schirmer scores for treatment regimens as described here with 19 patients, and basal Schirmer scores for standard treatment regimens of cyclosporine and an IL-1 agonist at 2.5% and 5%.

Figure 30:
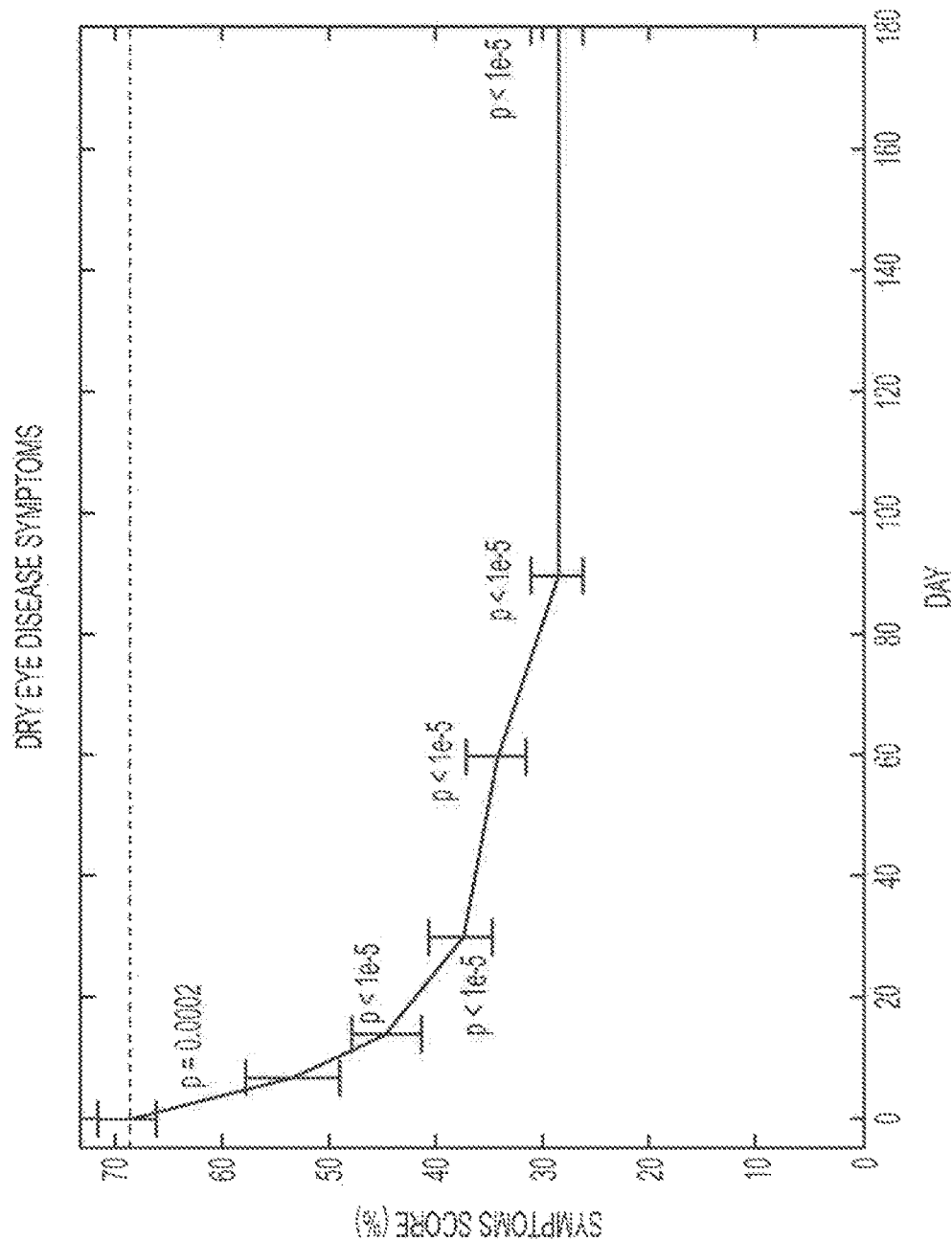
FIG. 30 shows patients' average dry eye symptoms over time with a treatment regimen as described here.

The average dry eye symptoms for 24 patients are shown in FIG. 30 and Table 3.

TABLE 3

| Day | DED Symptoms Value (%) |
| --- | --- |
| 0 | 69 |
| 7 | 53 |
| 14 | 45 |
| 30 | 38 |
| 60 | 34 |
| 90 | 29 |
| 180 | 28 |

As shown there, the patients' average dry eye symptoms decreased within one week of starting the treatment regimen, decreasing by about 16 percentage points on the scale during that time. The patients' average dry eye symptoms continued to decrease by about 8 percentage points on the scale in the following week, leading to a decrease of about 24 percentage points on the scale within two weeks. The patients' average dry eye symptoms decreased by about 31 percentage points on the scale within the first 30 days of starting the regimen, and decreased by about 40 percentage points on the scale within 60 days of starting the regimen. As shown, this decrease in average dry eye symptoms was maintained over 180 days.

Figure 31A:
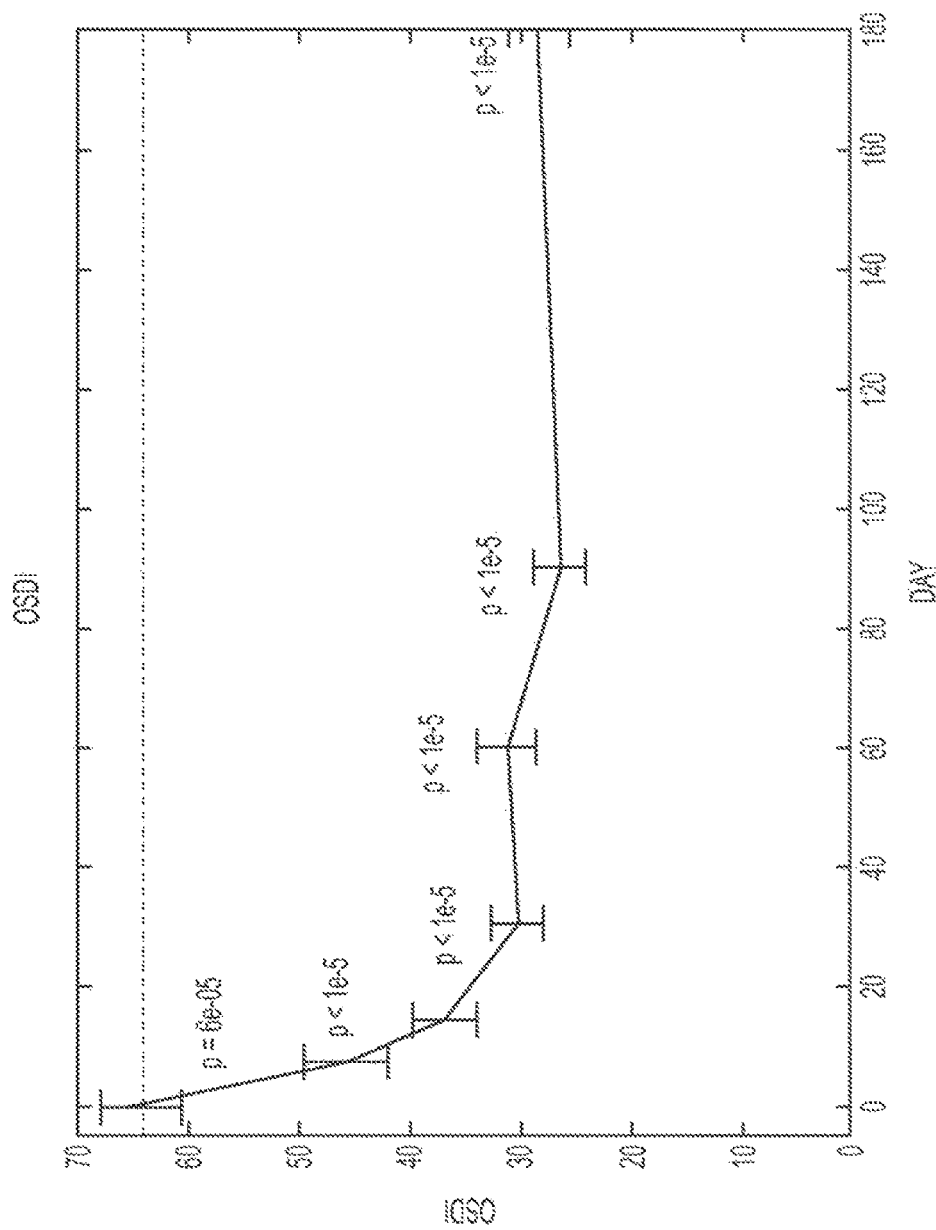
FIG. 31A shows patients' average Ocular Surface Disease Index scores over time with a treatment regimen as described here.

The average Ocular Surface Disease Index (OSDI) scores for 24 patients are shown in FIG. 31A and Table 4.

TABLE 4

| Day | OSDI |
|-----|------|
| 0   | 64   |
| 7   | 46   |
| 14  | 37   |
| 30  | 30   |
| 60  | 31   |
| 90  | 26   |
| 180 | 28   |

Figure 31B:
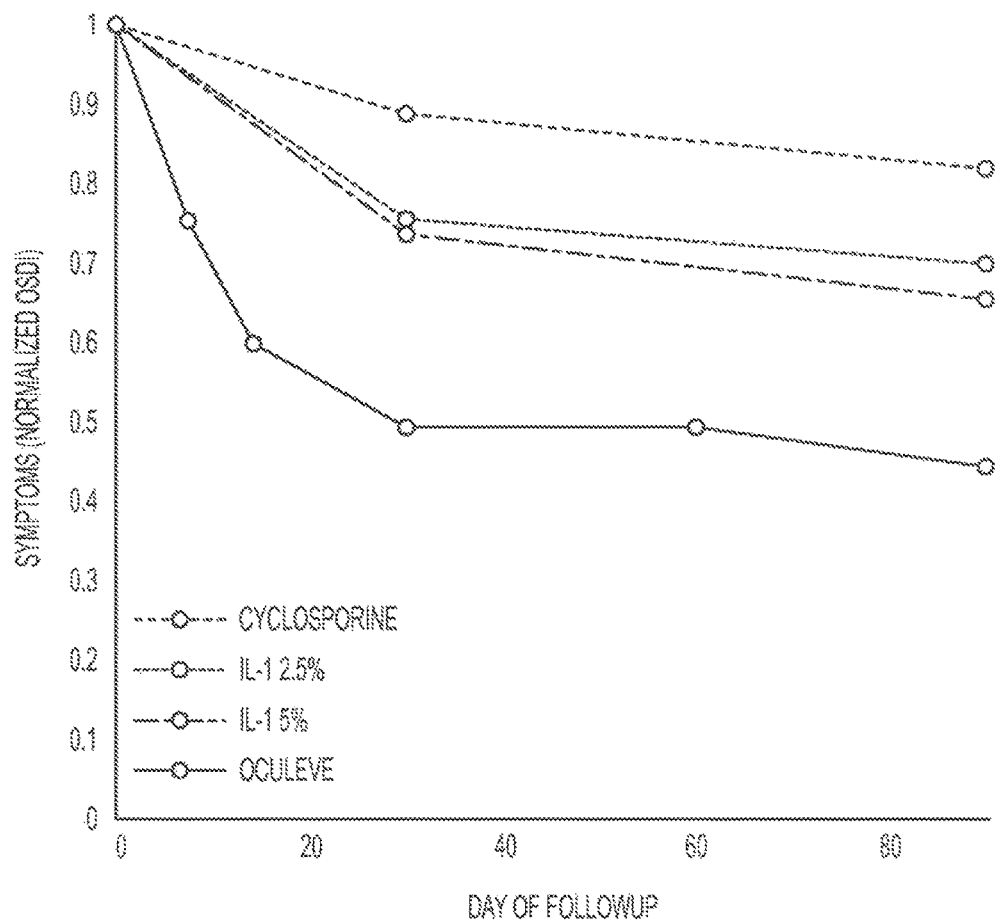
FIG. 31B shows comparative OSDI data.

As shown, the patients' average OSDI scores decreased within one week of starting the treatment regimen, decreasing by about 18 points (about 28%) within that time. Other treatment options may take significantly longer to relieve symptoms as measured by the OSDI, and even then the improvement in OSDI scores may be significantly less. After two weeks of a treatment regimen described herein, the patients' average OSDI scores had decreased by about 27 points (about 42%). After 30 days of a treatment regimen described herein, the patients' average OSDI scores had decreased by about 34 points (about 53%), and decreased by about 38 points (about 59%) after 90 days. In contrast, as shown in FIG. 31B, a treatment regimen of cyclosporine has been measured to decrease patients' average OSDI scores by about 15% after 90 days of treatment (Sall, et. al. Two Multicenter, Randomized Studies of the Efficacy and Safety of Cyclosporine Ophthalmic Emulsion in Moderate to Severe Dry Eye Disease. *Ophthalmology*, Vol 107(4). 2000; FDA Restasis Statistical Review, CDER 21-023. 1999). A treatment regimen of a topical IL-1 agonist has been measured to decrease patient's average OSDI scores by about 30% and 35% after 12 weeks of treatment with 2.5% and 5% IL-1 agonist, respectively (Amparo, et al. Topical Interleukin 1 Receptor Antagonist for Treatment of Dry Eye Disease. *JAMA Ophthalmol*, Vol 131(6). 2013). FIG. 31B shows comparative normalized average OSDI scores for 19 patients for treatment regimens as described here, and for treatment regimens of topical cyclosporine and topical IL-1 at 2.5% and 5%.

Figure 32A:
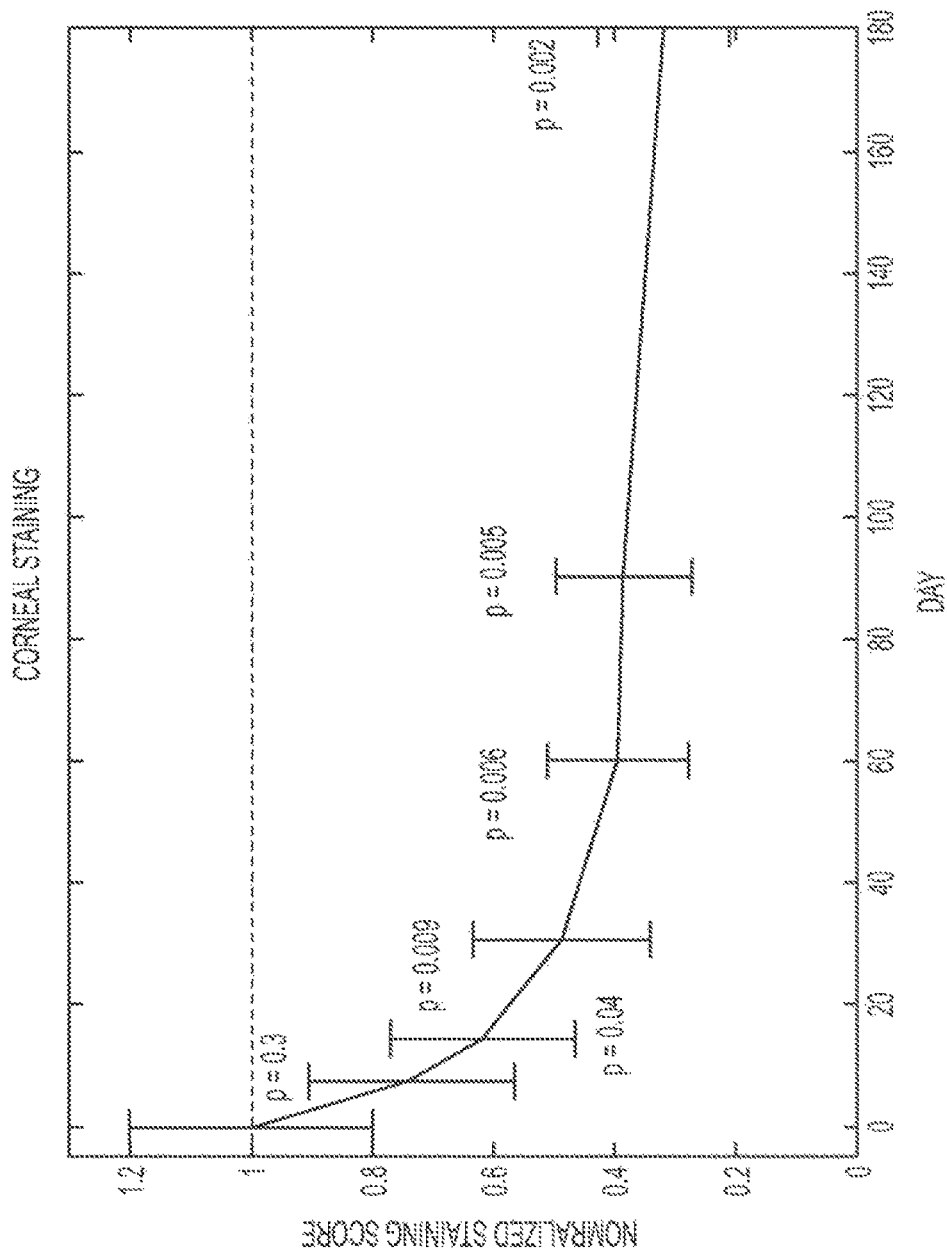
FIG. 32A shows patients' average normalized corneal staining over time with a treatment regimen as described here.

Average corneal staining for 24 patients is shown in FIG. 32A and Table 5, normalized to before starting the treatment regimen.

TABLE 5

| Day | Normalized Corneal Score |
|-----|--------------------------|
| 0   | 1    |
| 7   | 0.73 |
| 14  | 0.62 |
| 30  | 0.48 |
| 60  | 0.39 |
| 90  | 0.38 |
| 180 | 0.31 |

Figure 32B:
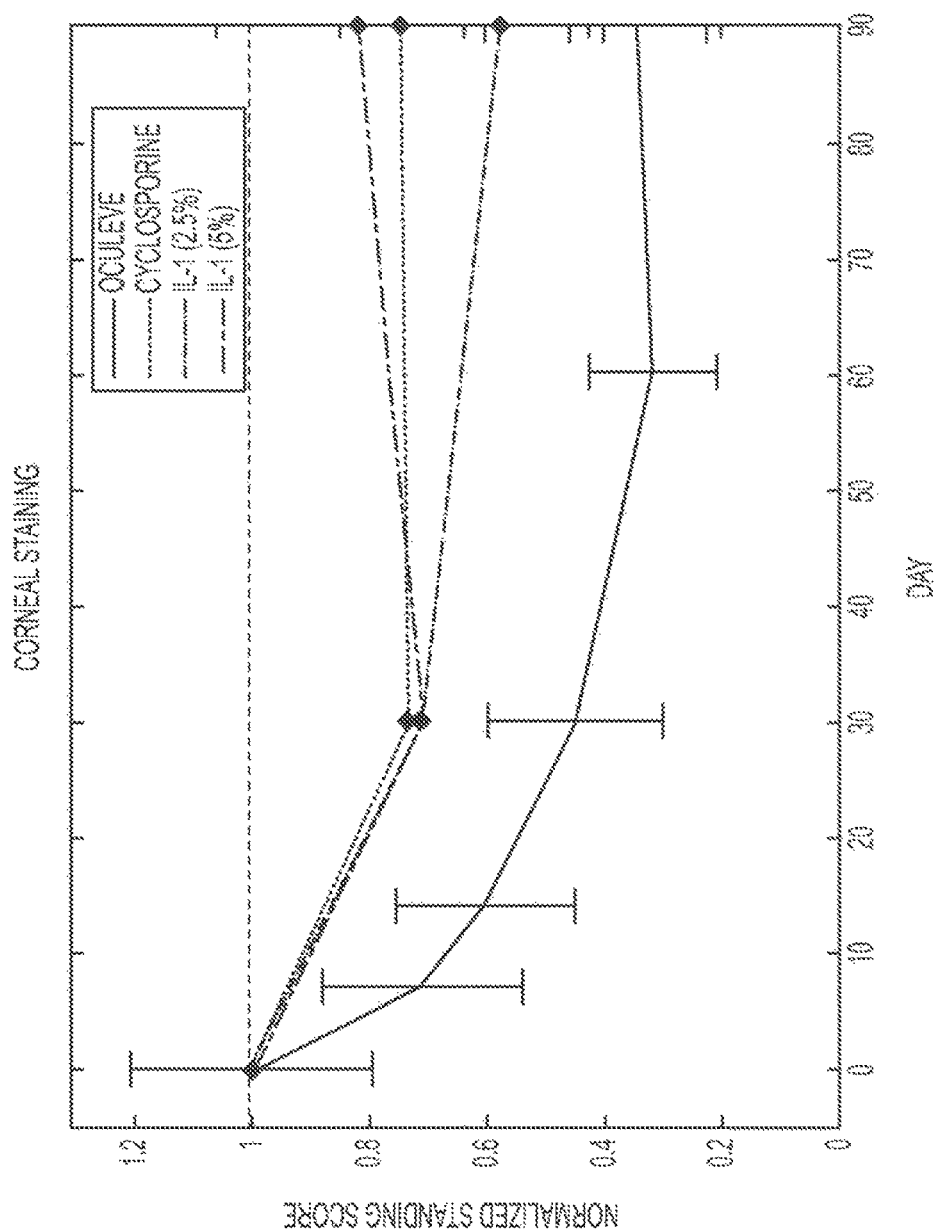
FIG. 32B shows comparative corneal staining data.

As shown there, the patients' average corneal staining decreased within one week of starting the treatment regimen, decreasing by about 27% during that time. Other treatment options may take significantly longer to show improved corneal staining. After two weeks of a treatment regimen described here, the patients' average corneal staining decreased by about 38%. The patients' average corneal staining decreased by about 52% within the first 30 days of starting the regimen, decreased by about 61% within 60 days of starting the regimen, and decreased by about 62% within 90 days of starting the regimen. In contrast, a treatment regimen of topical cyclosporine has been measured to decrease patients' average corneal staining by only about 23% after 90 days of treatment (Sall, et. al. Two Multicenter, Randomized Studies of the Efficacy and Safety of Cyclosporine Ophthalmic Emulsion in Moderate to Severe Dry Eye Disease. *Ophthalmology*, Vol 107(4). 2000; FDA Restasis Statistical Review, CDER 21-023. 1999). A treatment regimen of topical IL-1 agonist has been measured to decrease patient's average corneal staining by about 46% and 17% after 12 weeks of treatment with 2.5% and 5% IL-1 agonist, respectively. FIG. 32B shows comparative normalized average corneal staining for 19 patients with treatment regimens as described here, and for treatment regimens of topical cyclosporine and topical IL-1 at 2.5% and 5% (Amparo, et al. Topical Interleukin 1 Receptor Antagonist for Treatment of Dry Eye Disease. *JAMA Ophthalmol*, Vol 131(6). 2013).

Figure 33A:
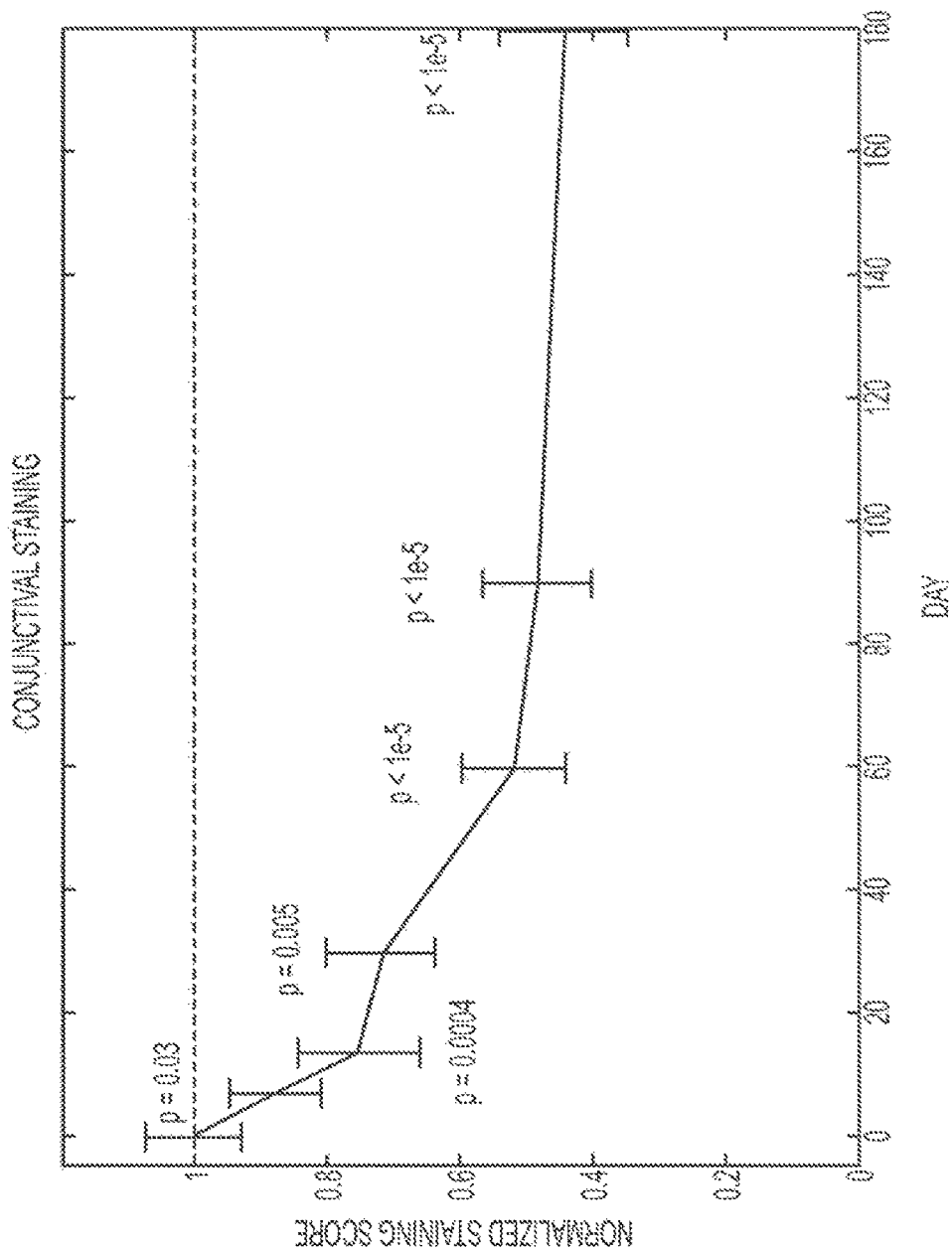
FIG. 33A shows patients' average normalized conjunctival staining over time with a treatment regimen as described here.

Average conjunctival staining for 24 patients is shown in FIG. 33A and Table 6, normalized to before starting the treatment regimen.

TABLE 6

| Day | Normalized Conjunctival Score |
|-----|-------------------------------|
| 0   | 1    |
| 7   | 0.87 |
| 14  | 0.75 |
| 30  | 0.71 |
| 60  | 0.51 |
| 90  | 0.48 |
| 180 | 0.44 |

Figure 33B:
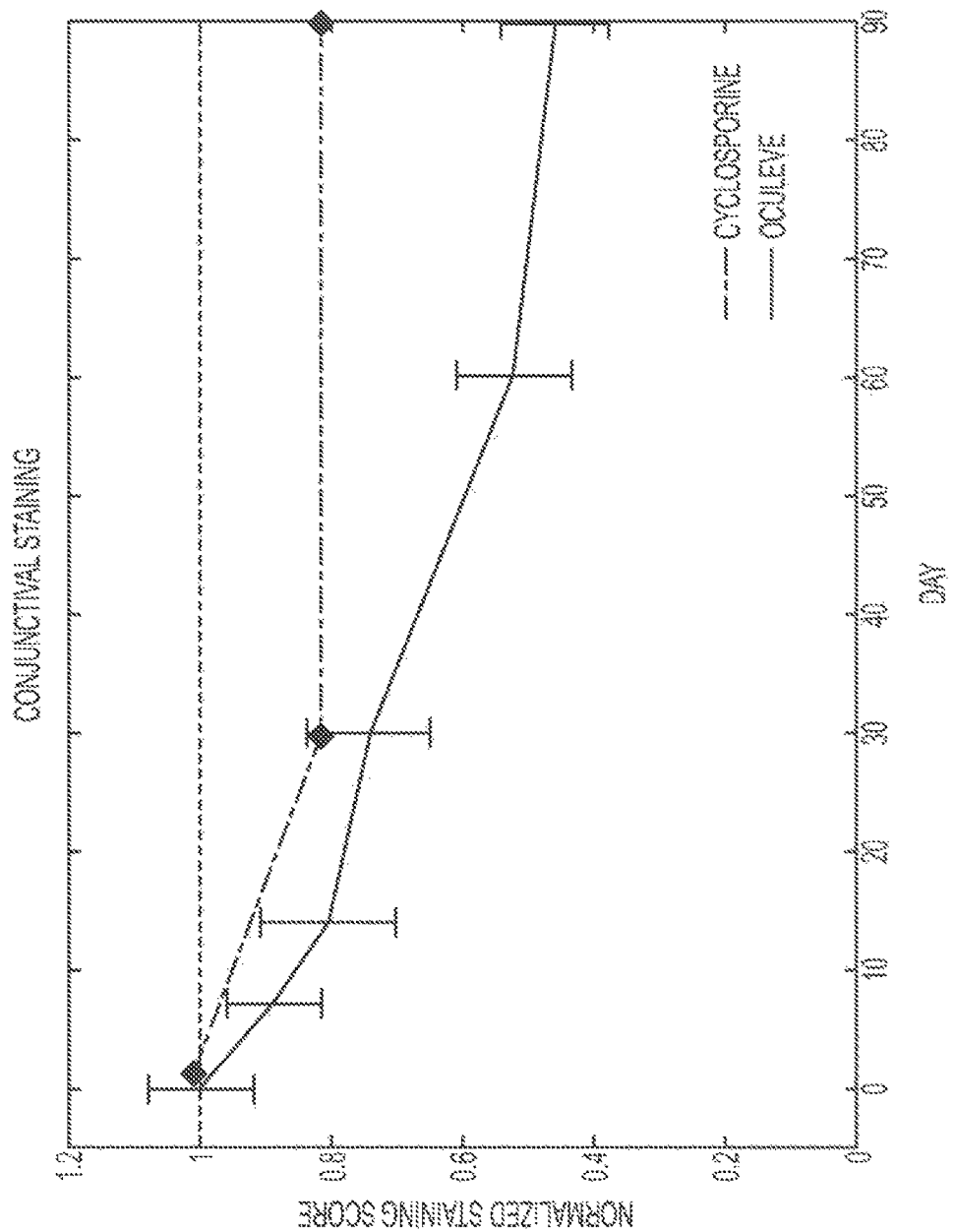
FIG. 33B shows comparative conjunctival staining data.

As shown there, the patients' average conjunctival staining decreased within one week of starting the treatment regimen, decreasing by about 13% within that time. Other treatment options may take significantly longer to show improved conjunctival staining. The patients' average conjunctival staining continued to decrease by about 12% in the following week as compared to before starting the treatment regimen, leading to a decrease of about 25% within two weeks. The patients' average conjunctival staining decreased by about 29% within the first 30 days of starting the regimen, decreased by about 49% within 60 days of starting the regimen, and decreased by about 52% within 90 days of starting the regimen. In contrast, a treatment regimen of topical cyclosporine has been measured to decrease patients' average conjunctival staining by only about 20% after 90 days of treatment. FIG. 33B shows comparative normalized average conjunctival staining for 19 patients for treatment regimens as described here, and for treatment regimens of topical cyclosporine. Tear film breakup time was observed to stay relatively constant over the study period for the patients observed.

For the patients shown in FIGS. 29-34, the stimulus delivered was a biphasic pulsed waveform with 300 µs per pulse at about 30 Hz and with amplitudes between about 0 mA and about 20 mA, using the handheld device of FIG. 14 without covers 1418. However, it should be appreciated that similar results may be found for other stimulus parameters (e.g., other waveforms as described above, other frequencies, other amplitudes, and the like) and other stimulators, such as described herein.

The invention claimed is:

1. A method of treating dry eye, comprising:
   delivering, by a handheld stimulator and in response to dry eye symptoms, an electrical stimulus via a first electrode and a second electrode to activate a nerve in the anterior nasal cavity of the subject and thereby increase an amount of tear production in the subject,
   wherein the first electrode and the second electrode are disposed on the handheld stimulator, wherein the handheld stimulator includes a user interface configured to allow a user to control the electrical stimulus, wherein the user interface includes an operating mechanism for allowing a user to adjust an intensity of the electrical stimulus delivered via the first electrode and the second electrode, and
   wherein the first electrode is positioned in a first nasal cavity of the subject and the second electrode is positioned in a second nasal cavity of the subject.

2. The method of claim 1, further comprising positioning the first electrode and the second electrode in contact with nasal mucosa of the subject.

3. The method of claim 1, wherein the electrical stimulus activates the nasolacrimal reflex.

4. The method of claim 1, wherein the electrical stimulus comprises a biphasic symmetric pulse waveform.

5. The method of claim 1, wherein the electrical stimulus comprises a waveform having a frequency between about 0.1 Hz and about 150 Hz.

6. The method of claim 1, wherein the electrical stimulus comprises a waveform having a maximum amplitude between about 10 μA and about 100 mA.

7. The method of claim 1, wherein the electrical stimulus comprises a waveform having varying peak-to-peak amplitude.

8. The method of claim 1, wherein the electrical stimulus comprises a waveform having varying frequency.

9. The method of claim 1, wherein the first electrode is positioned between about 20 mm and about 35 mm into the first nasal cavity of the subject and wherein the second electrode is positioned between about 20 mm and about 35 mm into the second nasal cavity of the subject.

10. The method of claim 1, further comprising positioning the first electrode and the second electrode in contact with nasal mucosa of the subject and delivering an electrical stimulus via the first electrode and the second electrode to activate a nerve to thereby produce tearing in the subject on a second occasion.

11. The method of claim 10, further comprising delivering an electrical stimulus via the first electrode and the second electrode at least once daily during a treatment period comprising a plurality of days.

12. The method of claim 1, wherein the handheld stimulator provides feedback to the subject to indicate intensity of the electrical stimulus.

13. The method of claim 1, wherein a stimulus pattern of the electrical stimulus is controlled by the subject through the user interface.

14. The method of claim 1, wherein duration of the electrical stimulus is controlled by the subject through the user interface.

15. The method of claim 1, wherein start and stop of the electrical stimulus is controlled by the subject through the user interface.

16. The method of claim 1, wherein the operating mechanism of the user interface comprises one or more buttons.

17. The method of claim 1, wherein the first electrode and the second electrode each comprises a hydrogel electrode.

18. The method of claim 1, wherein the handheld stimulator includes a stimulator body configured to be held in a hand of the subject, and wherein the user interface is positioned along the stimulator body.

* * * * *